(12) United States Patent
Gajewski et al.

(10) Patent No.: US 11,566,077 B2
(45) Date of Patent: Jan. 31, 2023

(54) DYSFUNCTIONAL ANTIGEN-SPECIFIC CD8+ T CELLS IN THE TUMOR MICROENVIRONMENT

(71) Applicant: The University of Chicago, Chicago, IL (US)

(72) Inventors: Thomas Gajewski, Chicago, IL (US); Jason Williams, Chicago, IL (US); Brendan Horton, Chicago, IL (US)

(73) Assignee: The University of Chicago, Chicago, IL (US)

( * ) Notice: Subject to any disclaimer, the term of this patent is extended or adjusted under 35 U.S.C. 154(b) by 18 days.

(21) Appl. No.: 16/476,219

(22) PCT Filed: Jan. 17, 2018

(86) PCT No.: PCT/US2018/014008
§ 371 (c)(1),
(2) Date: Jul. 5, 2019

(87) PCT Pub. No.: WO2018/186924
PCT Pub. Date: Oct. 11, 2018

(65) Prior Publication Data
US 2020/0010557 A1    Jan. 9, 2020

Related U.S. Application Data

(60) Provisional application No. 62/447,199, filed on Jan. 17, 2017.

(51) Int. Cl.
*C07K 16/28* (2006.01)
*A61K 35/17* (2015.01)
*G01N 33/569* (2006.01)

(52) U.S. Cl.
CPC .......... *C07K 16/2878* (2013.01); *A61K 35/17* (2013.01); *C07K 16/2803* (2013.01); *G01N 33/56972* (2013.01); *C07K 2317/75* (2013.01); *C07K 2317/76* (2013.01)

(58) Field of Classification Search
CPC ............ C07K 16/2878; C07K 16/2803; A61K 35/17; G01N 33/56972
See application file for complete search history.

(56) References Cited

U.S. PATENT DOCUMENTS

| | | | |
|---|---|---|---|
| 9,163,087 B2 * | 10/2015 | Kuchroo ................. | A61P 31/12 |
| 9,297,813 B2 * | 3/2016 | Lim ........................ | A61K 45/06 |
| 10,034,939 B2 * | 7/2018 | Gajewski ................ | A61P 35/00 |
| 2007/0072209 A1 | 3/2007 | Moses et al. | |
| 2013/0244255 A1 * | 9/2013 | Zhong ................. | G01N 33/6869 |
| | | | 435/7.23 |
| 2013/0296188 A1 | 11/2013 | Lim et al. | |
| 2015/0352206 A1 | 12/2015 | Gajewski et al. | |
| 2016/0024593 A1 * | 1/2016 | Zheng ..................... | G16B 25/10 |
| | | | 424/133.1 |
| 2017/0306416 A1 * | 10/2017 | Bedoya ................. | A61K 39/0011 |
| 2018/0187211 A1 * | 7/2018 | Jones ........................ | C12N 15/86 |
| 2018/0371093 A1 * | 12/2018 | Bilic ........................ | A61K 45/06 |

FOREIGN PATENT DOCUMENTS

| | | | |
|---|---|---|---|
| EP | 0265244 | 9/1992 | |
| WO | WO 2011/159877 | 12/2011 | |
| WO | WO 2015/119923 | 8/2015 | |
| WO | WO-2015119923 A1 * | 8/2015 | ......... C07K 16/3069 |
| WO | WO 2017/210523 | 12/2017 | |

OTHER PUBLICATIONS

Tang et al., "Facilitating T Cell Infiltration in Tumor Microenvironment Overcomes Resistance to PD-L1 Blockade", Cancer Cell. Mar. 14, 2016;29(3):285-296. (Year: 2016).*
Weigelin et al. "Anti-CD137 monoclonal antibodies and adoptive T cell therapy: a perfect marriage?", Cancer Immunol Immunother. May 2016;65(5):493-7. (Year: 2016).*
Kodomidu et al. "Immune Checkpoint Blockade to Improve Tumor Infiltrating Lymphocytes for Adoptive Cell Therapy", PLoS One. Apr. 6, 2016;11(4):e0153053. (Year: 2016).*
Carmona et al. "Deciphering the transcriptomic landscape of tumor-infiltrating CD8 lymphocytes in B16 melanoma tumors with single-cell RNA-Seq", OncoImmunology, 9:1, 1737369. (Year: 2020).*
The Merck Manuals Online Medical Library, [online]. Whitehouse Station, NJ: Merck Research Laboratories, 2006-2007. [retrieved on Dec. 8, 2020]. Retrieved from the Internet: < URL: https://www.merckmanuals.com/professional/neurologic-disorders/prion-diseases/creutzfeldt-jakob-disease-cjd?query=cjd#>. (Year: 2007).*
Alvarez et al. "Tumor Models in Cancer Research", Humana Press 2002, chapter 4 (Year: 2002).*
Ahmadzadeh et al., Tumor antigen-specific CD8 T cells infiltrating the tumor express high levels of PD-1 and are functionally impaired. Blood. 2009;114:1537-1544.
Ahmed et al., Unique proteome signature of post-chemotherapy ovarian cancer ascites-derived tumor cells. Scientific Reports 2016;6:30061.
Antibody mimetic definitition, Wikipedia, https://en.wikipedia.org/w/index.php?title=Antibody_mimetic&oldid=950419963, retrieved on Apr. 12, 2020, 3 pages.

(Continued)

*Primary Examiner* — Amy E Juedes
*Assistant Examiner* — Peter Johansen
(74) *Attorney, Agent, or Firm* — Casimir Jones SC; David W. Staple

(57) ABSTRACT

Provided herein are compositions and methods for detecting and/or targeting dysfunctional tumor antigen-specific CD8+ T cells in the tumor microenvironment for diagnostic, therapeutic and/or research applications. In particular, dysfunctional tumor antigen-specific CD8+ T cells are detected and/or targeted via their expression of cell surface receptors described herein, such as 4-1BB, LAG-3, or additional markers that correlate with 4-1BB and LAG-3 expression, such as markers differentially expressed on the surface of the T cells.

13 Claims, 51 Drawing Sheets
Specification includes a Sequence Listing.

(56) References Cited

OTHER PUBLICATIONS

Baitsch et al., Extended co-expression of inhibitory receptors by human CD8 T-cells depending on differentiation, antigen-specificity and anatomical localization. PLoS ONE. 2012;7:e30852.
Baitsch et al., Exhaustion of tumor-specific CD8+ T cells in metastases from melanoma patients. J. Clin. Invest. 2011;121:2350-2360.
Blackburn et al., Coregulation of CD8+ T cell exhaustion by multiple inhibitory receptors during chronic viral infection. Nature Publishing Group. 2009;10:29-37.
Brown et al., Homeostatic proliferation as an isolated variable reverses CD8+ T cell anergy and promotes tumor rejection. Journal of Immunology 2006;177:4521-4529.
Clouthier et al., Anti-GITR agonist therapy intrinsically enhances CD8 T cell responses to chronic lymphocytic choriomeningitis virus (LCMV), thereby circumventing LCMV-induced downregulation of costimulatory GITR ligand on APC. The Journal of Immunology. 2014;193:5033-5043.
Crawford et al., Molecular and Transcriptional Basis of CD4(+) T Cell Dysfunction during Chronic Infection. Immunity. 2014;40:289-302.
Cunningham et al., Type I and Type II Interferon Coordinately Regulate Suppressive Dendritic Cell Fate and Function during Viral Persistence. PLoS Pathog. 2016;12:e1005356.
Currier et al., Spectratype/Immunoscope Analysis of the Expressed TCR Repertoire. John Wiley & Sons, Inc., Hoboken, NJ, USA. 2011, 92544 pp.
Diamond et al., Type I interferon is selectively required by dendritic cells for immune rejection of tumors. J. Exp. Med. 2011;208:1989-2003.
Doering et al., Network analysis reveals centrally connected genes and pathways involved in CD8+ T cell exhaustion versus memory. Immunity. 2012;37:1130-1144.
Evaristo et al., Cutting Edge: Engineering Active IKKβ in T Cells Drives Tumor Rejection. The Journal of Immunology. 2016;196:2933-2938.
Fan et al., of the ICOS pathway markedly enhances efficacy of CTLA-4 blockade in cancer immunotherapy. J. Exp. Med. 2014;211:715-725.
Fourcade et al., CD8(+) T cells specific for tumor antigens can be rendered dysfunctional by the tumor microenvironment through upregulation of the inhibitory receptors BTLA and PD-1. Cancer Res. 2012;72:887-896.
Fridman et al., The immune contexture in human tumours: impact on clinical outcome. Nature Publishing Group. 2012;12:298-306.
Fuertes et al., Host type I IFN signals are required for antitumor CD8+ T cell responses through CD8{alpha}+ dendritic cells. J. Exp. Med. 2011;208:2005-2016.
Gajewski, The expanding universe of regulatory T cell subsets in cancer. Immunity. 2007;27:185-187.
Gajewski, Failure at the Effector Phase: Immune Barriers at the Level of the Melanoma Tumor Microenvironment. Clin. Cancer Res. 2007;13:5256-5261.
Gajewski et al., Innate and adaptive immune cells in the tumor microenvironment. Nat Immunol. 2013;14:1014-1022.
Gajewski et al., Immune resistance orchestrated by the tumor microenvironment. Immunological Reviews. 2006;1-15.
Goldszmid et al., Immune Response to Infection and Cancer: Unexpected Commonalities. Cell Host and Microbe. 2014;15:295-305.
Gros et al., PD-1 identifies the patient-specific CD8+ tumor-reactive repertoire infiltrating human tumors. J. Clin. Invest. 2014;124:2246-2259.
Halin et al., The S1P-analog FTY720 differentially modulates T-cell homing via HEV: T-cell-expressed S1P1 amplifies integrin activation in peripheral lymph nodes but not in Peyer patches. Blood. 2005;106:1314-1322.
Harlin et al., Tumor progression despite massive influx of activated CD8+ T cells in a patient with malignant melanoma ascites. Cancer Immunol Immunother. 2006;55:1185-1197.

Harlin et al., Chemokine expression in melanoma metastases associated with CD8+ T-cell recruitment. Cancer Res. 2009;69:3077-3085.
Hoelzinger et al., Blockade of CCL1 Inhibits T Regulatory Cell Suppressive Function Enhancing Tumor Immunity without Affecting T Effector Responses. The Journal of Immunology. 2010;184:6833-6842.
Jenkins et al., Molecular events in the induction of a nonresponsive state in interleukin 2-producing helper T-lymphocyte clones. PNAS. 1987;84:5409-5413.
Johnston et al., The immunoreceptor TIGIT regulates antitumor and antiviral CD8(+) T cell effector function. Cancer Cell. 2014;26:923-937.
Joshi et al., Inflammation Directs Memory Precursor and Short-Lived Effector CD8+ T Cell Fates via the Graded Expression of T-bet Transcription Factor. Immunity. 2007;27:281-295.
Kaech et al., Selective expression of the interleukin 7 receptor identifies effector CD8 T cells that give rise to long-lived memory cells. Nat Immunol. 2003;4:1191-1198.
Kearse et al., Geneious Basic: an integrated and extendable desktop software platform for the organization and analysis of sequence data. Bioinformatics. 2012;28:1647-1649.
Kim et al., NF-κB and AP-1 regulate activation-dependent CD137 (4-1BB) expression in T cells. FEBS Letters. 2003;541:163-170.
Kline et al., and molecular requirements for rejection of B16 melanoma in the setting of regulatory T cell depletion and homeostatic proliferation. The Journal of Immunology. 2012;188:2630-2642.
Kuchroo et al., Coinhibitory receptors and CD8 T cell exhaustion in chronic infections. Current Opinion in HIV and AIDS. 2014;9:439-445.
Larkin et al., Combined Nivolumab and Ipilimumab or Monotherapy in Untreated Melanoma. New England Journal of Medicine. 2015;373:1270-1271.
Li et al., The transcription factors Egr2 and Egr3 are essential for the control of inflammation and antigen-induced proliferation of B and T cells. Immunity. 2012;37:685-696.
Martinez et al., The Transcription Factor NFAT Promotes Exhaustion of Activated CD8+ T Cells. Immunity. 2015;42:265-278.
Odorizzi et al., absence of PD-1 promotes accumulation of terminally differentiated exhausted CD8+ T cells. J. Exp. Med. 2015;439:jem.20142237-1137.
Palazón et al., The HIF-1α hypoxia response in tumor-infiltrating T lymphocytes induces functional CD137 (4-1BB) for immunotherapy. Cancer Discov. 2012;2:608-623.
Pardoll, The blockade of immune checkpoints in cancer immunotherapy. Nat Rev Cancer. Mar. 22, 2012;12(4):252-64.
Pauken et al., Overcoming T cell exhaustion in infection and cancer. Trends in Immunology. 2015;36:265-276.
Pearce et al., Fueling immunity: insights into metabolism and lymphocyte function. Science. Oct. 11, 2013;342(6155):1242454.
Plaisier et al., Rank-rank hypergeometric overlap: identification of statistically significant overlap between gene-expression signatures. Nucl. Acids Res. 2010;38:e169-e169.
Safford et al., Egr-2 and Egr-3 are negative regulators of T cell activation. Nat Immunol. 2005;6:472-480.
Sarkar et al., Functional and genomic profiling of effector CD8 T cell subsets with distinct memory fates. J. Exp. Med. 2008;205:625-640.
Sarris et al., Neuropilin-1 Expression on Regulatory T Cells Enhances Their Interactions with Dendritic Cells during Antigen Recognition. Immunity. 2008;28:402-413.
Schietinger et al., and exhaustion: defining mechanisms of T cell dysfunction. Trends in Immunology. 2014;35:51-60.
Schietinger et al., Tumor-Specific T Cell Dysfunction Is a Dynamic Antigen-Driven Differentiation Program Initiated Early during Tumorigenesis. Immunity. Aug. 16, 2016;45(2):389-401.
Schwartz, T Cell Anergy. Annu. Rev. Immunol. 2003;21:305-334.
Schwartz et al., T-cell clonal anergy. Cold Spring Harb. Symp. Quant. Biol. 1989;54 Pt 2:605-610.
Shannon et al., Cytoscape: a software environment for integrated models of biomolecular interaction networks. Genome Res. 2003;13:2498-2504.

(56) References Cited

OTHER PUBLICATIONS

Snell et al., New insights into type 1 interferon and the immunopathogenesis of persistent viral infections. Curr. Opin. Immunol. 2015;34:91-98.

Spiotto et al., Increasing Tumor Antigen Expression Overcomes "Ignorance" to Solid Tumors via Crosspresentation by Bone Marrow-Derived Stromal Cells. Immunity. 2002;17:737-747.

Spranger et al., Mechanism of tumor rejection with doublets of CTLA-4, PD-1/PD-L1, or IDO blockade involves restored IL-2 production and proliferation of CD8(+) T cells directly within the tumor microenvironment. J Immunother Cancer. 2014;2:3.

Spranger et al., Up-Regulation of PD-L1, IDO, and Tregs in the Melanoma Tumor Microenvironment Is Driven by CD8+ T Cells. Science Translational Medicine. 2013;5:200ra116-200ra116.

Sumitomo et al., and Egr3 are the unique regulators for systemic autoimmunity. jak-stat. 2013;2:e23952.

Tang et al., Facilitating T Cell Infiltration in Tumor Microenvironment Overcomes Resistance to PD-L1 Blockade. Cancer Cell. Mar. 14, 2016;29(3):285-96.

Tumeh et al., PD-1 blockade induces responses by inhibiting adaptive immune resistance. Nature. 2014;515:568-571.

Twyman-Saint Victor et al., Radiation and dual checkpoint blockade activate non-redundant immune mechanisms in cancer. Nature. 2015;520:373-377.

Vesely et al., Natural Innate and Adaptive Immunity to Cancer. Annu. Rev. Immunol. 2011;29:235-271.

Waugh et al., Molecular Profile of Tumor-Specific CD8+ T Cell Hypofunction in a Transplantable Murine Cancer Model. The Journal of Immunology. 2016;197:1477-1488.

Weigelin et al., Anti-CD137 monoclonal antibodies and adoptive T cell therapy: a perfect marriage? Cancer Immunol Immunother. May 2016;65(5):493-7.

Wherry et al., Molecular and cellular insights into T cell exhaustion. Nat Rev Immunol. 2015;15:486-499.

Wherry et al., Molecular signature of CD8+ T cell exhaustion during chronic viral infection. Immunity. 2007;27:670-684.

Williams et al., The EGR2 targets LAG-3 and 4-1BB describe and regulate dysfunctional antigen-specific CD8+ T cells in the tumor microenvironment. J Environ Med. 2017;214(2):381-400.

Wu et al., PD-1(+) CD8(+) T cells are exhausted in tumours and functional in draining lymph nodes of colorectal cancer patients. Br. J. Cancer. 2014;111:1391-1399.

Xia et al., T Cell Dysfunction in Cancer Immunity and Immunotherapy. Front. Immunol. 2019;10:1719.

Zajac et al., Viral immune evasion due to persistence of activated T cells without effector function. J. Exp. Med. 1998;188:2205-2213.

Zha et al., T cell anergy is reversed by active Ras and is regulated by diacylglycerol kinase-alpha. Nat Immunol. 2006;7:1166-1173.

Zhang et al., PD-1/PD-L1 interactions inhibit antitumor immune responses in a murine acute myeloid leukemia model. Blood. 2009;114:1545-1552.

Zheng et al., Transcriptional regulator early growth response gene 2 (Egr2) is required for T cell anergy in vitro and in vivo. Journal of Experimental Medicine. 2012;209:2157-2163.

Zheng et al., Egr2-dependent gene expression profiling and ChIP-Seq reveal novel biologic targets in T cell anergy. Mol. Immunol. 2013;55:283-291.

Extended EP Search Report for EP18780614.6, dated Oct. 23, 2020, 10 pages.

International Search Report and Written Opinion for PCT/US2018/014008, dated Apr. 27, 2018, 12 pages.

Horton et al., Agonist anti-4-1BB plus neutralizing anti-CTLA-4 or -PD-L1 synergize to promote tumor regression by rescuing dying dysfunctional CD8+ T cells within the tumor microenvironment. Journal for ImmunoTherapy of Cancer 2015, 3(Suppl 2):O10.

Udono, Immune checkpoint regulation and cancer immunotherapy. Journal of the Okayama Medical Society. 2013; 125(1):13-18.

Williams et al., LAG-3 and 4-1BB identify dysfunctional antigen specific T cells in the tumor microenvironment and combinatorial LAG-3/4-1BB targeting gives synergistic tumor control. Journal for ImmunoTherapy of Cancer 2015, 3(Suppl 2):P328.

\* cited by examiner

DYSFUNCTIONAL ANTIGEN-SPECIFIC CD8+ T CELLS IN THE TUMOR MICROENVIRONMENT

CROSS-REFERENCE TO RELATED APPLICATIONS

The present invention claims priority to U.S. Provisional Patent Application Ser. No. 62/447,199, filed Jan. 17, 2017, which is incorporated by reference in its entirety.

STATEMENT OF GOVERNMENT SUPPORT

This invention was made with government support under Grant No. R01 CA161005 awarded by the National Institutes of Health. The government has certain rights in the invention.

FIELD

Provided herein are compositions and methods for detecting and/or targeting dysfunctional tumor antigen-specific CD8+ T cells in the tumor microenvironment for diagnostic, therapeutic and/or research applications. In particular, dysfunctional tumor antigen-specific CD8+ T cells are detected and/or targeted via their expression of cell surface receptors described herein, such as 4-1BB, LAG-3, or additional markers that correlate with 4-1BB and LAG-3 expression, such as markers differentially expressed on the surface of the T cells.

BACKGROUND

The immune system plays a critical role in protecting the host from cancer (Vesely et al., 2011; incorporated by reference in its entirety). Innate sensing of tumors leads to an adaptive T cell response through the presentation of tumor-associated antigens (TAAs) derived from mutations and epigenetic changes that contribute to carcinogenesis (Gajewski et al., 2013; incorporated by reference in its entirety). Spontaneously-primed CD8+ T cells home to tumor sites in mouse tumor models (Harlin et al., 2009; Fuertes et al., 2011; incorporated by reference in their entireties) and in a subset of patients with advanced cancer (Harlin et al., 2006; incorporated by reference in its entirety). These tumor-infiltrating lymphocytes (TIL) have the ability to recognize tumor antigens and are believed to contribute to tumor control in cancer patients, based on the correlation between activated CD8+ T cell infiltration with improved prognosis and response to immunotherapy (Fridman et al., 2012; Tumeh et al., 2014; incorporated by reference in their entireties). However, without additional manipulation, this endogenous anti-tumor response is usually not sufficient to mediate complete rejection of an established tumor (Gajewski, 2007b; Pardoll, 2012; Baitsch et al., 2011; Gajewski et al., 2006; Larkin et al., 2015). Data accumulated over the past several years have indicated that tumors with spontaneous anti-tumor T cell responses have high expression of immune-inhibitory pathways that subvert the effector phase of the response. These include PD-L1/PD-1 interactions (Pardoll, 2012; incorporated by reference in its entirety), recruitment of CD4+Foxp3+ regulatory T (Treg) cells (Gajewski, 2007a; incorporated by reference in its entirety), and metabolic dysregulation by indoleamine-2,3-dioxygenase (IDO) (Spranger et al., 2013; incorporated by reference in its entirety). However, even when CD8+ T cells specific for tumor antigens are isolated from tumors, away from these extrinsic immune inhibitory factors, they still show altered functional properties ex vivo (Harlin et al., 2006; Baitsch et al., 2011; incorporated by reference in their entireties).

Expression of PD-1 has been described to identify tumor-specific exhausted T cells (Ahmadzadeh et al., 2009; Fourcade et al., 2012; Wu et al., 2014; Gros et al., 2014; incorporated by reference in their entireties). However, T cells expressing PD-1 in the context of chronic infection can still retain effector function (Wherry and Kurachi, 2015; incorporated by reference in its entirety), and PD-1 is not required for the induction of T cell exhaustion (Odorizzi et al., 2015; incorporated by reference in its entirety). In addition to PD-1, several additional co-inhibitory receptors, including CD223 (LAG-3), CD244 (2B4), T-cell immunoreceptor with Ig and ITIM domains (TIGIT), hepatitis A virus cellular receptor 2 (TIM-3), and cytotoxic T-lymphocyte-associated protein 4 (CTLA-4), are also be expressed on dysfunctional T cells and expression of a greater number of inhibitory receptors has been correlated with diminished cytokine secretion (in particular IFN-g and TNF-α) as well as proliferative capacity (Blackburn et al., 2009; incorporated by reference in its entirety). Expression of these receptors has been observed in both viral and cancer models, however, a complete analysis of both co-inhibitory and co-stimulatory receptors on the same population is lacking in the tumor setting.

SUMMARY

Provided herein are compositions and methods for detecting and/or targeting dysfunctional tumor antigen-specific CD8+ T cells in the tumor microenvironment for diagnostic, therapeutic and/or research applications. In particular, dysfunctional tumor antigen-specific CD8+ T cells are detected and/or targeted via their expression of cell surface receptors described herein, such as 4-1BB, LAG-3, or additional markers that correlate with 4-1BB and LAG-3 expression, such as markers differentially expressed on the surface of the T cells (e.g., PD-1, TIM-3, OX-40ICOS, TIGIT, CD244, TNFRSF18, Nrn1, Nrp1, KLRG1, GM156, GPNMB, GPR65, TMEM205, and TMEM126A, CRTAM and Sema7a).

In some embodiments, provided herein are methods of treating a subject with cancer comprising administering an agent that specifically targets dysfunctional tumor antigen-specific CD8+ T cells. In some embodiments, the subject suffers from a solid tumor cancer. In some embodiments, the tumor allows T cell infiltration, but is resistant to immunotherapies. In some embodiments, the tumor environment comprises dysfunctional tumor antigen-specific CD8+ T cells. In some embodiments, contacting the dysfunctional tumor antigen-specific CD8+ T cells with an anti-4-1BB and/or anti-LAG3 agent. In some embodiments, the anti-4-1BB and/or anti-LAG3 agent is an antibody, antibody fragment, or antibody mimetic molecule. In some embodiments, methods further comprise co-administration of an additional therapeutic agent. In some embodiments, the additional therapeutic agent is a chemotherapeutic or an immunotherapeutic agent. In some embodiments, the additional therapeutic agent is an immunotherapeutic agent selected from the list consisting of cell-based therapies, monoclonal antibody (mAb) therapy, cytokine therapy, and adjuvant treatment. In some embodiments, the immunotherapeutic agent is a mAb therapy selected from the list consisting of anti-CTLA-4 monoclonal antibodies and/or anti-PD-L1 monoclonal antibodies. In some embodiments, the immunotherapeutic agent is a cell-based therapy selected from the list consisting of dendritic-cell therapy and T-cell therapy. In some embodiments, the additional therapeutic agent targets one of the markers/receptors listed in Table 2. In some embodiments, the additional therapeutic targets a marker/receptor expressed on the surface of the T cells. In some embodiments, the additional therapeutic targets PD-1, TIM-3, OX-40ICOS, TIGIT, CD244, TNFRSF18, Nrn1, Nrp1, KLRG1, GM156, GPNMB, GPR65, TMEM205, and TMEM126A, CRTAM or Sema7a. In some embodiments, the additional therapeutic agent targets Nrn1, Sema7a, or CRTAM.

In some embodiments, provided herein are methods of treating a subject with cancer comprising administering a therapeutic agent that specifically targets dysfunctional tumor antigen-specific $CD8^+$ T cells, wherein the agent targets one of the receptors listed in Table 2. In some embodiments, the therapeutic targets a marker/receptor expressed on the surface of the T cells. In some embodiments, the therapeutic targets PD-1, TIM-3, OX-40ICOS, TIGIT, CD244, TNFRSF18, Nrn1, Nrp1, KLRG1, GM156, GPNMB, GPR65, TMEM205, and TMEM126A, CRTAM or Sema7a. In some embodiments, the therapeutic agent targets Nrn1, Sema7a, or CRTAM. In some embodiments, the therapeutic agent is an antibody, antibody fragment, or antibody mimetic molecule that binds the target marker/receptor. In some embodiments, the therapeutic agent is an anti-Nrn antibody, antibody fragment, or antibody mimetic molecule. In some embodiments, the therapeutic agent is an anti-Sema7a antibody, antibody fragment, or antibody mimetic molecule. In some embodiments, the therapeutic agent is an anti-CRTAM antibody, antibody fragment, or antibody mimetic molecule.

In some embodiments, provided herein are compositions comprising: (a) one or more of an anti-4-1BB agent, an anti-LAG-3 agent, an anti-Nrn1 agent, an anti-Sema7a agent, and an anti-CRTAM agent; and (b) an immunotherapeutic agent, said composition formulated for therapeutic delivery to a subject. In some embodiments, the anti-4-1BB agent, anti-LAG-3 agent, anti-Nrn1 agent, anti-Sema7a agent, and/or anti-CRTAM agent is an antibody, antibody fragment, or antibody mimetic molecule.

In some embodiments, provided herein are compositions comprising: (a) an agent that targets and/or binds one of PD-1, TIM-3, OX-40ICOS, TIGIT, CD244, TNFRSF18, Nrn1, Nrp1, KLRG1, GM156, GPNMB, GPR65, TMEM205, and TMEM126A; and (b) an immunotherapeutic agent, said composition formulated for therapeutic delivery to a subject.

In some embodiments, provided herein are methods comprising: (a) testing $CD8^+$ T cells from a cell population to determine whether the CD8+ T Cells co-express LAG-3 and 4-1BB; and (b) administering one or more agents that target and/or bind one of PD-1, TIM-3, OX-40ICOS, TIGIT, CD244, TNFRSF18, Nrn1, Nrp1, KLRG1, GM156, GPNMB, GPR65, TMEM205, and TMEM126A. In some embodiments, the agent is an anti-Nrn1 agent, an anti-Sema7a agent, and an anti-CRTAM agent. In some embodiments, the anti-Nrn1 agent, anti-Sema7a agent, and/or anti-CRTAM agent is an antibody, antibody fragment, or antibody mimetic molecule. In some embodiments, testing is performed in vitro.

In some embodiments, provided herein are methods of identifying dysfunctional T cells by testing said cells for co-expression of 4-1BB and LAG-3. In some embodiments, provided herein are methods of identifying dysfunctional T cells by testing said cells for expression of one or more of the markers/receptors of Table 2 (e.g., a T-cell surface marker/receptor (e.g., PD-1, TIM-3, OX-40ICOS, TIGIT, CD244, TNFRSF18, Nrn1, Nrp1, KLRG1, GM156, GPNMB, GPR65, TMEM205, TMEM126A).

DEFINITIONS

Figure 1A:
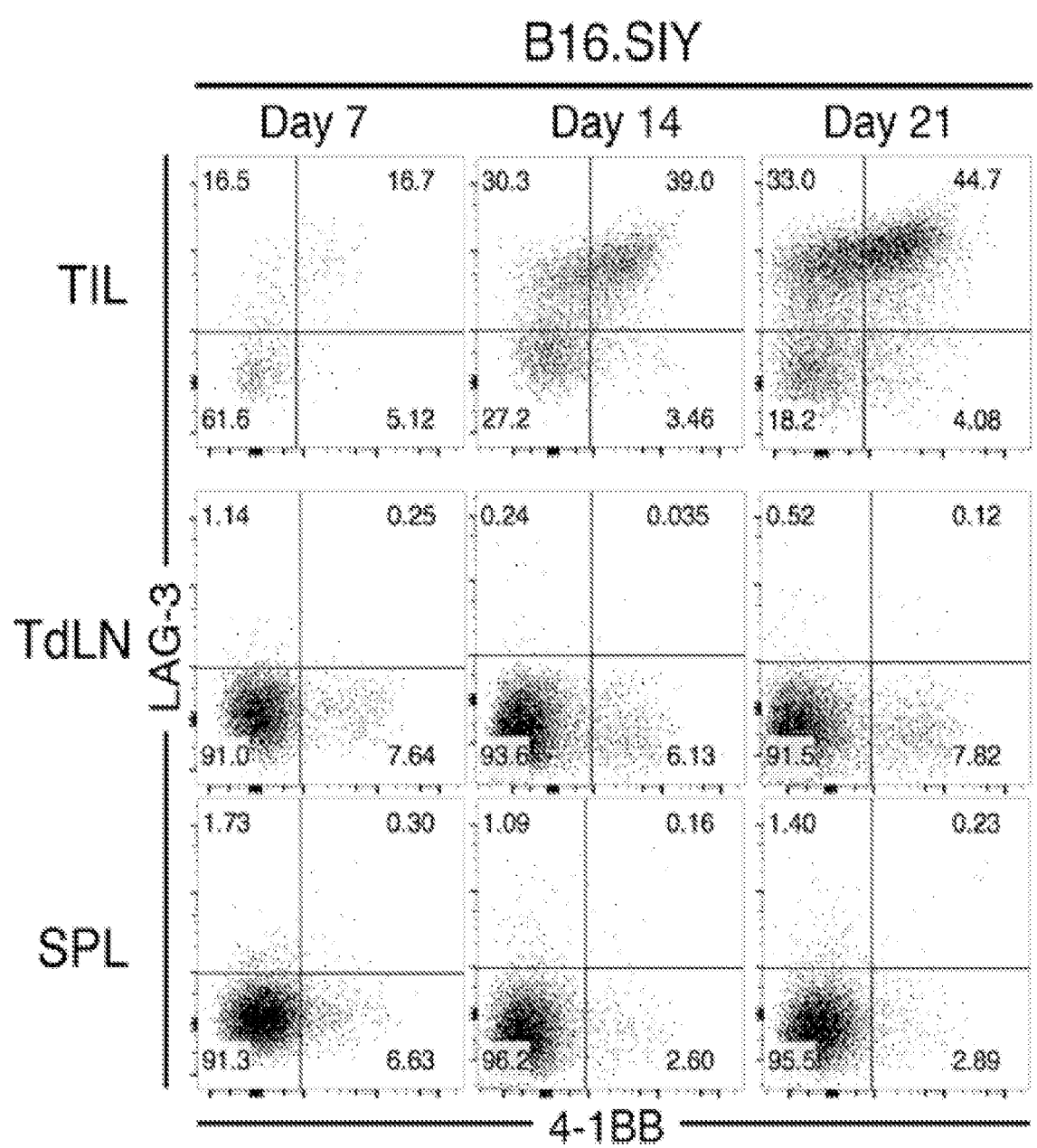
FIG. 1A-J. Co-expression of 4-1BB and LAG-3 identifies a significant fraction of the $CD8^+$ TIL compartment found in progressing tumors. (A) Representative analysis of 4-1BB and LAG-3 expression on $CD8^+$ T cells from B16.SIY tumors and the spleen and TdLN from tumor bearing mice on day 7, 14 and 21 after s.c. tumor inoculation. (B-D) Longitudinal summary of the composition, n=5; four to five independent experiments per time point, (C) absolute cell number, n=5; seven to nine independent experiments per time point, and (D) cellular density of the $CD8^+$4-1BB/LAG-3 TIL subpopulations, n=5; two to five independent experiments per time point. Absolute cell numbers were determined by acquiring the complete tumor sample by flow cytometery. (E) Day 14 summary of the proportion of the $CD8^+$4-1BB/LAG-3 TIL subpopulations that are $Ki67^+$. n=3-5; two independent experiments. (F) Summary of BrdU uptake on day 13 in the $CD8^+$4-1BB/LAG-3 TIL subpopulations after a 24 hour BrdU pulse. n=5; three independent experiments. (G-I) Representative flow plots (G and H) and summary (I) of the 4-1BB/LAG-3 populations in other tumor models. Mice were inoculated with $2 \times 10^6$ C1498.SIY, MC38.SIY, EL4.SIY, B16 Parental, MC57.SIY or 1969.SIY subcutaneously and analyzed for 4-1BB and LAG-3 expression on day 14 after tumor inoculation. n=3-5; two to 5 independent experiments for each time point. (J) Mice were inoculated on both flanks with $2 \times 10^6$ MC57.SIY or B16.SIY, at indicated time points tumors from each mouse were pooled and analyzed for co-expression of 4-1BB and LAG-3 in the $CD8^+$ TIL compartment. n=3-5; two independent experiments for each time point. All error bars indicate±SEM. *:P<0.05, :P<0.01, *:P<0.001. A two-way ANOVA with Bonferroni post-hoc test was used for (B, C, D, H) longitudinal studies and Kruskal-Wallis (non-parametric) test was used for (E and F) analysis at one time-point.
Figure 1B:
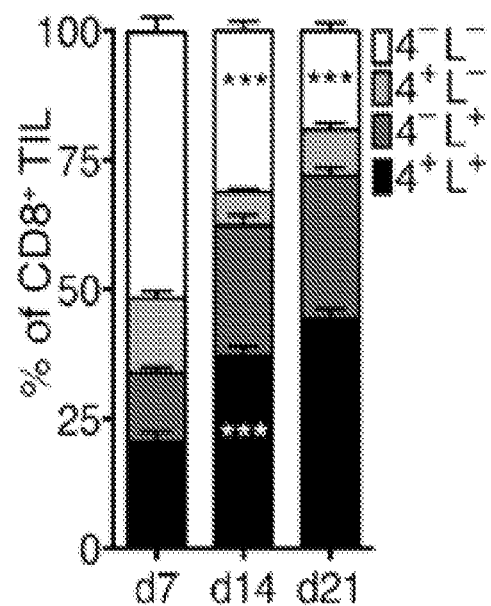

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "an antibody" is a reference to one or more antibodies and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition (e.g., cancer, solid tumor cancer, etc.).

As used herein, an "immune response" refers to the action of a cell of the immune system (e.g., T lymphocytes, B lymphocytes, natural killer (NK) cells, macrophages, eosinophils, mast cells, dendritic cells, neutrophils, etc.) and soluble macromolecules produced by any of these cells or the liver (including antibodies, cytokines, and complement) that results in selective targeting, binding to, damage to, destruction of, and/or elimination from a subject of invading pathogens, cells or tissues infected with pathogens, or cancerous or other abnormal cells.

As used herein, the term "immunoregulator" refers to a substance, an agent, a signaling pathway or a component thereof that regulates an immune response. "Regulating," "modifying" or "modulating" an immune response refers to any alteration in a cell of the immune system or in the activity of such cell. Such regulation includes stimulation or suppression of the immune system which may be manifested by an increase or decrease in the number of various cell types, an increase or decrease in the activity of these cells, or any other changes which can occur within the immune system. Both inhibitory and stimulatory immunoregulators have been identified, some of which may have enhanced function in the cancer microenvironment.

As used herein, the term "immunotherapy" refers to the treatment or prevention of a disease or condition by a method comprising inducing, enhancing, suppressing or otherwise modifying an immune response.

As used herein, "potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

As used herein, the term "antibody" refers to a whole antibody molecule or a fragment thereof (e.g., fragments such as Fab, Fab', and F(ab')$_2$), unless otherwise specified (e.g., "whole antibody," "antibody fragment"). An antibody may be a polyclonal or monoclonal antibody, a chimeric antibody, a humanized antibody, a human antibody, etc.

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, $V_H$, and three constant regions, $C_{H1}$, $C_{H2}$, and $C_{H3}$. The $V_H$ domain is at the amino-terminus of the heavy chain, and the $C_{H3}$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

As used herein, when an antibody or other entity "specifically recognizes" or "specifically binds" an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ M$^{-1}$ (e.g., >$10^7$ M$^{-1}$, >$10^8$ M$^{-1}$, >$10^9$ M$^{-1}$, >$10^{10}$ M$^{-1}$, >$10^{11}$ M$^{-1}$, >$10^{12}$ M$^{-1}$, >$10^{13}$ M$^{-1}$, etc.). In certain such embodiments, an antibody is capable of binding different antigens so long as the different antigens comprise that particular epitope. In certain instances, for example, homologous proteins from different species may comprise the same epitope.

As used herein, the term "anti-4-1BB antibody" or "4-1BB antibody" refers to an antibody which specifically recognizes an antigen and/or epitope presented by 4-1BB. Similarly, the terms "anti-LAG-3 antibody" and "LAG-3 antibody" refer to an antibody which specifically recognizes an antigen and/or epitope presented by LAG-3, the terms "anti-Nrn1 antibody" and "Nrn1 antibody" refer to an antibody which specifically recognizes an antigen and/or epitope presented by Nrn1, the terms "anti-CRTAM antibody" and "CRTAM antibody" refer to an antibody which specifically recognizes an antigen and/or epitope presented by CRTAM, and the terms "anti-Sema7a antibody" and "Sema7a antibody" refer to an antibody which specifically recognizes an antigen and/or epitope presented by Sema7a. Antibodies that recognize epitopes on other molecular entities may be referred to according to a similar scheme (e.g., anti-CTLA-4, anti-PD-L1, etc.).

As used herein, the term "monoclonal antibody" refers to an antibody which is a member of a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. See, e.g., Kohler and Milstein (1975) Nature 256: 495-499; herein incorporated by reference in its entirety. In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library. See, e.g., Clackson et al. (1991) Nature 352: 624-628; and Marks et al. (1991) J. Mol. Biol. 222: 581-597; herein incorporated by reference in their entireties. The modifying word "monoclonal" indicates properties of antibodies obtained from a substantially-homogeneous population of antibodies, and does not limit a method of producing antibodies to a specific method. For various other monoclonal antibody production techniques, see, e.g., Harlow and Lane (1988) Antibodies: A Laboratory Manual (Cold Spring Harbor Laboratory, Cold Spring Harbor, N.Y.); herein incorporated by reference in its entirety.

As used herein, the term "antibody fragment" refers to a portion of a full-length antibody, including at least a portion antigen binding region or a variable region. Antibody fragments include, but are not limited to, Fab, Fab', F(ab')$_2$, Fv, scFv, Fd, diabodies, and other antibody fragments that retain at least a portion of the variable region of an intact antibody. See, e.g., Hudson et al. (2003) Nat. Med. 9:129-134; herein incorporated by reference in its entirety. In certain embodiments, antibody fragments are produced by enzymatic or chemical cleavage of intact antibodies (e.g., papain digestion and pepsin digestion of antibody) produced by recombinant DNA techniques, or chemical polypeptide synthesis.

For example, a "Fab" fragment comprises one light chain and the $C_{H1}$ and variable region of one heavy chain. The heavy chain of a Fab molecule cannot form a disulfide bond with another heavy chain molecule. A "Fab'" fragment comprises one light chain and one heavy chain that comprises additional constant region, extending between the $C_{H1}$ and $C_{H2}$ domains. An interchain disulfide bond can be formed between two heavy chains of a Fab' fragment to form a "F(ab')$_2$" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203; herein incorporated by reference in their entireties. In certain instances, a single variable region (e.g., a heavy chain variable region or a light chain variable region) may have the ability to recognize and bind antigen.

Other antibody fragments will be understood by skilled artisans.

As used herein, the term "chimeric antibody" refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

A "humanized" antibody refers to a non-human antibody that has been modified so that it more closely matches (in amino acid sequence) a human antibody. A humanized antibody is thus a type of chimeric antibody. In certain embodiments, amino acid residues outside of the antigen binding residues of the variable region of the non-human antibody are modified. In certain embodiments, a humanized antibody is constructed by replacing all or a portion of a complementarity determining region (CDR) of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the framework regions (FRs) correspond to FRs of a human antibody. In certain such embodiments, a humanized antibody further comprises a constant region (Fc) of a human antibody.

The term "human antibody" refers to a monoclonal antibody that contains human antibody sequences and does not contain antibody sequences from a non-human animal. In certain embodiments, a human antibody may contain synthetic sequences not found in native antibodies. The term is not limited by the manner in which the antibodies are made. For example, in various embodiments, a human antibody may be made in a transgenic mouse, by phage display, by human B-lymphocytes, or by recombinant methods.

As used herein, the term "natural antibody" refers to an antibody in which the heavy and light chains of the antibody have been made and paired by the immune system of a multicellular organism. For example, the antibodies produced by the antibody-producing cells isolated from a first animal immunized with an antigen are natural antibodies. Natural antibodies contain naturally-paired heavy and light chains. The term "natural human antibody" refers to an antibody in which the heavy and light chains of the antibody have been made and paired by the immune system of a human subject.

Native human light chains are typically classified as kappa and lambda light chains. Native human heavy chains are typically classified as mu, delta, gamma, alpha, or epsilon, and define the antibody's isotype as IgM, IgD, IgG, IgA, and IgE, respectively. IgG has subclasses, including, but not limited to, IgG1, IgG2, IgG3, and IgG4. IgM has subclasses including, but not limited to, IgM1 and IgM2. IgA has subclasses including, but not limited to, IgA1 and IgA2. Within native human light and heavy chains, the variable and constant regions are typically joined by a "J" region of about 12 or more amino acids, with the heavy chain also including a "D" region of about 10 more amino acids. See, e.g., Fundamental Immunology (1989) Ch. 7 (Paul, W., ed., 2nd ed. Raven Press, N.Y.); herein incorporated by reference in its entirety.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or In vivo. In some embodiments, by neutralizing the polypeptide comprising the epitope, the neutralizing antibody inhibits the capacity of the cell displaying the epitope.

As used herein, the term "glycoengineered", as used herein, includes any manipulation of the glycosylation pattern of a naturally occurring or recombinant protein, polypeptide or a fragment thereof.

The term "antigen-binding site" refers to a portion of an antibody capable of specifically binding an antigen. In certain embodiments, an antigen-binding site is provided by one or more antibody variable regions.

The term "epitope" refers to any polypeptide determinant capable of specifically binding to an immunoglobulin or a T-cell or B-cell receptor. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three dimensional structural characteristics (e.g., a "conformational" epitope) and/or specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

A "conservative" amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution may encompass non-naturally occurring amino acid residues, which are typically incorporated by chemical peptide synthesis rather than by synthesis in biological systems. These include, but are not limited to, peptidomimetics and other reversed or inverted forms of amino acid moieties. Naturally occurring residues may be divided into classes based on common side chain properties, for example: hydrophobic: norleucine, Met, Ala, Val, Leu, and Ile; neutral hydrophilic: Cys, Ser, Thr, Asn, and Gln; acidic: Asp and Glu; basic: His, Lys, and Arg; residues that influence chain orientation: Gly and Pro; and aromatic: Trp, Tyr, and Phe. Non-conservative substitutions may involve the exchange of a member of one of these classes for a member from another class; whereas conservative substitutions may involve the exchange of a member of one of these classes for another member of that same class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) have similar polymer sequences. For example, similar amino acids are those that share the same biophysical characteristics and can be grouped into the families (see above). The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

The term "effective dose" or "effective amount" refers to an amount of an agent, e.g., an antibody, that results in the reduction of symptoms in a patient or results in a desired biological outcome. In certain embodiments, an effective dose or effective amount is sufficient to treat or reduce symptoms of a disease or condition.

As used herein, the terms "administration" and "administering" refer to the act of giving a drug, prodrug, or other agent, or therapeutic to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term "treatment" encompasses both therapeutic and prophylactic/preventative measures unless otherwise indicated. Those in need of treatment include, but are not limited to, individuals already having a particular condition as well as individuals who are at risk of acquiring a particular condition or disorder (e.g., those having a genetic or epigenetic predisposition; based on age, gender, lifestyle, etc.).

The term "treating" refers to administering an agent to a subject for therapeutic and/or prophylactic/preventative purposes.

A "therapeutic agent" refers to an agent that may be administered In vivo to bring about a therapeutic and/or prophylactic/preventative effect.

A "therapeutic antibody" refers to an antibody that may be administered In vivo to bring about a therapeutic and/or prophylactic/preventative effect.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term pharmaceutical composition" refers to the combination of an active agent (e.g., binding agent) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

As used herein, a "diagnostic" or "diagnostic test" includes the detection, identification, or characterization of a disease state or condition of a subject. For example, a disease or condition may be characterized to determine the likelihood that a subject with a disease or condition will respond to a particular therapy, determine the prognosis of a subject with a disease or condition (or its likely progression or regression), determine the effect of a treatment on a subject with a disease or condition, or determine a future treatment course of action.

DETAILED DESCRIPTION

Provided herein are compositions and methods for detecting and/or targeting dysfunctional tumor antigen-specific CD8+ T cells in the tumor microenvironment for diagnostic, therapeutic and/or research applications. In particular, dysfunctional tumor antigen-specific CD8+ T cells are detected and/or targeted via their expression of cell surface receptors described herein, such as 4-1BB, LAG-3, or additional markers that correlate with 4-1BB and LAG-3 expression, such as markers differentially expressed on the surface of the T cells (e.g., PD-1, TIM-3, OX-40ICOS, TIGIT, CD244, TNFRSF18, Nrn1, Nrp1, KLRG1, GM156, GPNMB, GPR65, TMEM205, and TMEM126A, CRTAM and Sema7a).

Experiments conducted during development of embodiments herein identified markers/receptors that correlate and/or are responsible for tumor antigen-specific CD8+ T cell dysfunction. In some embodiments, the markers/receptors are overexpressed in dysfunctional tumor antigen-specific CD8+ T cells. In such embodiments, detecting the level (e.g., above a threshold) of such markers provides a diagnostic for detecting tumor antigen-specific CD8+ T cell dysfunction. Further, in such embodiments, targeting (e.g., inhibiting (e.g., expression and/or activity of)) such markers/receptors provides a therapeutic. In other embodiments, the markers/receptors are underexpressed in dysfunctional tumor antigen-specific CD8+ T cells. In such embodiments, detecting the level (e.g., below a threshold) of such markers provides a diagnostic for detecting tumor antigen-specific CD8+ T cell dysfunction. Further, in such embodiments, targeting (e.g., enhancing (e.g., expression and/or activity of)) such markers/receptors provides a therapeutic.

Transcription factor Egr2 is a critical regulator of the anergic state in CD4+ T cell clones manipulated in vitro (Zheng et al., 2013; 2012; incorporated by reference in their entireties). Egr2 has also been shown to be involved in negative regulation of T cell activation in several in vivo model systems (Sumitomo et al., 2013; incorporated by reference in its entirety). Egr2 contributes to upregulation of DGKa and -z which act to blunt TCR-mediated Ras pathway activation (Zha et al., 2006; incorporated by reference in its entirety). By comparing gene expression profiling of anergized cells along with Egr2 ChIP-Seq analysis multiple additional Egr2-driven gene targets were identified (Zheng et al., 2013; incorporated by reference in its entirety). These gene targets include 4-1BB (Tnfrsf9 or CD137), Lag3, Nrn1, Sema7a, Crtam, and Rankl, which encode cell surface proteins.

4-1BB is a co-stimulatory molecule transiently expressed after TCR engagement. Lag3 (lymphocyte-activation gene 3 or CD223) is a CD4 homologue and functions as an inhibitory receptor. Expression of 4-1BB and Lag3 is regulated following TCR engagement and continues throughout differentiation. In humans, 4-1BB and LAG-3 are expressed on CD8+ TILs from human melanoma tumors (Gros et al., 2014; Baitsch et al., 2012; incorporated by reference in their entireties). In both mice and humans, either molecule alone are expressed on populations of activated T cells. However, co-expression is more limited and is rarely observed in circulating T cells. The function of CD8+ TILs co-expressing these markers is unknown.

Experiments were conducted during development of embodiments herein to investigate the detailed characteristics of CD8+ TILs expressing 4-1BB and LAG-3 using mouse tumor models. It was found that the co-expression of 4-1BB and LAG-3 was sufficient to identify tumor antigen-specific dysfunctional CD8+ TILs enriched in the expression of Egr2 target genes. These CD8+ TILs failed to make IL-2 following in vitro stimulation, yet still produced IFN-g and Treg-recruiting chemokines and lysed target cells ex vivo, indicating they are not completely functionally inert. Combinatorial treatment with anti-LAG-3/anti-4-1BB restored the function of this population and promoted in situ acquisition of KLRG-1hi effector cells. Additional gene expression profiling provided a complete phenotyping of this T cell subset, which revealed expression of a broad panel of both inhibitory receptors and co-stimulatory receptors (e.g., receptors of Table 2 (e.g. Nrn1, Sema7a, CRTAM, etc.)). Inhibitory receptors and co-stimulatory receptors identified in this profiling that are displayed on the surface of T cells include PD-1, TIM-3, OX-40ICOS, TIGIT, CD244, TNFRSF18, Nrn1, Nrp1, KLRG1, GM156, GPNMB, GPR65, TMEM205, and TMEM126A. These approaches have thus enabled the characterization of the population of tumor antigen-specific CD8+ T cells that arise specifically within the tumor microenvironment having altered functional properties. In some embodiments, this population is a target for immunotherapeutic approaches to restore desired functionality and promote tumor regression. In some embodiments, the receptors/markers identified herein (e.g., 4-1BB, LAG-3, receptors/markers of Table 2 (e.g., surface markers/receptors (e.g. Nrn1, Sema7a, CRTAM, etc.), etc.) etc.) are targeted (e.g., via immunotherapeutic approaches) to restore desired immunoresponsiveness, to promote tumor regression, and/or for the treatment of cancer.

Experiments conducted during development of embodiments herein applied knowledge of Egr2 targets to evaluate applicability of these markers toward understanding dysfunctional T cells within tumors in vivo. The data indeed confirm that co-expression of LAG-3 and 4-1BB is sufficient to identify the majority of tumor antigen-specific CD8+ T cells within the tumor microenvironment. Co-expression of these markers was not observed within peripheral lymphoid organs in tumor-bearing mice, indicating that a property unique to the tumor context drives 4-1BB and LAG-3 expression. In addition, acquisition of LAG-3 and 4-1BB expression was not observed within tumors that were undergoing successful rejection, indicating that the acquisition of this phenotype occurs under conditions of incomplete antigen clearance.

In some embodiments, cancer treatment methods described herein comprise administration (or co-administration with one or more additional therapies/therapeutics) of one or more anti-4-1BB and/or anti-LAG-3 agents (e.g., antibodies, antibody fragments, antibody mimetic molecules (e.g., DARPins, affibodies, aptamers, nanobodies, etc.), etc.). In some embodiments, an anti-4-1BB and/or anti-LAG-3 agents is administered to render cancer cells, tumor(s), and/or the tumor microenvironment accessible or susceptible to treatment with additional therapies/therapeutics (e.g., immunotherapeutics). Anti-4-1BB and/or anti-LAG-3 agents that find use in embodiments described herein are not limited by their mechanism of action. Agents may be small molecules, peptide, polypeptides, proteins, nucleic acids (e.g., antisense, RNAi, etc.), antibodies, antibody fragments, etc.

In some embodiments, cancer treatment methods described herein comprise enhancing the activity or expression of a marker/receptor identified herein that negatively correlates with tumor antigen-specific CD8+ T cell dysfunction.

Experiments conducted during development of embodiments herein identified receptors/markers that are differentially expressed in dysfunctional CD8+ TILs (See Table 2). Testing of targets of interest identified in that screen demonstrate that at least neuritin 1 (Nrn1), cytotoxic and regulatory t-cell molecule (CRTAM), and Semaphorin 7A (Sema7a) are regulators of anti-tumor immunity, with Nrn1 and CRTAM blockade correlating with increased tumor area, and Sema7a blockade correlating with decreased tumor area.

In some embodiments, cancer treatment methods described herein comprise administration (or co-administration with one or more additional therapies/therapeutics) of agents (e.g., antibodies, antibody fragments, antibody mimetic molecules (e.g., DARPins, affibodies, aptamers, nanobodies, etc.), etc.) that target one or more receptors/markers of Table 2 (e.g. PD-1, TIM-3, OX-40ICOS, TIGIT, CD244, TNFRSF18, Nrn1, Nrp1, KLRG1, GM156, GPNMB, GPR65, TMEM205, and TMEM126A, Nrn1, CRTAM, Sema7a, etc.). In some embodiments, an agent is administered to render cancer cells, tumor(s), and/or the tumor microenvironment accessible or susceptible to treatment with additional therapies/therapeutics (e.g., immunotherapeutics). Agents targeting one or more receptors/markers of Table 2 (e.g. PD-1, TIM-3, OX-40ICOS, TIGIT, CD244, TNFRSF18, Nrn1, Nrp1, KLRG1, GM156, GPNMB, GPR65, TMEM205, and TMEM126A, Nrn1, CRTAM, Sema7a, etc.) that find use in embodiments described herein are not limited by their mechanism of action. Agents may be small molecules, peptide, polypeptides, proteins, nucleic acids (e.g., antisense, RNAi, etc.), antibodies, antibody fragments, etc. In some embodiments, an antagonist of Nrn1 is administered. In some embodiments, an antagonist of CRTAM is administered. In some embodiments, an agonist of Sema7a is administered.

In some embodiments, antibodies, antibody fragments, antibody mimetic molecules (e.g., DARPins, affibodies, aptamers, nanobodies, etc.) targeting 4-1BB, LAG-3 and/or one or more receptors/markers of Table 2 (e.g. PD-1, TIM-3, OX-40ICOS, TIGIT, CD244, TNFRSF18, Nrn1, Nrp1, KLRG1, GM156, GPNMB, GPR65, TMEM205, and TMEM126A, CRTAM, Sema7a, etc.), or fragments thereof, are provided. Such agents may be naked, deriving their effect by target binding (e.g., neutralizing the target), or may be conjugated to a functional moiety (e.g., drug, toxin, effector moiety, etc.).

In some embodiments, a subject is treated with (i) one or more agents (e.g., antibodies, antibody fragments, antibody mimetic molecules (e.g., DARPins, affibodies, aptamers, nanobodies, etc.), etc.) that target 4-1BB, LAG-3 and/or one or more receptors/markers of Table 2 (e.g. PD-1, TIM-3, OX-40ICOS, TIGIT, CD244, TNFRSF18, Nrn1, Nrp1, KLRG1, GM156, GPNMB, GPR65, TMEM205, and TMEM126A, CRTAM, Sema7a, etc.), as well as (ii) one or more additional cancer therapies. Such therapies include chemotherapy, immunotherapy, radiation, surgery, etc. In some embodiments, agents targeting the receptors/markers described herein are co-administered with one or more additional agents for the treatment of cancer.

In some embodiments, exemplary anticancer agents suitable for use in compositions and methods described herein include, but are not limited to: 1) alkaloids, including microtubule inhibitors (e.g., vincristine, vinblastine, and vindesine, etc.), microtubule stabilizers (e.g., paclitaxel (Taxol), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosfamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies (e.g., conjugated with anticancer drugs, toxins, and/or radionuclides, etc.; neutralizing antibodies; etc.); 9) biological response modifiers (e.g., interferons (e.g., IFN-.alpha., etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); and 22) modulators of p53 protein function.

In some embodiments, agents targeting 4-1BB, LAG-3 and/or one or more receptors/markers of Table 2 (e.g. Nrn1, Sema7a, CRTAM, etc.) are administered to overcome immune invasion of the cancer cells, tumor, tumor microenvironment, etc. In some embodiments, one or more additional cancer immunotherapies are employed (e.g., concurrently or serially) to make use of the immune-responsiveness of the treated cells/tumor. Suitable immunotherapies may include, but are not limited to: cell-based therapies (e.g., dendritic cell or T cell therapy, etc.), monoclonal antibody (mAb) therapy (e.g., naked mAbs, conjugated mAbs), cytokine therapy (e.g., interferons, interleukins, etc.), adjuvant treatment (e.g., polysaccharide-K), etc.

In some embodiments, agents targeting 4-1BB, LAG-3 and/or one or more receptors/markers of Table 2 (e.g. PD-1, TIM-3, OX-40ICOS, TIGIT, CD244, TNFRSF18, Nrn1, Nrp1, KLRG1, GM156, GPNMB, GPR65, TMEM205, and TMEM126A, CRTAM, Sema7a, etc.) are co-administered with agents (e.g., small molecules, peptides, antibodies, antibody fragments, etc.) that target one or more cancer cell or tumor) markers or components. In some embodiments, such co-administration renders the cancer cells, tumor, and/or tumor microenvironment susceptible and/or accessible to the treatment with the additional agent.

In some embodiments, agents for use in the methods and compositions described herein target and/or binds a cancer or tumor cell marker or component, selected from the group including but not limited to, epidermal growth factor receptor (EGFR, EGFR1, ErbB-1, HER1). ErbB-2 (HER2/neu), ErbB-3/HER3, ErbB-4/HER4, EGFR ligand family; insulin-like growth factor receptor (IGFR) family, IGF-binding proteins (IGFBPs), IGFR ligand family (IGF-1R); platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family: TRK receptor family; ephrin (EPH) receptor family: AXL receptor family; leukocyte tyrosine kinase (LTK) receptor family; TIE receptor family, angiopoietin 1, 2; receptor tyrosine kinase-like orphan receptor (ROR) receptor family; discoidin domain receptor (DDR) family; RET receptor family; KLG receptor family; RYK receptor family; MuSK receptor family; Transforming growth factor alpha (TGF-α), TGF-α receptor; Transforming growth factor-beta (TGF-β), TGF-β receptor; Interleukin β receptor alpha2 chain (IL13Ralpha2), Interleukin-6 (IL-6), 1L-6 receptor, interleukin-4, IL-4 receptor, Cytokine receptors, Class I (hematopoietin family) and Class II (interferon/1L-10 family) receptors, tumor necrosis factor (TNF) family, TNF-α, tumor necrosis factor (TNF) receptor superfamily (TNTRSF), death receptor family, TRAIL-receptor; cancer-testis (CT) antigens, lineage-specific antigens, differentiation antigens, alpha-actinin-4, ARTC1, breakpoint cluster region-Abelson (Bcr-abl) fusion products, B-RAF, caspase-5 (CASP-5), caspase-8 (CASP-8), beta-catenin (CTNNB1), cell division cycle 27 (CDC27), cyclin-dependent kinase 4 (CDK4), CDKN2A, COA-1, dek-can fusion protein, EFTUD-2, Elongation factor 2 (ELF2), Ets variant gene 6/acute myeloid leukemia 1 gene ETS (ETC6-AML1) fusion protein, fibronectin (FN), GPNMB, low density lipid receptor/GDP-L fucose: beta-Dgalactose 2-alpha-Lfucosyl-traosferase (LDLR/FUT) fusion protein, HLA-A2, MLA-A11, heat shock protein 70-2 mutated (HSP70-2M), KIAA0205, MART2, melanoma ubiquitous mutated 1, 2, 3 (MUM-1, 2, 3), prostatic acid phosphatase (PAP), neo-PAP, Myosin class 1, NFYC, OGT, OS-9, pml-RARalpha fusion protein, PRDX5, PTPRK, K-ras (KRAS2), N-ras (NRAS), HRAS, RBAF600, SIRT12, SNRPD1, SYT-SSX1 or -SSX2 fusion protein, Triosephosphate Isomerase, BAGE, BAGE-1, BAGE-2, 3, 4, 5, GAGE-1, 2, 3, 4, 5, 6, 7, 8, GnT-V (aberrant N-acetyl glucosaminyl transferase V, MGAT5), HERV-K MEL, KK-LC, KM-HN-1, LAGE, LAGE-1, CTL-recognized antigen on melanoma (CAMEL), MAGE-A1 (MAGE-1). MAGE-A2, MAGE-A3, MAGE-A4, MAGE-AS, MAGE-A6, MAGE-A8, MAGE-A9, MAGE-A10. MAGE-All, MAGE-A12, MAGE-3, MAGE-B1, MAGE-B2, MAGE-B5. MAGE-B6, MAGE-C1, MAGE-C2, mucin 1 (MUC1), MART-1/Melan-A (MLANA), gp100, gp100/Pme117 (S1LV), tyrosinase (TYR), TRP-1, HAGE, NA-88, NY-ESO-1, NY-ESO-1/LAGE-2, SAGE, Sp17. SSX-1, 2, 3, 4, TRP2-1NT2, carcino-embryonic antigen (CEA), Kallikrein 4, mammaglobin-A, OA1 prostate specific antigen (PSA), prostate specific membrane antigen, TRP-1/, 75. TRP-2 adipophilin, interferon inducible protein absent in melanoma 2 (AIM-2). BING-4, CPSF, cyclin D1, epithelial cell adhesion molecule (Ep-CAM), EpbA3, fibroblast growth factor-5 (FGF-5), glycoprotein 250 (gp250intestinal carboxyl esterase (iCE), alpha-feto protein (AFP), M-CSF, mdm-2, MUCI, p53 (TP53), PBF, PRAME, PSMA, RAGE-1, RNF43, RU2AS, SOX10, STEAP1, survivin (BIRCS), human telomerase reverse transcriptase (hTERT), telomerase, Wilms' tumor gene (WT1), SYCP1, BRDT, SPANX, XAGE, ADAM2, PAGE-5, LIP1, CTAGE-1, CSAGE, MMA1, CAGE, BORIS, HOM-TES-85, AF15q14, HCA66I, LDHC, MORC, SGY-1, SPO11, TPX1, NY-SAR-35, FTHLI7, NXF2 TDRD1, TEX 15, FATE, TPTE, immunoglobulin idiotypes, Bence-Jones protein, estrogen receptors (ER), androgen receptors (AR), CD40, CD30, CD20, CD19, CD33, CD4, CD25, CD3, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), beta-human chorionic gonadotropin, 1-2 microglobulin, squamous cell carcinoma antigen, neuron-specific enolase, heat shock protein gp96. GM2, sargramostim, CTLA-4, 707 alanine proline (707-AP), adenocarcinoma antigen recognized by T cells 4 (ART-4), carcinoembryogenic antigen peptide-1 (CAP-1), calcium-activated chloride channel-2 (CLCA2), cyclophilin B (Cyp-B), human signet ring tumor-2 (HST-2), etc.

Examples of antibodies which can be incorporated into compositions and methods disclosed herein include, but are not limited, to antibodies such as trastuzumab (anti-HER2/neu antibody); Pertuzumab (anti-HER2 mAb); cetuximab (chimeric monoclonal antibody to epidermal growth factor receptor EGFR); panitumumab (anti-EGFR antibody); nimotuzumab (anti-EGFR antibody); Zalutumumab (anti-EGFR mAb); Necitumumab (anti-EGFR mAb); MDX-210 (humanized anti-HER-2 bispecific antibody); MDX-210 (humanized anti-HER-2 bispecific antibody); MDX-447 (humanized anti-EGF receptor bispecific antibody); Rituximab (chimeric murine/human anti-CD20 mAb); Obinutuzumab (anti-CD20 mAb); Ofatumumab (anti-CD20 mAb); Tositumumab-1131 (anti-CD20 mAb); Ibritumomab tiuxetan (anti-CD20 mAb); Bevacizumab (anti-VEGF mAb); Ramucirumab (anti-VEGFR2 mAb); Ranibizumab (anti-VEGF mAb); Aflibercept (extracellular domains of VEGFR1 and VEGFR2 fused to IgG1 Fc); AMG386 (angiopoietin-1 and -2 binding peptide fused to IgG1 Fc); Dalotuzumab (anti-IGF-1R mAb); Gemtuzumab ozogamicin (anti-CD33 mAb); Alemtuzumab (anti-Campath-1/CD52 mAb); Brentuximab vedotin (anti-CD30 mAb): Catumaxomab (bispecific mAb that targets epithelial cell adhesion molecule and CD3); Naptumomab (anti-5T4 mAb); Girentuximab (anti-Carbonic anhydrase ix); or Farletuzumab (anti-folate receptor). Other examples include antibodies such as Panorex™ (17-1A) (murine monoclonal antibody); Panorex (@(17-1A)) (chimeric murine monoclonal antibody); BEC2 (ami-idiotypic mAb, mimics the GD epitope) (with BCG); Oncolym (Lym-1 monoclonal antibody); SMART M195 Ab, humanized 13' 1 LYM-1 (Oncolym). Ovarex (B43.13, anti-idiotypic mouse mAb); 3622W94 mAb that binds to EGP40 (17-1A) pancarcinoma antigen on adenocarcinomas; Zenapax (SMART Anti-Tac (IL-2 receptor); SMART M195 Ab, humanized Ab, humanized); NovoMAb-G2 (pancarcinoma specific Ab); TNT (chimeric mAb to histone antigens); TNT (chimeric mAb to histone antigens); Gliomab-H (Monoclonals—Humanized Abs); GNI-250 Mab; EMD-72000 (chimeric-EGF antagonist); LymphoCide (humanized IL.L.2 antibody); and MDX-260 bispecific, targets GD-2, ANA Ab, SMART IDIO Ab, SMART ABL 364 Ab, or ImmuRAIT-CEA.

In some embodiments, an agent that finds use in embodiments herein specifically binds a component of a regulatory T cell, myeloid suppressor cell, or dendritic cell. In another aspect, the targeting moiety specifically binds one of the following molecules: CD4; CD25 (IL-2α receptor; IL-2αR); cytotoxic T-lymphocyte antigen-4 (CTLA-4; CD152); Interleukin-10 (IL-10); Transforming growth factor-beta receptor (TGF-βR); Transforming growth factor-beta (TGF-β); Programmed Death-1 (PD-1); Programmed death-1 ligand (PD-L1 or PD-L2); Receptor activator of nuclear factor-κB (RANK); Receptor activator of nuclear factor-κB (RANK) ligand (RANKL); LAG-3; glucocorticoid-induced tumor necrosis factor receptor family-related gene (GITR; TNFRSF18); or Interleukin-4 receptor (IL-4R). In some embodiments, the agent is an agonist that increases the function of the targeted molecule. In other embodiments, the agent is an antagonist that inhibits the function of the targeted molecule.

In some embodiments, an agent that finds use in embodiments herein binds a specific cytokine, cytokine receptor, co-stimulatory molecule, co-inhibitory molecule, or immunomodulatory receptor that modulates the immune system. In another aspect, the targeting moiety specifically binds one of the following molecules: tumor necrosis factor (TNF) superfamily; tumor necrosis factor-α (TNF-α); tumor necrosis factor receptor (TNFR) superfamily; Interleukin-12 (IL-12); IL-12 receptor; 4-1BB (CD137); 4-1BB ligand (4-1BBL; CD137L); OX40 (CD134; TNR4); OX40 ligand (OX40L; CD40; CD40 ligand (CD40L); CTLA-4; Programmed death-1 (PD-1); PD-1 ligand I (PD-L1: B7-H1); or PD-1 ligand 2 (PD-L2; B7-DC); B7 family; B7-1 (CD80); B7-2 (CD86); B7-H3; B7-H4; GITR/AITR: GITRL/AITRL; BTLA; CD70; CD27; LIGHT; HVEM: Toll-like receptor (TLR) (TLR 1, 2, 3, 4, 5, 6, 7, 8, 9, 10). In some embodiments, the agent is an agonist that increases the function of the targeted molecule. In other embodiments, the agent is an antagonist that inhibits the function of the targeted molecule.

In some embodiments, agents (e.g., immunotherapeutics) targeting 4-1BB, LAG-3 and/or one or more receptors/markers of Table 2 (e.g. PD-1, TIM-3, OX-40ICOS, TIGIT, CD244, TNFRSF18, Nrn1, Nrp1, KLRG1, GM156, GPNMB, GPR65, TMEM205, and TMEM126A, CRTAM, Sema7a, etc.) are co-administered (e.g., serially or sequentially) with one or more adjuvants. Suitable adjuvants include, but are not limited to, one or more of: oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor. In addition to variant B7-DC polypeptides, other co-stimulatory molecules, including other polypeptides of the B7 family, may be administered. Proteinaceous adjuvants may be provided as the full-length polypeptide or an active fragment thereof, or in the form of DNA, such as plasmid DNA.

Pharmaceutical and immunotherapeutic compositions described herein may be delivered by any suitable route of administration (e.g., oral delivery, parenteral delivery, mucous membrane delivery, pulmonary delivery, intravenous delivery, etc.). Appropriate formulations for such delivery routes are understood in the field.

Non-limiting examples of cancers that may be treated with the compositions and methods described herein include, but are not limited to: melanoma (e.g., metastatic malignant melanoma), renal cancer (e.g. clear cell carcinoma), prostate cancer (e.g. hormone refractory prostate adenocarcinoma), pancreatic cancer (e.g., adenocarcinoma), breast cancer, colon cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. In some embodiments, the cancer is a solid tumor cancer.

Some embodiments described herein are particularly useful for the treatment of tumors that do not otherwise respond to immunotherapeutic approaches. In some embodiments, provided herein is the treatment of cancers that are non-responsive (or have a reduced response) to T cells or antigen presenting cells (e.g., dendritic cells (e.g., CD103$^+$DCs, etc.), etc.). In some embodiments, provided herein is the treatment of cancers that are non-responsive to treatments, despite T cell infiltration. In some embodiments, compositions and methods described herein find use in the treatment of cancers in which T cells are not appropriately primed against tumor-associated antigens. In some embodiments, compositions and methods described herein find use in the treatment of cancers comprising tumors or cells that are defective in recruitment of dendritic cells (e.g., CD103$^+$ DCs, etc.). In some embodiments, compositions and methods described herein find use in the treatment of cancers comprising tumors or cells that are defective in production of the chemokine CCL4.

In some embodiments, the therapeutic compositions and methods herein find use with those described in, for example WO 2016/141312; incorporated by reference in its entirety.

In some embodiments, methods are provided for testing sample (e.g., cell, tissue, population of cells, tumor, blood, urine, saliva, etc.) from a subject for one or more biomarkers (e.g., biomarkers of dysfunctional tumor antigen-specific CD8$^+$ T cells). Such biomarkers may comprise nucleic acids, small molecules, proteins, peptides, etc., and may be detected using any suitable assay of technique. In some embodiments, provided herein are DNA-, RNA-, small molecule, and/or protein-based diagnostic methods that either directly or indirectly detect the biomarkers of the evasion of immune response or immunotherapy by cancer cells or tumors. The present invention also provides compositions, reagents, and kits for such diagnostic purposes.

In some embodiments, biomarkers are detected at the nucleic acid (e.g., RNA) level. For example, the presence or amount of biomarker nucleic acid (e.g., mRNA) in a sample is determined (e.g., to determine the presence or level of biomarker expression). Biomarker nucleic acid (e.g., RNA, amplified cDNA, etc.) may be detected/quantified using a variety of nucleic acid techniques known to those of ordinary skill in the art, including but not limited to nucleic acid sequencing, nucleic acid hybridization, nucleic acid amplification (e.g., by PCR, RT-PCR, qPCR, etc.), microarray, Southern and Northern blotting, sequencing, etc. Non-amplified or amplified nucleic acids can be detected by any conventional means. For example, in some embodiments, nucleic acids are detected by hybridization with a detectably labeled probe and measurement of the resulting hybrids. Nucleic acid detection reagents may be labeled (e.g., fluorescently) or unlabeled, and may by free in solution or immobilized (e.g., on a bead, well, surface, chip, etc.).

In some embodiments, biomarkers are detected at the protein level. For example, the presence or amount of biomarker protein in a sample is determined (e.g., to determine the presence or level of biomarker expression or localization). In some embodiments, reagents are provided for the detection and/or quantification of biomarker proteins. Suitable reagents include primary antibodies (e.g., that bind to the biomarkers), secondary antibodies (e.g., that bind primary antibodies), antibody fragments, aptamers, etc. Protein detection reagents may be labeled (e.g., fluorescently) or unlabeled, and may by free in solution or immobilized (e.g., on a bead, well, surface, chip, etc.).

In some embodiments, biomarker capture reagents are provided to localize, concentrate, aggregate, etc. a biomarker. For example, in some embodiments a biomarker capture reagent that interacts with the biomarker is linked to a solid support (e.g., a bead, surface, resin, column, and the like) that allows manipulation by the user on a macroscopic scale. Often, the solid support allows the use of a mechanical means to isolate and purify the biomarker from a heterogeneous solution. For example, when linked to a bead, separation is achieved by removing the bead from the heterogeneous solution, e.g., by physical movement. In embodiments in which the bead is magnetic or paramagnetic, a magnetic field is used to achieve physical separation of the capture reagent (and thus the target) from the heterogeneous solution. Magnetic beads used to isolate targets are described in the art, e.g., as described in European Patent Application No. 87309308, incorporated herein in its entirety for all purposes.

Compositions for use in the diagnostic methods or testing steps described herein include, but are not limited to, probes, amplification oligonucleotides, and antibodies. Any of the detection and/or diagnostic reagents used in embodiments described herein may be provided alone or in combination with other compositions in the form of a kit. Kits may include any and all components necessary or sufficient for assays including, but not limited to, the detection reagents, buffers, control reagents (e.g., tissue samples, positive and negative control sample, etc.), solid supports, labels, written and/or pictorial instructions and product information, inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered.

In some embodiments, a computer-based analysis program is used to translate the raw data generated by the detection assay (e.g., the presence, absence, or amount of expression a biomarker) into data of predictive value for a clinician. In some embodiments, computer analysis combines various data into a single score or value that is predictive and/or diagnostic. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject. Contemplated herein are any methods capable of receiving, processing, and transmitting the information to and from laboratories conducting the assays, information providers, medical personal, and subjects. For example, in some embodiments of the present invention, a sample (e.g., a biopsy, cell, or blood sample) is obtained from a subject and submitted to a profiling service (e.g., clinical lab at a medical facility, third-party testing service, genomic profiling business, etc. to generate raw data. Where the sample comprises a tissue or other biological sample, the subject may visit a medical center to have the sample obtained and sent to the profiling center, or subjects may collect the sample themselves and directly send it to a profiling center. In some embodiments, a report is generated (e.g., by a clinician, by a testing center, by a computer or other automated analysis system, etc.). A report may contain test results, diagnoses, and/or treatment recommendations.

EXPERIMENTAL

Materials and Methods

Mice and Tumor Inoculation

Female C57BL/6 mice ranging from 6 to 8 weeks were purchased from Taconic Farms. CD45.1 and Rag2$^{-/-}$ mice on the C57BL/6 background were obtained from Taconic Farms and bred at the University of Chicago. 2C/Rag2$^{-/-}$ and P14/Rag2$^{-/-}$ mice have been previously described (Brown et al., 2006; incorporated by reference in its entirety). pLCK-CreERT2×ROSA-YFP mice were generated and have been described (Evaristo et al., 2016; incorporated by reference in its entirety). B16.SIY.dsRed (Kline et al., 2012; incorporated by reference in its entirety), C1498.SIY.GFP (Zhang et al., 2009; incorporated by reference in its entirety), and MC57.SIY.GFP (Spiotto et al., 2002; incorporated by reference in its entirety) tumor cells were engineered to express either dsRed or GFP in frame with the H2-K$^b$-restricted model antigen SIYRYYGL. The 1969.SIY.GFP cell line was engineered by retroviral transduction of the 1969 cell line (Diamond et al., 2011; incorporated by reference in its entirety) using the pLEGFP plasmid expressing cDNA for SIYRYYGL (Spiotto et al., 2002; incorporated by reference in its entirety). For experiments, mice 6 to 9 weeks of age and received 2×10$^6$ tumor cells subcutaneously on either the left flank or both the left and right flank. All mice were maintained according to the National Institute of Health Animal Care guidelines and studied under IACUC-approved protocols.

To generate the targeting construct for the Egr2$^{EGFP}$ knock-in reporter mice, a 12.6 kb mouse genomic DNA fragment including the egr2 gene was excised with SacII and cloned into a pEasy-Flox vector adjacent to the thymidine kinase (TK) selection marker. A cassette containing IRES2-eGFP and a LoxP-flanked neomycin selection marker was inserted into an Nhe1 site between the translation stop codon (TGA) and the polyadenylation signal of the egr2 gene. ES cell clones from 129 mice were electroporated and selected for Neomycin resistance. ES cell clones were verified for homologous insertion in the endogenous locus by PCR and southern blot with 5' and 3' probes. Mice were backcrossed to C57BL/6 for over 8 generations.

TIL Isolation

Tumors were harvested from mice at the indicated time points. Tumors were dissociated through a 50 μm filter and washed with PBS. TILs were further enriched by layering Ficoll-Hypaque beneath the cell suspension followed by centrifugation without breaks for 30 min at 400×g. The buffy-layer was isolated and washed twice with PBS before staining. For isolating specific cell populations by FACS, tumors were pooled when indicated and the cell layer was re-purified by Ficoll-Hypaque centrifugation twice. For day 28 tumors, after Ficoll-Hypaque separation, T cells were further purified by negative bead selection according to manufacturer's instructions (MAGNISORT, eBiosciences). Cells were then washed with PBS, stained at 4° C. for 15 minutes before resuspending in complete DMEM (cDMEM: 10% FBS, 100U/mL Penicillin-Streptomycin, 1% MEM Non-Essential Amino Acids, 50 μM β-ME, 0.01M MOPS), and were sorted into either RLT lysis buffer (QIAGEN) or cDMEM depending on the experimental assay. Cells sorted into RLT buffer were put directly on dry ice as soon as the sort was finished.

Flow Cytometry and Antibodies

Cell suspensions were washed twice in PBS before staining an FACS buffer (10% FBS, 2 mM EDTA, 0.001% NaN$_3$). Cells were stained for 30 min on ice and fixed in 1% PFA. Antibodies against the following molecules were used: CD3 (17A2, AX700), 2B4 (2B4, FITC), CD127 (A7R34, PE), OX-40 (OX-86, PE), 4-1BB (17B5, Biotin, APC), CD160 (7H1, PE-Cy7), LAG-3 (C9B7W, PerCPeFluor710), PD-1 (RMP1-30, PE-Cy7), NRP1 (3E12, BV421), GITR (DTA-1, FITC), ICOS (7E.17G9, BV421), KLRG-1 (2F1, eF450, BV605), TIGIT (1G9, APC), TIM-3 (RMT3-23, PE), CD4 (RM4-5, BV605), CD45.1 (A20, FITC), CD45.2 (104, PE), CD8a (53-6.7, BV711). Fixable Viability Dye 506 (eBioscience) was used for live/dead discrimination. Staining of SIY-specific T cells was performed utilizing the SIYRYYGL-Pentamer (PE) (Proimmune); a SIINFEKL-pentamer (PE) was used as a non-specific control. All flow cytometric analysis was conducted on an LSRFortessa (BD) and analyzed using FlowJo software (Tree Star).

Quantitative Real-Time PCR

Total RNA was extracted from sorted cell populations using the RNEasy Micro Kit (QIAGEN) following the manufacturer's protocol. cDNA was synthesized using the High Capacity cDNA Reverse Transcription kit (Applied Biosystems) according to manufacturer's instructions. Transcript levels were determined using primer-probe sets (Tables 1a and 1b) developed through the online ProbeFinder Software and the Universal Probe Library (Roche) with the exception of IL-2 (Mm00434256_m1) and 18S (Hs99999901_s1). To minimize batch effect, when possible, all samples probed for a gene were run on the same 96-well qRT-PCR plate. All primer-probe sets either contained a primer spanning an exon-exon boundary or primers spanning an intron. Expression levels of transcripts were normalized to 18S expression.

TABLE 1a

Primer Sequences

| # | Wilson | IMGT | Sequence | SEQ ID NO: |
|---|---|---|---|---|
| 0 | Cβ1.1 | TRBC1 | CTCAAACAAGGAGACCTTGGGTGG | 1 |
| 1 | Vβ1 | TRVB5 | CAGACAGCTCCAAGCTACTTTTAC | 2 |

TABLE 1a -continued

Primer Sequences

| # | Wilson | IMGT | Sequence | SEQ ID NO: |
|---|---|---|---|---|
| 2 | Vβ2 | TRVB1 | ATGAGCCAGGGCAGAACCTTGTAC | 3 |
| 3 | Vβ3 | TRVB26 | GAAATTCAGTCCTCTGAGGCAGGA | 4 |
| 4 | Vβ4 | TRVB2 | CTAAAGCCTGATGACTCGGCCACA | 5 |
| 5 | Vβ5.1 | TRVB12-2 | CTTTGGAGCTAGAGGACTCTGCCG | 6 |
| 6 | Vβ5.2 | TRVB12-1 | CCTTGGAACTGGAGGACTCTGCTA | 7 |
| 7 | Vβ6 | TRVB19 | GCCCAGAAGAACGAGATGGCCGTT | 8 |
| 8 | Vβ7 | TRVB29 | GGATTCTGCTAAAACAAACCAGACATCTGT | 9 |
| 9 | Vβ8.1 | TRVB13-3 | GCTTCCCTTTCTCAGACAGCTGTA | 10 |
| 10 | Vβ8.2 | TRVB13-2 | GCTACCCCCTCTCAGACATCAGTG | 11 |
| 11 | Vβ8.3 | TRVB13-3 | GGCTTCTCCCTCTCAGACATCTT | 12 |
| 12 | Vβ9 | TRVB17 | CTCTCTCTACATTGGCTCTGCAGG | 13 |
| 13 | Vβ10 | TRVB4 | CTTCGAATCAAGTCTGTAGAGCCG | 14 |
| 14 | Vβ11 | TRVB16 | TGAAGATCCAGAGCAGCGGGCCCC | 15 |
| 15 | Vβ12 | TRVB15 | CCACTCTGAAGATTCAACCTACAGAACCC | 16 |
| 16 | Vβ13 | TRVB14 | CAAGATCCAGTCTGCAAAGCAGGG | 17 |
| 17 | Vβ14 | TRVB31 | GCACGGAGAAGCTGCTTCTCAGCC | 18 |
| 18 | Vβ15 | TRVB20 | GCATATCTTGAAGACAGAGGC | 19 |
| 19 | Vβ16 | TRVB3 | CTCTGAAAATCCAACCCACAGCACTGG | 20 |
| 20 | Vβ17 | TRVB24 | TCTGAAGAAGACGACTCAGCACTG | 21 |
| 21 | Vβ18 | TRVB30 | GCAAGGCCTGGAGACAGCAGTATC | 22 |

TABLE 1b

Primer/Probe

| Gene | SEQ ID NO: | Primer1 | Primer2 | SEQ ID NO: | Roche Probe # |
|---|---|---|---|---|---|
| Lag3 | 23 | tgctttgggaagctccagt | gctgcagggaagatggac | 42 | 79 |
| Tnfrsf9 | 24 | ccggtcttaagcacagacct | gaacggtactggcgtctgtc | 43 | 108 |
| Egr2 | 25 | ctacccggtggaagacctc | aatgttgatcatgccatctcc | 44 | 60 |
| Sema7a | 26 | tcaatcggctgcaagatgt | cgcagacagctgagtagttcc | 45 | 15 |
| Crtam | 27 | agatccaacaacgaggagaca | tcatgcaacgcttagactgg | 46 | 71 |
| Ccl1 | 28 | tcaccatgaaacccactgc | agcagcagctattggagacc | 47 | 71 |

TABLE 1b -continued

Primer/Probe

| Gene | SEQ ID NO: | Primer1 | Primer2 | SEQ ID NO: | Roche Probe # |
|---|---|---|---|---|---|
| Ngn | 29 | caccctagcctaacctcaacc | tgaaaacctcctccctctt | 48 | 45 |
| Arl3 | 30 | ctggcagatccagtcctgtt | acccagttcatgccatcct | 49 | 100 |
| Exph5 | 31 | atgagggaggagagcggtat | cagcttgttgtccaaatcgtc | 50 | 67 |
| Fhl2 | 32 | agaaaaccatcatgccaggt | acaggtgaagcaggtctcgt | 51 | 74 |
| Nrn1 | 33 | atcctcgcggtgcaaata | gcccttaaagactgcatcaca | 52 | 108 |
| Ptgfrn | 34 | ccggggagatctcatcaaa | tcgaaggccatgtcatctg | 53 | 12 |
| Rankl | 35 | tgaagacacactacctgactcctg | cccacaatgtgttgcagttc | 54 | 88 |
| Tnfa | 36 | gctgctcactgtgaaggaagt | tggggaatgcattttaccat | 55 | 2 |
| Egr3 | 37 | caatctgtacccgaggaga | ccgatgtccatcacattctct | 56 | 74 |
| Tnfa | 38 | ctgtagcccacgtcgtagc | ttgagatccatgccgttg | 57 | 25 |
| Gzmb | 39 | gctgctcactgtgaaggaagt | tggggaatgcattttaccat | 58 | 2 |
| Ccl1 | 40 | tcaccatgaaacccactgc | agcagcagctattggagacc | 59 | 71 |
| Ccl22 | 41 | tcttgctgtggcaattcaga | gcagagggtgacggatgtag | 60 | 74 |

In Vivo Proliferation Assay

In vivo proliferation was measured by a BrdU pulse 24 hours prior to flow cytometric analysis. Each mouse received 0.8 mg BrdU injected i.p. (intraperitoneal) on day 12 after tumor inoculation. TILs were isolated and surface stain was performed as described above. Following surface staining, cells were fixed and permeabilized using the Foxp3 staining kit (BD), according to manufacturer's protocol, and incubated with 100 µl PBS/DNase solution (300 µg/ml) for 30 minutes at 37° C. Cells were washed and incubated for 30 minutes at room temperature with anti-BrdU (FITC, Bu20a) and then washed with and resuspended in PBS.

In Vitro Stimulation Assays

Tissue culture-treated 96-well round bottom plates were coated with anti-CD3E (1 µg/ml; 2C11) in DPBS overnight at 4° C. or for 2 hours at 37° C. Cells were sorted into cold cDMEM media and put on ice as soon as the sort was finished. Cells were then pelleted, resuspended in 50 µl cDMEM and incubated with soluble anti-CD28 (2 µg/ml; PV-1) for 10-12 hours for a final volume of 100 µl. After stimulation supernatants were removed for ELISA or bead-based immunoassay (LegendPlex), and cells were washed once with DPBS and resuspended in 15 µl of RNAlater Stabilization Solution (QIAGEN) or 300 µl of RLT buffer. Cells were stored at −80° C. until RNA isolation was performed.

Protein Quantification

Measurement of protein concentration was determined either by a standard ELISA or bead-based immunoassay (LEGENDplex, BioLegend). ELISAs were performed according to manufacturer's protocol (Ready-SET-Go ELISA; eBioscience) on supernatants from in vitro stimulations. Absorbance values were obtained at 450 nm using an Emax microplate reader (Molecular Devices) and IL-2 concentration was determined by standard curve. Protein concentration values were normalized to the number of sorted cells plated. LEGENDplex assays were performed according to manufacturer's protocols. IL-2 concentration (FIG. 4B) was confirmed by both methods in separate experiments with no significant difference in IL-2 concentration between the two methods.

Spectratype Analysis and Sequencing Mice were injected with 2×10⁶ B16.SIY.dsRed tumor cells. 14 days later, tumors were harvested and specific CD8⁺ TIL subpopulations were sorted into RLT buffer (QIAGEN) and immediately frozen. cDNA was synthesized from sorted cell populations and CDR3 regions were amplified by PCR with 21 different Vβ-5' primers paired with a FAM-Cβ1.1 primer (Table 1). Three Vβ PCR reactions did not reach significant amplification for analysis and were removed from the analysis. For sequencing, Cβ-Vβ PCR products were purified using the QIAquick PCR purification kit (QIAGEN) and sequenced at the University of Chicago Genomics Core Facility. Cβ-Vβ PCR products were analyzed by capillary electrophoresis at the University of Chicago Genomics core and CDR3 peaks were aligned using the Liz500 ladder. Spectratype graphs were displayed using the GeneiousR9 software (Kearse et al., 2012). To generate the frequency profile for each Vβ spectratype, the area under each peak was measured using peak studio. The Hamming Distance (Currier and Robinson, 2001; incorporated by reference in its entirety) was calculated between each Vβ spectratype from each CD8⁺ spleen and TIL population within a given mouse. To determine significance between the HD from each comparison the HDs for each Vβ from mice were averaged and a One-Way ANOVA with Dunn's correction for multiple comparisons was performed.

TCR Transgenic T Cell Transfer Experiments

Cell suspensions were generated from spleens and lymph nodes from congenic 2C/Rag2⁻/⁻/CD45.1/2 and/or P14/Rag2⁻/⁻/CD45.2 mice and T cells were purified by CD8⁺ negative selection (Miltenyi Biotechnologies) over magnetic columns according to the manufacturer's protocol. TCR Transgenic (Tg) T cells were washed with PBS, resuspended at a concentration of 10×10⁶/ml and 1×10⁶ TCR Tg cells were adoptively transferred into CD45.1 tumor bearing mice by tail vein transfer in a volume of 0.1 mL. After indicated times, 2C T cells and corresponding host CD8⁺ T cells were sorted and stimulated as described above.

In Vitro Cytotoxicity Assay

Per individual experiment, 10 C57BL/6 mice were injected s.c. (subcutaneous) with 2×10⁶B16.SIY cells on both left and right flanks. On day 14, all 20 tumors were pooled and dissociated using the Tumor Dissociation Kit (Miltenyi Biotec) following the manufacturer's protocol. Tumor cell suspensions were washed 3-5 times with PBS and TILs were enriched for by Ficoll-Hypaque gradient centrifugation. TILs were stained, sorted and put directly on ice. TILs were titrated and added directly to a 96-well plate containing 50,000 P815 mastocytoma cells and 1 µg/mL anti-CD3. For a positive control, OT-I cells were isolated from OT-I/Rag2$^{-/-}$ mice and stimulated with plate-bound anti-CD3 (0.25 µg/mL), anti-CD28 (2 µg/mL) and 100 U/mL IL-2 for 2-3 days. For a negative control, P815 cells were cultured alone or cultured with naïve CD8⁺ T cells isolated from lymph nodes. After 12 hours of incubation, cells were stained for Thy1, CD45, CD8α, Fixable Viability Dye 450 (eBioscience) and/or propidium Iodide.

Gene Expression Analysis

Total RNA for the CD8⁺ TIL subpopulations was isolated following the manufacturer's protocol (RNEasy Micro Kit: QIAGEN) from sorted cells pooled from 10 mice. Samples were analyzed by the University of Chicago Genomics Facility using Illumina MouseRef8 microarray chips. Two experimental replicates were performed, and the results were $\log_2$ transformed and averaged. Probe sets that revealed a 1.5-fold difference abs($\log_2$(ratio)>1.5)) relative to CD8⁺4-1BB⁻LAG-3⁻PD-1⁻ cells were identified and used for subsequent analysis. The microarray data are available in the Gene Expression Omnibus database under accession number GSE79919. For cross-study comparisons, log 2-fold change values were extracted using the GEO2R online software from the hypofunctional CD8⁺ TIL data set, GSE79858 ((GSM2107353, GSM2107353 and GSM2107355) versus (GSM2107350, GSM2107351, GSM210732)) and the CD8⁺ T cell exhausted data set, GSE41870 ((GSM1026819, GSM1026820, GSM1026821) versus (GSM1026786, GSM1026787, GSM1026788, GSM1026789)). Upregulated genes showing a 2-fold difference were used for analysis. Multiple genes names with from the GEO2R extracted data were identified and matched to gene names from the Illumina data set. The rank-rank hypergeometric overlap (RRHO) analysis (Plaisier et al., 2010; incorporated by reference in its entirety) was conducted (Rosenblatt and Stein, 2014; incorporated by reference in its entirety).

Gene Ontology Enrichment Analysis

In a pair-wise fashion, shared upregulated genes were used as the input for the ClueGO software with the Cytoscape application (Shannon et al., 2003; incorporated by reference in its entirety). Both the Biological Process and Immune System Process Gene Ontology Annotations were used for analysis. Only pathways with a Bonferroni step down correction p-value>0.01 were considered when generating pathway nodes. Non-redundant pathways with the greatest number of genes found within each node were used as examples in FIG. 6A.

Antibody and FTY720 Treatments

Mice were treated i.p. with 100 µg/mouse of anti-4-1BB (Bio-X-Cell; LOB12.3) antibody and/or 100 µg/mouse anti-LAG-3 (Bio-X-Cell; C9B7W). For tumor outgrowth experiments, mice were treated on day 7, 10, 13 and 16 after tumor inoculation. For ex vivo functional experiments mice were treated on day 7, 10 and 13 and cells were sorted on day 14. For experiments blocking lymph node egress, 25 µg of FTY720 was given by gavage one day prior to first antibody treatment (day 6) and continued every day until endpoint on day 14.

Results 4-1BB and LAG-3 Identify a Major Population of CD8⁺ TILs

Figure 1C:
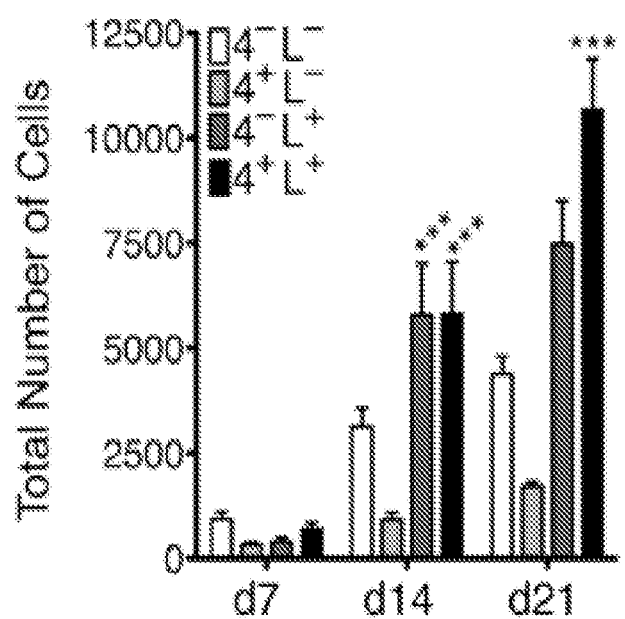
Figure 1D:
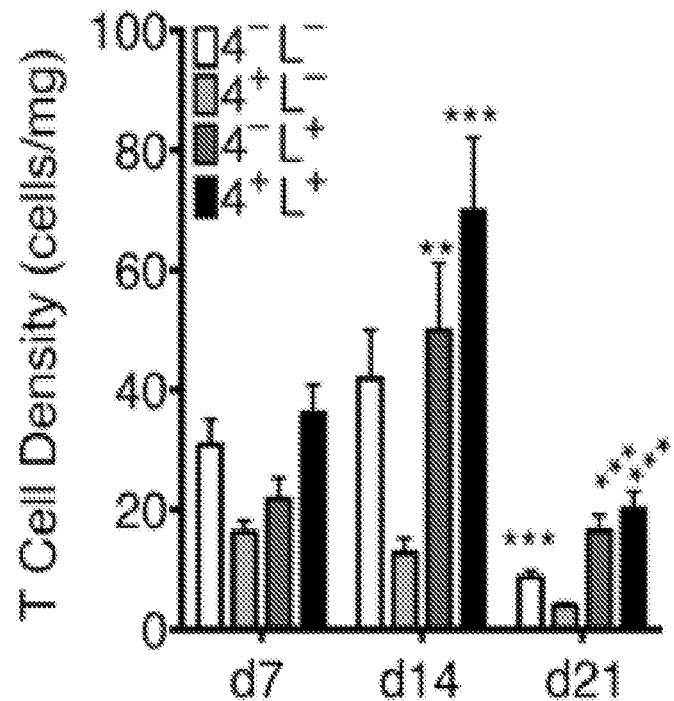

To determine whether 4-1BB and LAG-3 could identify dysfunctional CD8⁺ TILs, the expression pattern of LAG-3 and 4-1BB was examined using the well-characterized B16.SIY model of melanoma. On day 7 following tumor inoculation, the 4-1BB⁺LAG-3⁺ population comprised 15.8% of all CD8⁺ TILs. The frequency of this population significantly increased to 44% by day 21. The frequency of 4-1BB⁻LAG-3⁺ (4⁻L⁺) population also increased 1.9-fold from day 7 to day 14 to comprise 25% of the CD8⁺ TIL compartment. In contrast, the frequency of the 4-1BB⁻LAG-3⁻ (4⁻L⁻) population decreased by 2.7-fold by day 21. There was no significant increase in the proportion or number of 4-1BB⁺LAG-3⁻CD8⁺ TILs within the time frame of the experiment (FIGS. 1A and B). Similar patterns were seen when analyzing absolute numbers of cell subsets (FIGS. 1C and D). Acquisition of these phenotypes was specific for the tumor microenvironment, as they were not observed in the spleen or tumor-draining lymph node (TdLN) (FIG. 1A). These data indicate that the tumor microenvironment preferentially supports the induced co-expression of LAG-3 and 4-1BB.

Figure 1E:
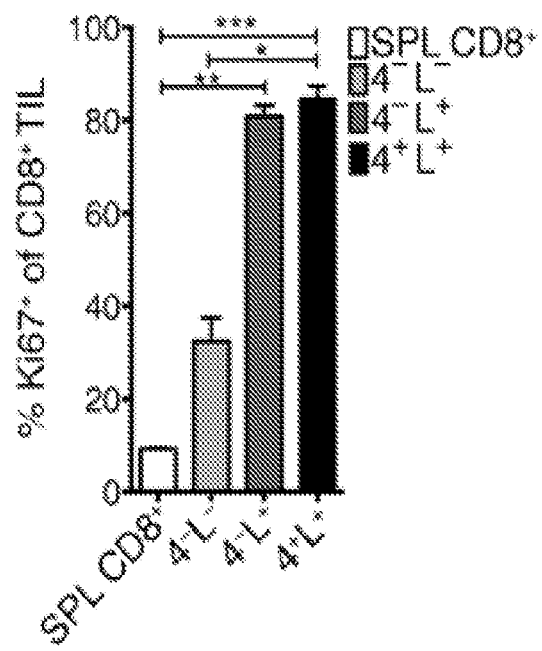
Figure 1F:
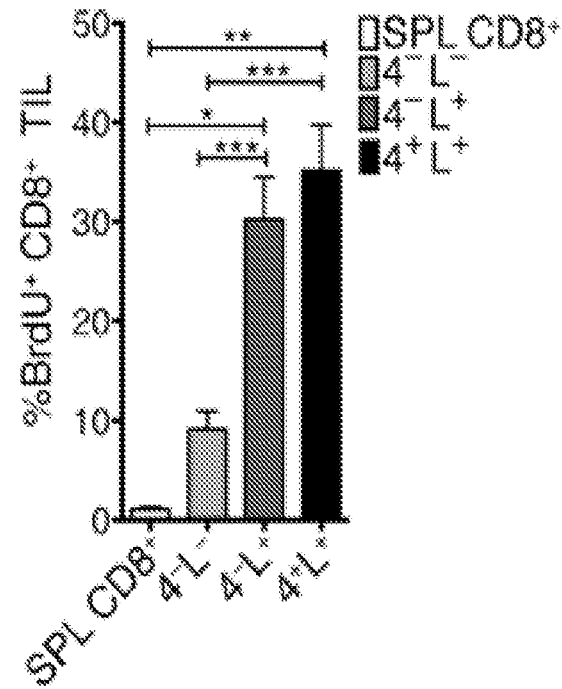

The selective increase in cell numbers and proportional shift towards the 4-1BB⁻ LAG-3⁺ and 4-1BB⁺LAG-3⁺ populations during tumor progression indicated that expansion of these populations was occurring within the tumor microenvironment. CD8⁺ TILs were stained for Ki67 at day 14 after tumor inoculation and analyzed by flow cytometry. 81% of 4-1BB⁻LAG-3⁺ cells and 85% of 4-1BB⁺LAG-3⁺ cells were Ki67⁺ compared to only 32% of the 4-1BB⁻LAG-3⁻ TILs (FIG. 1E). Mice were pulsed with BrdU on day 12, and 24 hours later the CD8⁺ TIL subpopulations were analyzed for BrdU incorporation. Indeed, the 4-1BB⁻LAG-3⁺ and 4-1BB⁺LAG-3⁺ populations incorporated more BrdU compared to the 4-1BB⁻LAG-3⁻ population (FIG. 1F). These data indicate that once CD8⁺ T cells arrive at the tumor site, a fraction of TILs expands within the tumor, and that these expanding TILs are identified by increased expression of 4-1BB and LAG-3.

Figure 1J:
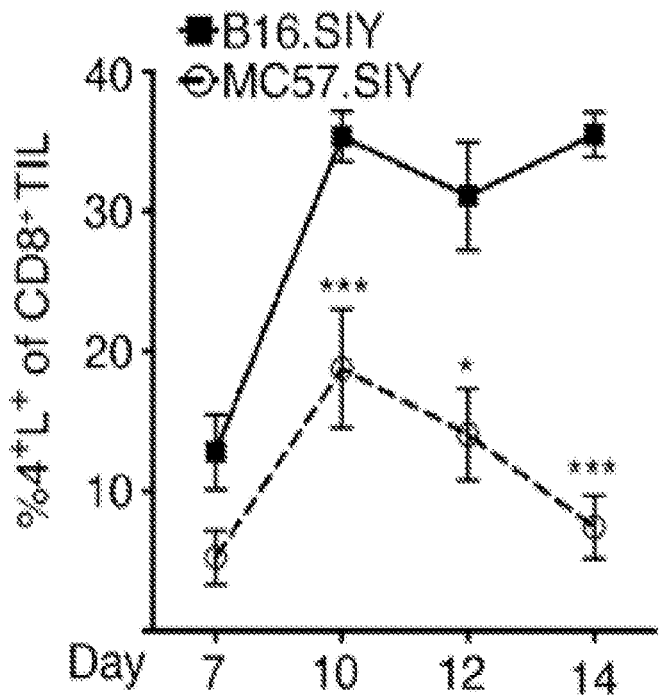
Figure 1G:
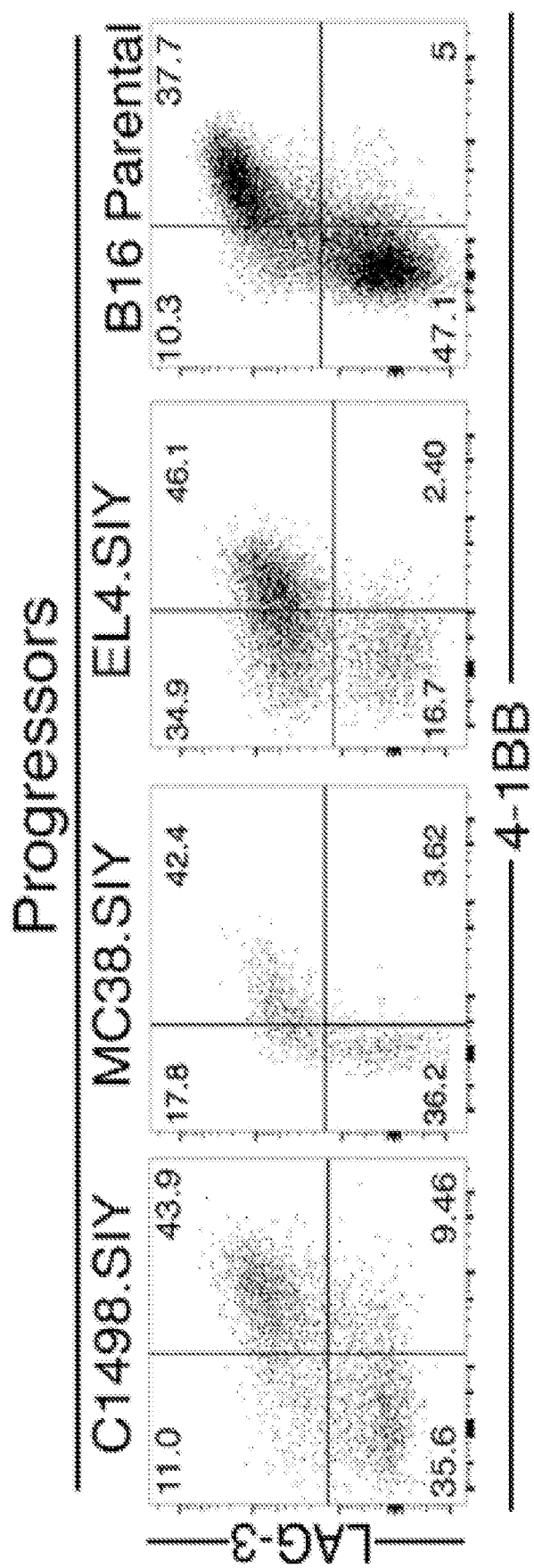
Figure 1H:
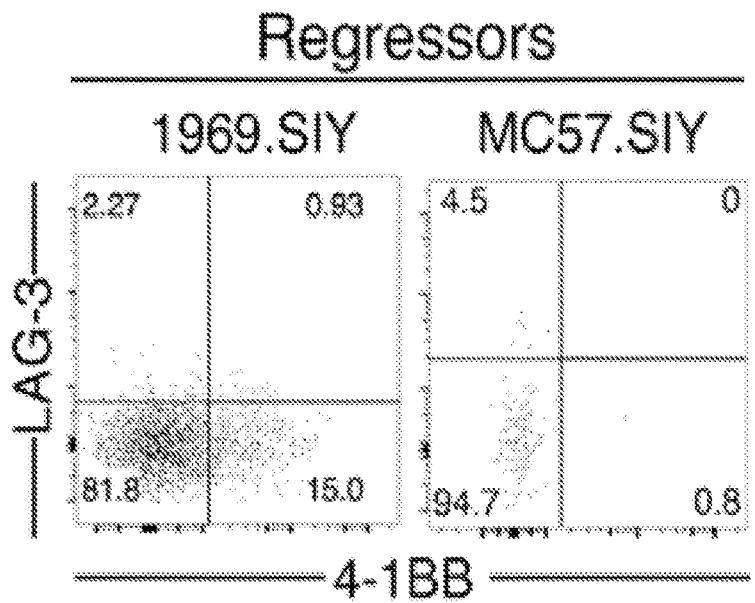
Figure 1I:
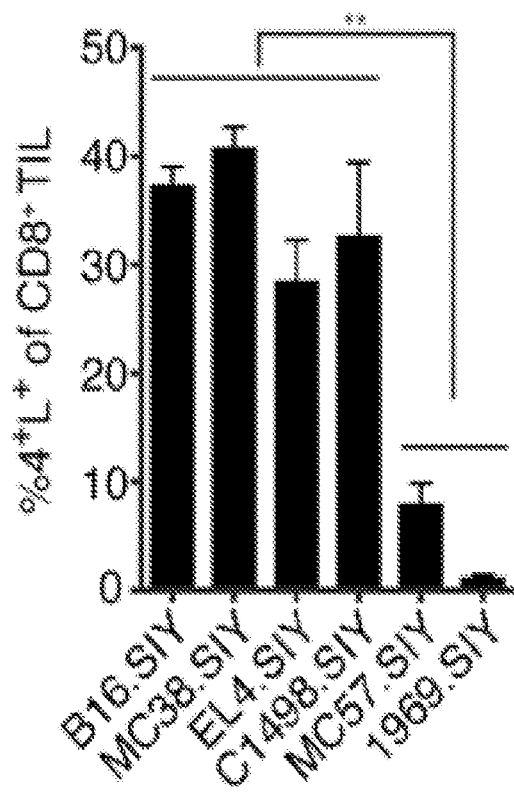

To determine if upregulation of LAG-3 and 4-1BB was simply a product of the B16.SIY tumor model or if it is a more general feature of CD8⁺ T cells within tumors, T cells from three additional progressively growing tumor models, C1498.SIY, MC38.SIY, EL4.SIY and B16F10 parental were analyzed. TILs were analyzed for expression of 4-1BB and LAG-3 at day 14. A pattern of expression was found that is similar to that seen in CD8⁺ TILs isolated from B16.SIY tumors (FIGS. 1G and I). The results from the B16F10 parental tumor confirm that presence of SIY is not required to see co-expression of 4-1BB and LAG-3. In order to determine whether the 4-1BB⁺LAG-3⁺ TIL subset was generated only in progressing tumors or also in tumors that were rejected, T cell phenotypes in the 1969.SIY and MC57.SIY fibrosarcoma tumor models were analyzed, which are more immunogenic and undergo spontaneous rejection. Distinctly fewer 4-1BB⁺LAG-3⁺ cells were found among the CD8⁺ TIL compartment in the 1969.SIY and MC57.SIY tumors (Figure H and I). Over time, co-expression of 4-1BB and LAG-3 was maintained in B16.SIY tumors but not MC57.SIY tumors (FIG. 1J). These data indicate that the acquisition of the LAG-3$^+$4-1BB$^+$ TIL phenotype preferentially occurs within the tumor microenvironment and only upon conditions of tumor progression rather than regression.

CD8$^+$ 4-1BB$^+$LAG-3$^+$ TILs Express Egr2 and Multiple Egr2 Gene Targets

Figure 2A:
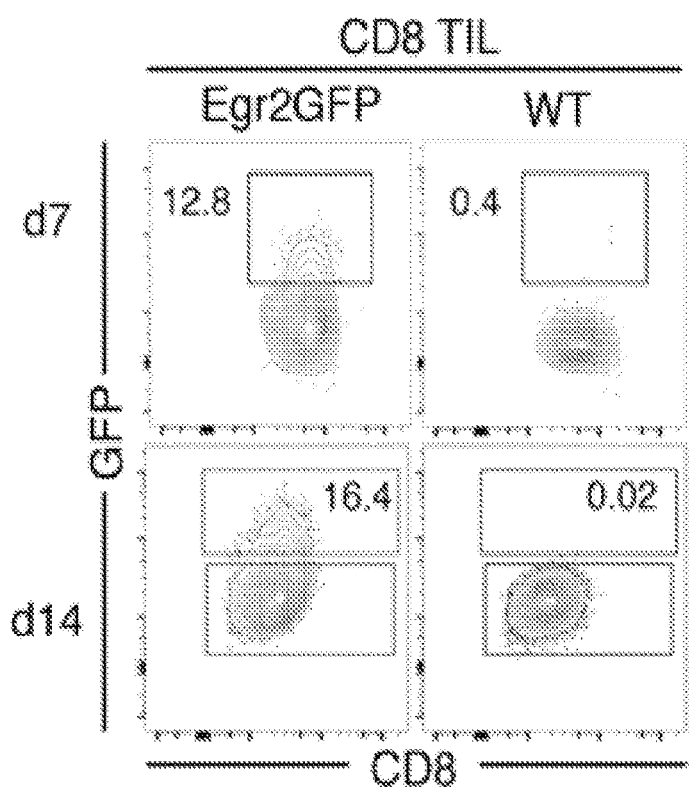
FIG. 2A-G. Egr2 and a component of the Egr2-transcriptional network are enriched in 4-1BB$^+$LAG-3$^+$CD8$^+$ TILs. (A) Representative flow plot and summary of $Egr2^{EGFP}$ expression. $Egr2^{EGFP}$ mice were inoculated with $2 \times 10^6$ B16.SIY tumors s.c. $CD8^+$ T cells from the tumor, TdLN and spleen were analyzed for $Egr2^{EGFP}$ expression on day 7 and day 14. n=4-5; two-independent experiments. (B) Expression of Egr2 target genes (Zheng et al., 2013). $CD8^+$ TILs from day 14 tumor bearing mice were sorted based on high or low expression of $Egr2^{EGFP}$ and analyzed directly for expression of Egr2 targets by qRT-PCR. Two tumors on opposite flanks pooled per mouse. n=3; two independent experiments. (C) Representative flow plots and summary of the 4-1BB/LAG-3 subpopulations in $CD8^+$ $Egr2GFP^{hi}$ and $Egr2GFP^{lo}$ TILs on day 7 and 14. n=4-5. Two-independent experiments per time point. (D) Expression of Egr2 targets in the 4-1BB$^+$LAG-3$^+$ and 4-1BB$^-$LAG-3$^-$ subpopulations. The subpopulations were sorted and analyzed directly for the expression of targets by qRT-PCR. Two tumors on opposite flanks pooled per mouse. n=4; two-independent experiments. (E) $Egr2^{flox/flox}$×pLCKCreERT2×YFP-Rosa26 mice given 5 doses of tamoxifen by gavage and inoculated 3 days later with $2 \times 10^6$ B16.SIY cells. $YFP^+$ or $YFP^-$CD8$^+$ TILs were sorted and analyzed for Egr2 transcript directly and after in vitro stimulation. Two tumors on opposite flanks pooled per mouse. n=3; two independent experiments. (F) Representative flow plots and summary of 4-1BB/LAG-3 co-expression in YFP$^+$ or YFP$^-$CD8$^+$ TILs on day 7 and 14. n=3; two independent experiments. (G) Expression of Egr3 and Hif1α in Egr2GFP$^{hi}$ and Egr2GFP$^{lo}$ from day 7 CD8$^+$ TILs isolated from Egr2GFP mice. n=5; two-independent experiments. Error bars indicate±SEM. *:P<0.05, :P<0.01, *:P<0.001. A two-way ANOVA with Bonferroni post-hoc test was used for longitudinal studies (A and C) and a Mann-Whitney test was used to compute significance in (B, D, E, F and G).
Figure 2A:
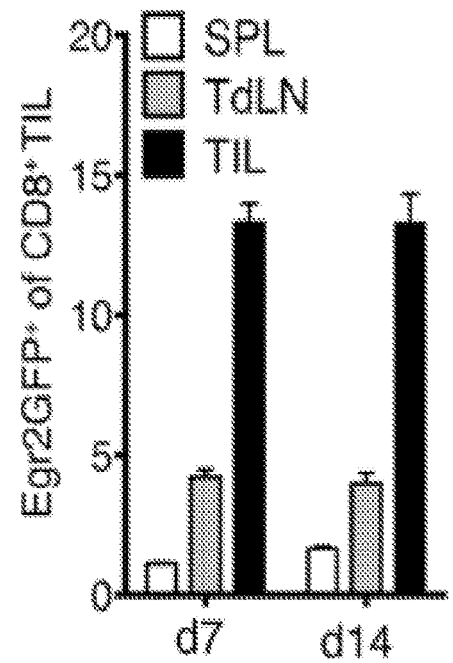
Figure 2B:
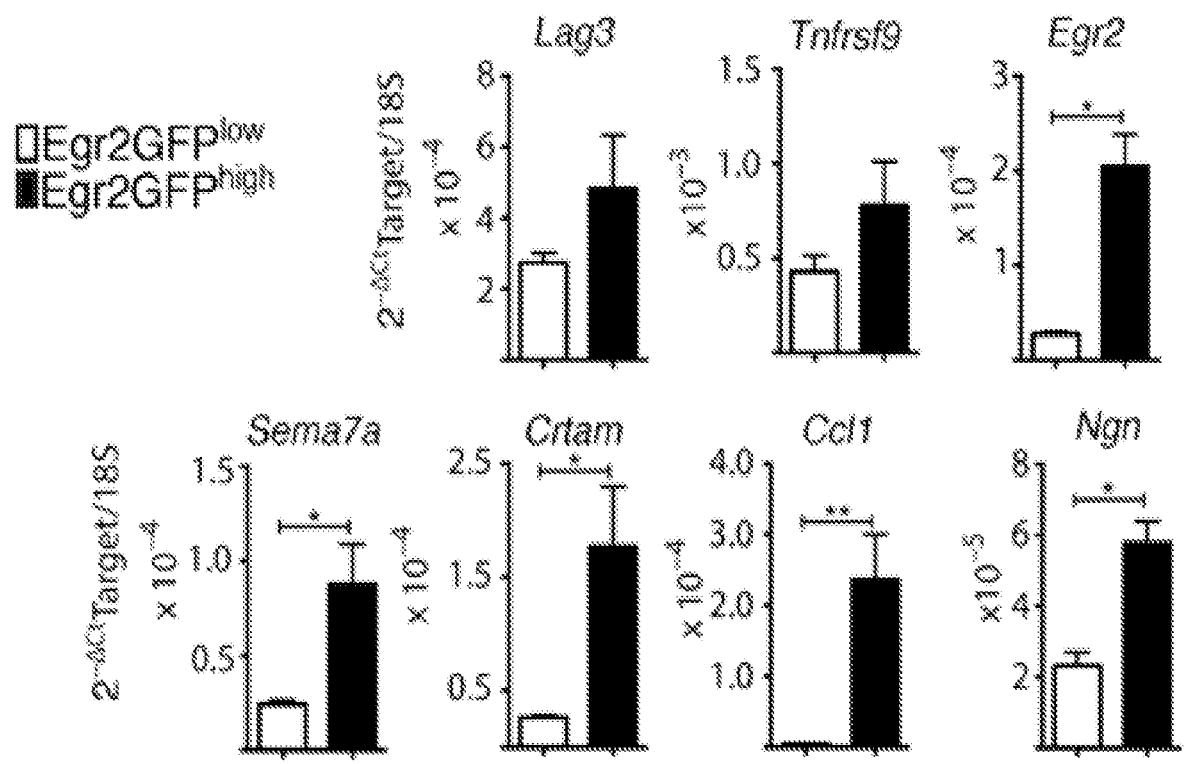
Figure 2C:
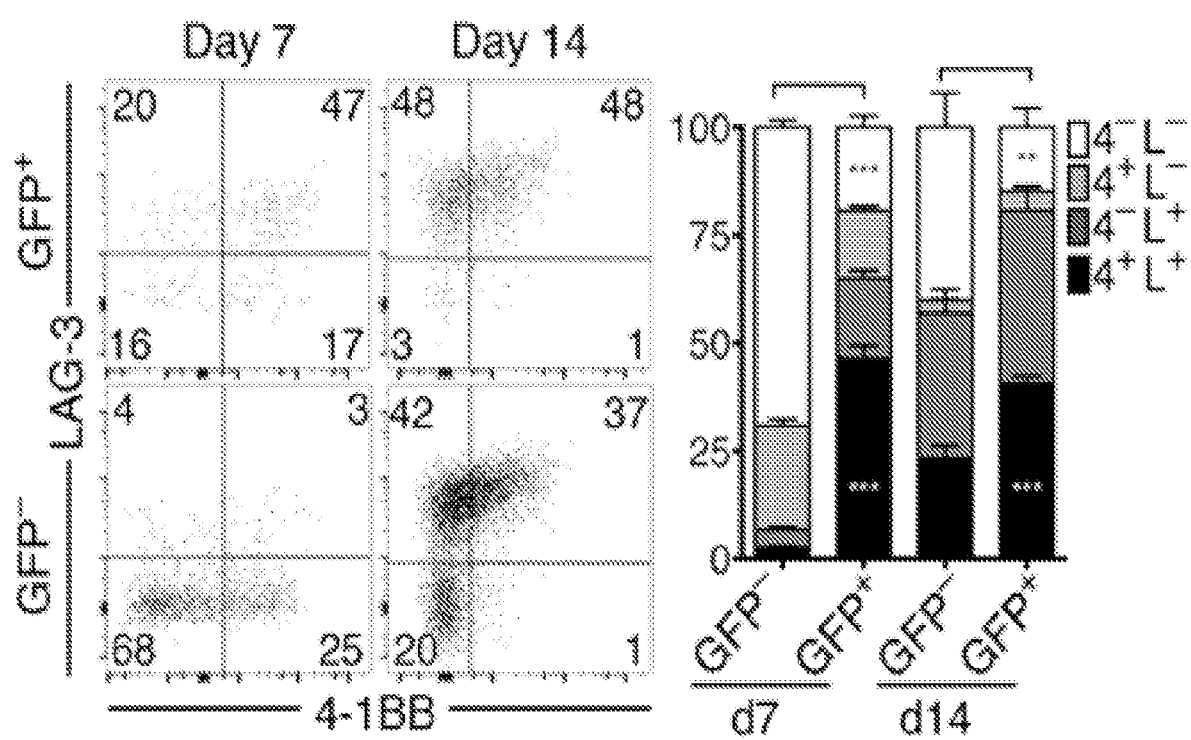

Experiments conducted during development of embodiments herein to determine whether Egr2 expression itself was also characteristic of T cells within the CD8$^+$ TIL compartment; an Egr2-IRES-GFP (Egr2$^{GFP}$) knock-in reporter mouse was utilized. Approximately 14% of all CD8$^+$ TILs were GFP$^+$ on both day 7 and day 14 (FIG. 2A). To confirm that Egr2 is faithfully reported, CD8$^+$ TILs expressing high and low levels of EGFP were sorted and screened for Egr2 and several Egr2 targets by qRT-PCR. The Egr2-GFP$^{hi}$ population expressed greater levels of Egr2 and many Egr2-target genes previously defined using in vitro anergy models. These include Tnfrsf9, Lag3, Ngn, Sema7a, Crtam, Ccl1 and Nrn1 (FIG. 2B). Expression of 4-1BB and LAG-3 in the Egr2-GFP$^{hi}$ CD8$^+$ TILs was confirmed by flow cytometry. The majority of Egr2-GFP$^{hi}$ cells expressed LAG-3 and/or 4-1BB. The Egr2GFP$^{lo}$ cells also showed expression of 4-1BB and LAG-3 on a subpopulation at day 14 (FIG. 2C). This result indicates either that CD8$^+$ TILs expressing Egr2 encompass only a subset of the TILs expressing LAG-3 and/or 4-1BB, or that Egr2 is transiently expressed and is subsequently downregulated after the induction of LAG-3 and 4-1BB.

Figure 2D:
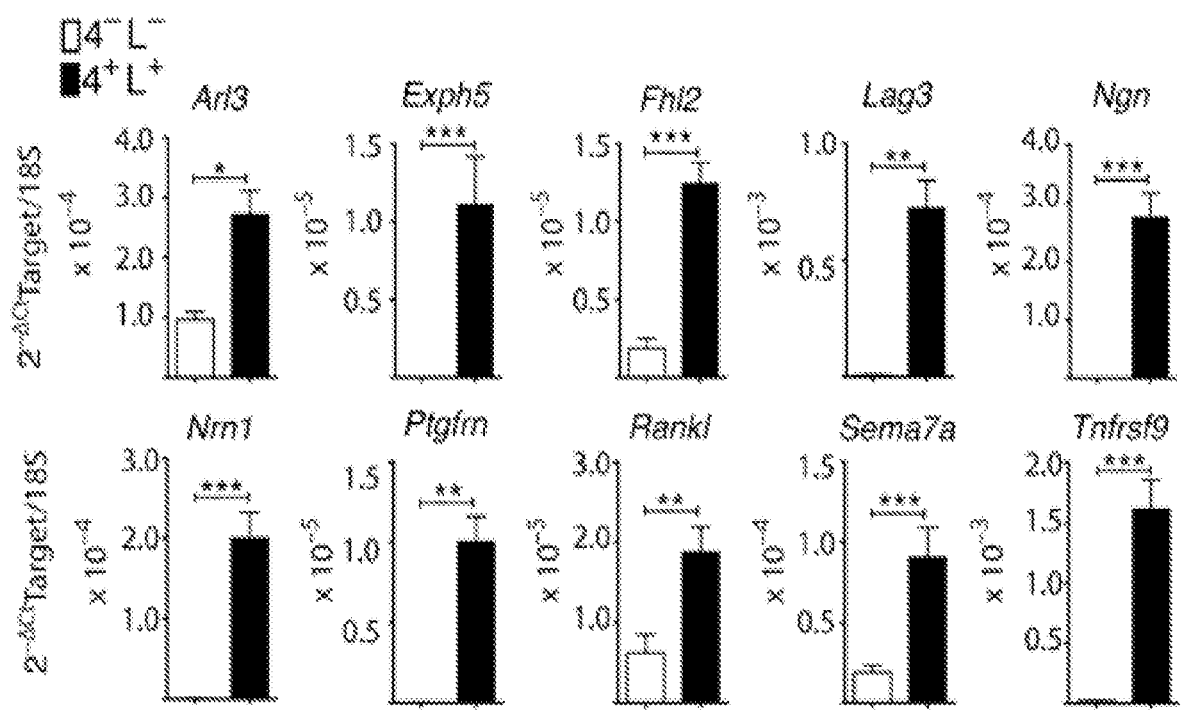

Using Egr2 target genes from in vitro anergic CD4$^+$ T cell clones (Zheng et al., 2013; incorporated by reference in its entirety), the Egr2-driven transcriptional program was examined in sorted 4-1BB$^-$LAG-3$^-$ and 4-1BB$^+$LAG-3$^+$ cells by qRT-PCR. Of the 43 Egr2 target genes examined, 10 showed detectably increased expression in 4-1BB$^+$LAG-3$^+$ population, while expression of a similar subset of genes was increased in the 4-1BB$^-$LAG-3$^+$ population (FIG. 2D). Collectively, these data demonstrate that Egr2 is expressed in a subpopulation of CD8$^+$ TILs expressing LAG-3 and/or 4-1BB, and that a subset of known Egr2 targets was detected in these larger T cell populations as a whole.

Figure 2E:
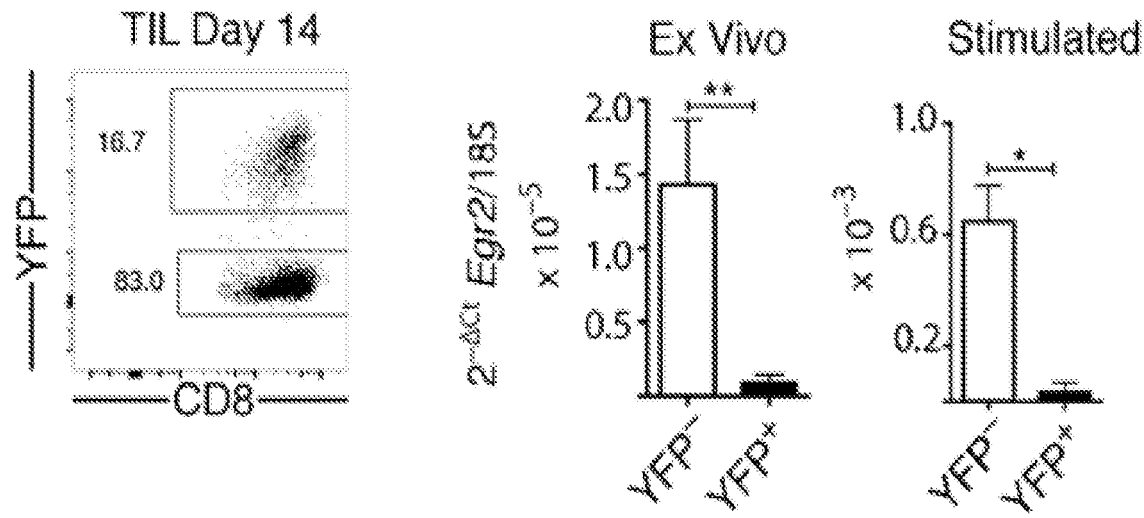
Figure 2F:
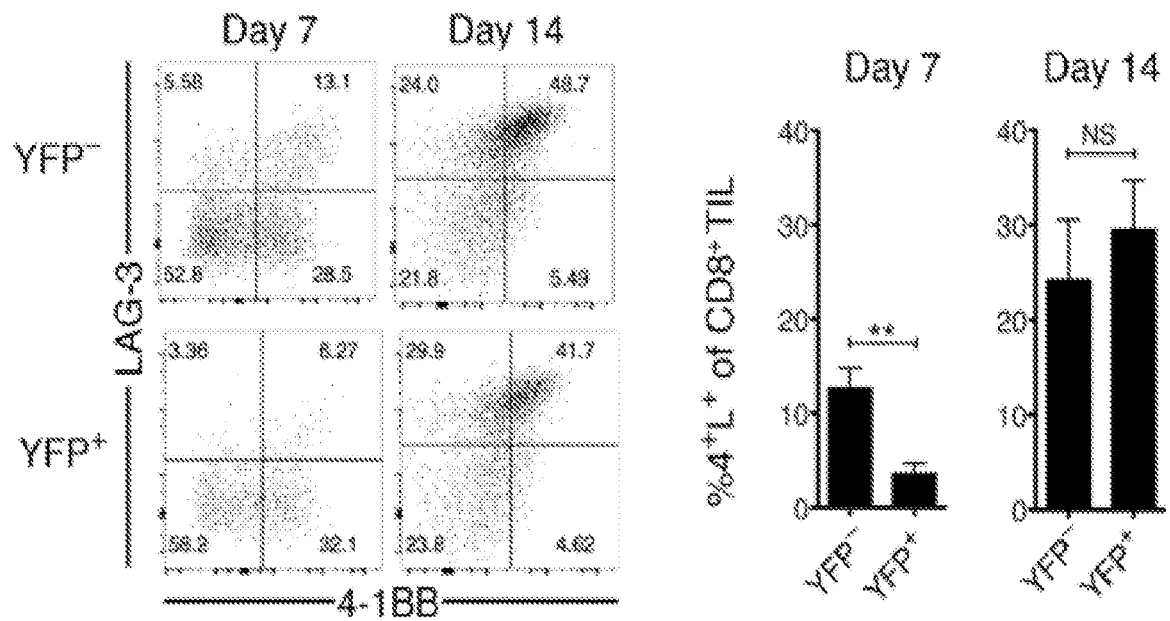

It was next examined whether Egr2 was required for expression of LAG-3 and 4-1BB among CD8$^+$ TIL in vivo. To this end Egr2$^{flox/flox}$×pLCK-CreERT2×ROSA-YFP mice were utilized, in which oral tamoxifen administration results in a fraction of the CD8$^+$ T cells deleting Egr2 and expressing YFP (FIG. 2E). This allowed comparison of both Egr2-sufficient (YFP$^-$) and Egr2-deficient (YFP$^+$) CD8$^+$ within the same tumor. To determine that Egr2 was in fact deleted from the YFP$^+$ fraction, both YFP$^+$ and YFP$^-$CD8$^+$ TILs were sorted and Egr2 transcripts were measured directly ex vivo and upon ex vivo stimulation. The YFP$^+$CD8$^+$ TILs expressed substantially less Egr2 transcripts compared to the YFP$^-$ counterparts (FIG. 2E). To determine if Egr2 is required for 4-1BB and LAG-3 expression, CD8$^+$ TILs were analyzed at day 7 and 14 after tumor inoculation and compared the YFP$^+$ and YFP$^-$ populations to mice not treated with tamoxifen. At day 7, the YFP$^+$ fraction expressed less 4-1BB and LAG-3 compared to the YFP$^-$ population and the WT CD8$^+$ TILs. However, expression of 4-1BB and LAG-3 was not significantly different at day 14 (FIG. 2F). This indicates that other transcriptional regulators compensate and contribute to the expression of LAG-3 and 4-1BB, especially at later time points.

Figure 2G:
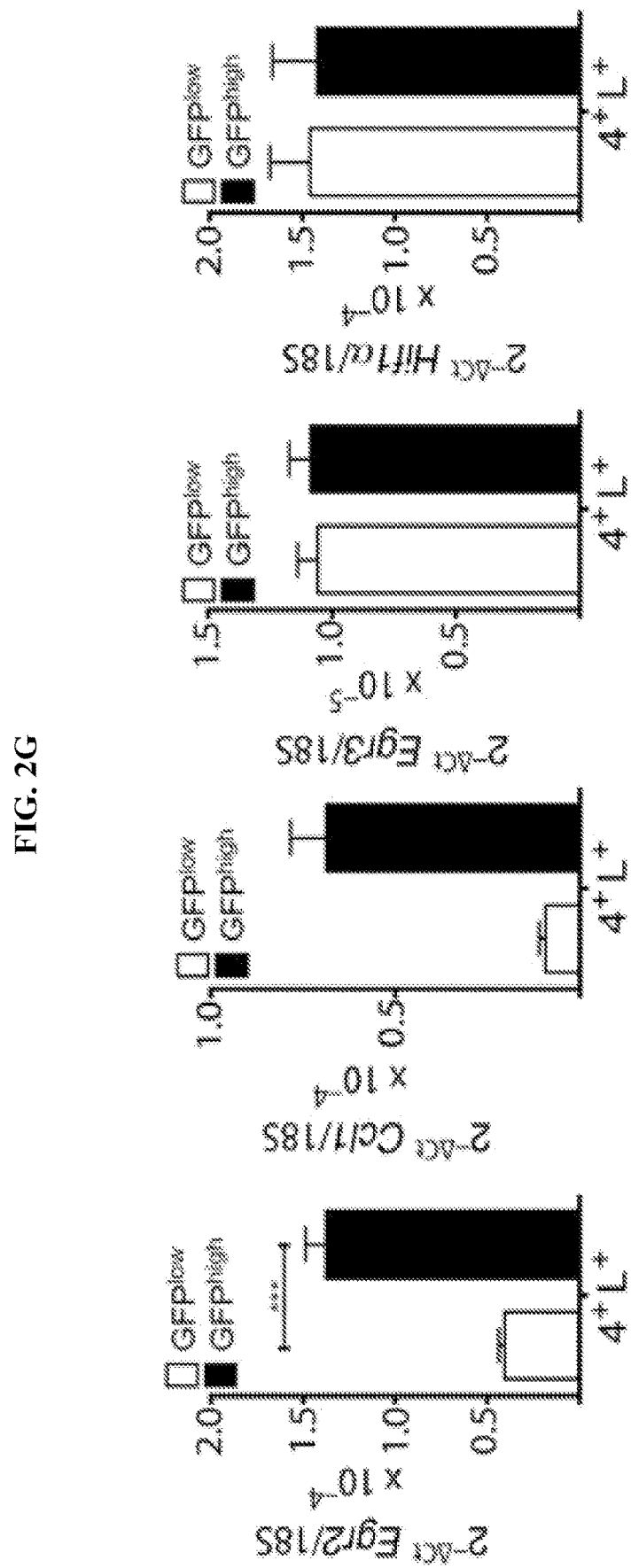

Egr3 has been shown to have overlapping function with Egr2 (Safford et al., 2005; incorporated by reference in its entirety) and HIF1α can contribute to 4-1BB expression (Palazón et al., 2012). To investigate whether these transcription factors may compensate for 4-1BB and/or LAG-3 expression we sorted Egr2GFP$^{hi}$ and Egr2GFP$^{lo}$ CD8$^+$ TILs expressing 4-1BB and LAG-3 on day 7 and analyzed expression of Egr3 and HIF1α by qRT-PCR. Egr3 and HIF1α were indeed expressed in both the Egr2GFP$^{hi}$ and Egr2GFP$^{lo}$ populations. It was confirmed differential expression of Egr2 and CCL1 to between the Egr2GFP$^{hi}$ and Egr2GFP$^{lo}$ populations to assure sort purity (FIG. 2G). Together, these data indicate that Egr2 contributes to upregulation of 4-1BB and LAG-3 expression at early time points, but that other transcriptional regulators compensate and drive expression of LAG-3 and 4-1BB as the T cell-tumor interaction progresses.

Figure 3A:
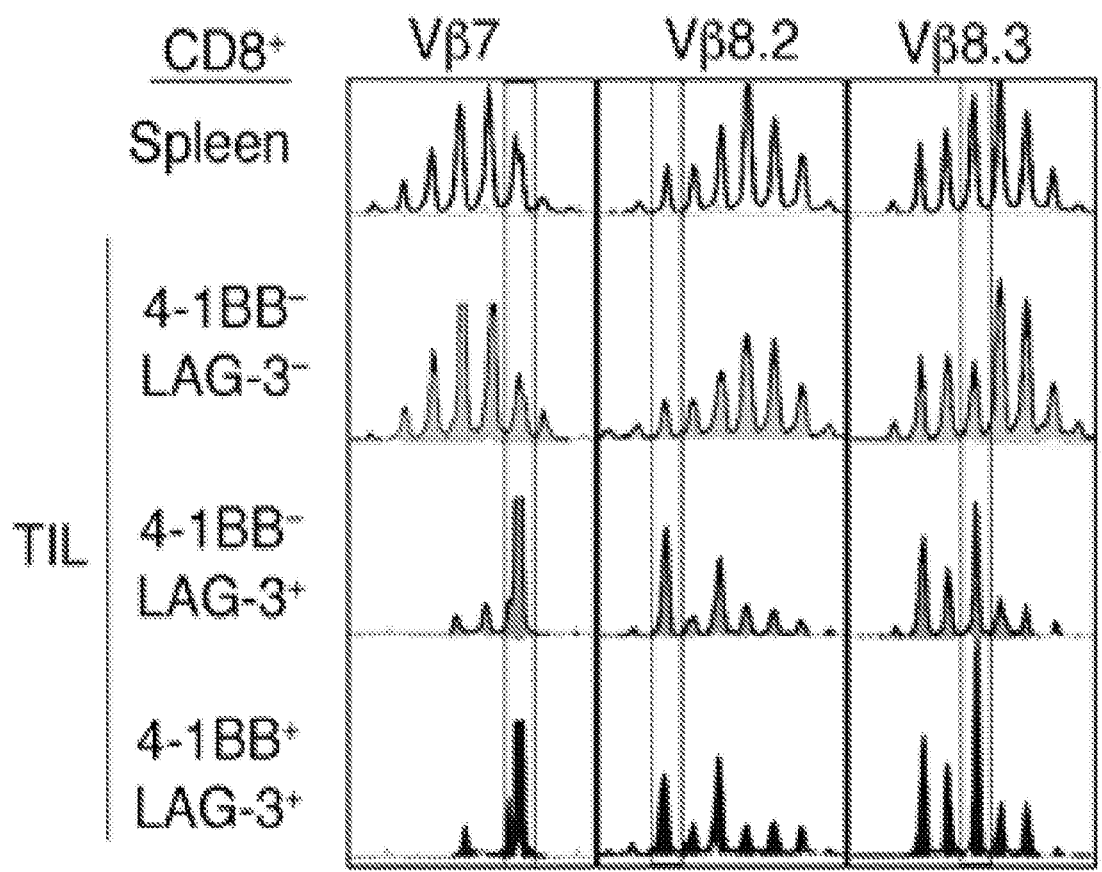
FIG. 3A-H. Co-expression of 4-1BB and LAG-3 identifies tumor antigen-specific TILs in progressing tumors. (A) Representative CDR3β distributions from the different 4-1BB/LAG-3 subpopulations and CD8$^+$ T cells isolated from the spleen. Boxed regions represent dominant peaks in the 4-1BB$^+$LAG-3$^+$CD8$^+$ TIL subpopulation. (B) As a measure of skewness, the Hamming Distance (HD) for each Vβ spectratype was calculated between each TIL subpopulation and CD8$^+$ T cell spleen population within the same mouse. As a control the HDs from CD8$^+$ splenocyte populations between mice (grey bar) were calculated. n=3; one independent experiment. (C-D) Representative flow analysis of the 4-1BB/LAG-3 subpopulation in H-2K$^b$/SIY$^+$ and H-2K$^b$/SIY$^-$ CD8$^+$ TILs on day 14 after B16.SIY and MC38.SIY or (D) MC57.SIY and 1969.SIY tumor inoculation. n=3-4; three to five independent experiments. (E) Summary of the composition of H-2K$^b$/SIY$^+$ and H-2K$^b$/SIY$^-$ CD8$^+$ TILs co-expressing 4-1BB and LAG-3 comparing B16.SIY, MC38.SIY, MC57.SIY and 1969.SIY tumors on day 14 after tumor inoculation. n=5; three to four independent experiments. (F-H) On day 7 after tumor inoculation 1×10$^6$ P14/CD45.2 and 2C/CD45.1/2 Tg T cells were adoptively transferred, via tail vein, into CD45.1 congenic tumor bearing hosts and analyzed for the (F) total number of recovered cells in the tumor, (G and H) profile of 4-1BB and LAG-3 expression in 2C, P14 and host CD8$^+$ TILs. n=5; two-independent experiments. All error bars indicate±SEM. *:P<0.05, P<0.01, *:P<0.001. A Kruskal-Wallis (non-parameteric) test was used for (B) spectratype analysis and (E and F) H-2K$^b$/SIY analysis. A two-way ANOVA with Bonferroni post-hoc test was used for (H) 2C, Host and P14 composition analysis.
Figure 3B:
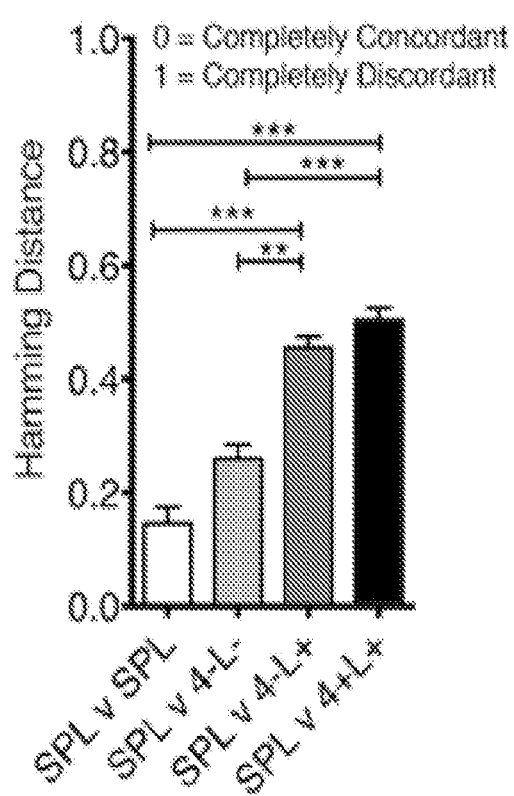
Figure 8:
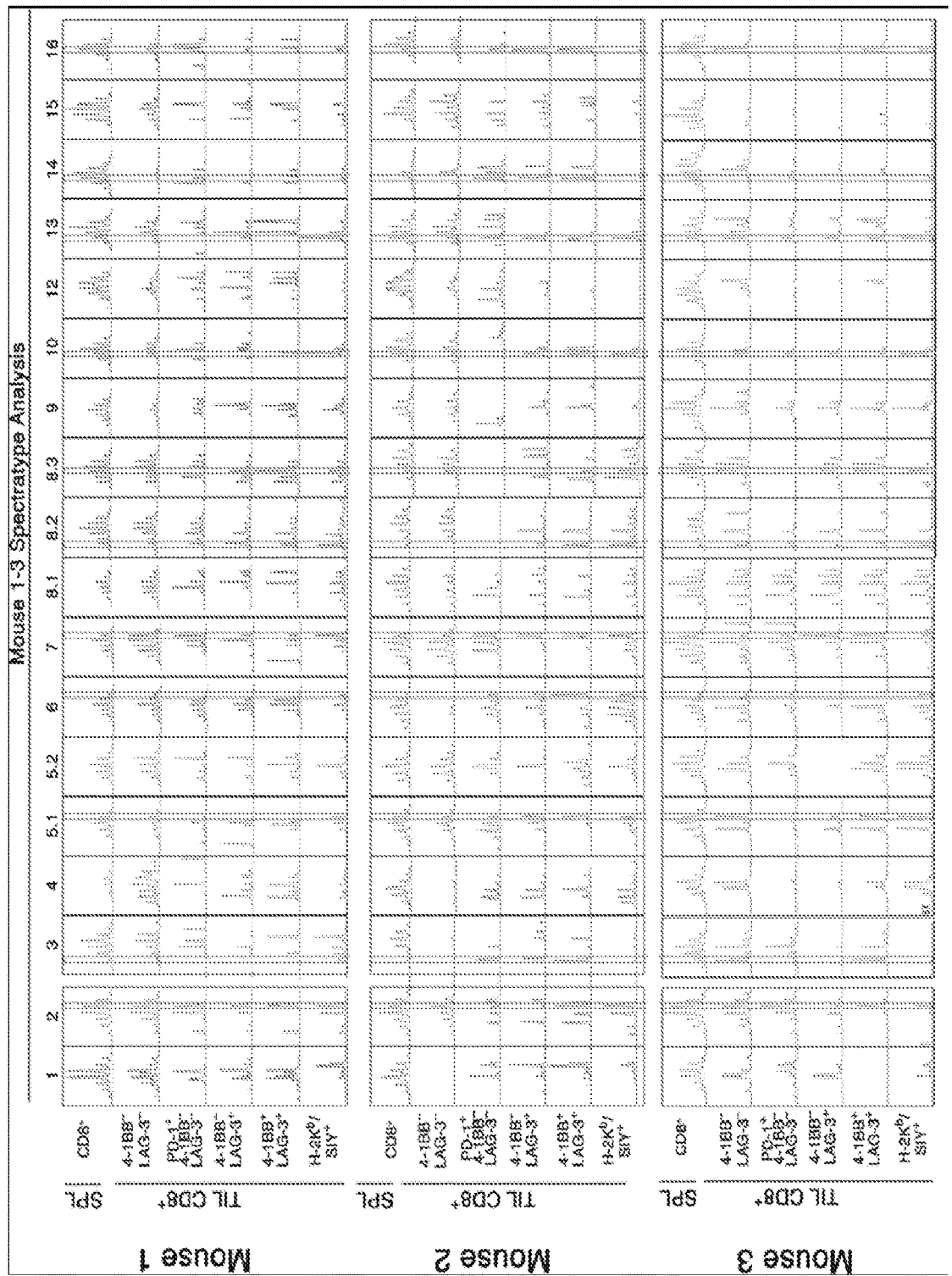
FIG. 8. Spectratype graphs used in the analysis in FIG. 3B.

CD8$^+$ 4-1BB$^+$LAG-3$^+$ TILs are Oligoclonal and Enriched for Tumor Antigen Specificity Not all T cells in the tumor microenvironment are specific for tumor-associated antigens, as memory T cells specific for irrelevant antigens are often found among TIL, and non-specific T cell trafficking has been documented in vivo (Harlin et al., 2006; incorporated by reference in its entirety). Experiments conducted during development of embodiments herein to determine whether 4-1BB$^+$LAG-3$^+$ CD8$^+$ TILs are tumor-antigen specific. LAG-3, 4-1BB and Egr2 are upregulated after TCR stimulation and experiments indicate that this population expands within the tumor microenvironment in situ. Three complementary techniques were employed. First, the CD8$^+$ TILs were isolated based on LAG-3 and 4-1BB expression by cell sorting and performed TCRβ spectratype analysis. Compared to the 4-1BB$^-$LAG-3$^-$ TILs and CD8$^+$ splenocytes, the 4-1BB$^+$LAG-3$^+$ TILs had a non-Gaussian distribution and shared one or two dominant peaks (FIG. 3A). Analysis of several Vβs displaying one dominant peak revealed that Vβ7 contained a single CDR3β sequence shared between the 4-1BB$^-$LAG-3$^+$ and 4-1BB$^+$LAG-3$^+$ populations, indicating a clonal relationship (FIG. 3A). To measure the oligoclonality of the CDR3β repertoires the Hamming Distance (HD) was calculated for each Vβ between the CD8$^+$ TIL subpopulations and the splenic CD8$^+$ population within three separate mice (FIG. 8). By transforming each spectratype into area under the curve frequency profiles the Hamming Distance computes the changes in frequency and reports a value of comparison between 0 and 1, with 0 indicating a completely identical frequency profile and 1 signifying a completely discordant profile. As a control, the HD of the splenic CD8$^+$ populations between different mice was calculated (FIG. 3B, black bar). Since the splenic CD8$^+$ spectratypes are largely Gaussian this value represents the HD between two similar distributions. Analysis of the HD between the CD8$^+$ TIL subpopulations revealed that the 4-1BB$^+$LAG-3$^+$ and 4-1BB$^-$LAG-3$^+$ but not the 4-1BB$^-$LAG-3$^-$CDR3β distributions are significantly different (less Gaussian) compared to the splenic CD8$^+$ population (FIG. 3B). These data indicate that the 4-1BB$^+$LAG-3$^+$ and 4-1BB$^-$LAG-3$^+$ populations are oligoclonal expanded subsets of TILs, indicating antigen specificity in these subpopulations.

Figure 3C:
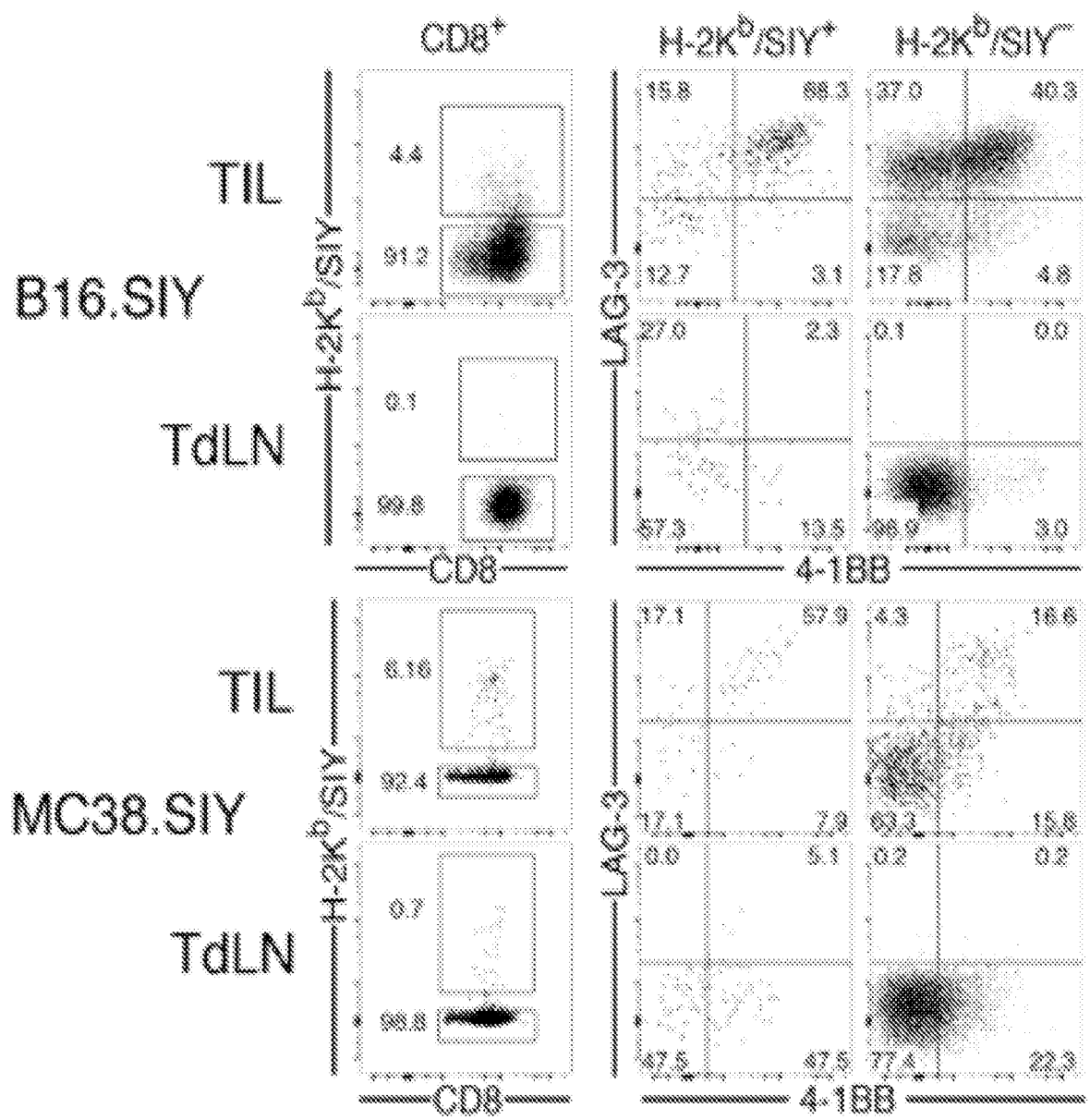

As a second approach, the B16.SIY melanoma and MC38.SIY adenocarcinoma models were utilized. CD8$^+$ T cells specific for the H-2K$^b$-restricted SIY epitope (SIYRYYGL) were monitored. SIYRYYGL/K$^b$ pentamer$^+$ (H-2K$^b$/SIY) cells were found in expanded numbers within B16.SIY and MC38.SIY tumors at day 14 after tumor inoculation (FIG. 3C). Nearly 47% of the H-2K$^b$/SIY$^+$ cells expressed both 4-1BB and LAG-3, in contrast to 32% of the H-2K$^b$/SIY$^-$ population (FIGS. 3C and E). This enrichment of antigen-specific CD8$^+$ TILs in the 4-1BB$^+$LAG-3$^+$ populations indicates that these markers identify tumor antigen-specific TILs. The H-2K$^b$/SIY$^-$ cells also contained significant numbers of 4-1BB$^+$LAG-3$^+$ cells, which is consistent with the notion that tumor antigens other than SIY are also recognized by subsets of CD8$^+$ TILs in vivo (FIG. 3C). H-2K$^b$/SIY$^+$ cells in the spleen or TdLN did not co-express 4-1BB and LAG-3, indicating that this phenotype is acquired within the tumor microenvironment.

Figure 3D:
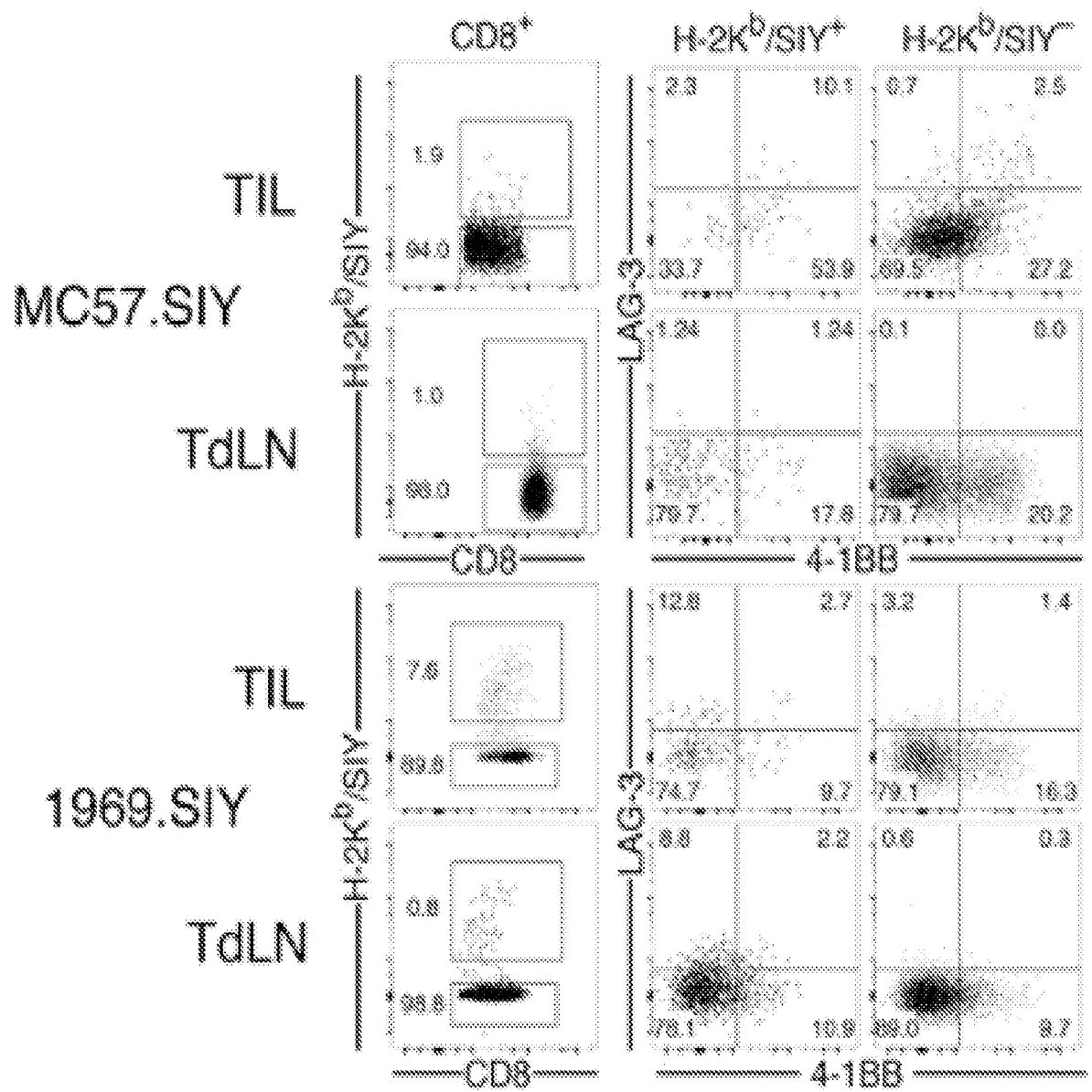
Figure 3E:
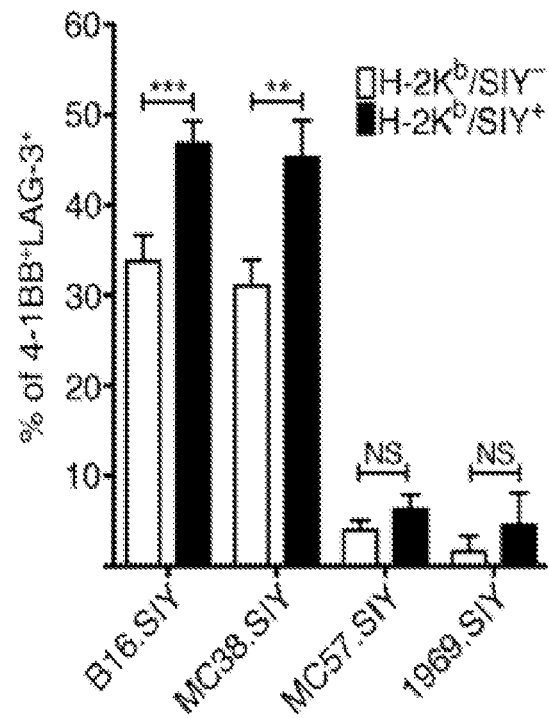

These features were also analyzed in the context of tumor-antigen specific CD8$^+$ TILs in two spontaneously rejected tumor models. To this end, H-2K$^b$/SIY-specific CD8$^+$ TILs cells were evaluated from MC57.SIY and 1969.SIY tumors. At day 14 after tumor inoculation, approximately 5% of the H-2K$^b$/SIY-specific CD8$^+$ TILs were found in the 4-1BB$^+$LAG-3$^+$ fraction. As with the B16.SIY tumors, no H-2K$^b$/SIY-specific CD8 T cells co-expressed 4-1BB and LAG-3 in the TdLN or spleen (not shown) (FIG. 3D). Unlike the B16.SIY and MC38.SIY tumors, no significant enrichment of 4-1BB$^+$LAG-3$^+$ H-2K$^b$/SIY-specific CD8$^+$ TILs was observed (FIGS. 3D and E). These data indicate that tumor antigen specificity per se does not determine dysfunctionality, and that this is a feature unique to the microenvironment of progressing tumors.

Figure 3F:
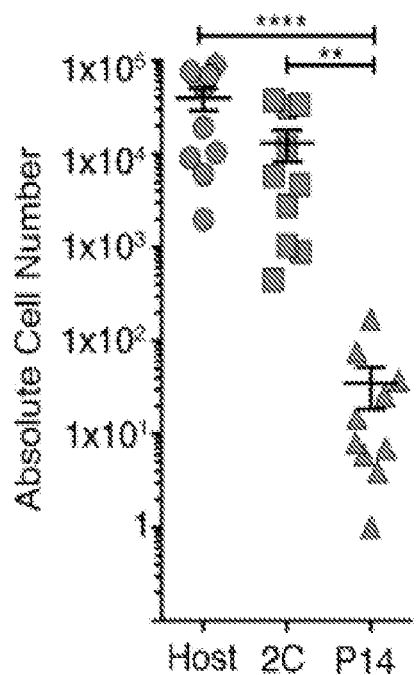
Figure 3G:
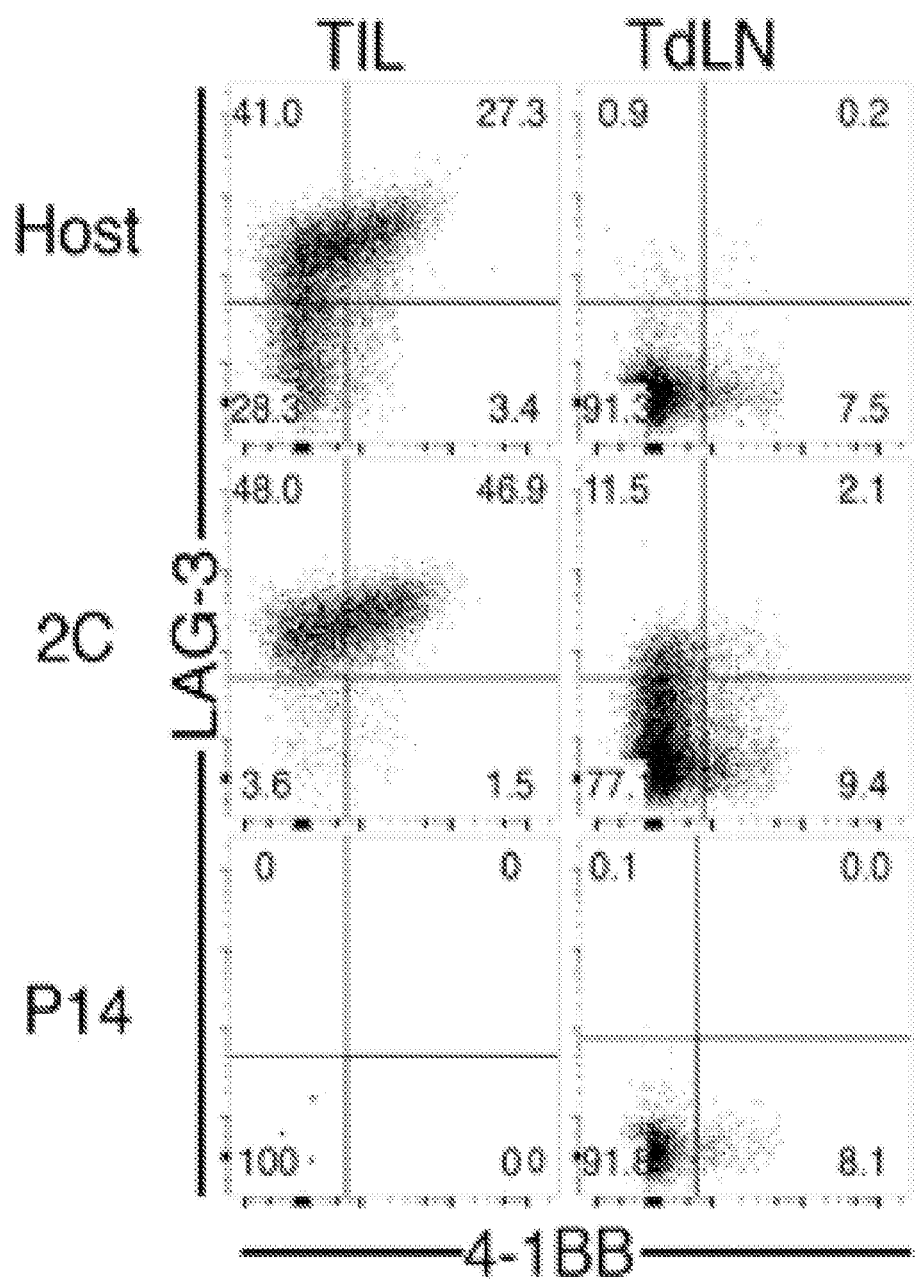
Figure 3H:
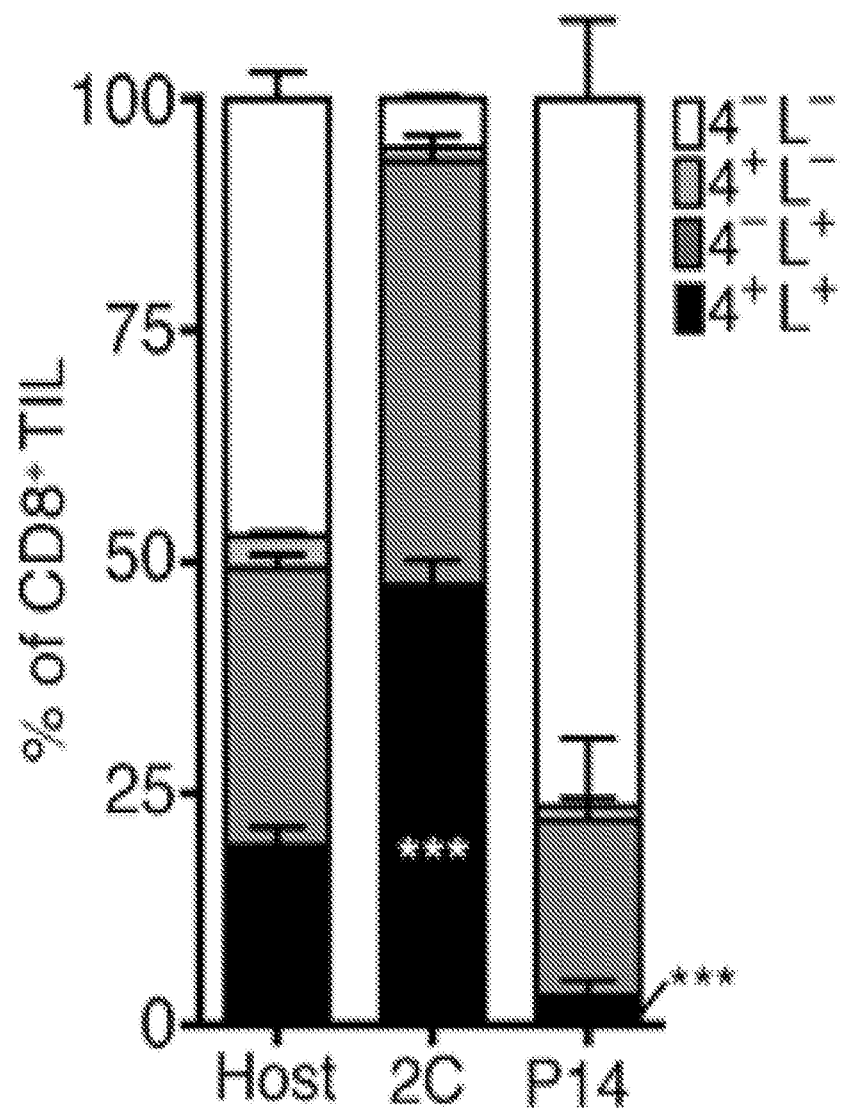

As a third measure to determine if tumor-antigen specific CD8$^+$ T cells acquire the 4-1BB$^+$LAG-3$^+$ phenotype, congenically marked 2C and P14 transgenic (Tg) T cells, isolated from 2C/Rag2$^{-/-}$ and P14/Rag2$^{-/-}$ mice, were transferred into tumor-bearing hosts. The 2C TCR is specific for the SIY model antigen expressed by B16.SIY tumor cells, while P14 is an irrelevant TCR specific for the LCMV-derived gp$_{33-41}$ epitope; both TCRs are H-2K$^b$-restricted. 2C and P14 Tg CD8$^+$ T cells were transferred via tail vein 7 days after tumor inoculation. Seven days after transfer, tumors and TdLNs were extracted and the phenotypic profile of the transferred populations was analyzed. This system allowed for the analysis of two T cell populations with defined antigen specificities within the same tumor microenvironment, as well as the polyclonal host CD8$^+$ T cells. The 2C T cells were more efficiently recruited and expanded within the tumor microenvironment compared to the P14 T cells and encompassed a large fraction of the total CD8$^+$ TIL population (FIG. 3F). Of the 2C T cells, nearly all expressed LAG-3 and or 4-1BB while this was true for only a small percentage of the P14 cells (FIGS. 3G and H). Consistent with the SIY-K$^b$ pentamer analysis, the co-expression of LAG-3 and 4-1BB on 2C T cells was not observed in the TdLN. Together, these results demonstrate that the 4-1BB$^+$LAG-3$^+$ phenotype is a property of tumor antigen-specific TIL under conditions of tumor progression.

Figure 4A:
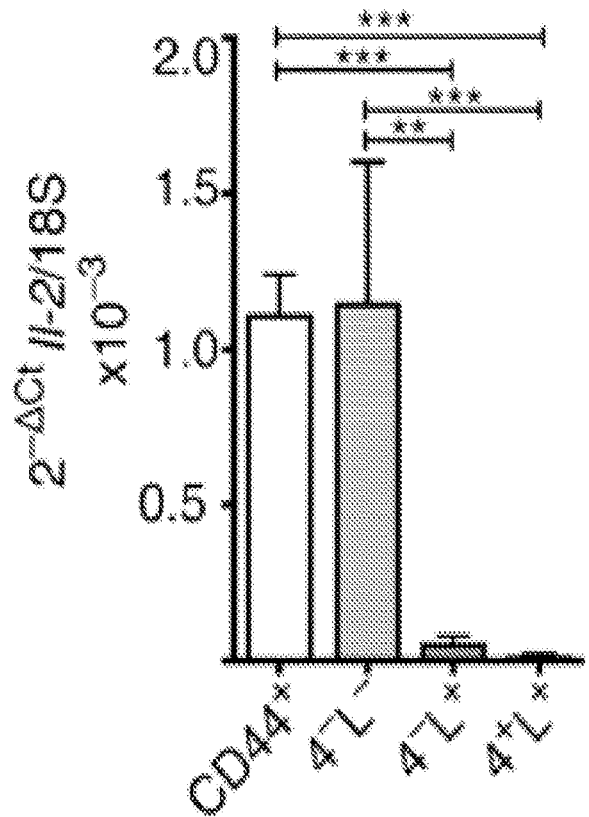
FIG. 4A-G. Co-expression of 4-1BB and LAG-3 but not PD-1 define dysfunctional CD8$^+$ TILs with diminished IL-2. (A and B) Sorted cells from day 14 B16.SIY tumor bearing mice were stimulated in vitro with anti-CD3ε and anti-CD28 for 12 hours and analyzed for (A) Il-2 transcript by qRT-PCR and (B) IL-2 protein by ELISA. Two tumors on opposite flanks pooled per mouse. n=4-5; three independent experiments. (C) Egr2GFP$^{hi}$ and Egr2GFP$^{lo}$ TILs were sorted from day 14 B16.SIY tumor bearing Egr2$^{GFP}$ mice and stimulated in vitro for 12 hours and analyzed for Il-2 transcript by qRT-PCR. Two tumors on opposite flanks pooled per mouse. n=5; two independent experiments. (D) On day 7 after tumor inoculation 1×10$^6$ 2 C/CD45.1/2 Tg T cells were transferred into mice, 7 days later host 4-1BB$^+$LAG-3$^+$ T cells sorted from the tumor and 2C T cells sorted from the tumor or TdLN were stimulated in vitro and analyzed for expression of Il-2 transcript by qRT-PCR. Two tumors on opposite flanks pooled per mouse. n=3; two independent experiments. (E and F) Representative flow analysis of PD-1 expression on 4-1BB/LAG-3 CD8$^+$ TIL subpopulations and (F) summary of the composition of the 4-1BB$^-$LAG-3$^-$PD-1$^+$ subpopulation in the CD8$^+$ TIL compartment on day 14 and 21. n=5; three independent experiments. (G) 4-1BB$^-$LAG-3$^-$PD-1$^+$ and LAG-3$^+$4-1BB$^+$CD8$^+$ TILs were sorted from day 14 tumor bearing mice, stimulated in vitro and analyzed for Il-2 transcript by qRT-PCR. Two tumors on opposite flanks pooled per mouse. n=3; two independent experiments. All error bars indicate±SEM. *:P<0.05, :P<0.01, *:P<0.001 ****:P<0.0001. A Kruskal-Wallis (non-parametric) test was used for analysis of multiple comparisons (A, B, and D) and a Mann-Whitney test was used for pair-wise comparisons (C and G).
Figure 4B:
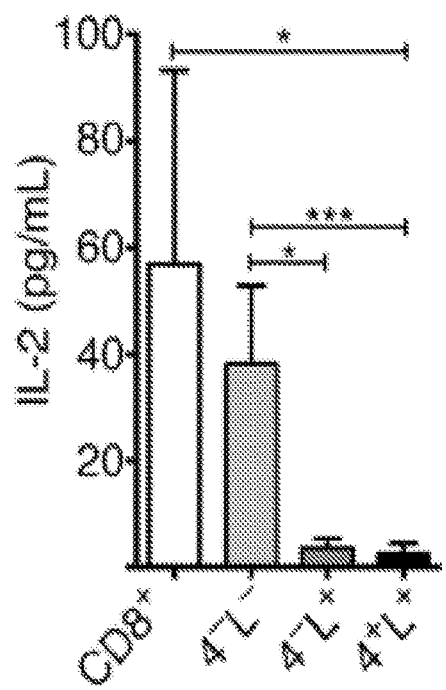
Figure 4C:
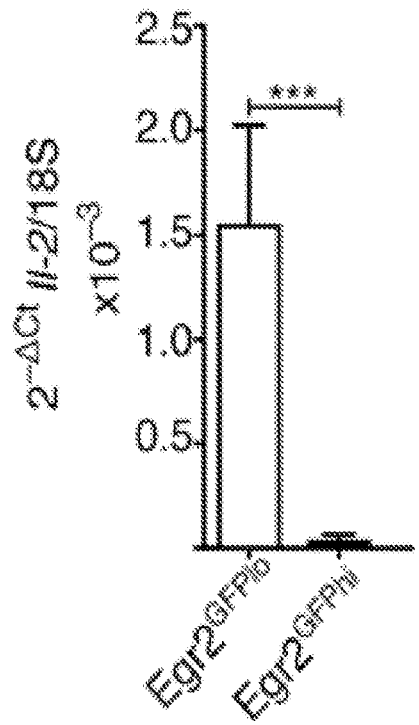
Figure 4D:
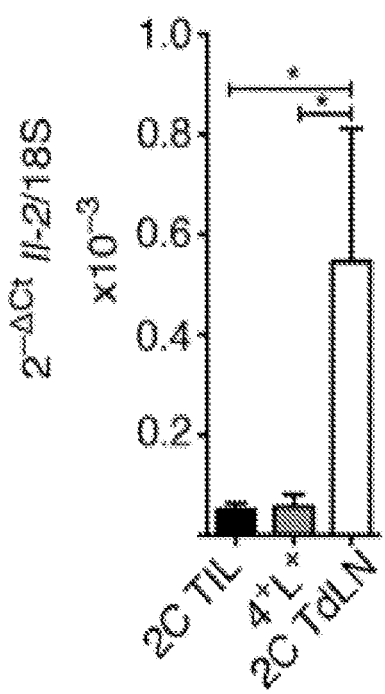
Figure 4E:
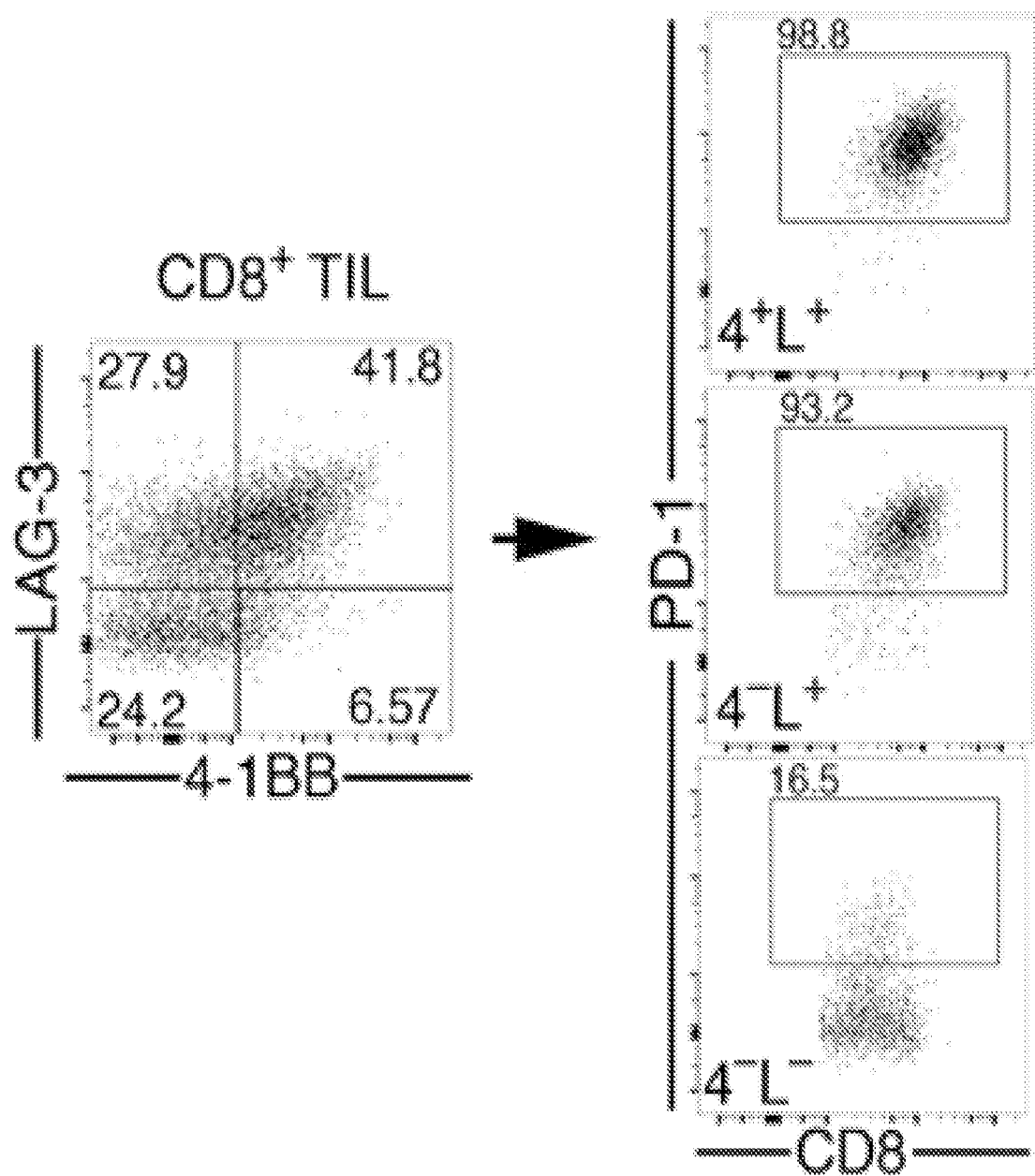
Figure 4F:
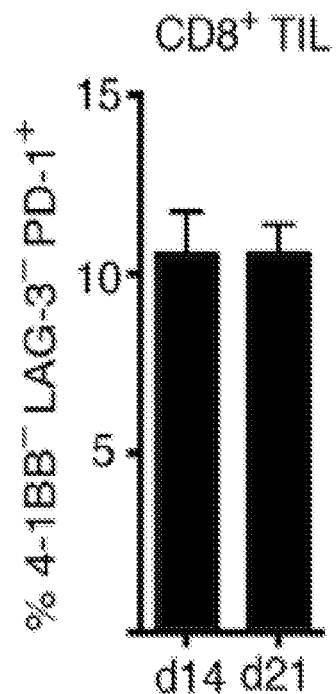
Figure 4G:
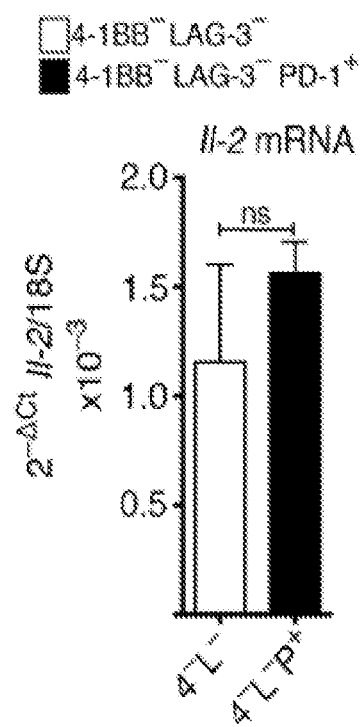

CD8$^+$ TILs Expressing LAG-3 and 4-1BB Exhibit Defective IL-2 Production Yet Produce IFN-γ and Treg-Recruiting Chemokines Based on the characteristics of the in vitro T cell anergy model that led to the identification of Egr2 as an important regulator, experiments conducted during development of embodiments herein to determine whether the tumor-antigen specific 4-1BB$^+$LAG-3$^+$CD8$^+$ TIL population is dysfunctional in their capacity to produce IL-2. To this end each subpopulation was sorted and stimulated with anti-CD3 and anti-CD28 mAb and analyzed IL-2 production by qRT-PCR and ELISA. Since nearly all CD8$^+$ TILs displayed an activated phenotype, CD8$^+$CD44$^+$ splenocytes were used as a positive control. Indeed, the 4-1BB$^+$LAG-3$^+$ cells showed a 100-fold reduction in Il-2 mRNA and as much as a 40-fold reduction in IL-2 protein levels compared to the 4-1BB$^-$LAG-3$^-$ population (FIGS. 4A and 4B). As a second approach, Egr2$^{hi}$ TIL (which are also largely 4-1BB$^+$LAG-3$^+$) was examined by utilizing the Egr2-GFP reporter mice. Indeed, ex vivo stimulated Egr2-GFP$^{hi}$ CD8$^+$ TILs also exhibited reduced Il-2 transcript compared to Egr2-GFP$^{lo}$ cells (FIG. 4C). As a final approach, congenically marked 2C T cells were adoptively transferred intravenously into tumor-bearing hosts and recovered the 2C T cells 7 days later from the tumor and TdLN. 2C T cells isolated from tumors exhibited a reduced capacity to produce Il-2 transcripts, at a level equivalent to 4-1BB$^+$LAG-3$^+$ TILs, compared to 2C CD44$^+$ T cells isolated from the TdLN (FIG. 4D). In chronic infection models, expression of PD-1 has been suggested to identify intrinsically dysfunctional or "exhausted" CD8$^+$ T cells. To determine if PD-1 alone might be sufficient to identify cells that lack the capacity to produce IL-2, CD8$^+$ TILs that lacked expression of LAG-3 and 4-1BB were isolated and tested for the ability of the PD-1$^+$ fraction to produce IL-2. Approximately ~10% of CD8$^+$ TILs were 4-1BB$^-$LAG-3$^-$PD-1$^+$ on day 14 and 21 (FIGS. 4E and F). Upon ex vivo stimulation, this population retained the capacity to produce ll-2 mRNA at a level comparable to the 4-1BB$^-$LAG-3$^-$ cells (FIG. 4G). These results indicate that PD-1 expression alone is not sufficient to identify dysfunctional TIL in the tumor microenvironment.

Figure 5A:
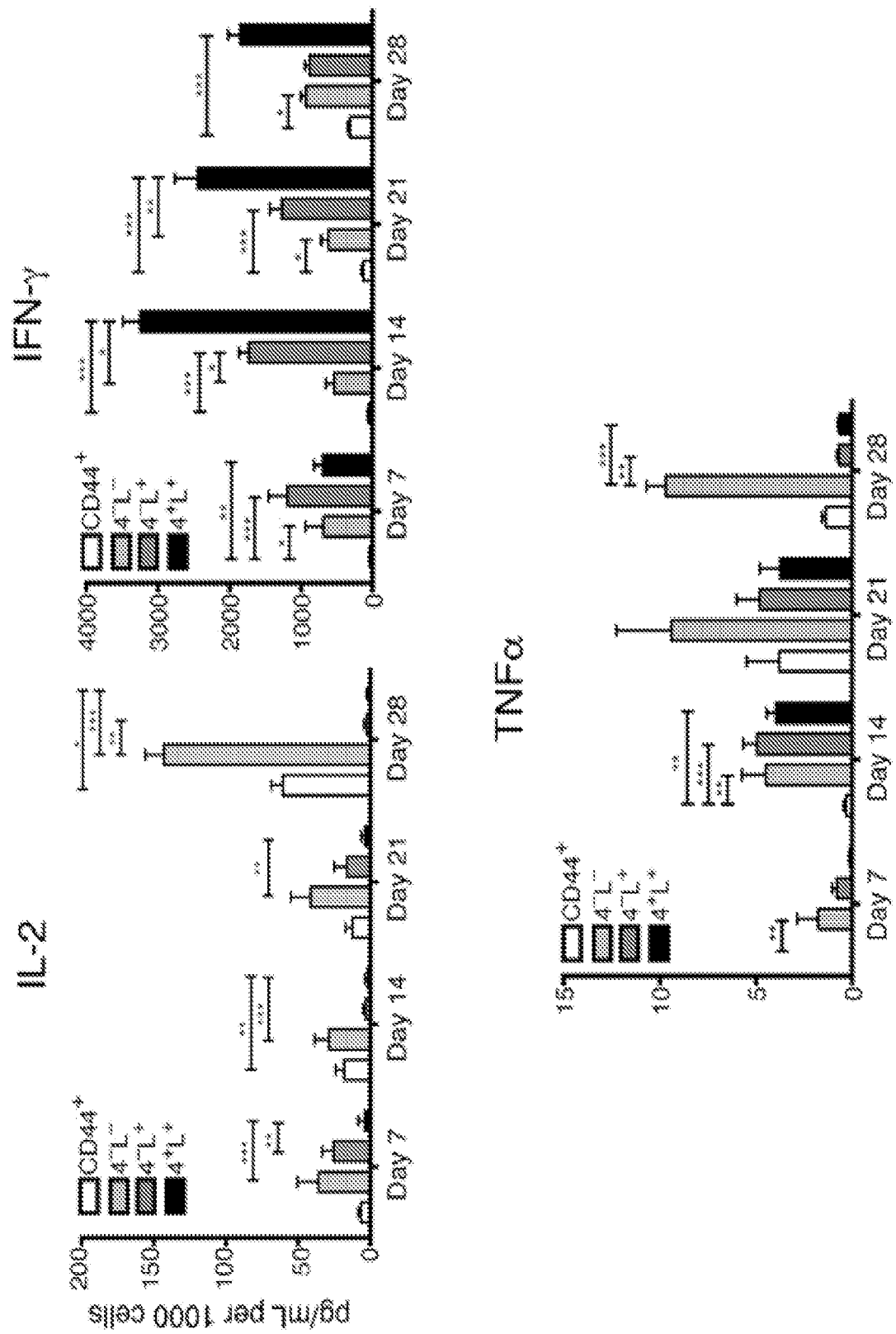
FIG. 5A-E. Dysfunctional CD8$^+$ TILs retain IFN-γ production, cytolytic capacity and produce Treg-recruiting chemokines. (A) Longitudinal analysis CD8$^+$ TIL subpopulation cytokine production capacity. CD8$^+$ TIL subpopulations were sorted and stimulated with anti-CD3ε and anti-CD28 for 10-12 hours and the concentration of IL-2, IFN-γ and TNF-α was measured. Concentration was normalized to cell number. Two tumors on opposite flanks pooled for day 7 and 14. n=4-5; two-independent experiments. (B) Ifn-γ Tnf-α and Gzmb transcript levels in the 4-1BB/LAG-3 subpopulations analyzed directly ex vivo. Two tumors on opposite flanks pooled per mouse. n=3-5; three-independent experiments. (C) Representative flow plot and summary of IFN-γ production analyzed directly ex vivo. Briefly, 100 μl of PBS containing 2 mg/mL GolgiPlug was injected intratumorally on day 14 after tumor inoculation. 8 hours later TILs were isolated. All steps were performed on ice with media containing 1 mg/mL GolgiStop until fixation. n=5; two independent experiments. (D) CD8$^+$ TIL subpopulations at indicated time points were sorted and plated with 50,000 P815 target cells and 1 μg/mL anti-CD3ε. Lysed target cells were measured by positive staining for propidium iodide and/or live/dead fixable viability dye. P815 target cells plated without CTLs were used as a negative control (black bar). Primed OTI cells were used as a positive control. Tumors from 10 mice with 2 tumors on opposite flank were pooled to obtain sufficient quantities of CD8$^+$ TILS. Data are representative of three independent experiments. (E) Ccl1 and Ccl22 transcript levels in the 4-1BB/LAG-3 subpopulations analyzed directly ex vivo by qRT-PCR. n=4; two independent experiments. *:P<0.05, :P<0.01, *: P<0.001, ****:P<0.0001. A Kruskal-Wallis (non-parametric) test was used for (A-C, E) cytokine/chemokine analysis and a two-way ANOVA with Bonferroni post-hoc test was used for (D) cytolytic assay.

To further examine functional alterations during tumor progression protein levels of IL-2, IFN-γ and TNF-α were tested after TCR stimulation. As the loss of the ability of CD8$^+$ TILs to produce cytokines is suggested to be a temporal process reported initiated following entry into the tumor microenvironment (Waugh et al., 2016; Schietinger et al., 2016; incorporated by reference in their entireties) or progressively after 30 days in the chronic LCMV model (Wherry et al., 2007; incorporated by reference in its entirety), cytokine production was tested on day 7, 14, 21 and 28. The 4-1BB$^+$LAG-3$^+$ population lost the capacity to produce IL-2 as early as day 7 while the 4-1BB$^-$LAG-3$^+$ population lost IL-2 production between day 7 and day 14 (FIG. 5A). The 4-1BB$^-$LAG-3$^-$ population did not lose the ability to produce IL-2 at any time point tested (FIG. 5A), supporting the notion that this population is not tumor antigen specific and that differentiation into the dysfunctional state is an antigen-dependent process (Schietinger et al., 2016; incorporated by reference in its entirety). The 4-1BB$^+$LAG-3$^+$ population produced more IFN-γ at all time points after day 7 compared to their negative counterparts, albeit with a slight decrease in IFN-γ production over time. While the increase in IFN-γ was maintained until later time points, TNF-α production was lost by day 28 (FIG. 5A).

Figure 5B:
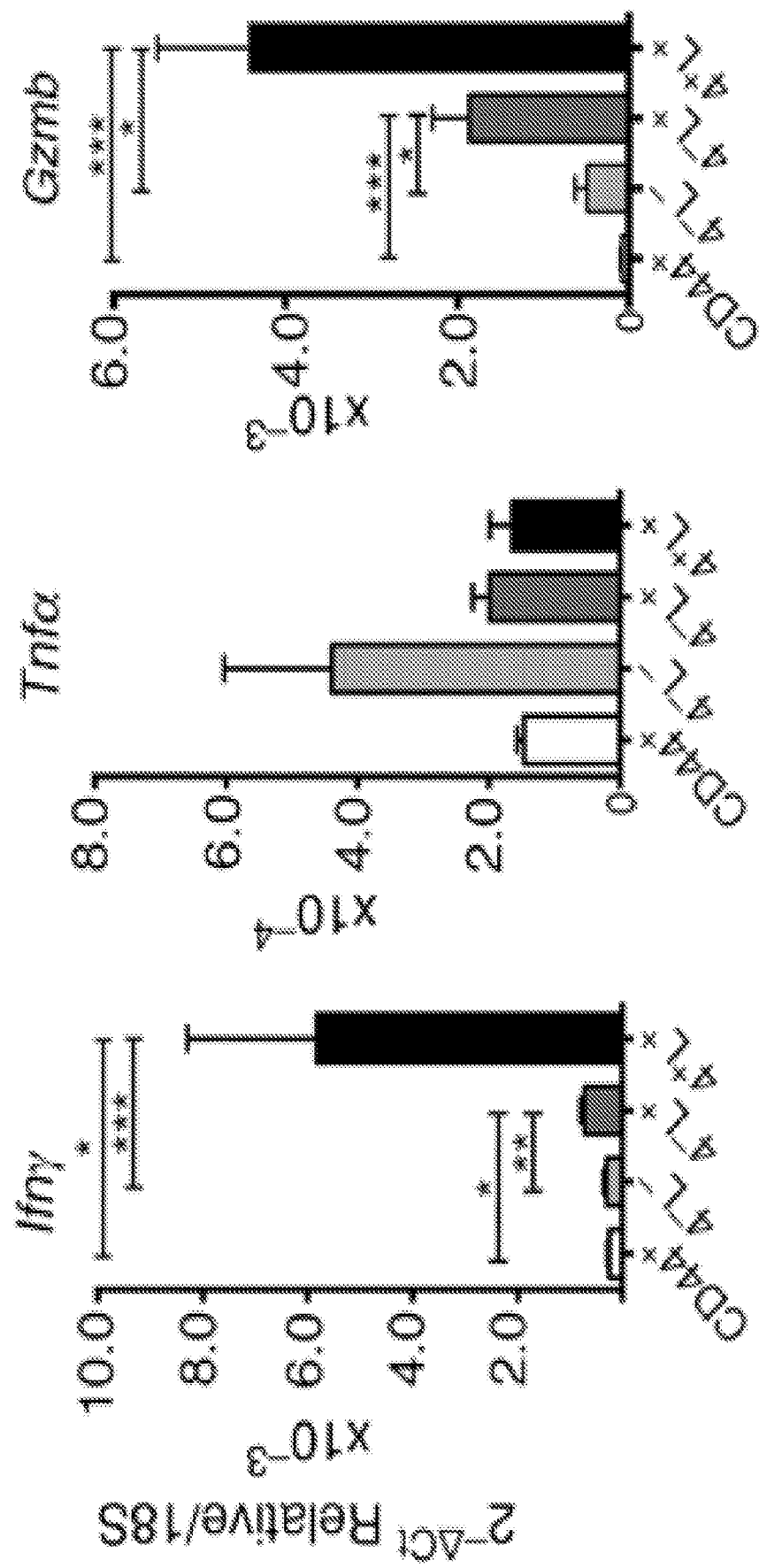
Figure 5C:
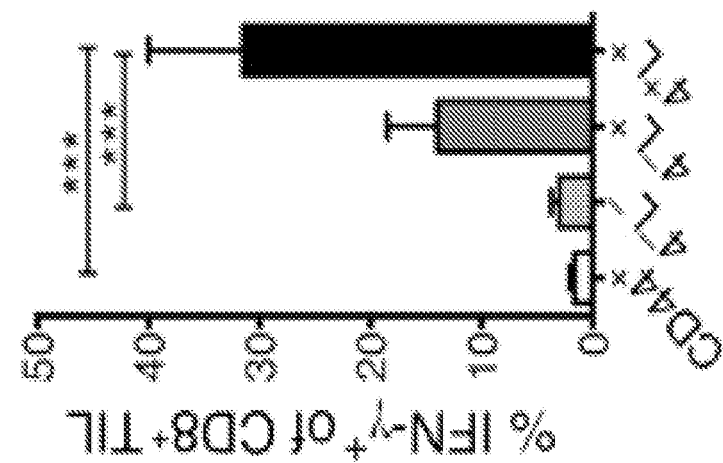
Figure 5C:
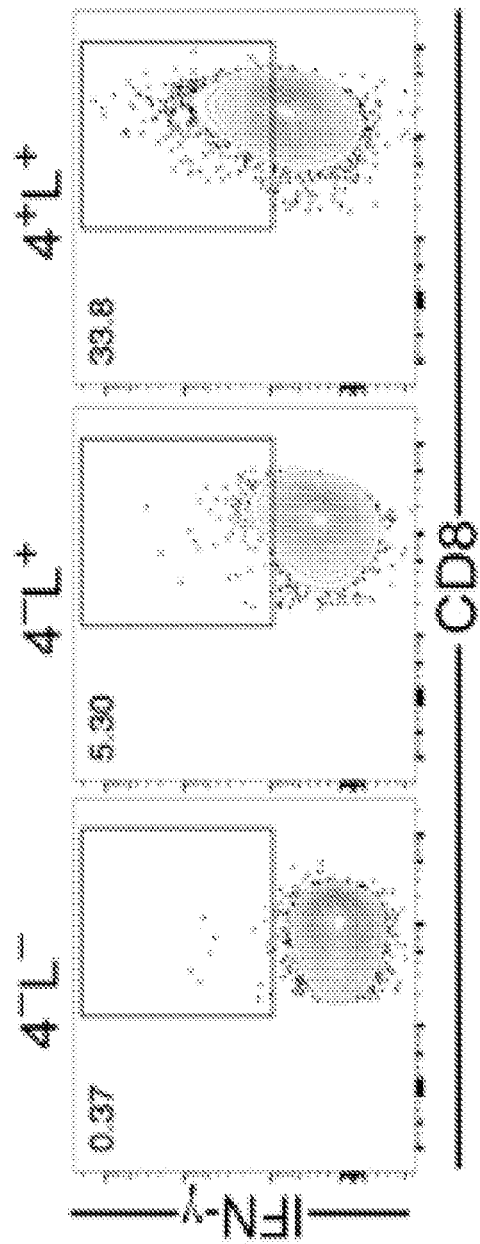

Experiments were conducted during development of embodiments herein to evaluate production of cytokines directly in the tumor without in vitro restimulation, which may more closely reflect which T cells were receiving TCR stimulation in situ. Each T cell population was sorted directly ex vivo without any culturing and mRNA levels were measured by qRT-PCR. Elevated Ifn-γ and Gzmb transcripts were observed from the 4-1BB$^+$LAG-3$^+$ subpopulation, along with a slight decrease in Tnf-α levels, compared to the 4-1BB$^-$LAG-3$^-$ cells (FIG. 5B). Production of IFN-γ in primary TILs was confirmed by injecting tumors with Brefeldin A prior to analysis by intracellular cytokine staining. Consistent with the mRNA expression, the 4-1BB$^+$LAG-3$^+$ population produced significantly greater amounts of IFN-γ protein (FIG. 5C). Thus, the 4-1BB$^+$LAG-3$^+$ TIL are not completely devoid of functionality, as they continue to produce IFN-γ despite defective production of IL-2. This phenotype is consistent with in vitro T cell anergy models (Jenkins et al., 1987; incorporated by reference in its entirety).

Figure 5D:
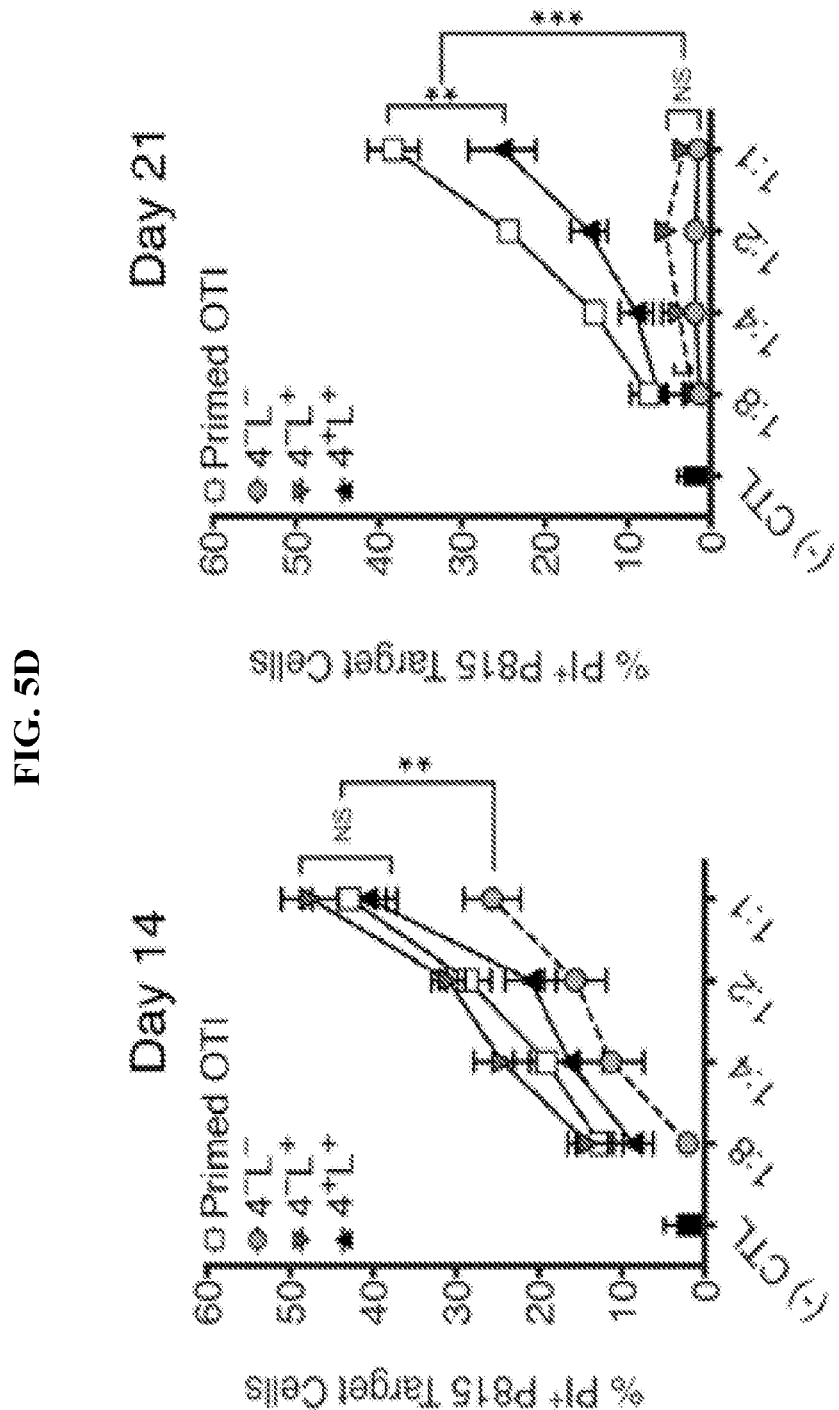
Figure 5E:
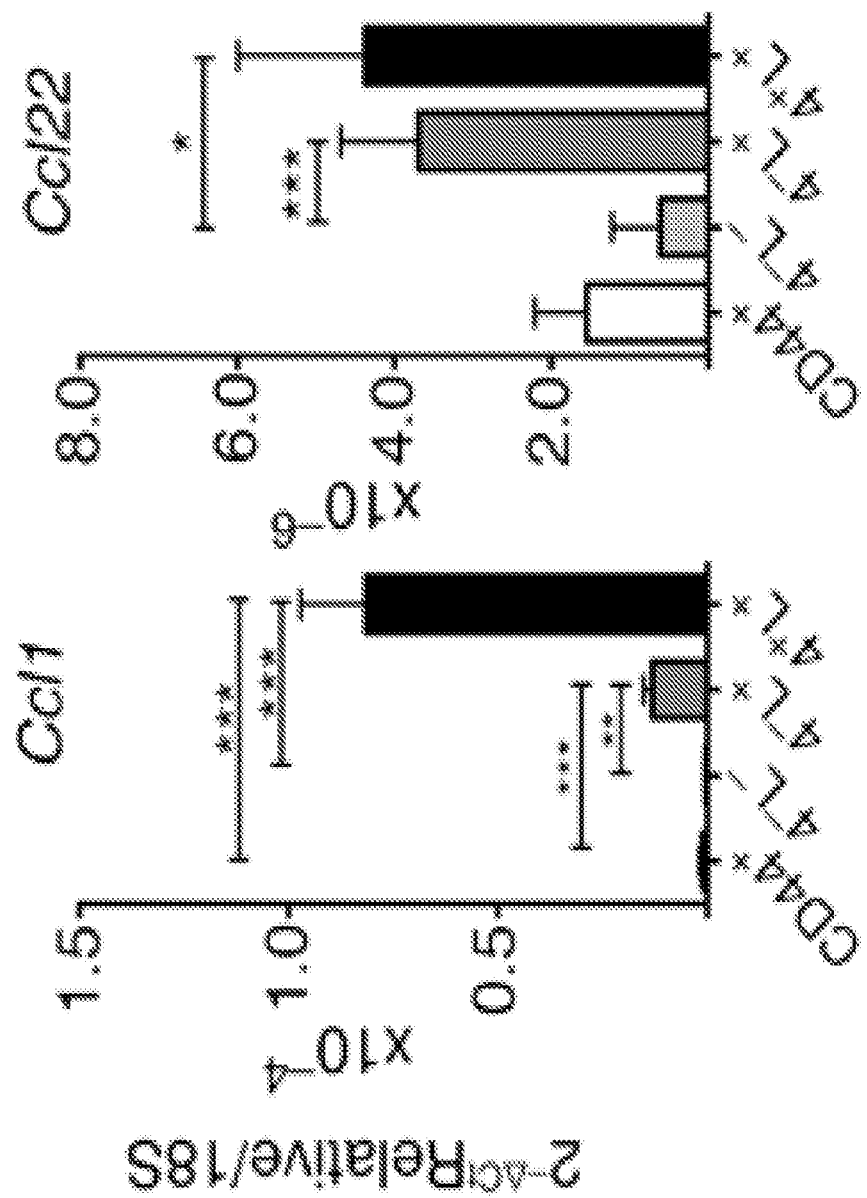

To test whether the 4-1BB⁺LAG-3⁺ population still retains cytotoxic capacity, re-directed lysis was performed by co-culturing anti-CD3 bound P815 mastocytoma target cells with the different CD8⁺ TIL subpopulations directly after sorting. 4-1BB⁺LAG-3⁺CD8⁺ TILs isolated from day 14 tumors were able to lyse target cells at a comparable efficacy to in vitro primed OT-I cells. 4-1BB⁺LAG-3⁺ TILs isolated from day 21 tumors were still able to lyse target cells, albeit to a lesser extent compared to primed OT-I cells (FIG. 5D).

CD8⁺ T cells in the tumor can be the source of the chemokine CCL22 that recruits FoxP3⁺ regulatory T cells (Tregs) to the tumor microenvironment (Spranger et al., 2013; incorporated by reference in its entirety). In addition, the chemokine Ccl1 was an Egr2 target in anergic T cells (Zheng et al., 2013; incorporated by reference in its entirety), and it has been suggested that CCL1 also contribute to Treg recruitment in the tumor context in vivo (Hoelzinger et al., 2010; incorporated by reference in its entirety). However, whether all CD8⁺ T cells in the tumor produce these chemokines or if they are only produced by subpopulations of T cells had not been determined. To address this the CD8⁺ TIL phenotypic subpopulations were analyzed for Ccl1 and Ccl22 mRNA expression directly ex vivo by qRT-PCR. Indeed, the 4-1BB⁺LAG-3⁺ TIL population produced substantially greater Ccl1 and Ccl22 compared to their negative counterparts or to splenic CD8⁺CD44⁺ T cells (FIG. 4K). As a control, expression of a distinct chemokine Ccl5 was found not to be differentially expressed.

Together, these data show that co-expression of 4-1BB and LAG-3 delineates tumor antigen-specific CD8⁺ TIL that lack the ability to produce IL-2 yet retain the ability to produce IFN-γ, kill target cells in vitro, and secrete chemokines capable of Treg recruitment. Given the fact that IFN-γ is responsible for the upregulation of PD-L1 and IDO in the tumor microenvironment, and that chemokines produced by CD8⁺ TIL contribute to Treg recruitment (Spranger et al., 2013; incorporated by reference in its entirety), these data indicate that the 4-1BB⁺LAG-3⁺ population contributes to the network of immune suppressive mechanisms within the tumor microenvironment that limit the efficacy of anti-tumor immunity.

Figure 6A:
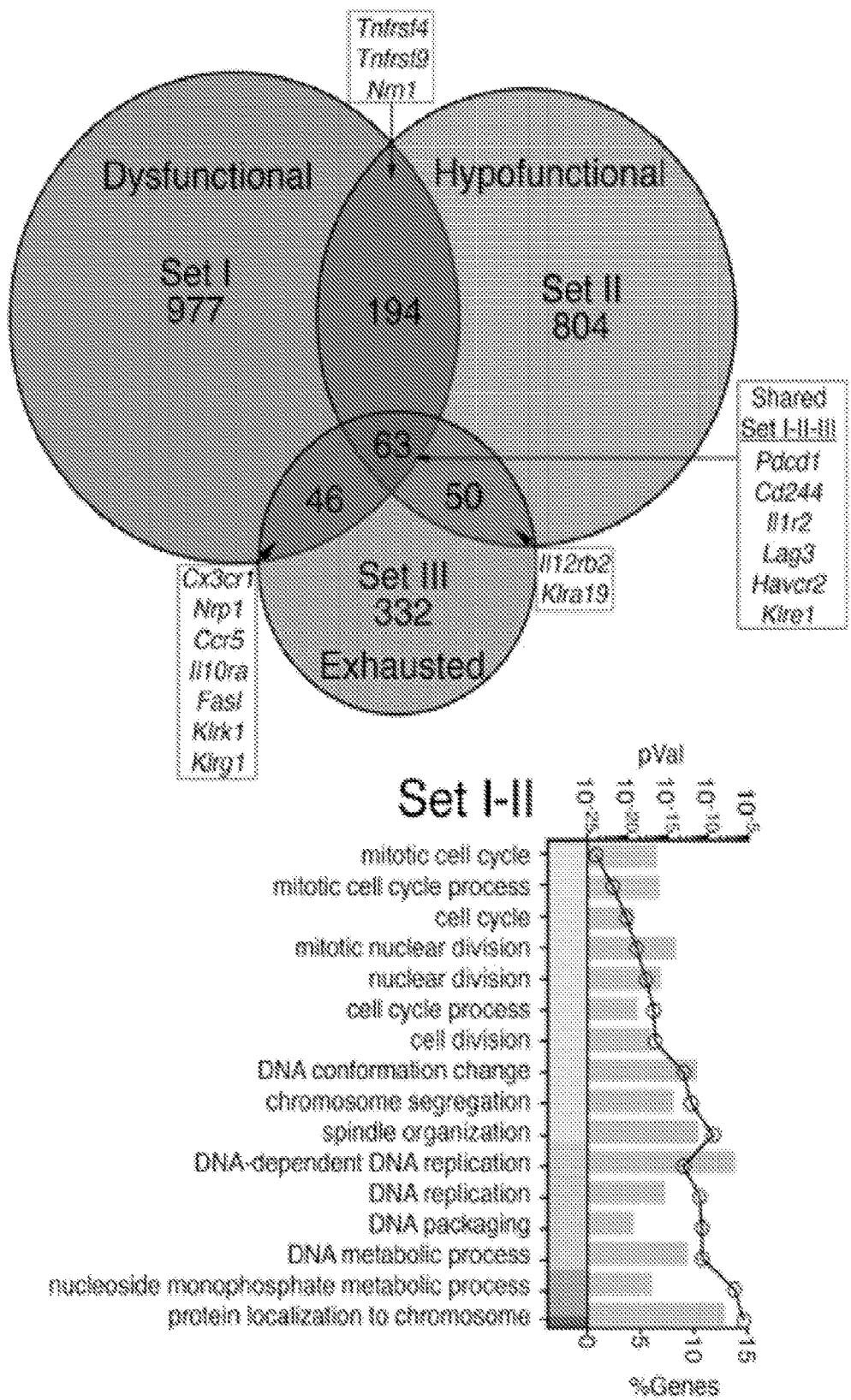
FIG. 6A-D. Dysfunctional CD8$^+$ TILS express a wide range of co-inhibitory and co-stimulatory receptors. (B) Gene expression profile of cell surface receptors in the 4-1BB/LAG-3 CD8$^+$ TIL subsets. Probe sets that revealed a 1.5-fold increase in the 4-1BB$^+$LAG-3$^+$ population relative to the 4-1BB$^-$LAG-3$^-$PD-1$^-$ population are displayed. Columns show the log$_2$-transformed signal intensity. (C) Longitudinal study of selected un-regulated cell surface receptors. Flow plots are representative of the CD8$^+$ TIL subsets on day 14. n=5; two to five independent experiments for each time point. (D) Representative flow plot and summary of KLRG-1 and IL-7Rα expression among the 4-1BB/LAG-3 subpopulations on day 14 after tumor inoculation. n=5; two independent experiments. *:P<0.05, :P<0.01, *:P<0.001, ****:P<0.0001. A two-way ANOVA with Bonferroni post-hoc test was used for all analyses.
Figure 6A:
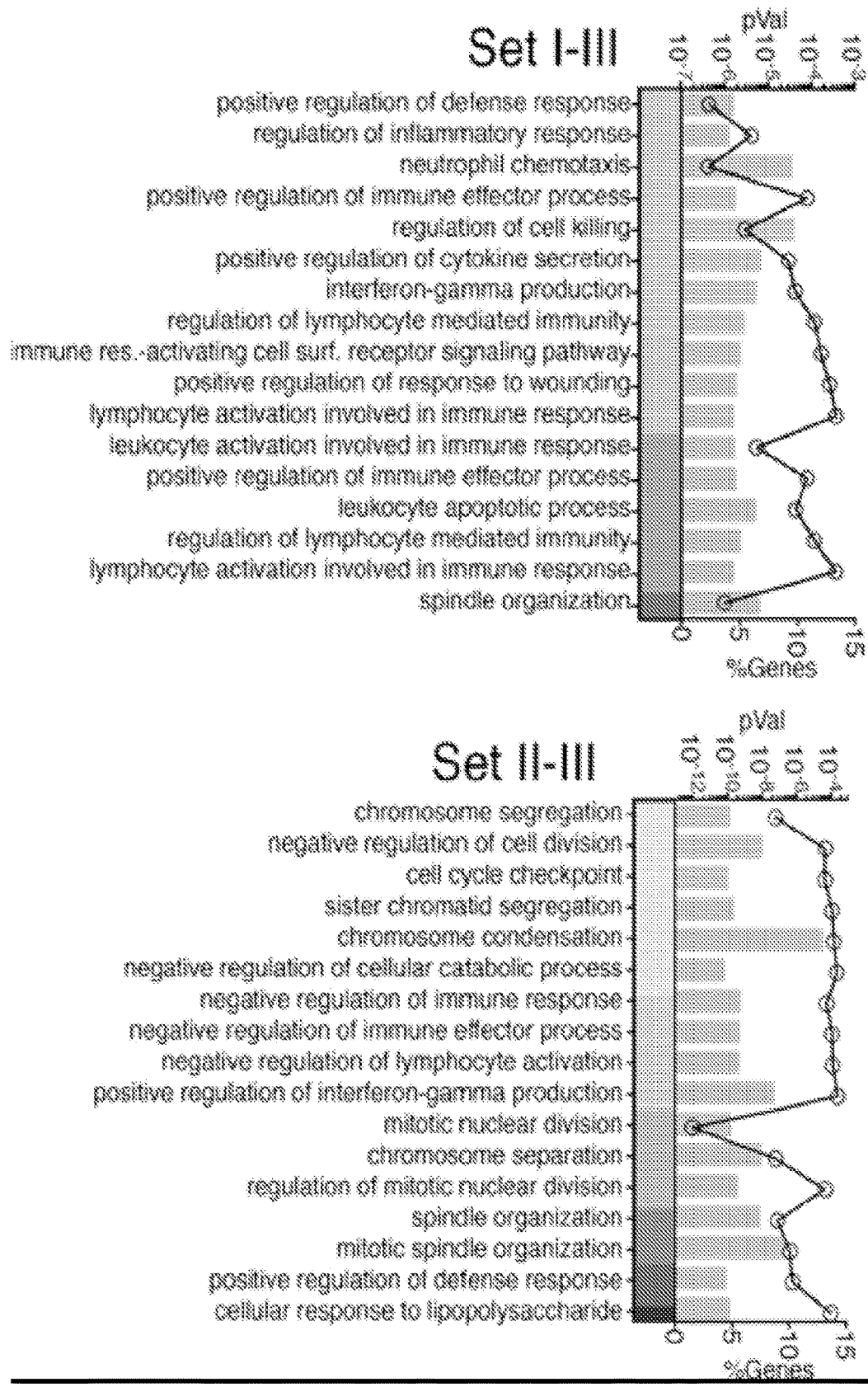
Figure 6B:
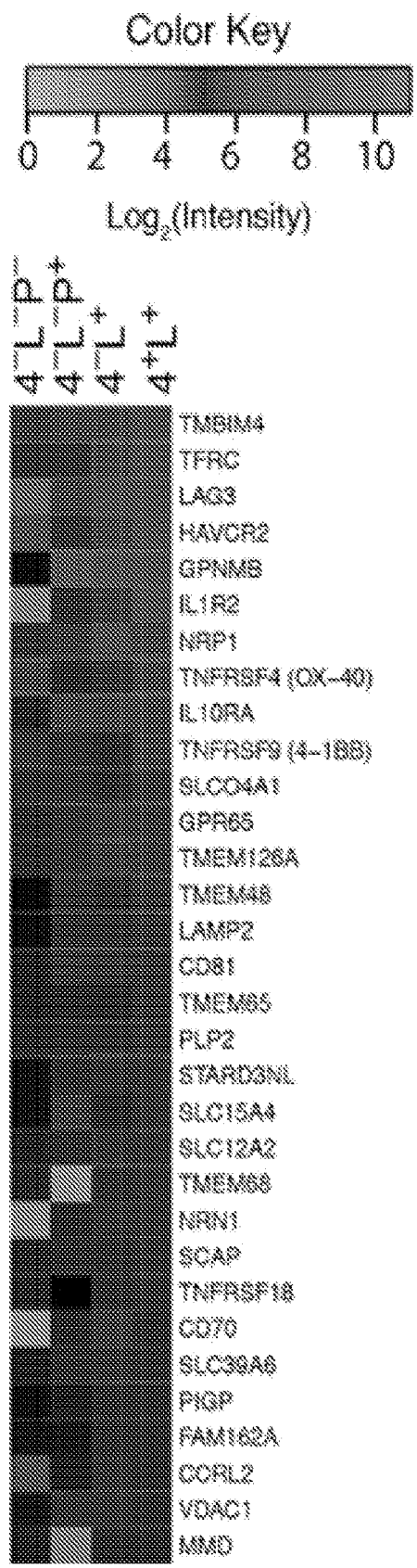
Figure 6B:
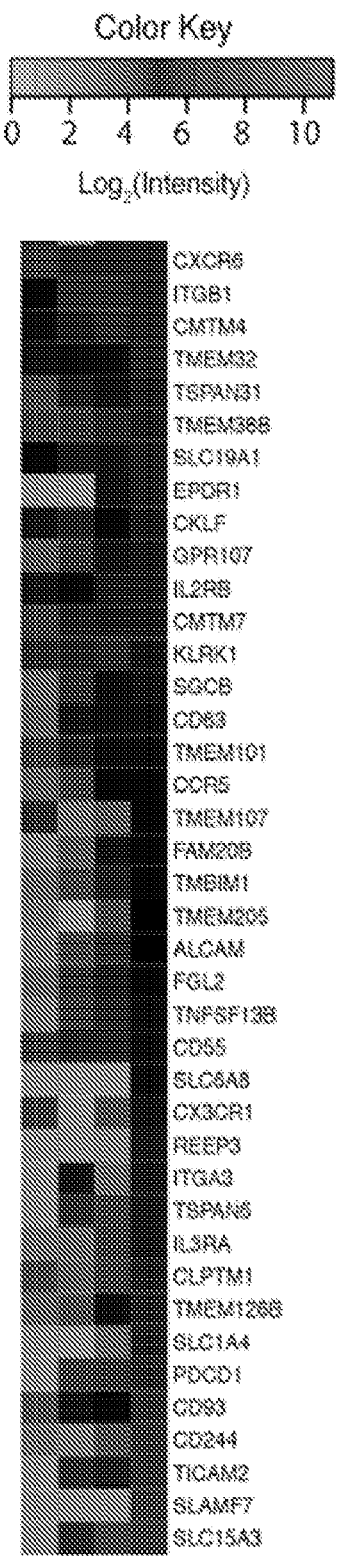
Figure 10A:
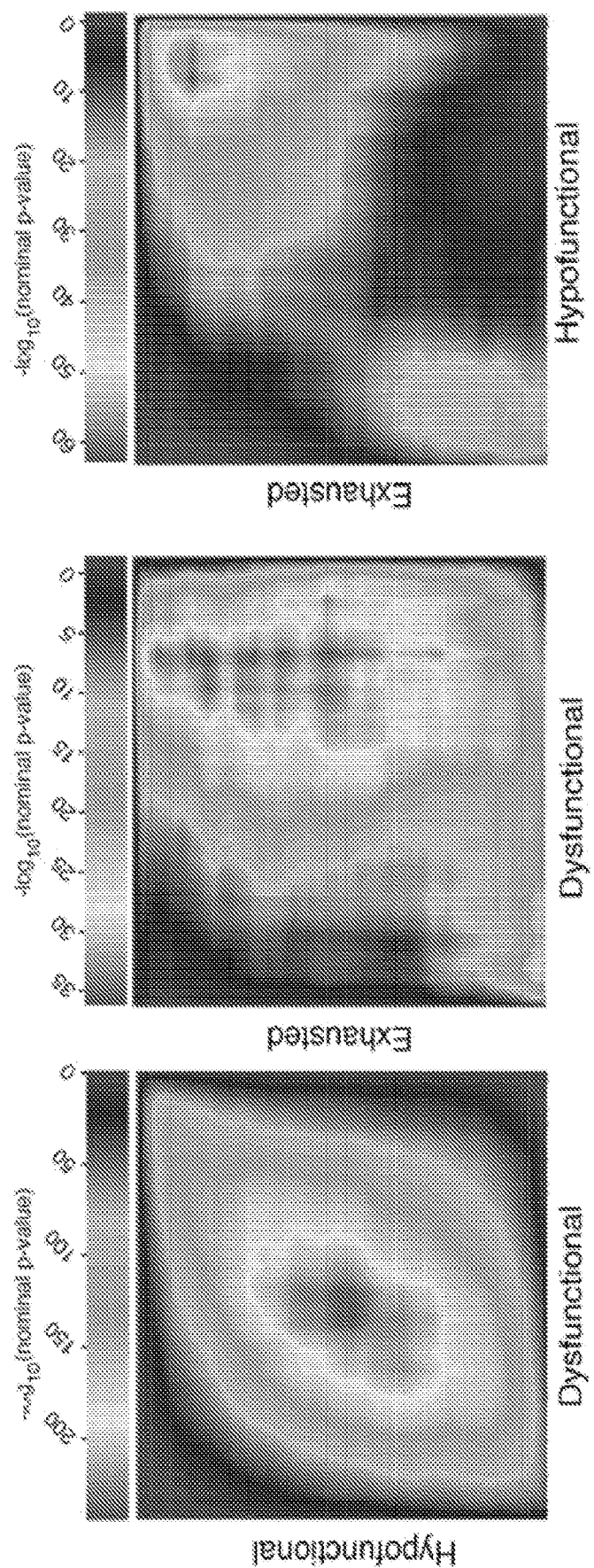
FIG. 10A-B. Statistical analysis of the cross-study comparison of gene expression profiles. (A) Rank-Rank Hypergeometric plots of each pair-wise comparison. (B) Pair-wise correlation of expression values between each data set. Rho (ρ) is the spearman rank correlation coefficient.
Figure 10A:
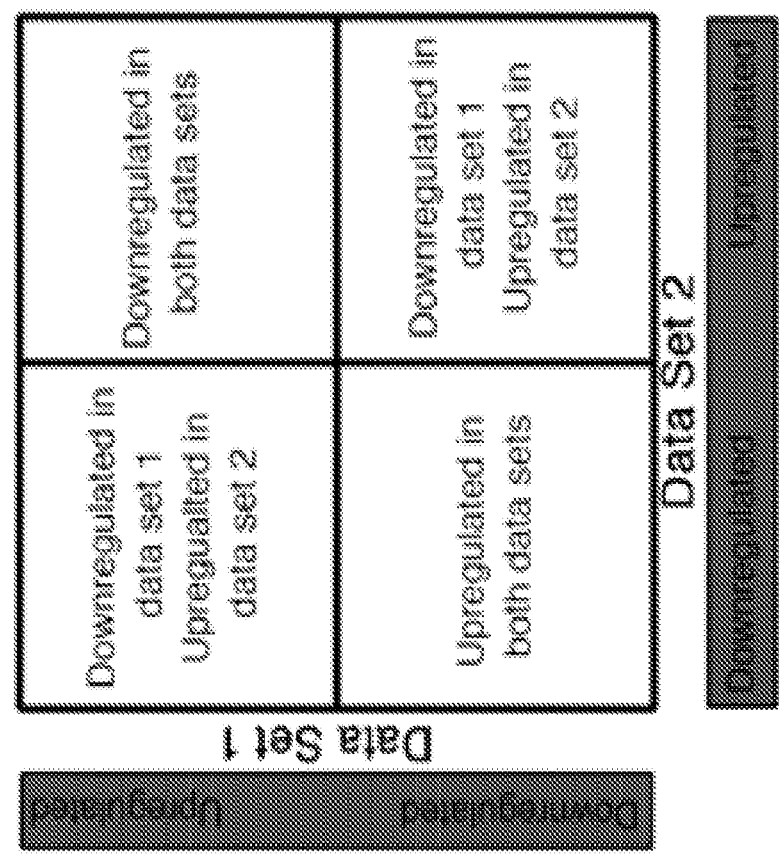
Figure 10B:
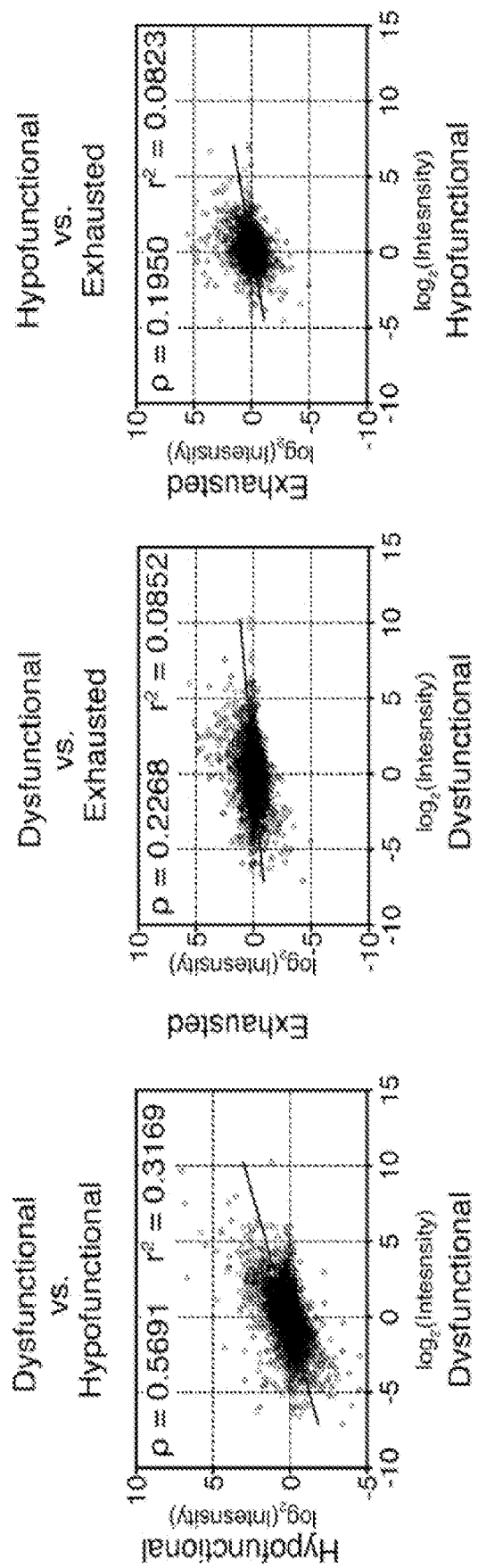

Gene Expression Profiling Reveals that CD8⁺ 4-1BB⁺LAG-3⁺ TILs Express an Extensive Array of Additional Co-Stimulatory and Co-Inhibitory Receptors Having in hand surface markers that define tumor antigen-specific dysfunctional CD8⁺ TILs, experiments conducted during development of embodiments herein to compare the gene expression profile of this population to other published profiles of dysfunctional CD8⁺ T cells to determine genes that regulate or are differentially expressed in cells in this dysfunctional state. To this end, a cross-study comparison was conducted of the transcriptional profiles of the "dysfunctional" 4-1BB⁺LAG-3⁺CD8⁺ TILs, "hypofunctional" CD8⁺ TILs from a study utilizing the murine CT26 tumor model (Waugh et al., 2016; incorporated by reference in its entirety) and LCMV "exhausted" GP33 specific CD8⁺ T cells (Doering et al., 2012; incorporated by reference in its entirety). The results are depicted in Table 2. Only genes with a 2-fold increase over controls from each study independently were considered. Over a 2-fold greater number of genes was found to be shared between the dysfunctional TIL dataset and the previously published hypofunctional CD8⁺ TIL data, than with the exhausted T cell profile (FIG. 6A). In addition, a rank-rank hypergeometric overlap (RRHO) analysis indicated a greater statistically significant overlap (FIG. 10A) and a greater correlation (FIG. 10B) between the current dysfunctional TIL and the published hypofunctional CD8⁺ TIL gene expression profiles compared to the virally-induced exhausted CD8⁺ T cell profile, indicating a more similar molecular program between CD8⁺ T cells isolate from tumors compared to chronic viral infection.

TABLE 2

Differentially regulated genes in CD8⁺4-1BB⁺LAG-3⁺ TILs

| Gene | Gene Description | Log2-Fold Change | Gene Symbol | Gene Description | Log2-Fold Change |
| --- | --- | --- | --- | --- | --- |
| GLDC | glycine decarboxylase | 11.25109772 | CRY2 | cryptochrome circadian clock 2 | −1.546648257 |
| GZMD | Granzyme D | 10.66720027 | KCMF1 | potassium channel modulatory factor 1 | −1.546835341 |
| SLC17A6 | solute carrier family 17 member 6 | 8.946467699 | RHOB | ras homolog family member B | −1.548813112 |
| IL1R2 | interleukin 1 receptor type 2 | 7.595353131 | KRT15 | keratin 15 | −1.549018071 |
| LTF | lactotransferrin | 7.530211233 | RRAD | RRAD, Ras related glycolysis inhibitor and calcium channel regulator | −1.549530357 |
| NRGN | neurogranin | 7.334049768 | C3 | complement component 3 | −1.549960037 |
| GZME | granzyme E | 7.160375687 | ITFG3 | Description Not Found | −1.550162812 |
| RPL6 | ribosomal protein L6 | 7.142107057 | HAAO | 3-hydroxyanthranilate 3,4-dioxygenase | −1.550553207 |
| NRN1 | neuritin 1 | 7.087993146 | RNF138 | ring finger protein 138 | −1.551449524 |
| LPL | lipoprotein lipase | 7.004501392 | UNC93B1 | unc-93 homolog B1 (C. elegans) | −1.551767491 |
| CLGN | calmegin | 6.933690655 | ANKZF1 | ankyrin repeat and zinc finger domain containing 1 | −1.552214097 |
| CD70 | CD70 molecule | 6.906890596 | IFITM3 | interferon induced transmembrane protein 3 | −1.552644542 |
| AREG | amphiregulin | 6.712870868 | TXNIP | thioredoxin interacting protein | −1.552785452 |
| ZRANB3 | zinc finger RANBP2-type containing 3 | 6.595443985 | LMAN1L | lectin, mannose binding 1 like | −1.554588852 |

TABLE 2-continued

Differentially regulated genes in CD8⁺4-1BB⁺LAG-3⁺ TILs

| Gene | Gene Description | Log2-Fold Change | Gene Symbol | Gene Description | Log2-Fold Change |
|---|---|---|---|---|---|
| ASNS | asparagine synthetase (glutamine-hydrolyzing) | 6.59496878 | ALDH3B1 | aldehyde dehydrogenase 3 family member B1 | −1.554711558 |
| FANCD2 | Fanconi anemia complementation group D2 | 6.353146826 | GIP | gastric inhibitory polypeptide | −1.555511104 |
| GM156 | predicted gene 156(Gm156) | 6.293701542 | COX7A2L | cytochrome c oxidase subunit 7A2 like | −1.555572553 |
| ACAA1B | acetyl-Coenzyme A acyltransferase 1B(Acaa1b) | 6.293701542 | APPL2 | adaptor protein, phosphotyrosine interacting with PH domain and leucine zipper 2 | −1.555598704 |
| IGF2BP3 | insulin like growth factor 2 mRNA binding protein 3 | 6.186857067 | KLHL22 | kelch like family member 22 | −1.555929583 |
| GZMG | granzyme G | 6.093813673 | OLFR272 | olfactory receptor 272(Olfr272) | −1.557482156 |
| CIB2 | calcium and integrin binding family member 2 | 6.007868243 | LRRC29 | leucine rich repeat containing 29 | −1.559366716 |
| ATG9B | autophagy related 9B | 5.986410935 | A630095E13RIK | Description Not Found | −1.560714954 |
| XKR8 | XK related 8 | 5.977279924 | OLFR194 | olfactory receptor 194(Olfr194) | −1.560714954 |
| EPDR1 | ependymin related 1 | 5.956521363 | OLFR1013 | olfactory receptor 1013(Olfr1013) | −1.560714954 |
| SPP1 | secreted phosphoprotein 1 | 5.797769502 | GLRA4 | glycine receptor alpha 4 | −1.560714954 |
| RGS8 | regulator of G-protein signaling 8 | 5.753805672 | P2RY6 | pyrimidinergic receptor P2Y6 | −1.560714954 |
| MDFIC | MyoD family inhibitor domain containing | 5.730639956 | RASGEF1B | RasGEF domain family member 1B | −1.560714954 |
| DMWD | dystrophia myotonica, WD repeat containing | 5.687200695 | IL22RA2 | interleukin 22 receptor subunit alpha 2 | −1.560714954 |
| KIF11 | kinesin family member 11 | 5.669593751 | LIN7C | lin-7 homolog C, crumbs cell polarity complex component | −1.560714954 |
| LGI2 | leucine rich repeat LGI family member 2 | 5.655351829 | DMRT1 | doublesex and mab-3 related transcription factor 1 | −1.560714954 |
| ZFP41 | ZFP41 zinc finger protein | 5.615445725 | TSPAN12 | tetraspanin 12 | −1.560714954 |
| MLKL | mixed lineage kinase domain-like | 5.605849867 | PAK3 | p21 (RAC1) activated kinase 3 | −1.560714954 |
| CENPH | centromere protein H | 5.563768278 | COL2A1 | collagen type II alpha 1 chain | −1.560714954 |
| SERPINF1 | serpin family F member 1 | 5.5360529 | SLC37A1 | solute carrier family 37 member 1 | −1.560714954 |
| UNC13B | unc-13 homolog B (*C. elegans*) | 5.503030646 | PSD3 | pleckstrin and Sec7 domain containing 3 | −1.560714954 |
| MLANA | melan-A | 5.496654083 | RDH5 | retinol dehydrogenase 5 | −1.560714954 |
| PES1 | pescadillo ribosomal biogenesis factor 1 | 5.484376709 | ABCA3 | ATP binding cassette subfamily A member 3 | −1.561263453 |
| 2900026A02RIK | Description Not Found | 5.477353527 | PLA2G4E | phospholipase A2 group IVE | −1.561650879 |
| OSR2 | odd-skipped related transcription factor 2 | 5.416164165 | DDIT3 | DNA damage inducible transcript 3 | −1.563566526 |
| MPP6 | membrane palmitoylated protein 6 | 5.408506442 | ZFP12 | zinc finger protein 12(Zfp12) | −1.564308646 |
| HIST1H3C | histone cluster 1, H3c | 5.397460726 | PIGYL | phosphatidylinositol glycan anchor biosynthesis, class Y-like(Pigyl) | −1.564585219 |
| PI4K2B | phosphatidylinositol 4-kinase type 2 beta | 5.375039431 | CCDC97 | coiled-coil domain containing 97 | −1.565355117 |
| SH3YL1 | SH3 and SYLF domain containing 1 | 5.375039431 | OLFR1112 | olfactory receptor 1112(Olfr1112) | −1.56589319 |
| RAD51 | RAD51 recombinase | 5.371558863 | ACTN2 | actinin alpha 2 | −1.566931646 |
| ZBTB32 | zinc finger and BTB domain containing 32 | 5.318316841 | POLG | polymerase (DNA) gamma, catalytic subunit | −1.567265595 |
| MSC | musculin | 5.285402219 | FBXO32 | F-box protein 32 | −1.567281905 |
| TG | thyroglobulin | 5.259272487 | MRPL15 | mitochondrial ribosomal protein L15 | −1.570722678 |
| RSPH1 | radial spoke head 1 homolog | 5.236492618 | FCHSD2 | FCH and double SH3 domains 2 | −1.571821211 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| ARL11 | ADP ribosylation factor like GTPase 11 | 5.21916852 | RECQL | RecQ like helicase | −1.572889668 |
| NUDT11 | nudix hydrolase 11 | 5.215290306 | NDUFB11 | NADH: ubiquinone oxidoreductase subunit B11 | −1.572889668 |
| APBB1 | amyloid beta precursor protein binding family B member 1 | 5.197708158 | SOX8 | SRY-box 8 | −1.573341535 |
| SPINK2 | serine peptidase inhibitor, Kazal type 2 | 5.189824559 | 1700030J22RIK | Description Not Found | −1.57662394 |
| HMGN3 | high mobility group nucleosomal binding domain 3 | 5.168922782 | EMB | embigin | −1.577890585 |
| FAM20B | family with sequence similarity 20 member B | 5.12722055 | CELSR1 | cadherin EGF LAG seven-pass G-type receptor 1 | −1.578201987 |
| CDC25C | cell division cycle 25C | 5.11997861 | COL1A2 | collagen type I alpha 2 chain | −1.580682782 |
| FAM20A | family with sequence similarity 20 member A | 5.108524457 | 1700080E11RIK | Description Not Found | −1.581046002 |
| PPP1R16B | protein phosphatase 1 regulatory subunit 16B | 5.09592442 | GALNT12 | polypeptide N-acetylgalactosaminyltransferase 12 | −1.581363645 |
| SBNO1 | strawberry notch homolog 1 (*Drosophila*) | 5.050936965 | RMND5B | required for meiotic nuclear division 5 homolog B | −1.583960816 |
| ST14 | suppression of tumorigenicity 14 | 5.026800059 | LRRC28 | leucine rich repeat containing 28 | −1.583987499 |
| LRRC49 | leucine rich repeat containing 49 | 5.024704311 | OLFR622 | olfactory receptor 622(Olfr622) | −1.584962501 |
| TIAM1 | T-cell lymphoma invasion and metastasis 1 | 5.004501392 | OLFR339 | olfactory receptor 339(Olfr339) | −1.584962501 |
| APLF | aprataxin and PNKP like factor | 4.951867504 | NEIL3 | nei like DNA glycosylase 3 | −1.584962501 |
| PGPEP1 | pyroglutamyl-peptidase I | 4.927185358 | SNX24 | sorting nexin 24 | −1.584962501 |
| ALCAM | activated leukocyte cell adhesion molecule | 4.909293086 | SLC7A11 | solute carrier family 7 member 11 | −1.584962501 |
| B9D1 | B9 domain containing 1 | 4.906890596 | FOXJ1 | forkhead box J1 | −1.584962501 |
| SCIN | scinderin | 4.87282876 | TAF3 | TATA-box binding protein associated factor 3 | −1.584962501 |
| EXOC3L | exocyst complex component 3-like(Exoc3l) | 4.844013973 | MATN2 | matrilin 2 | −1.584962501 |
| SLC35D3 | solute carrier family 35 member D3 | 4.840463234 | ADHFE1 | alcohol dehydrogenase, iron containing 1 | −1.586280668 |
| ALDOC | aldolase, fructose-bisphosphate C | 4.832890014 | NANOS1 | nanos C2HC-type zinc finger 1 | −1.586914831 |
| TMEM205 | transmembrane protein 205 | 4.830182468 | PPP2R5B | protein phosphatase 2 regulatory subunit B'beta | −1.586914831 |
| PLEKHA8 | pleckstrin homology domain containing A8 | 4.820178962 | USP22 | ubiquitin specific peptidase 22 | −1.588703598 |
| SPC25 | SPC25, NDC80 kinetochore complex component | 4.817623258 | DAGLB | diacylglycerol lipase beta | −1.588817933 |
| PCYT1B | phosphate cytidylyltransferase 1, choline, beta | 4.749534268 | KCTD6 | potassium channel tetramerization domain containing 6 | −1.589690033 |
| SLC6A8 | solute carrier family 6 member 8 | 4.749534268 | ACTL6B | actin like 6B | −1.591351555 |
| TUBB6 | tubulin beta 6 class V | 4.749241128 | FAM129B | family with sequence similarity 129 member B | −1.5915039 |
| BSPRY | B-box and SPRY domain containing | 4.711494907 | APOE | apolipoprotein E | −1.591683393 |
| ICA1 | islet cell autoantigen 1 | 4.708739041 | GPR18 | G protein-coupled receptor 18 | −1.592384168 |
| TNFSF13B | tumor necrosis factor superfamily member 13b | 4.703211467 | GSTP2 | glutathione S-transferase, pi 2(Gstp2) | −1.592559885 |
| GSTCD | glutathione S-transferase C-terminal domain containing | 4.700439718 | GPR114 | Description Not Found | −1.593829527 |
| CCNB1 | cyclin B1 | 4.699051844 | CHUK | conserved helix-loop-helix ubiquitous kinase | −1.594823937 |
| 4930539E08RIK | Description Not Found | 4.693211287 | TAS1R3 | taste 1 receptor member 3 | −1.596595048 |
| SRXN1 | sulfiredoxin 1 | 4.66106548 | SLC7A7 | solute carrier family 7 member 7 | −1.596935142 |

TABLE 2-continued

Differentially regulated genes in CD8⁺4-1BB⁺LAG-3⁺ TILs

| Gene | Gene Description | Log2-Fold Change | Gene Symbol | Gene Description | Log2-Fold Change |
|---|---|---|---|---|---|
| SERF1 | small EDRK-rich factor 1(Serf1) | 4.632268216 | SPIB | Spi-B transcription factor | −1.597677703 |
| CCDC77 | coiled-coil domain containing 77 | 4.62935662 | POLR3A | polymerase (RNA) III subunit A | −1.599588488 |
| RHBDF1 | rhomboid 5 homolog 1 | 4.626439137 | OLFR952 | olfactory receptor 952(Olfr952) | −1.599679175 |
| REEP3 | receptor accessory protein 3 | 4.599912842 | 1700021F05RIK | Description Not Found | −1.601623253 |
| ITGA3 | integrin subunit alpha 3 | 4.590961241 | CCDC79 | Description Not Found | −1.602195565 |
| SCCPDH | saccharopine dehydrogenase (putative) | 4.590961241 | FAM134B | family with sequence similarity 134 member B | −1.602715966 |
| MYADM | myeloid associated differentiation marker | 4.587964989 | SEMA3B | semaphorin 3B | −1.602884409 |
| FAM132A | family with sequence similarity 132 member A | 4.581953751 | FA2H | fatty acid 2-hydroxylase | −1.604494406 |
| FOXRED2 | FAD dependent oxidoreductase domain containing 2 | 4.572889668 | ULK1 | unc-51 like autophagy activating kinase 1 | −1.604653903 |
| CENPK | centromere protein K | 4.569855608 | MCOLN1 | mucolipin 1 | −1.606242992 |
| DCXR | dicarbonyl and L-xylulose reductase | 4.562242424 | BMP5 | bone morphogenetic protein 5 | −1.606760033 |
| TSPAN6 | tetraspanin 6 | 4.54225805 | ANKRD50 | ankyrin repeat domain 50 | −1.607137028 |
| UPP1 | uridine phosphorylase 1 | 4.53838296 | OLFR560 | olfactory receptor 560(Olfr560) | −1.608809243 |
| DOK4 | docking protein 4 | 4.520422249 | OLFR366 | olfactory receptor 366(Olfr366) | −1.608809243 |
| ELOVL4 | ELOVL fatty acid elongase 4 | 4.501439145 | OLFR273 | olfactory receptor 273(Olfr273) | −1.608809243 |
| KNDC1 | kinase non-catalytic C-lobe domain containing 1 | 4.499790117 | FHIT | fragile histidine triad | −1.608809243 |
| KRT17 | keratin 17 | 4.491853096 | AQP11 | aquaporin 11 | −1.608809243 |
| CHST2 | carbohydrate sulfotransferase 2 | 4.487315031 | TMEM176A | transmembrane protein 176A | −1.608809243 |
| TPX2 | TPX2, microtubule nucleation factor | 4.475733431 | ENAH | enabled homolog (Drosophila) | −1.608809243 |
| DUSP14 | dual specificity phosphatase 14 | 4.456149035 | CLDN6 | claudin 6 | −1.608809243 |
| BGN | biglycan | 4.449561375 | SP1 | Sp1 transcription factor | −1.608809243 |
| FKBP9 | FK506 binding protein 9 | 4.442943496 | SP140 | SP140 nuclear body protein | −1.608809243 |
| CAPN5 | calpain 5 | 4.385431037 | RASGRP3 | RAS guanyl releasing protein 3 | −1.608809243 |
| SLC1A4 | solute carrier family 1 member 4 | 4.375039431 | HIF3A | hypoxia inducible factor 3 alpha subunit | −1.609422664 |
| IDI2 | isopentenyl-diphosphate delta isomerase 2 | 4.357552005 | FYCO1 | FYVE and coiled-coil domain containing 1 | −1.611220598 |
| AKR1E1 | aldo-keto reductase family 1, member E1(Akr1e1) | 4.346596388 | FBXL12 | F-box and leucine rich repeat protein 12 | −1.6119368 |
| GNB4 | G protein subunit beta 4 | 4.336088936 | KLRA10 | killer cell lectin-like receptor subfamily A, member 10(Klra10) | −1.618484777 |
| CPNE2 | copine 2 | 4.318640898 | ABAT | 4-aminobutyrate aminotransferase | −1.62058641 |
| FAM132B | family with sequence similarity 132, member B(Fam132b) | 4.259272487 | AMHR2 | anti-Mullerian hormone receptor type 2 | −1.62058641 |
| SLC6A12 | solute carrier family 6 member 12 | 4.259272487 | DDX3Y | DEAD-box helicase 3, Y-linked | −1.620649859 |
| CPLX1 | complexin 1 | 4.240314329 | LGALS4 | galectin 4 | −1.621550215 |
| PDCD1 | programmed cell death 1 | 4.221103725 | SPG20 | spastic paraplegia 20 (Troyer syndrome) | −1.621653602 |
| UTF1 | undifferentiated embryonic cell transcription factor 1 | 4.201633861 | CTRL | chymotrypsin like | −1.62729369 |
| WDR60 | WD repeat domain 60 | 4.14974712 | GREM2 | gremlin 2, DAN family BMP antagonist | −1.627927342 |
| EGFL7 | EGF like domain multiple 7 | 4.137503524 | ZMAT3 | zinc finger matrin-type 3 | −1.628362075 |
| ASPM | abnormal spindle microtubule assembly | 4.133399125 | AP4M1 | adaptor related protein complex 4 mu 1 subunit | −1.628898157 |
| TMBIM1 | transmembrane BAX inhibitor motif containing 1 | 4.104628811 | NT5C2 | 5'-nucleotidase, cytosolic II | −1.63059747 |

TABLE 2-continued

Differentially regulated genes in CD8$^+$4-1BB$^+$LAG-3$^+$ TILs

| Gene | Gene Description | Log2-Fold Change | Gene Symbol | Gene Description | Log2-Fold Change |
|---|---|---|---|---|---|
| KNTC1 | kinetochore associated 1 | 4.093952772 | TMIE | transmembrane inner ear | −1.631606148 |
| 1700019D03RIK | Description Not Found | 4.087462841 | OLFR556 | olfactory receptor 556(Olfr556) | −1.632268216 |
| TM4SF5 | transmembrane 4 L six family member 5 | 4.087462841 | OLFR463 | olfactory receptor 463(Olfr463) | −1.632268216 |
| BIRC5 | baculoviral IAP repeat containing 5 | 4.027905997 | CTS3 | cathepsin 3(Cts3) | −1.632268216 |
| SYNGR3 | synaptogyrin 3 | 4.022367813 | OAS1B | 2'-5' oligoadenylate synthetase 1B(Oas1b) | −1.632268216 |
| PLSCR4 | phospholipid scramblase 4 | 4 | KCNF1 | potassium voltage-gated channel modifier subfamily F member 1 | −1.632268216 |
| KIF15 | kinesin family member 15 | 3.962376898 | GCGR | glucagon receptor | −1.632268216 |
| TICAM2 | toll like receptor adaptor molecule 2 | 3.958842675 | NR1I3 | nuclear receptor subfamily 1 group I member 3 | −1.632268216 |
| CENPM | centromere protein M | 3.957682486 | FSTL1 | follistatin like 1 | −1.632268216 |
| KIF4 | kinesin family member 4(Kif4) | 3.956097191 | ASAP3 | ArfGAP with SH3 domain, ankyrin repeat and PH domain 3 | −1.632268216 |
| E2F2 | E2F transcription factor 2 | 3.93191939 | IHH | indian hedgehog | −1.632268216 |
| MSN | moesin | 3.930737338 | SEMA3A | semaphorin 3A | −1.632268216 |
| PTPRA | protein tyrosine phosphatase, receptor type A | 3.928989949 | RAMP1 | receptor activity modifying protein 1 | −1.632575446 |
| BC026585 | cDNA sequence BC026585(BC026585) | 3.882643049 | NFKBID | NFKB inhibitor delta | −1.633158642 |
| IQGAP3 | IQ motif containing GTPase activating protein 3 | 3.867896464 | KLK15 | kallikrein related peptidase 15 | −1.633773522 |
| CD244 | CD244 molecule | 3.867896464 | CYP1B1 | cytochrome P450 family 1 subfamily B member 1 | −1.634684534 |
| HIST1H3G | histone cluster 1, H3g | 3.837943242 | DNAJA1 | DnaJ heat shock protein family (Hsp40) member A1 | −1.635111002 |
| SLC15A3 | solute carrier family 15 member 3 | 3.832890014 | SDSL | serine dehydratase like | −1.635807742 |
| GIPC2 | GIPC PDZ domain containing family member 2 | 3.817623258 | CCDC137 | coiled-coil domain containing 137 | −1.636838653 |
| UTP15 | UTP15, small subunit processome component | 3.812498225 | ZSWIM4 | zinc finger SWIM-type containing 4 | −1.638152805 |
| PDIA6 | protein disulfide isomerase family A member 6 | 3.812498225 | BBC3 | BCL2 binding component 3 | −1.638336813 |
| JDP2 | Jun dimerization protein 2 | 3.807354922 | SOCS3 | suppressor of cytokine signaling 3 | −1.638876738 |
| MESDC1 | mesoderm development candidate 1 | 3.806723946 | 2900092C05RIK | Description Not Found | −1.639157339 |
| GAS2 | growth arrest specific 2 | 3.802193217 | CSRNP2 | cysteine and serine rich nuclear protein 2 | −1.639383642 |
| IL4I1 | interleukin 4 induced 1 | 3.802193217 | BLOC1S3 | biogenesis of lysosomal organelles complex 1 subunit 3 | −1.639585785 |
| PHF19 | PHD finger protein 19 | 3.802193217 | ELL | elongation factor for RNA polymerase II | −1.64021945 |
| CKAP2L | cytoskeleton associated protein 2 like | 3.797012978 | GTF3C4 | general transcription factor IIIC subunit 4 | −1.640658029 |
| GSTT1 | glutathione S-transferase theta 1 | 3.791814071 | MYLPF | myosin light chain, phosphorylatable, fast skeletal muscle | −1.640660074 |
| ADAM3 | a disintegrin and metallopeptidase domain 3 (cyritestin)(Adam3) | 3.781359714 | CYP2A12 | cytochrome P450, family 2, subfamily a, polypeptide 12(Cyp2a12) | −1.641947141 |
| SLAMF7 | SLAM family member 7 | 3.781359714 | RNF139 | ring finger protein 139 | −1.642010395 |
| MCPT8 | mast cell protease 8(Mcpt8) | 3.770829046 | C78339 | Description Not Found | −1.643573868 |
| DGKG | diacylglycerol kinase gamma | 3.765534746 | EDEM1 | ER degradation enhancing alpha-mannosidase like protein 1 | −1.64385619 |
| NLGN2 | neuroligin 2 | 3.716990894 | UBE2E1 | ubiquitin conjugating enzyme E2 E1 | −1.645859791 |
| SERPINE2 | serpin family E member 2 | 3.694880193 | PALMD | palmdelphin | −1.646322067 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| IL10 | interleukin 10 | 3.689299161 | AMICA1 | adhesion molecule, interacts with CXADR antigen 1(Amica1) | −1.647478619 |
| SLC6A13 | solute carrier family 6 member 13 | 3.689299161 | KLHL11 | kelch like family member 11 | −1.650611828 |
| STAU2 | staufen double-stranded RNA binding protein 2 | 3.666756592 | IFNGR2 | interferon gamma receptor 2 (interferon gamma transducer 1) | −1.651050175 |
| ARHGDIG | Rho GDP dissociation inhibitor gamma | 3.655351829 | DECR1 | 2,4-dienoyl-CoA reductase 1, mitochondrial | −1.651406438 |
| TK1 | thymidine kinase 1 | 3.637477097 | SAMD3 | sterile alpha motif domain containing 3 | −1.653213853 |
| PCYT1A | phosphate cytidylyltransferase 1, choline, alpha | 3.617728231 | 9130409I23RIK | Description Not Found | −1.655351829 |
| LAMB3 | laminin subunit beta 3 | 3.608809243 | 2010107G12RIK | Description Not Found | −1.655351829 |
| UBE2N | ubiquitin conjugating enzyme E2 N | 3.590961241 | ZFP354B | zinc finger protein 354B(Zfp354b) | −1.655351829 |
| STARD8 | StAR related lipid transfer domain containing 8 | 3.578938713 | TAS2R143 | taste receptor, type 2, member 143(Tas2r143) | −1.655351829 |
| PRR5 | proline rich 5 | 3.578938713 | OLFR65 | olfactory receptor 65(Olfr65) | −1.655351829 |
| BDH2 | 3-hydroxybutyrate dehydrogenase, type 2 | 3.554588852 | NRP | neural regeneration protein(Nrp) | −1.655351829 |
| FAM124B | family with sequence similarity 124 member B | 3.548436625 | DOK3 | docking protein 3 | −1.655351829 |
| MGAT3 | mannosyl (beta-1,4-)-glycoprotein beta-1,4-N-acetylglucosaminyltransferase | 3.548436625 | HIGD1A | HIG1 hypoxia inducible domain family member 1A | −1.655351829 |
| LAG3 | lymphocyte activating 3 | 3.542346309 | CCDC13 | coiled-coil domain containing 13 | −1.655351829 |
| GDPD5 | glycerophosphodiester phosphodiesterase domain containing 5 | 3.538812733 | ANGPTL2 | angiopoietin like 2 | −1.655351829 |
| RNF168 | ring finger protein 168 | 3.5360529 | CNGB3 | cyclic nucleotide gated channel beta 3 | −1.655351829 |
| LYPLA1 | lysophospholipase I | 3.529820947 | HOXD4 | homeobox D4 | −1.655351829 |
| TUBGCP4 | tubulin gamma complex associated protein 4 | 3.523561956 | KIFC3 | kinesin family member C3 | −1.655351829 |
| PYGL | phosphorylase, glycogen, liver | 3.51412226 | AMACR | alpha-methylacyl-CoA racemase | −1.655351829 |
| CCL3 | C-C motif chemokine ligand 3 | 3.510281539 | 2310014L17RIK | Description Not Found | −1.655707015 |
| BCAT1 | branched chain amino acid transaminase 1 | 3.508163667 | BRAP | BRCA1 associated protein | −1.657090723 |
| ATP6V0A1 | ATPase H+ transporting V0 subunit a1 | 3.501439145 | SLC39A1 | solute carrier family 39 member 1 | −1.657631089 |
| EIF4E | eukaryotic translation initiation factor 4E | 3.498250868 | OLFR419 | olfactory receptor 419(Olfr419) | −1.65813796 |
| HIST1H4B | histone cluster 1, H4b | 3.491853096 | NHP2L1 | NHP2 non-histone chromosome protein 2-like 1 (S. cerevisiae)(Nhp2l1) | −1.658298045 |
| LAD1 | ladinin 1 | 3.49085426 | STOML2 | stomatin like 2 | −1.659357735 |
| ITGAV | integrin subunit alpha V | 3.485426827 | SAMM50 | SAMM50 sorting and assembly machinery component | −1.662400762 |
| MRPL47 | mitochondrial ribosomal protein L47 | 3.485426827 | CCDC91 | coiled-coil domain containing 91 | −1.6632299 |
| CAMK2N1 | calcium/calmodulin dependent protein kinase II inhibitor 1 | 3.484460783 | ATF3 | activating transcription factor 3 | −1.663483642 |
| UEVLD | UEV and lactate/malate dehydrogenase domains | 3.465974465 | RAI1 | retinoic acid induced 1 | −1.663885989 |
| SFXN4 | sideroflexin 4 | 3.462706751 | RRAS2 | related RAS viral (r-ras) oncogene homolog 2 | −1.665826896 |
| 2810417H13RIK | Description Not Found | 3.461634298 | UROS | uroporphyrinogen III synthase | −1.665923156 |
| RAD51AP1 | RAD51 associated protein 1 | 3.459431619 | SCOC | short coiled-coil protein | −1.666272349 |
| FUT4 | fucosyltransferase 4 | 3.452858965 | DUSP10 | dual specificity phosphatase 10 | −1.666485948 |
| CTNNBIP1 | catenin beta interacting protein 1 | 3.44625623 | CYB5R4 | cytochrome b5 reductase 4 | −1.666756592 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| ZBTB8OS | zinc finger and BTB domain containing 8 opposite strand | 3.426264755 | 9930104L06RIK | Description Not Found | −1.667150978 |
| LYSMD4 | LysM domain containing 4 | 3.42259008 | ZFP579 | zinc finger protein 579(Zfp579) | −1.669023741 |
| DIAP3 | Description Not Found | 3.40599236 | RGP1 | RGP1 homolog, RAB6A GEF complex partner 1 | −1.669393721 |
| PTGIS | prostaglandin I2 (prostacyclin) synthase | 3.399171094 | PIAS2 | protein inhibitor of activated STAT 2 | −1.672137196 |
| MOAP1 | modulator of apoptosis 1 | 3.392317423 | METTL1 | methyltransferase like 1 | −1.672425342 |
| SLC27A3 | solute carrier family 27 member 3 | 3.392317423 | POU5F1 | POU class 5 homeobox 1 | −1.673854965 |
| MRPL39 | mitochondrial ribosomal protein L39 | 3.371492175 | SERPINB6C | serine (or cysteine) peptidase inhibitor, clade B, member 6c(Serpinb6c) | −1.673932658 |
| WTAP | Wilms tumor 1 associated protein | 3.364572432 | STXBP4 | syntaxin binding protein 4 | −1.675552278 |
| RAD54L | RAD54-like (S. cerevisiae) | 3.356589854 | RIMS3 | regulating synaptic membrane exocytosis 3 | −1.676120648 |
| CETN4 | centrin 4(Cetn4) | 3.336283388 | XYLT2 | xylosyltransferase 2 | −1.676976793 |
| CEP55 | centrosomal protein 55 | 3.329123596 | TAS2R107 | taste receptor, type 2, member 107(Tas2r107) | −1.678071905 |
| CYP4F39 | cytochrome P450, family 4, subfamily f, polypeptide 39(Cyp4f39) | 3.321928095 | SKP1A | S-phase kinase-associated protein 1A(Skp1a) | −1.678071905 |
| PTPN5 | protein tyrosine phosphatase, non-receptor type 5 | 3.314696526 | OLFR165 | olfactory receptor 165(Olfr165) | −1.678071905 |
| TUBE1 | tubulin epsilon 1 | 3.292781749 | OLFR111 | olfactory receptor 111(Olfr111) | −1.678071905 |
| TCAM1 | testicular cell adhesion molecule 1(Tcam1) | 3.285402219 | CYP4A12A | cytochrome P450, family 4, subfamily a, polypeptide 12a(Cyp4a12a) | −1.678071905 |
| MID1IP1 | MID1 interacting protein 1 | 3.263034406 | TLR6 | toll like receptor 6 | −1.678071905 |
| ABHD6 | abhydrolase domain containing 6 | 3.260682276 | KCNS3 | potassium voltage-gated channel modifier subfamily S member 3 | −1.678071905 |
| ZCCHC4 | zinc finger CCHC-type containing 4 | 3.255500733 | FARSA | phenylalanyl-tRNA synthetase alpha subunit | −1.678071905 |
| MGST3 | microsomal glutathione S-transferase 3 | 3.25353624 | SLC2A4 | solute carrier family 2 member 4 | −1.678071905 |
| BC022687 | cDNA sequence BC022687(BC022687) | 3.247927513 | GDPD4 | glycerophosphodiester phosphodiesterase domain containing 4 | −1.678071905 |
| ACSF3 | acyl-CoA synthetase family member 3 | 3.24325855 | RCAN1 | regulator of calcineurin 1 | −1.678071905 |
| ADAM8 | ADAM metallopeptidase domain 8 | 3.240314329 | CCDC82 | coiled-coil domain containing 82 | −1.678071905 |
| SGCB | sarcoglycan beta | 3.237034772 | CDYL2 | chromodomain protein, Y-like 2 | −1.678071905 |
| SOCS2 | suppressor of cytokine signaling 2 | 3.232660757 | MBD5 | methyl-CpG binding domain protein 5 | −1.678071905 |
| HIST1H2AG | histone cluster 1, H2ag | 3.223000387 | ACSL1 | acyl-CoA synthetase long-chain family member 1 | −1.678071905 |
| CRMP1 | collapsin response mediator protein 1 | 3.201633861 | OTUB2 | OTU deubiquitinase, ubiquitin aldehyde binding 2 | −1.678071905 |
| RPS19BP1 | ribosomal protein S19 binding protein 1 | 3.201633861 | NPPA | natriuretic peptide A | −1.678071905 |
| 1700020L24RIK | Description Not Found | 3.193771743 | LY96 | lymphocyte antigen 96 | −1.679594789 |
| CCDC109B | coiled-coil domain containing 109B(Ccdc109b) | 3.181276986 | OLFR351 | olfactory receptor 351(Olfr351) | −1.680730557 |
| UBE2C | ubiquitin conjugating enzyme E2 C | 3.177917792 | TGFBR1 | transforming growth factor beta receptor 1 | −1.681068055 |
| SLC25A16 | solute carrier family 25 member 16 | 3.177917792 | KLHL6 | kelch like family member 6 | −1.683531539 |
| ARHGAP19 | Rho GTPase activating protein 19 | 3.167705534 | ELMO2 | engulfment and cell motility 2 | −1.683696454 |
| TYMS-PS | thymidylate synthase, pseudogene(Tyms-ps) | 3.166362514 | POLR3D | polymerase (RNA) III subunit D | −1.683942043 |
| IL3RA | interleukin 3 receptor subunit alpha | 3.145793675 | RALGPS1 | Ral GEF with PH domain and SH3 binding motif 1 | −1.685524532 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| TMEM53 | transmembrane protein 53 | 3.141596278 | ATL2 | atlastin GTPase 2 | −1.685731341 |
| THNSL2 | threonine synthase like 2 | 3.141596278 | RAD52 | RAD52 homolog, DNA repair protein | −1.689523672 |
| 2810408M09RIK | Description Not Found | 3.129283017 | GPC1 | glypican 1 | −1.689646894 |
| ADAMDEC1 | ADAM like decysin 1 | 3.121015401 | ARHGAP15 | Rho GTPase activating protein 15 | −1.690804518 |
| ASB2 | ankyrin repeat and SOCS box containing 2 | 3.118792343 | GPRC5B | G protein-coupled receptor class C group 5 member B | −1.693999744 |
| SLC37A4 | solute carrier family 37 member 4 | 3.112700133 | ZBTB1 | zinc finger and BTB domain containing 1 | −1.694046727 |
| NICN1 | nicolin 1 | 3.108478268 | NARFL | nuclear prelamin A recognition factor like | −1.694880193 |
| 2310067B10RIK | Description Not Found | 3.087462841 | SLC26A6 | solute carrier family 26 member 6 | −1.695252347 |
| PIGL | phosphatidylinositol glycan anchor biosynthesis class L | 3.077239787 | MAPKBP1 | mitogen-activated protein kinase binding protein 1 | −1.695908738 |
| 1190005I06RIK | Description Not Found | 3.070389328 | RAB6B | RAB6B, member RAS oncogene family | −1.697541036 |
| DHFR | dihydrofolate reductase | 3.070389328 | ARL2 | ADP ribosylation factor like GTPase 2 | −1.700349879 |
| FABP5 | fatty acid binding protein 5 | 3.06608919 | ZFP646 | zinc finger protein 646(Zfp646) | −1.700439718 |
| POMT2 | protein O-mannosyltransferase 2 | 3.055794286 | SELENBP2 | selenium binding protein 2(Selenbp2) | −1.700439718 |
| F2RL2 | coagulation factor II thrombin receptor like 2 | 3.053111336 | ACOT3 | acyl-CoA thioesterase 3(Acot3) | −1.700439718 |
| GRB7 | growth factor receptor bound protein 7 | 3.048852907 | REG3G | regenerating family member 3 gamma | −1.700439718 |
| SNX21 | sorting nexin family member 21 | 3.044394119 | GAB1 | GRB2 associated binding protein 1 | −1.700439718 |
| SUFU | SUFU negative regulator of hedgehog signaling | 3.044394119 | LCN10 | lipocalin 10 | −1.700439718 |
| RFC3 | replication factor C subunit 3 | 3.029288361 | MTHFD2L | methylenetetrahydrofolate dehydrogenase (NADP+ dependent) 2-like | −1.700439718 |
| CLDN12 | claudin 12 | 3.017921908 | PTCD3 | pentatricopeptide repeat domain 3 | −1.700439718 |
| C1QTNF6 | C1q and tumor necrosis factor related protein 6 | 3.014450679 | NTHL1 | nth-like DNA glycosylase 1 | −1.700439718 |
| PLCXD1 | phosphatidylinositol specific phospholipase C X domain containing 1 | 2.99095486 | NUDT3 | nudix hydrolase 3 | −1.700439718 |
| SULT4A1 | sulfotransferase family 4A member 1 | 2.99095486 | CLEC12A | C-type lectin domain family 12 member A | −1.700439718 |
| CTTNBP2NL | CTTNBP2 N-terminal like | 2.981852653 | ZBTB3 | zinc finger and BTB domain containing 3 | −1.700439718 |
| SNX5 | sorting nexin 5 | 2.977279924 | AMT | aminomethyltransferase | −1.700439718 |
| HPS5 | HPS5, biogenesis of lysosomal organelles complex 2 subunit 2 | 2.972692654 | ZDHHC14 | zinc finger DHHC-type containing 14 | −1.700439718 |
| WISP1 | WNT1 inducible signaling pathway protein 1 | 2.968090752 | NKX2-5 | NK2 homeobox 5 | −1.700491519 |
| PTPN9 | protein tyrosine phosphatase, non-receptor type 9 | 2.963474124 | FOXA3 | forkhead box A3 | −1.702815694 |
| USP37 | ubiquitin specific peptidase 37 | 2.95419631 | WASF1 | WAS protein family member 1 | −1.706412734 |
| SH3BGRL | SH3 domain binding glutamate rich protein like | 2.935459748 | OLFR690 | olfactory receptor 690(Olfr690) | −1.707192688 |
| NCALD | neurocalcin delta | 2.935459748 | ENTPD5 | ectonucleoside triphosphate diphosphohydrolase 5 | −1.707764551 |
| CDC42EP4 | CDC42 effector protein 4 | 2.916476644 | PCDHGA4 | protocadherin gamma subfamily A, 4 | −1.709042655 |
| IGFBP7 | insulin like growth factor binding protein 7 | 2.910553168 | TCF12 | transcription factor 12 | −1.710308209 |
| ABHD4 | abhydrolase domain containing 4 | 2.908868748 | MTRR | 5-methyltetrahydrofolate-homocysteine methyltransferase reductase | −1.711494907 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| CSF1 | colony stimulating factor 1 | 2.906890596 | CDKN1C | cyclin dependent kinase inhibitor 1C | −1.711690028 |
| COX7A1 | cytochrome c oxidase subunit 7A1 | 2.897240426 | PRICKLE1 | prickle planar cell polarity protein 1 | −1.713410822 |
| TTYH2 | tweety family member 2 | 2.892391026 | ATXN7L1 | ataxin 7 like 1 | −1.71669984 |
| ACO1 | aconitase 1 | 2.87774425 | SLCO3A1 | solute carrier organic anion transporter family member 3A1 | −1.719235762 |
| BARD1 | BRCA1 associated RING domain 1 | 2.867896464 | TMEM110 | transmembrane protein 110 | −1.720046704 |
| GPN1 | GPN-loop GTPase 1 | 2.867896464 | KLF2 | Kruppel like factor 2 | −1.721374729 |
| PTTG1 | pituitary tumor-transforming 1 | 2.867896464 | FGG | fibrinogen gamma chain | −1.722466024 |
| 2810408A11RIK | Description Not Found | 2.857980995 | ASAH2 | N-acylsphingosine amidohydrolase 2 | −1.722466024 |
| BBX | BBX, HMG-box containing | 2.857980995 | LAP3 | leucine aminopeptidase 3 | −1.722466024 |
| LTBP3 | latent transforming growth factor beta binding protein 3 | 2.837943242 | STAB2 | stabilin 2 | −1.722466024 |
| ACTG2 | actin, gamma 2, smooth muscle, enteric | 2.827819025 | IL22RA1 | interleukin 22 receptor subunit alpha 1 | −1.722466024 |
| ISLR | immunoglobulin superfamily containing leucine rich repeat | 2.827819025 | SERINC4 | serine incorporator 4 | −1.722466024 |
| NARS2 | asparaginyl-tRNA synthetase 2, mitochondrial (putative) | 2.823087408 | GPR180 | G protein-coupled receptor 180 | −1.722466024 |
| ICAM4 | intercellular adhesion molecule 4 (Landsteiner-Wiener blood group) | 2.81452379 | TIPARP | TCDD inducible poly(ADP-ribose) polymerase | −1.722466024 |
| ABCB8 | ATP binding cassette subfamily B member 8 | 2.813358991 | USP11 | ubiquitin specific peptidase 11 | −1.722466024 |
| IDI1 | isopentenyl-diphosphate delta isomerase 1 | 2.811782922 | TRIP6 | thyroid hormone receptor interactor 6 | −1.722466024 |
| GLS2 | glutaminase 2 | 2.797012978 | KCNH2 | potassium voltage-gated channel subfamily H member 2 | −1.722466024 |
| HDAC8 | histone deacetylase 8 | 2.797012978 | ESR2 | estrogen receptor 2 | −1.722466024 |
| BRIP1 | BRCA1 interacting protein C-terminal helicase 1 | 2.797012978 | FGF13 | fibroblast growth factor 13 | −1.722639247 |
| USP6NL | USP6 N-terminal like | 2.794415866 | KBTBD7 | kelch repeat and BTB domain containing 7 | −1.724237927 |
| TLCD2 | TLC domain containing 2 | 2.791814071 | UHRF1BP1 | UHRF1 binding protein 1 | −1.725835292 |
| GUCY1A3 | guanylate cyclase 1 soluble subunit alpha | 2.787502763 | BCAM | basal cell adhesion molecule (Lutheran blood group) | −1.726509704 |
| OCA2 | OCA2 melanosomal transmembrane protein | 2.786596362 | ELOVL6 | ELOVL fatty acid elongase 6 | −1.726565554 |
| VAT1 | vesicle amine transport 1 | 2.772502543 | PPM1K | protein phosphatase, Mg2+/Mn2+ dependent 1K | −1.726643643 |
| HIST1H2AB | histone cluster 1, H2ab | 2.767914142 | SPATA6 | spermatogenesis associated 6 | −1.727673077 |
| PIGC | phosphatidylinositol glycan anchor biosynthesis class C | 2.760220946 | NAV1 | neuron navigator 1 | −1.727920455 |
| PARG | poly(ADP-ribose) glycohydrolase | 2.756558208 | ANK3 | ankyrin 3, node of Ranvier (ankyrin G) | −1.727920455 |
| ESCO2 | establishment of sister chromatid cohesion N-acetyltransferase 2 | 2.754887502 | KCNAB1 | potassium voltage-gated channel subfamily A member regulatory beta subunit 1 | −1.727920455 |
| HIPK2 | homeodomain interacting protein kinase 2 | 2.754887502 | CYP27A1 | cytochrome P450 family 27 subfamily A member 1 | −1.727920455 |
| IMPA1 | inositol monophosphatase 1 | 2.752945007 | MAP4K4 | mitogen-activated protein kinase kinase kinase kinase 4 | −1.729756006 |
| COQ4 | coenzyme Q4 | 2.744161096 | ANKRD7 | ankyrin repeat domain 7 | −1.730646873 |
| ZBTB7A | zinc finger and BTB domain containing 7A | 2.744161096 | IFRD1 | interferon related developmental regulator 1 | −1.732447522 |

TABLE 2-continued

Differentially regulated genes in CD8⁺4-1BB⁺LAG-3⁺ TILs

| Gene | Gene Description | Log2-Fold Change | Gene Symbol | Gene Description | Log2-Fold Change |
|---|---|---|---|---|---|
| GAMT | guanidinoacetate N-methyltransferase | 2.744161096 | ALX3 | ALX homeobox 3 | −1.733354341 |
| BIK | BCL2 interacting killer | 2.744161096 | SNURF | SNRPN upstream reading frame | −1.733354341 |
| PMS1 | PMS1 homolog 1, mismatch repair system component | 2.733354341 | AMZ2 | archaelysin family metallopeptidase 2 | −1.73350053 |
| HAVCR2 | hepatitis A virus cellular receptor 2 | 2.729769667 | ROGDI | rogdi homolog | −1.73419198 |
| FHL2 | four and a half LIM domains 2 | 2.727254747 | DAGLA | diacylglycerol lipase alpha | −1.734471203 |
| CHAF1A | chromatin assembly factor 1 subunit A | 2.725248783 | 4930432K21RIK | Description Not Found | −1.736243886 |
| 2810004N23RIK | Description Not Found | 2.722466024 | KRCC1 | lysine rich coiled-coil 1 | −1.73665741 |
| TBC1D14 | TBC1 domain family member 14 | 2.722466024 | OLFR1331 | olfactory receptor 1331(Olfr1331) | −1.736826447 |
| EHD2 | EH domain containing 2 | 2.711494907 | SLC25A25 | solute carrier family 25 member 25 | −1.73690749 |
| APH1A | aph-1 homolog A, gamma-secretase subunit | 2.705977902 | CXCR4 | C-X-C motif chemokine receptor 4 | −1.737779353 |
| TMEM2 | transmembrane protein 2 | 2.703211467 | EPB4.1L3 | Description Not Found | −1.738767837 |
| LCAT | lecithin-cholesterol acyltransferase | 2.700439718 | CEP164 | centrosomal protein 164 | −1.738795736 |
| FBXO15 | F-box protein 15 | 2.689299161 | AGER | advanced glycosylation end product-specific receptor | −1.73961488 |
| ADAP1 | ArfGAP with dual PH domains 1 | 2.674391397 | B3GALT5 | beta-1,3-galactosyltransferase 5 | −1.740215306 |
| PPAPDC1B | Description Not Found | 2.666756592 | OLFR450 | olfactory receptor 450(Olfr450) | −1.74228265 |
| CD48 | CD48 molecule | 2.666756592 | ZFP780B | zinc finger protein 780B(Zfp780b) | −1.744161096 |
| CAMK4 | calcium/calmodulin dependent protein kinase IV | 2.655351829 | OLFR485 | olfactory receptor 485(Olfr485) | −1.744161096 |
| SAC3D1 | SAC3 domain containing 1 | 2.64385619 | OLFR47 | olfactory receptor 47(Olfr47) | −1.744161096 |
| ECHDC2 | enoyl-CoA hydratase domain containing 2 | 2.640725033 | CYP4F18 | cytochrome P450, family 4, subfamily f, polypeptide 18(Cyp4f18) | −1.744161096 |
| INCENP | inner centromere protein | 2.638460117 | PLOD2 | procollagen-lysine,2-oxoglutarate 5-dioxygenase 2 | −1.744161096 |
| INTS9 | integrator complex subunit 9 | 2.634920268 | OSBPL1A | oxy sterol binding protein like 1A | −1.744161096 |
| KLRA17 | killer cell lectin-like receptor, subfamily A, member 17(Klra17) | 2.632268216 | CHRNA5 | cholinergic receptor nicotinic alpha 5 subunit | −1.744161096 |
| MAN2B2 | mannosidase alpha class 2B member 2 | 2.632268216 | TSSK4 | testis specific serine kinase 4 | −1.744161096 |
| DOLK | dolichol kinase | 2.632268216 | ALKBH8 | alkB homolog 8, tRNA methyltransferase | −1.744161096 |
| SAP30BP | SAP30 binding protein | 2.632268216 | GPX2 | glutathione peroxidase 2 | −1.744161096 |
| RTN1 | reticulon 1 | 2.627898616 | ATG4D | autophagy related 4D cysteine peptidase | −1.744161096 |
| ADAM15 | ADAM metallopeptidase domain 15 | 2.626439137 | SCRN3 | secernin 3 | −1.744161096 |
| STAG3 | stromal antigen 3 | 2.62058641 | NOTCH3 | notch 3 | −1.744161096 |
| NUDT2 | nudix hydrolase 2 | 2.610775705 | OLFR113 | olfactory receptor 113(Olfr113) | −1.744357436 |
| GLT8D2 | glycosyltransferase 8 domain containing 2 | 2.609988757 | CD28 | CD28 molecule | −1.744605653 |
| CAPSL | calcyphosine like | 2.608809243 | SAG | S-antigen; retina and pineal gland (arrestin) | −1.745224161 |
| CALR | calreticulin | 2.608809243 | AGTRAP | angiotensin II receptor associated protein | −1.749107415 |
| CRYBG3 | crystallin beta-gamma domain containing 3 | 2.605393551 | BLK | BLK proto-oncogene, Src family tyrosine kinase | −1.749534268 |
| DIXDC1 | DIX domain containing 1 | 2.596940379 | MGAT5 | mannosyl (alpha-1,6-)-glycoprotein beta-1,6-N-acetyl-glucosaminyltransferase | −1.749534268 |
| TACSTD2 | tumor-associated calcium signal transducer 2 | 2.593926161 | RNF2 | ring finger protein 2 | −1.750890228 |

TABLE 2-continued

Differentially regulated genes in CD8$^+$4-1BB$^+$LAG-3$^+$ TILs

| Gene | Gene Description | Log2-Fold Change | Gene Symbol | Gene Description | Log2-Fold Change |
|---|---|---|---|---|---|
| TRP53RK | Description Not Found | 2.588066506 | COL14A1 | collagen type XIV alpha 1 chain | −1.752093722 |
| PDCD1LG2 | programmed cell death 1 ligand 2 | 2.584962501 | PLEKHG3 | pleckstrin homology and RhoGEF domain containing G3 | −1.752109698 |
| SEC23IP | SEC23 interacting protein | 2.584962501 | ARHGEF18 | Rho/Rac guanine nucleotide exchange factor 18 | −1.754100479 |
| ORM1 | orosomucoid 1 | 2.584962501 | LEF1 | lymphoid enhancer binding factor 1 | −1.754887502 |
| ZFP322A | zinc finger protein 322A(Zfp322a) | 2.575024164 | COMMD9 | COMM domain containing 9 | −1.75490709 |
| 4931406C07RIK | Description Not Found | 2.560714954 | SLC20A1 | solute carrier family 20 member 1 | −1.758637847 |
| ZFP382 | zinc finger protein 382(Zfp382) | 2.560714954 | ACTR5 | ARP5 actin-related protein 5 homolog | −1.759244091 |
| CLIP2 | CAP-Gly domain containing linker protein 2 | 2.560714954 | UBQLN3 | ubiquilin 3 | −1.765109548 |
| TNFAIP8L1 | TNF alpha induced protein 8 like 1 | 2.560714954 | ZFP770 | zinc finger protein 770(Zfp770) | −1.765534746 |
| NRCAM | neuronal cell adhesion molecule | 2.560714954 | PCDHB18 | protocadherin beta 18(Pcdhb18) | −1.765534746 |
| HPSE | heparanase | 2.560714954 | OLFR700 | olfactory receptor 700(Olfr700) | −1.765534746 |
| RTKN | rhotekin | 2.558985655 | FOXP4 | forkhead box P4 | −1.765534746 |
| DLGAP5 | DLG associated protein 5 | 2.550125328 | CDC34 | cell division cycle 34 | −1.765534746 |
| ENPP2 | ectonucleotide pyrophosphatase/phosphodiesterase 2 | 2.548436625 | HIST1H1E | histone cluster 1, H1e | −1.765534746 |
| GCNT1 | glucosaminyl (N-acetyl) transferase 1, core 2 | 2.548436625 | G6PC2 | glucose-6-phosphatase catalytic subunit 2 | −1.765534746 |
| SASS6 | SAS-6 centriolar assembly protein | 2.548436625 | FUT1 | fucosyltransferase 1 (H blood group) | −1.765534746 |
| AMIGO3 | adhesion molecule with Ig-like domain 3 | 2.548436625 | ZFP69 | ZFP69 zinc finger protein | −1.765534746 |
| APH1B | aph-1 homolog B, gamma-secretase subunit | 2.548436625 | WBSCR27 | Williams Beuren syndrome chromosome region 27 | −1.765534746 |
| ABCC5 | ATP binding cassette subfamily C member 5 | 2.547846505 | METTL8 | methyltransferase like 8 | −1.766880868 |
| YIPF6 | Yip1 domain family member 6 | 2.543805176 | TMEM170 | transmembrane protein 170(Tmem170) | −1.767462508 |
| FFAR1 | free fatty acid receptor 1 | 2.5360529 | TRP53INP1 | transformation related protein 53 inducible nuclear protein 1(Trp53inp1) | −1.767518474 |
| TSSK6 | testis specific serine kinase 6 | 2.5360529 | H2-Q5 | histocompatibility 2, Q region locus 5(H2-Q5) | −1.769676967 |
| ETV6 | ETS variant 6 | 2.535385323 | ADCK1 | aarF domain containing kinase 1 | −1.770033995 |
| PTGDS | prostaglandin D2 synthase | 2.529838423 | IMPAD1 | inositol monophosphatase domain containing 1 | −1.771434505 |
| SH3D19 | SH3 domain containing 19 | 2.523561956 | E4F1 | E4F transcription factor 1 | −1.772427885 |
| KIF5C | kinesin family member 5C | 2.518298014 | ZFYVE20 | Description Not Found | −1.772942676 |
| PTGER2 | prostaglandin E receptor 2 | 2.517275693 | PNPLA6 | patatin like phospholipase domain containing 6 | −1.775074114 |
| INSR | insulin receptor | 2.510961919 | TRIB3 | tribbles pseudokinase 3 | −1.775215233 |
| MAPK6 | mitogen-activated protein kinase 6 | 2.504620392 | GM614 | predicted gene 614(Gm614) | −1.776103988 |
| OXSR1 | oxidative stress responsive 1 | 2.502211192 | D5ERTD579E | DNA segment, Chr 5, ERATO Doi 579, expressed(D5Ertd579e) | −1.776306798 |
| EZH2 | enhancer of zeste 2 polycomb repressive complex 2 subunit | 2.501439145 | SCAND1 | SCAN domain containing 1 | −1.77785827 |
| BNIP1 | BCL2 interacting protein 1 | 2.498250868 | ASB13 | ankyrin repeat and SOCS box containing 13 | −1.782205107 |
| LPCAT4 | lysophosphatidylcholine acyltransferase 4 | 2.495285165 | ARHGEF4 | Rho guanine nucleotide exchange factor 4 | −1.784072601 |
| PPAP2C | Description Not Found | 2.485426827 | H1FNT | H1 histone family member N, testis specific | −1.78485543 |

TABLE 2-continued

Differentially regulated genes in CD8$^+$4-1BB$^+$LAG-3$^+$ TILs

| Gene | Gene Description | Log2-Fold Change | Gene Symbol | Gene Description | Log2-Fold Change |
|---|---|---|---|---|---|
| IFNA12 | interferon alpha 12(Ifna12) | 2.485426827 | BLOC1S1 | biogenesis of lysosomal organelles complex 1 subunit 1 | −1.784911393 |
| DCLK1 | doublecortin like kinase 1 | 2.485426827 | ZFYVE27 | zinc finger FYVE-type containing 27 | −1.7851013 |
| MX1 | MX dynamin like GTPase 1 | 2.485426827 | RHOX4B | reproductive homeobox 4B(Rhox4b) | −1.786596362 |
| SMTN | smoothelin | 2.485426827 | OLFR1134 | olfactory receptor 1134(Olfr1134) | −1.786596362 |
| PLA2G15 | phospholipase A2 group XV | 2.48194563 | CAR11 | carbonic anhydrase 11(Car11) | −1.786596362 |
| OLFR192 | olfactory receptor 192(Olfr192) | 2.472487771 | LRRIQ4 | leucine rich repeats and IQ motif containing 4 | −1.786596362 |
| ITGB5 | integrin subunit beta 5 | 2.472487771 | CASP12 | caspase 12 (gene/pseudogene) | −1.786596362 |
| RAPSN | receptor associated protein of the synapse | 2.465974465 | ODF3L1 | outer dense fiber of sperm tails 3 like 1 | −1.786596362 |
| SNX3 | sorting nexin 3 | 2.459431619 | CCDC3 | coiled-coil domain containing 3 | −1.786596362 |
| FERMT2 | fermitin family member 2 | 2.459431619 | SSPN | sarcospan | −1.786596362 |
| CCR5 | C-C motif chemokine receptor 5 (gene/pseudogene) | 2.444410478 | KLK1 | kallikrein 1 | −1.786596362 |
| UPK1A | uroplakin 1A | 2.439623138 | SENP7 | SUMO1/sentrin specific peptidase 7 | −1.786897131 |
| BCL2L2 | BCL2 like 2 | 2.43629512 | CAML | calcium modulating ligand(Caml) | −1.787735284 |
| 2610002M06RIK | Description Not Found | 2.432959407 | YEATS2 | YEATS domain containing 2 | −1.788627083 |
| CENPN | centromere protein N | 2.432959407 | SERPINF2 | serpin family F member 2 | −1.791814071 |
| HBEGF | heparin binding EGF like growth factor | 2.43096254 | KCNMB1 | potassium calcium-activated channel subfamily M regulatory beta subunit 1 | −1.792597191 |
| TYMS | thymidylate synthetase | 2.427103287 | FCHO2 | FCH domain only 2 | −1.792666489 |
| MGA | MGA, MAX dimerization protein | 2.426939834 | BBS9 | Bardet-Biedl syndrome 9 | −1.792734984 |
| RAI14 | retinoic acid induced 14 | 2.426264755 | OLFR323 | olfactory receptor 323(Olfr323) | −1.794609131 |
| CFI | complement factor I | 2.419538892 | CD247 | CD247 molecule | −1.796081585 |
| PLK4 | polo like kinase 4 | 2.419538892 | HIST2H2AA1 | histone cluster 2, H2aal(Hist2h2aa1) | −1.796847743 |
| SLC6A9 | solute carrier family 6 member 9 | 2.419538892 | PDK1 | pyruvate dehydrogenase kinase 1 | −1.800563818 |
| TMED2 | transmembrane p24 trafficking protein 2 | 2.419538892 | NRARP | NOTCH-regulated ankyrin repeat protein | −1.803049246 |
| TMEM120B | transmembrane protein 120B | 2.41857423 | BTBD11 | BTB domain containing 11 | −1.804793263 |
| TRIM36 | tripartite motif containing 36 | 2.417852515 | CSF2RA | colony stimulating factor 2 receptor alpha subunit | −1.805089518 |
| CCDC93 | coiled-coil domain containing 93 | 2.416164165 | DEXI | Dexi homolog | −1.806998156 |
| SLC25A35 | solute carrier family 25 member 35 | 2.409367225 | OLFR1276 | olfactory receptor 1276(Olfr1276) | −1.807354922 |
| BNC1 | basonuclin 1 | 2.40599236 | TCSTV3 | 2-cell-stage, variable group, member 3(Tcstv3) | −1.807354922 |
| FOXL2 | forkhead box L2 | 2.40599236 | SPRR2D | small proline rich protein 2D | −1.807354922 |
| TFPI2 | tissue factor pathway inhibitor 2 | 2.40599236 | SEMA4G | semaphorin 4G | −1.807354922 |
| NET1 | neuroepithelial cell transforming 1 | 2.40599236 | KCNK9 | potassium two pore domain channel subfamily K member 9 | −1.807354922 |
| SLCO2A1 | solute carrier organic anion transporter family member 2A1 | 2.40599236 | SNAPC3 | small nuclear RNA activating complex polypeptide 3 | −1.807385513 |
| A730008H23RIK | Description Not Found | 2.399275037 | AXIN2 | axin 2 | −1.808429403 |
| CDKN2B | cyclin dependent kinase inhibitor 2B | 2.397264578 | PCNXL3 | Description Not Found | −1.808995133 |
| ZFP532 | zinc finger protein 532(Zfp532) | 2.393138801 | KLHL7 | kelch like family member 7 | −1.809016035 |
| GTSE1 | G2 and S-phase expressed 1 | 2.392428431 | ZFP281 | zinc finger protein 281(Zfp281) | −1.811556991 |

TABLE 2-continued

Differentially regulated genes in CD8⁺4-1BB⁺LAG-3⁺ TILs

| Gene | Gene Description | Log2-Fold Change | Gene Symbol | Gene Description | Log2-Fold Change |
|---|---|---|---|---|---|
| CCDC14 | coiled-coil domain containing 14 | 2.392317423 | CHRNB2 | cholinergic receptor nicotinic beta 2 subunit | −1.812498225 |
| ADAT1 | adenosine deaminase, tRNA specific 1 | 2.392317423 | TBC1D15 | TBC1 domain family member 15 | −1.812909044 |
| DGKH | diacylglycerol kinase eta | 2.392317423 | GALNT9 | polypeptide N-acetylgalactosaminyltransferase 9 | −1.813407449 |
| ZRSR1 | zinc finger CCCH-type, RNA binding motif and serine/arginine rich 1 | 2.392317423 | DYNC1I1 | dynein cytoplasmic 1 intermediate chain 1 | −1.813434179 |
| NFE2 | nuclear factor, erythroid 2 | 2.391529377 | MYH8 | myosin heavy chain 8 | −1.81403224 |
| CD63 | CD63 molecule | 2.387853137 | CEP57 | centrosomal protein 57 | −1.815684972 |
| MIB1 | mindbomb E3 ubiquitin protein ligase 1 | 2.38645559 | LTK | leukocyte receptor tyrosine kinase | −1.817623258 |
| TSN | translin | 2.382349023 | COMMD2 | COMM domain containing 2 | −1.817623258 |
| 2510003E04RIK | Description Not Found | 2.378511623 | MEF2C | myocyte enhancer factor 2C | −1.817623258 |
| BC043934 | cDNA sequence BC043934(BC043934) | 2.378511623 | LONRF2 | LON peptidase N-terminal domain and ring finger 2 | −1.817941412 |
| AHCYL1 | adenosylhomocysteinase like 1 | 2.366734247 | PDCD6IP | programmed cell death 6 interacting protein | −1.820575529 |
| OLFR731 | olfactory receptor 731(Olfr731) | 2.364572432 | DHX16 | DEAH-box helicase 16 | −1.820661084 |
| CDKN2A | cyclin dependent kinase inhibitor 2A | 2.364572432 | ZFYVE19 | zinc finger FYVE-type containing 19 | −1.825281028 |
| SLC29A4 | solute carrier family 29 member 4 | 2.364572432 | H2-T10 | histocompatibility 2, T region locus 10(H2-T10) | −1.826218639 |
| SLC4A10 | solute carrier family 4 member 10 | 2.364572432 | ARID1A | AT-rich interaction domain 1A | −1.827043205 |
| CYCS | cytochrome c, somatic | 2.351872866 | NOD1 | nucleotide binding oligomerization domain containing 1 | −1.827185706 |
| COL5A1 | collagen type V alpha 1 | 2.350497247 | 2610318N02RIK | Description Not Found | −1.827819025 |
| UTRN | utrophin | 2.350497247 | BC048644 | cDNA sequence BC048644(BC048644) | −1.827819025 |
| AURKA | aurora kinase A | 2.349678136 | CDC42EP2 | CDC42 effector protein 2 | −1.827819025 |
| KREMEN2 | kringle containing transmembrane protein 2 | 2.349431709 | CCL25 | C-C motif chemokine ligand 25 | −1.827819025 |
| FGL2 | fibrinogen like 2 | 2.346409407 | TBX6 | T-box 6 | −1.827819025 |
| NCAM1 | neural cell adhesion molecule 1 | 2.343407822 | PLEKHG4 | pleckstrin homology and RhoGEF domain containing G4 | −1.827819025 |
| ALG8 | ALG8, alpha-1,3-glucosyltransferase | 2.343407822 | RAD18 | RAD18, E3 ubiquitin protein ligase | −1.830642494 |
| OLFR703 | olfactory receptor 703(Olfr703) | 2.336283388 | SLC12A9 | solute carrier family 12 member 9 | −1.830807586 |
| SLC39A10 | solute carrier family 39 member 10 | 2.336283388 | NR1D2 | nuclear receptor subfamily 1 group D member 2 | −1.837943242 |
| HIST1H2AH | histone cluster 1, H2ah | 2.322141712 | NLK | nemo like kinase | −1.840170811 |
| TSGA8 | testis specific gene A8(Tsga8) | 2.321928095 | TTC37 | tetratricopeptide repeat domain 37 | −1.840462743 |
| ELOVL2 | ELOVL fatty acid elongase 2 | 2.321928095 | DLG3 | discs large MAGUK scaffold protein 3 | −1.841507525 |
| MLF1 | myeloid leukemia factor 1 | 2.321928095 | PCF11 | PCF11 cleavage and polyadenylation factor subunit | −1.843349827 |
| FZD6 | frizzled class receptor 6 | 2.321928095 | HIST1H4D | histone cluster 1, H4d | −1.846386944 |
| PLD1 | phospholipase D1 | 2.321928095 | PEX26 | peroxisomal biogenesis factor 26 | −1.847440096 |
| IFRD2 | interferon-related developmental regulator 2 | 2.321928095 | CYP2B10 | cytochrome P450, family 2, subfamily b, polypeptide 10(Cyp2b10) | −1.847996907 |
| OLA1 | Obg-like ATPase 1 | 2.321928095 | GDF3 | growth differentiation factor 3 | −1.847996907 |
| ASPA | aspartoacylase | 2.321928095 | GPR33 | G protein-coupled receptor 33 (gene/pseudogene) | −1.847996907 |
| TGFB3 | transforming growth factor beta 3 | 2.321928095 | TDG | thymine DNA glycosylase | −1.847996907 |
| PKIG | protein kinase (cAMP-dependent, catalytic) inhibitor gamma | 2.314696526 | HIPK3 | homeodomain interacting protein kinase 3 | −1.847996907 |
| TNFRSF4 | tumor necrosis factor receptor superfamily member 4 | 2.308832886 | PAPOLA | poly(A) polymerase alpha | −1.847996907 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| IQCB1 | IQ motif containing B1 | 2.307984443 | MAPK4 | mitogen-activated protein kinase 4 | −1.847996907 |
| SLC16A11 | solute carrier family 16 member 11 | 2.307662797 | FRAT2 | frequently rearranged in advanced T-cell lymphomas 2 | −1.84969115 |
| 1190002N15RIK | Description Not Found | 2.307428525 | HEXIM1 | hexamethylene bisacetamide inducible 1 | −1.851035845 |
| LCE1L | late cornified envelope 1L(Lce1l) | 2.307428525 | TATDN2 | TatD DNase domain containing 2 | −1.851433223 |
| RGS13 | regulator of G-protein signaling 13 | 2.307428525 | KLRB1C | killer cell lectin-like receptor subfamily B member 1C(Klrb1c) | −1.854253843 |
| FBXW8 | F-box and WD repeat domain containing 8 | 2.299987517 | SLC16A9 | solute carrier family 16 member 9 | −1.855083462 |
| SNCA | synuclein alpha | 2.296457407 | ACBD4 | acyl-CoA binding domain containing 4 | −1.855739032 |
| OSGIN1 | oxidative stress induced growth inhibitor 1 | 2.294491702 | REXO1 | RNA exonuclease 1 homolog | −1.857980995 |
| BC004004 | cDNA sequence BC004004(BC004004) | 2.292781749 | OLFR1442 | olfactory receptor 1442(Olfr1442) | −1.859286959 |
| WNT10A | Wnt family member 10A | 2.292781749 | PHOSPHO1 | phosphoethanolamine/phosphocholine phosphatase | −1.859747926 |
| THG1L | tRNA-histidine guanylyltransferase 1 like | 2.292781749 | ITPKA | inositol-trisphosphate 3-kinase A | −1.859881803 |
| MLH1 | mutL homolog 1 | 2.292781749 | ZFHX2 | zinc finger homeobox 2 | −1.860513882 |
| RRM2 | ribonucleotide reductase regulatory subunit M2 | 2.289435485 | TOR1A | torsin family 1 member A | −1.860949348 |
| SHISA4 | shisa family member 4 | 2.277984747 | CDKAL1 | CDK5 regulatory subunit associated protein 1 like 1 | −1.862794137 |
| DDAH2 | dimethylarginine dimethylaminohydrolase 2 | 2.277984747 | SMAD1 | SMAD family member 1 | −1.863462947 |
| APBA1 | amyloid beta precursor protein binding family A member 1 | 2.269085766 | ZC3H13 | zinc finger CCCH-type containing 13 | −1.863535399 |
| MMAB | methylmalonic aciduria (cobalamin deficiency) cblB type | 2.264911693 | ZSCAN20 | zinc finger and SCAN domain containing 20 | −1.863962106 |
| DIAP1 | Description Not Found | 2.263034406 | EPB4.1L4A | Description Not Found | −1.867896464 |
| CAR14 | carbonic anhydrase 14(Car14) | 2.263034406 | ZFP280C | zinc finger protein 280C(Zfp280c) | −1.867896464 |
| C2 | complement component 2 | 2.263034406 | GM1322 | predicted gene 1322(Gm1322) | −1.867896464 |
| MAG | myelin associated glycoprotein | 2.263034406 | OLFR472 | olfactory receptor 472(Olfr472) | −1.867896464 |
| KCNIP3 | potassium voltage-gated channel interacting protein 3 | 2.263034406 | OLFR171 | olfactory receptor 171(Olfr171) | −1.867896464 |
| CFD | complement factor D | 2.263034406 | OLFR1249 | olfactory receptor 1249(Olfr1249) | −1.867896464 |
| CCNE1 | cyclin E1 | 2.262723645 | PRH1 | proline rich protein HaeIII subfamily 1 | −1.867896464 |
| RYR1 | ryanodine receptor 1 | 2.261305322 | ARSI | arylsulfatase family member I | −1.867896464 |
| PROC | protein C, inactivator of coagulation factors Va and VIIIa | 2.255500733 | KRT7 | keratin 7 | −1.867896464 |
| ZFP27 | zinc finger protein 27(Zfp27) | 2.247927513 | PCGF3 | polycomb group ring finger 3 | −1.867896464 |
| TBX1 | T-box 1 | 2.247927513 | PCTP | phosphatidylcholine transfer protein | −1.867896464 |
| DHRS13 | dehydrogenase/reductase 13 | 2.247927513 | CALD1 | caldesmon 1 | −1.867896464 |
| HSPG2 | heparan sulfate proteoglycan 2 | 2.247927513 | TREML2 | triggering receptor expressed on myeloid cells like 2 | −1.867896464 |
| FRMD8 | FERM domain containing 8 | 2.24777312 | RTN4RL1 | reticulon 4 receptor like 1 | −1.867896464 |
| MIOX | myo-inositol oxygenase | 2.240579987 | PARVA | parvin alpha | −1.868479018 |
| LYRM1 | LYR motif containing 1 | 2.232660757 | NPCD | neuronal pentraxin chromo domain(Npcd) | −1.871902039 |
| STAP1 | signal transducing adaptor family member 1 | 2.232660757 | RFXANK | regulatory factor X associated ankyrin containing protein | −1.87206109 |

TABLE 2-continued

Differentially regulated genes in CD8⁺4-1BB⁺LAG-3⁺ TILs

| Gene | Gene Description | Log2-Fold Change | Gene Symbol | Gene Description | Log2-Fold Change |
| --- | --- | --- | --- | --- | --- |
| NAT2 | N-acetyltransferase 2 | 2.232660757 | MAP3K14 | mitogen-activated protein kinase kinase kinase 14 | −1.872291304 |
| SRGAP3 | SLIT-ROBO Rho GTPase activating protein 3 | 2.232660757 | KLHL9 | kelch like family member 9 | −1.874528943 |
| NXT2 | nuclear transport factor 2 like export factor 2 | 2.232660757 | SESN1 | sestrin 1 | −1.875260951 |
| RCOR1 | REST corepressor 1 | 2.232660757 | ADAMTS7 | ADAM metallopeptidase with thrombospondin type 1 motif 7 | −1.879404807 |
| SRR | serine racemase | 2.230836503 | SNAPC1 | small nuclear RNA activating complex polypeptide 1 | −1.88488993 |
| IKBKAP | inhibitor of kappa light polypeptide gene enhancer in B-cells, kinase complex-associated protein | 2.226177109 | ADAR | adenosine deaminase, RNA specific | −1.885299379 |
| AI597479 | expressed sequence AI597479(AI597479) | 2.225819675 | LCE1C | late cornified envelope 1C | −1.885626461 |
| POP1 | POP1 homolog, ribonuclease P/MRP subunit | 2.224966365 | FBXO21 | F-box protein 21 | −1.886155099 |
| SLC35E4 | solute carrier family 35 member E4 | 2.217230716 | 2610524H06RIK | Description Not Found | −1.887525271 |
| XAB2 | XPA binding protein 2 | 2.217230716 | 1700016K19RIK | Description Not Found | −1.887525271 |
| MREG | melanoregulin | 2.2129258 | ZFP715 | zinc finger protein 715(Zfp715) | −1.887525271 |
| FKBP11 | FK506 binding protein 11 | 2.210721954 | OLFR446 | olfactory receptor 446(Olfr446) | −1.887525271 |
| IGF2BP2 | insulin like growth factor 2 mRNA binding protein 2 | 2.207789851 | PTK7 | protein tyrosine kinase 7 (inactive) | −1.887525271 |
| NUP133 | nucleoporin 133 | 2.207447199 | TMEM117 | transmembrane protein 117 | −1.887525271 |
| OLFR1183 | olfactory receptor 1183(Olfr1183) | 2.201633861 | ITIH2 | inter-alpha-trypsin inhibitor heavy chain 2 | −1.887525271 |
| IL1F6 | interleukin 1 family, member 6(Il1f6) | 2.201633861 | TAGLN3 | transgelin 3 | −1.887525271 |
| OTX1 | orthodenticle homeobox 1 | 2.201633861 | IFI203 | interferon activated gene 203(Ifi203) | −1.887644112 |
| MSH3 | mutS homolog 3 | 2.201633861 | ATP1B1 | ATPase Na+/K+ transporting subunit beta 1 | −1.887664186 |
| SCN4B | sodium voltage-gated channel beta subunit 4 | 2.201633861 | BLCAP | bladder cancer associated protein | −1.888596201 |
| CROCC | ciliary rootlet coiled-coil, rootletin | 2.201633861 | IGF1R | insulin like growth factor 1 receptor | −1.89024137 |
| NSUN2 | NOP2/Sun RNA methyltransferase family member 2 | 2.194349986 | HMG20A | high mobility group 20A | −1.890579593 |
| GAS2L1 | growth arrest specific 2 like 1 | 2.193771743 | WDR24 | WD repeat domain 24 | −1.891527175 |
| 3110007F17RIK | Description Not Found | 2.190740399 | CDX4 | caudal type homeobox 4 | −1.892655439 |
| DEFB15 | defensin beta 15(Defb15) | 2.185866545 | CLDN18 | claudin 18 | −1.893449375 |
| C1QTNF2 | C1q and tumor necrosis factor related protein 2 | 2.185866545 | IL4RA | interleukin 4 receptor, alpha(Il4ra) | −1.895369594 |
| RAP1GAP | RAP1 GTPase activating protein | 2.185866545 | RETNLA | resistin like alpha(Retnla) | −1.895739477 |
| SNTB1 | syntrophin beta 1 | 2.185866545 | AA388235 | expressed sequence AA388235(AA388235) | −1.895739477 |
| FAH | fumarylacetoacetate hydrolase | 2.182925576 | ZC3H6 | zinc finger CCCH-type containing 6 | −1.896127489 |
| AVPI1 | arginine vasopressin induced 1 | 2.174393775 | D930015E06RIK | RIKEN cDNA D930015E06 gene(D930015E06Rik) | −1.899656973 |
| RPA2 | replication protein A2 | 2.172751912 | NPFFR2 | neuropeptide FF receptor 2 | −1.902073579 |
| BRCA2 | BRCA2, DNA repair associated | 2.168732488 | IRAK1 | interleukin 1 receptor associated kinase 1 | −1.90243374 |
| RBM47 | RNA binding motif protein 47 | 2.165911939 | CWF19L2 | CWF19-like 2, cell cycle control (S. pombe) | −1.903704505 |
| MSL3L2 | male-specific lethal 3-like 2 (Drosophila)(Msl3l2) | 2.159061455 | STK40 | serine/threonine kinase 40 | −1.903964448 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| TNFRSF9 | tumor necrosis factor receptor superfamily member 9 | 2.156071704 | MARS2 | methionyl-tRNA synthetase 2, mitochondrial | −1.904571951 |
| TRF | transferrin(Trf) | 2.154588207 | RAB5A | RAB5A, member RAS oncogene family | −1.906350687 |
| ZDHHC15 | zinc finger DHHC-type containing 15 | 2.154372546 | OLFR1037 | olfactory receptor 1037(Olfr1037) | −1.906890596 |
| IGJ | Description Not Found | 2.153805336 | ARHGAP22 | Rho GTPase activating protein 22 | −1.906890596 |
| FBXO27 | F-box protein 27 | 2.153805336 | DENND1B | DENN domain containing 1B | −1.906890596 |
| ZDHHC24 | zinc finger DHHC-type containing 24 | 2.153805336 | EAPP | E2F associated phosphoprotein | −1.906890596 |
| SPCS2 | signal peptidase complex subunit 2 | 2.153805336 | ANKRD13D | ankyrin repeat domain 13D | −1.906890596 |
| UCN3 | urocortin 3 | 2.153805336 | EFCAB2 | EF-hand calcium binding domain 2 | −1.906890596 |
| SLC35A1 | solute carrier family 35 member A1 | 2.153805336 | HOXC9 | homeobox C9 | −1.906890596 |
| PODXL | podocalyxin like | 2.153805336 | SENP6 | SUMO1/sentrin specific peptidase 6 | −1.907956932 |
| FAM154B | Description Not Found | 2.153792145 | SIDT1 | SID 1 transmembrane family member 1 | −1.908286674 |
| NRP1 | neuropilin 1 | 2.147470553 | 2310057J18RIK | Description Not Found | −1.916476644 |
| ERGIC1 | endoplasmic reticulum-golgi intermediate compartment 1 | 2.147104727 | SPRYD4 | SPRY domain containing 4 | −1.916476644 |
| RNF26 | ring finger protein 26 | 2.146810011 | LY6D | lymphocyte antigen 6 complex, locus D | −1.916476644 |
| LCN3 | lipocalin 3(Lcn3) | 2.137503524 | PPARGC1B | PPARG coactivator 1 beta | −1.917291956 |
| FMO1 | flavin containing monooxygenase 1 | 2.137503524 | SH3TC1 | SH3 domain and tetratricopeptide repeats 1 | −1.917906346 |
| RAB20 | RAB20, member RAS oncogene family | 2.137503524 | FOXO1 | forkhead box O1 | −1.920209106 |
| KATNAL1 | katanin catalytic subunit A1 like 1 | 2.137503524 | DHX40 | DEAH-box helicase 40 | −1.920623917 |
| GPR107 | G protein-coupled receptor 107 | 2.136424717 | RECQL5 | RecQ like helicase 5 | −1.920664575 |
| MELK | maternal embryonic leucine zipper kinase | 2.133399125 | RBM15 | RNA binding motif protein 15 | −1.922616041 |
| KCTD9 | potassium channel tetramerization domain containing 9 | 2.13207329 | EGLN2 | egl-9 family hypoxia inducible factor 2 | −1.924079933 |
| PBK | PDZ binding kinase | 2.130417144 | GPR112 | Description Not Found | −1.925999419 |
| ENPP5 | ectonucleotide pyrophosphatase/phosphodiesterase 5 (putative) | 2.124112676 | OLFR829 | olfactory receptor 829(Olfr829) | −1.925999419 |
| ZDHHC16 | zinc finger DHHC-type containing 16 | 2.12361008 | OLFR684 | olfactory receptor 684(Olfr684) | −1.925999419 |
| OLFR1346 | olfactory receptor 1346(Olfr1346) | 2.121015401 | RETN | resistin | −1.925999419 |
| MILL1 | MHC I like leukocyte 1(Mill1) | 2.121015401 | ST6GALNAC2 | ST6N-acetylgalactosaminide alpha-2,6-sialyltransferase 2 | −1.925999419 |
| RHCG | Rh family C glycoprotein | 2.121015401 | FES | FES proto-oncogene, tyrosine kinase | −1.925999419 |
| CLDN1 | claudin 1 | 2.121015401 | KIF13A | kinesin family member 13A | −1.925999419 |
| LHX3 | LIM homeobox 3 | 2.121015401 | TRPT1 | tRNA phosphotransferase 1 | −1.926457816 |
| TUBB2A | tubulin beta 2A class IIa | 2.121015401 | PLCB2 | phospholipase C beta 2 | −1.927343833 |
| GSG2 | germ cell associated 2, haspin | 2.119412265 | NADSYN1 | NAD synthetase 1 | −1.929674394 |
| HYAL2 | hyaluronoglucosaminidase 2 | 2.107345942 | 4833420G17RIK | Description Not Found | −1.93060469 |
| 1700003F12RIK | Description Not Found | 2.10433666 | P2RY10 | purinergic receptor P2Y10 | −1.930737338 |
| RUSC2 | RUN and SH3 domain containing 2 | 2.10433666 | PPAPDC3 | Description Not Found | −1.935459748 |
| LRRIQ3 | leucine rich repeats and IQ motif containing 3 | 2.10433666 | DIP2B | disco interacting protein 2 homolog B | −1.935459748 |
| CHSY1 | chondroitin sulfate synthase 1 | 2.10433666 | RHAG | Rh-associated glycoprotein | −1.935459748 |
| DUSP23 | dual specificity phosphatase 23 | 2.10433666 | EMID1 | EMI domain containing 1 | −1.935459748 |

TABLE 2-continued

Differentially regulated genes in CD8⁺4-1BB⁺LAG-3⁺ TILs

| Gene | Gene Description | Log2-Fold Change | Gene Symbol | Gene Description | Log2-Fold Change |
|---|---|---|---|---|---|
| RRAGB | Ras related GTP binding B | 2.10433666 | RNF4 | ring finger protein 4 | −1.938834579 |
| KCNAB3 | potassium voltage-gated channel subfamily A regulatory beta subunit 3 | 2.10433666 | UBL5 | ubiquitin like 5 | −1.938952478 |
| GRPEL2 | GrpE like 2, mitochondrial | 2.103129681 | PROSC | proline synthetase cotranscribed homolog (bacterial) | −1.94016675 |
| TRAF2 | TNF receptor associated factor 2 | 2.102029095 | FZD5 | frizzled class receptor 5 | −1.942503137 |
| COQ7 | coenzyme Q7, hydroxylase | 2.100205246 | UBE2D1 | ubiquitin conjugating enzyme E2 D1 | −1.942775467 |
| TMEM126B | transmembrane protein 126B | 2.099187297 | KLRA7 | killer cell lectin-like receptor, subfamily A, member 7(Klra7) | −1.943510757 |
| SGPL1 | sphingosine-1-phosphate lyase 1 | 2.097112667 | TMEM63C | transmembrane protein 63C | −1.94425562 |
| CAPN2 | calpain 2 | 2.096447979 | 2810006K23RIK | Description Not Found | −1.944858446 |
| CHEK2 | checkpoint kinase 2 | 2.088457439 | OLFR672 | olfactory receptor 672(Olfr672) | −1.944858446 |
| GLRP1 | glutamine repeat protein 1(Glrp1) | 2.087462841 | OLFR1347 | olfactory receptor 1347(Olfr1347) | −1.944858446 |
| RTN4R | reticulon 4 receptor | 2.087462841 | MTTP | microsomal triglyceride transfer protein | −1.944858446 |
| TRIM37 | tripartite motif containing 37 | 2.087462841 | MSX1 | msh homeobox 1 | −1.944858446 |
| NUCB2 | nucleobindin 2 | 2.087462841 | BSND | barttin CLCNK type accessory beta subunit | −1.944858446 |
| UBE2T | ubiquitin conjugating enzyme E2 T | 2.073616696 | MARK1 | microtubule affinity regulating kinase 1 | −1.944858446 |
| CREB3L3 | cAMP responsive element binding protein 3 like 3 | 2.070389328 | CHRNB1 | cholinergic receptor nicotinic beta 1 subunit | −1.944858446 |
| CHRM4 | cholinergic receptor muscarinic 4 | 2.070389328 | CRYL1 | crystallin lambda 1 | −1.946419425 |
| SLC16A13 | solute carrier family 16 member 13 | 2.070389328 | TEC | tec protein tyrosine kinase | −1.947330641 |
| OLFML2B | olfactomedin like 2B | 2.070389328 | XKR6 | XK related 6 | −1.95031589 |
| CSNK1G1 | casein kinase 1 gamma 1 | 2.070389328 | ARC | activity-regulated cytoskeleton-associated protein | −1.953636949 |
| S100A14 | S100 calcium binding protein A14 | 2.070389328 | WFDC10 | WAP four-disulfide core domain 10(Wfdc10) | −1.95419631 |
| SMYD4 | SET and MYND domain containing 4 | 2.070389328 | OLFR866 | olfactory receptor 866(Olfr866) | −1.959768144 |
| CH25H | cholesterol 25-hydroxylase | 2.070389328 | WIPI2 | WD repeat domain, phosphoinositide interacting 2 | −1.960171668 |
| TEX2 | testis expressed 2 | 2.067875748 | OLFR948 | olfactory receptor 948(Olfr948) | −1.963474124 |
| SYN1 | synapsin I | 2.063429187 | CRTAM | cytotoxic and regulatory T-cell molecule | −1.963474124 |
| CYP3A13 | cytochrome P450, family 3, subfamily a, polypeptide 13(Cyp3a13) | 2.060581758 | CCDC116 | coiled-coil domain containing 116 | −1.963474124 |
| CBX8 | chromobox 8 | 2.060297534 | ALAS2 | 5'-aminolevulinate synthase 2 | −1.963474124 |
| TOR2A | torsin family 2 member A | 2.056535553 | SDC4 | syndecan 4 | −1.963474124 |
| E230025N22RIK | Riken cDNA E230025N22 gene(E230025N22Rik) | 2.053111336 | LENG1 | leukocyte receptor cluster member 1 | −1.963474124 |
| OLFR963 | olfactory receptor 963(Olfr963) | 2.053111336 | TRIM65 | tripartite motif containing 65 | −1.963474124 |
| OLFR694 | olfactory receptor 694(Olfr694) | 2.053111336 | ADRA2B | adrenoceptor alpha 2B | −1.963474124 |
| AKR1B8 | aldo-keto reductase family 1, member B8(Akr1b8) | 2.053111336 | CPSF4 | cleavage and polyadenylation specific factor 4 | −1.964016356 |
| UGDH | UDP-glucose 6-dehydrogenase | 2.053111336 | LRCH1 | leucine rich repeats and calponin homology domain containing 1 | −1.966068313 |
| CLPB | ClpB homolog, mitochondrial AAA ATPase chaperonin | 2.053111336 | CPXM1 | carboxypeptidase X (M14 family), member 1 | −1.96782195 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| KLHDC9 | kelch domain containing 9 | 2.053111336 | PARP6 | poly(ADP-ribose) polymerase family member 6 | −1.968362498 |
| MCPH1 | microcephalin 1 | 2.051211057 | GTF3C2 | general transcription factor IIIC subunit 2 | −1.975687807 |
| IL2RA | interleukin 2 receptor subunit alpha | 2.049225103 | NEDD4L | neural precursor cell expressed, developmentally down-regulated 4-like, E3 ubiquitin protein ligase | −1.978518523 |
| CAR9 | carbonic anhydrase 9(Car9) | 2.044394119 | DICER1 | dicer 1, ribonuclease III | −1.97959126 |
| USP10 | ubiquitin specific peptidase 10 | 2.044394119 | GBA2 | glucosylceramidase beta 2 | −1.980387638 |
| FASTKD2 | FAST kinase domains 2 | 2.044394119 | OLFR1269 | olfactory receptor 1269(Olfr1269) | −1.981852653 |
| STRA13 | stimulated by retinoic acid 13 | 2.044394119 | EAR10 | eosinophil-associated, ribonuclease A family, member 10(Ear10) | −1.981852653 |
| HIST1H2AD | histone cluster 1, H2ad | 2.044111161 | ADAM5 | ADAM metallopeptidase domain 5 (pseudogene) | −1.981852653 |
| PLA1A | phospholipase A1 member A | 2.037157781 | MED1 | mediator complex subunit 1 | −1.981852653 |
| MCM3 | minichromosome maintenance complex component 3 | 2.036462274 | FGFRL1 | fibroblast growth factor receptor-like 1 | −1.981852653 |
| PIF1 | PIF1 5'-to-3' DNA helicase | 2.036094966 | EXTL1 | exostosin like glycosyltransferase 1 | −1.981852653 |
| GALR1 | galanin receptor 1 | 2.03562391 | ZFHX3 | zinc finger homeobox 3 | −1.981852653 |
| DLD | dihydrolipoamide dehydrogenase | 2.03562391 | FBXO30 | F-box protein 30 | −1.981852653 |
| GGCX | gamma-glutamyl carboxylase | 2.03562391 | RNF112 | ring finger protein 112 | −1.984681148 |
| CEP68 | centrosomal protein 68 | 2.03562391 | PARP3 | poly(ADP-ribose) polymerase family member 3 | −1.98599548 |
| MMP11 | matrix metallopeptidase 11 | 2.03562391 | AIRE | autoimmune regulator | −1.986410935 |
| STMN1 | stathmin 1 | 2.033316653 | CYB561D1 | cytochrome b561 family member D1 | −1.987107951 |
| SLCO4A1 | solute carrier organic anion transporter family member 4A1 | 2.03217627 | TRAPPC5 | trafficking protein particle complex 5 | −1.987269174 |
| TIAL1 | TIA1 cytotoxic granule-associated RNA binding protein-like 1 | 2.02888965 | RFTN2 | raftlin family member 2 | −1.98749308 |
| 0610009B22RIK | Description Not Found | 2.017921908 | FRAT1 | frequently rearranged in advanced T-cell lymphomas 1 | −1.999894159 |
| GM1673 | predicted gene 1673(Gm1673) | 2.017921908 | DMC1 | DNA meiotic recombinase 1 | −2 |
| CCL26 | C-C motif chemokine ligand 26 | 2.017921908 | RIPK4 | receptor interacting serine/threonine kinase 4 | −2 |
| ZWILCH | zwilch kinetochore protein | 2.017921908 | PVR | poliovirus receptor | −2 |
| GABRA1 | gamma-aminobutyric acid type A receptor alpha1 subunit | 2.017921908 | LPIN2 | lipin 2 | −2 |
| ACP2 | acid phosphatase 2, lysosomal | 2.017143376 | THAP2 | THAP domain containing 2 | −2 |
| FAM131A | family with sequence similarity 131 member A | 2.013219985 | SHE | Src homology 2 domain containing E | −2 |
| PXMP4 | peroxisomal membrane protein 4 | 2.012497517 | ARHGAP25 | Rho GTPase activating protein 25 | −2.005618551 |
| CDC6 | cell division cycle 6 | 2.011166077 | CSF1R | colony stimulating factor 1 receptor | −2.006350699 |
| AXL | AXL receptor tyrosine kinase | 2.008131619 | ZFP1 | ZFP1 zinc finger protein | −2.007904843 |
| RBBP7 | RB binding protein 7, chromatin remodeling factor | 2.006746832 | SFN | stratifin | −2.008988783 |
| PABPC4 | poly(A) binding protein cytoplasmic 4 | 2.005260152 | COL17A1 | collagen type XVII alpha 1 | −2.010386372 |

TABLE 2-continued

Differentially regulated genes in CD8⁺4-1BB⁺LAG-3⁺ TILs

| Gene | Gene Description | Log2-Fold Change | Gene Symbol | Gene Description | Log2-Fold Change |
|---|---|---|---|---|---|
| HIST1H2AK | histone cluster 1, H2ak | 2.003307679 | XKRX | XK related, X-linked | −2.0105696 |
| MTFMT | mitochondrial methionyl-tRNA formyltransferase | 2.001754595 | BRD8 | bromodomain containing 8 | −2.01346226 |
| ZFP449 | zinc finger protein 449(Zfp449) | 2 | ZFP213 | zinc finger protein 213(Zfp213) | −2.013532276 |
| D930020B18RIK | RIKEN cDNA D930020B18 gene(D930020B18Rik) | 2 | ZFY2 | zinc finger protein 2, Y-linked(Zfy2) | −2.015657249 |
| LCE1D | late cornified envelope 1D | 2 | MAP3K3 | mitogen-activated protein kinase kinase kinase 3 | −2.01612652 |
| UCN | urocortin | 2 | ZFP445 | zinc finger protein 445(Zfp445) | −2.017921908 |
| SYT4 | synaptotagmin 4 | 2 | MTAP7D3 | MAP7 domain containing 3(Mtap7d3) | −2.017921908 |
| GPR132 | G protein-coupled receptor 132 | 2 | TMPRSS11A | transmembrane protease, serine 11A | −2.017921908 |
| SDHD | succinate dehydrogenase complex subunit D | 2 | OLFM2 | olfactomedin 2 | −2.017921908 |
| PANK3 | pantothenate kinase 3 | 2 | GRM4 | glutamate metabotropic receptor 4 | −2.017921908 |
| SBSN | suprabasin | 1.99095486 | ONECUT2 | one cut homeobox 2 | −2.017921908 |
| WDR59 | WD repeat domain 59 | 1.989976974 | HNRNPH3 | heterogeneous nuclear ribonucleoprotein H3 | −2.017921908 |
| MTMR9 | myotubularin related protein 9 | 1.987844644 | ZMYM5 | zinc finger MYM-type containing 5 | −2.020204421 |
| IL15RA | interleukin 15 receptor subunit alpha | 1.985628881 | RAPGEF6 | Rap guanine nucleotide exchange factor 6 | −2.020953989 |
| RHBDF2 | rhomboid 5 homolog 2 | 1.984681148 | CD34 | CD34 molecule | −2.026714044 |
| NHLRC2 | NHL repeat containing 2 | 1.98375117 | ACVR2B | activin A receptor type 2B | −2.026714044 |
| NMRAL1 | NmrA-like family domain containing 1 | 1.983370163 | RILP | Rab interacting lysosomal protein | −2.026800059 |
| OLFR120 | olfactory receptor 120(Olfr120) | 1.981852653 | EMR1 | Description Not Found | −2.031218731 |
| OLFR1051 | olfactory receptor 1051(Olfr1051) | 1.981852653 | DNAJA2 | DnaJ heat shock protein family (Hsp40) member A2 | −2.031291874 |
| PCDHGA9 | protocadherin gamma subfamily A, 9 | 1.981852653 | SEMA4B | semaphorin 4B | −2.031985281 |
| FST | follistatin | 1.981852653 | 1700015E13RIK | Description Not Found | −2.03562391 |
| RECQL4 | RecQ like helicase 4 | 1.976611605 | RHOX1 | reproductive homeobox 1(Rhox1) | −2.03562391 |
| NFKBIL1 | NFKB inhibitor like 1 | 1.970969489 | TCP11 | t-complex 11 | −2.03562391 |
| TUBD1 | tubulin delta 1 | 1.964367355 | FBXW11 | F-box and WD repeat domain containing 11 | −2.03562391 |
| FSD1 | fibronectin type III and SPRY domain containing 1 | 1.963474124 | ALX1 | ALX homeobox 1 | −2.03562391 |
| GDF5 | growth differentiation factor 5 | 1.963474124 | BST1 | bone marrow stromal cell antigen 1 | −2.03562391 |
| TREML4 | triggering receptor expressed on myeloid cells like 4 | 1.963474124 | GPR83 | G protein-coupled receptor 83 | −2.03562391 |
| SORD | sorbitol dehydrogenase | 1.963474124 | RECK | reversion inducing cysteine rich protein with kazal motifs | −2.036112118 |
| HEBP1 | heme binding protein 1 | 1.963474124 | ABHD14B | abhydrolase domain containing 14B | −2.040460993 |
| KDELR2 | KDEL endoplasmic reticulum protein retention receptor 2 | 1.96155465 | GPRC6A | G protein-coupled receptor class C group 6 member A | −2.042122888 |
| TRPV4 | transient receptor potential cation channel subfamily V member 4 | 1.958842675 | GRAMD3 | GRAM domain containing 3 | −2.042296131 |
| ABHD5 | abhydrolase domain containing 5 | 1.957389419 | IMPACT | impact RWD domain protein | −2.042436285 |
| YOD1 | YOD1 deubiquitinase | 1.95419631 | TOP1 | topoisomerase (DNA) I | −2.044394119 |
| MAGOHB | mago homolog B, exon junction complex core component | 1.952932368 | NACC2 | NACC family member 2 | −2.044394119 |
| TSPAN2 | tetraspanin 2 | 1.95176103 | PKNOX1 | PBX/knotted 1 homeobox 1 | −2.045797958 |
| LDB3 | LIM domain binding 3 | 1.94850842 | TMEM79 | transmembrane protein 79 | −2.046628729 |
| 1700067P10RIK | Description Not Found | 1.944858446 | MYCBP2 | MYC binding protein 2, E3 ubiquitin protein ligase | −2.047368853 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| 9530091C08RIK | Description Not Found | 1.944858446 | MAS1 | MAS1 proto-oncogene, G protein-coupled receptor | −2.048055651 |
| RHOJ | ras homolog family member J | 1.944858446 | GEMIN6 | gem nuclear organelle associated protein 6 | −2.053111336 |
| SFRP1 | secreted frizzled related protein 1 | 1.944858446 | TMEM100 | transmembrane protein 100 | −2.053111336 |
| XPNPEP2 | X-prolyl aminopeptidase (aminopeptidase P) 2, membrane-bound | 1.944858446 | FOXI1 | forkhead box I1 | −2.053111336 |
| RNASE4 | ribonuclease A family member 4 | 1.935459748 | OPLAH | 5-oxoprolinase (ATP-hydrolysing) | −2.053111336 |
| NAPSA | napsin A aspartic peptidase | 1.931586931 | BC094916 | Description Not Found | −2.058337935 |
| TIMM22 | translocase of inner mitochondrial membrane 22 homolog (yeast) | 1.931202999 | GZMM | granzyme M | −2.061193332 |
| MTCH2 | mitochondrial carrier 2 | 1.929774464 | RCOR2 | REST corepressor 2 | −2.06280495 |
| ADCK4 | aarF domain containing kinase 4 | 1.927921426 | NR2E1 | nuclear receptor subfamily 2 group E member 1 | −2.06366268 |
| PDSS1 | prenyl (decaprenyl) diphosphate synthase, subunit 1 | 1.926245513 | NT5DC1 | 5'-nucleotidase domain containing 1 | −2.065994119 |
| ZFP94 | zinc finger protein 94(Zfp94) | 1.925999419 | SCN8A | sodium voltage-gated channel alpha subunit 8 | −2.06750099 |
| FABP9 | fatty acid binding protein 9 | 1.925999419 | CBX7 | chromobox 7 | −2.06750099 |
| RNF170 | ring finger protein 170 | 1.925999419 | FHAD1 | forkhead associated phosphopeptide binding domain 1 | −2.068114527 |
| TLR3 | toll like receptor 3 | 1.925999419 | KCNQ3 | potassium voltage-gated channel subfamily Q member 3 | −2.068885643 |
| LIPH | lipase H | 1.925999419 | BC025920 | zinc finger protein pseudogene(BC025920) | −2.070389328 |
| PLEKHA7 | pleckstrin homology domain containing A7 | 1.925999419 | FCGR1 | Fc receptor, IgG, high affinity I(Fcgr1) | −2.070389328 |
| LXN | latexin | 1.9244606 | SYN3 | synapsin III | −2.070389328 |
| PPCS | phosphopantothenoylcysteine synthetase | 1.92294738 | KLHL5 | kelch like family member 5 | −2.070389328 |
| BTRC | beta-transducin repeat containing E3 ubiquitin protein ligase | 1.92065845 | EDA2R | ectodysplasin A2 receptor | −2.070389328 |
| APIP | APAF1 interacting protein | 1.920326443 | STK38 | serine/threonine kinase 38 | −2.070389328 |
| ANK1 | ankyrin 1 | 1.916476644 | CDKN2D | cyclin dependent kinase inhibitor 2D | −2.072205467 |
| TOMM70A | translocase of outer mitochondrial membrane 70 homolog A (yeast)(Tomm70a) | 1.913107017 | IL6ST | interleukin 6 signal transducer | −2.072660321 |
| ABCB1B | ATP-binding cassette, sub-family B (MDR/TAP), member 1B(Abcb1b) | 1.908033945 | OLFR427 | olfactory receptor 427(Olfr427) | −2.074318985 |
| ACN9 | Description Not Found | 1.906890596 | BAIAP2 | BAI1 associated protein 2 | −2.078951341 |
| DLX1AS | distal-less homeobox 1, antisense(Dlx1as) | 1.906890596 | TIMP2 | TIMP metallopeptidase inhibitor 2 | −2.079805224 |
| MRGPRD | MAS related GPR family member D | 1.906890596 | CDCP1 | CUB domain containing protein 1 | −2.083991945 |
| WDHD1 | WD repeat and HMG-box DNA binding protein 1 | 1.906890596 | RGS14 | regulator of G-protein signaling 14 | −2.084198537 |
| USP46 | ubiquitin specific peptidase 46 | 1.906890596 | VASP | vasodilator-stimulated phosphoprotein | −2.086359868 |
| PKN3 | protein kinase N3 | 1.906890596 | ZFP318 | zinc finger protein 318(Zfp318) | −2.087462841 |
| OSCAR | osteoclast associated, immunoglobulin-like receptor | 1.906890596 | PSG25 | pregnancy-specific glycoprotein 25(Psg25) | −2.087462841 |
| CDK2 | cyclin dependent kinase 2 | 1.906746727 | PDZD8 | PDZ domain containing 8 | −2.087462841 |
| TRIM62 | tripartite motif containing 62 | 1.905520967 | DET1 | de-etiolated homolog 1 (Arabidopsis) | −2.087462841 |
| SQLE | squalene epoxidase | 1.903767694 | CHST3 | carbohydrate sulfotransferase 3 | −2.087462841 |

TABLE 2-continued

Differentially regulated genes in CD8⁺4-1BB⁺LAG-3⁺ TILs

| Gene | Gene Description | Log2-Fold Change | Gene Symbol | Gene Description | Log2-Fold Change |
|---|---|---|---|---|---|
| MCM10 | minichromosome maintenance 10 replication initiation factor | 1.89598378 | EHHADH | enoyl-CoA, hydratase/3-hydroxyacyl CoA dehydrogenase | −2.087462841 |
| CCDC90B | coiled-coil domain containing 90B | 1.894803124 | FCGRT | Fc fragment of IgG receptor and transporter | −2.090735607 |
| SPATS1 | spermatogenesis associated serine rich 1 | 1.892848083 | CFP | complement factor properdin | −2.09437407 |
| GPNMB | glycoprotein nmb | 1.891427809 | SOCS6 | suppressor of cytokine signaling 6 | −2.094638136 |
| MST1 | macrophage stimulating 1 | 1.88993148 | SYT11 | synaptotagmin 11 | −2.09592442 |
| LTB4R1 | leukotriene B4 receptor 1(Ltb4r1) | 1.887644112 | MBTPS2 | membrane bound transcription factor peptidase, site 2 | −2.09592442 |
| DNAJC5B | DnaJ heat shock protein family (Hsp40) member C5 beta | 1.887525271 | MEFV | Mediterranean fever | −2.097059135 |
| PCDHGC4 | protocadherin gamma subfamily C, 4 | 1.887525271 | SRPK2 | SRSF protein kinase 2 | −2.10044313 |
| HMX2 | H6 family homeobox 2 | 1.887525271 | DUSP16 | dual specificity phosphatase 16 | −2.102740277 |
| NDUFAB1 | NADH: ubiquinone oxidoreductase subunit AB1 | 1.887525271 | SLC6A7 | solute carrier family 6 member 7 | −2.103129681 |
| MGP | matrix Gla protein | 1.887525271 | HBB-B1 | hemoglobin, beta adult major chain(Hbb-b1) | −2.10433666 |
| ZKSCAN2 | zinc finger with KRAB and SCAN domains 2 | 1.887525271 | TNPO3 | transportin 3 | −2.10433666 |
| CCDC51 | coiled-coil domain containing 51 | 1.887525271 | CSNK2B | casein kinase 2 beta | −2.10433666 |
| CTSK | cathepsin K | 1.887525271 | BCAS1 | breast carcinoma amplified sequence 1 | −2.10433666 |
| PRDM9 | PR domain 9 | 1.887525271 | INO80 | INO80 complex subunit | −2.10433666 |
| C8A | complement component 8 alpha subunit | 1.887525271 | MPG | N-methylpurine DNA glycosylase | −2.10433666 |
| NEUROG1 | neurogenin 1 | 1.887082413 | FOXP1 | forkhead box P1 | −2.107557734 |
| NUSAP1 | nucleolar and spindle associated protein 1 | 1.886951242 | USP21 | ubiquitin specific peptidase 21 | −2.107658353 |
| LZIC | leucine zipper and CTNNBIP1 domain containing | 1.877899051 | LIMS1 | LIM zinc finger domain containing 1 | −2.112700133 |
| ZFP609 | zinc finger protein 609(Zfp609) | 1.87774425 | FXYD1 | FXYD domain containing ion transport regulator 1 | −2.112700133 |
| GPR87 | G protein-coupled receptor 87 | 1.87774425 | POU3F1 | POU class 3 homeobox 1 | −2.113574207 |
| GMPPB | GDP-mannose pyrophosphorylase B | 1.871523637 | OLFR591 | olfactory receptor 591(Olfr591) | −2.114494844 |
| TMEM115 | transmembrane protein 115 | 1.870364796 | GRAMD4 | GRAM domain containing 4 | −2.114673101 |
| DSN1 | DSN1 homolog, MIS12 kinetochore complex component | 1.868479018 | BCL2 | BCL2, apoptosis regulator | −2.115878669 |
| A530099J19RIK | Description Not Found | 1.867896464 | PELI3 | pellino E3 ubiquitin protein ligase family member 3 | −2.118915146 |
| 1700007K09RIK | Description Not Found | 1.867896464 | PPP1CB | protein phosphatase 1 catalytic subunit beta | −2.119236221 |
| 1810043G02RIK | Description Not Found | 1.867896464 | TFF2 | trefoil factor 2 | −2.121015401 |
| UCHL1 | ubiquitin C-terminal hydrolase L1 | 1.867896464 | GCA | grancalcin | −2.121015401 |
| PTCH2 | patched 2 | 1.867896464 | LYL1 | LYL1, basic helix-loop-helix family member | −2.121015401 |
| APBB3 | amyloid beta precursor protein binding family B member 3 | 1.867896464 | ATG4B | autophagy related 4B cysteine peptidase | −2.121015401 |
| PTER | phosphotriesterase related | 1.867896464 | CCDC102A | coiled-coil domain containing 102A | −2.121015401 |
| PRKCE | protein kinase C epsilon | 1.867896464 | ATP2A1 | ATPase sarcoplasmic/endoplasmic reticulum Ca2+ transporting 1 | −2.121015401 |

TABLE 2-continued

Differentially regulated genes in CD8$^+$4-1BB$^+$LAG-3$^+$ TILs

| Gene | Gene Description | Log2-Fold Change | Gene Symbol | Gene Description | Log2-Fold Change |
| --- | --- | --- | --- | --- | --- |
| PLEKHM3 | pleckstrin homology domain containing M3 | 1.867896464 | TERF2 | telomeric repeat binding factor 2 | -2.123585568 |
| HIST1H4C | histone cluster 1, H4c | 1.867896464 | LCN5 | lipocalin 5(Lcn5) | -2.124432612 |
| PLS3 | plastin 3 | 1.867896464 | TM6SF1 | transmembrane 6 superfamily member 1 | -2.124533495 |
| DUSP4 | dual specificity phosphatase 4 | 1.867686654 | SSBP2 | single stranded DNA binding protein 2 | -2.129283017 |
| SCLY | selenocysteine lyase | 1.862802277 | KRTAP6-2 | keratin associated protein 6-2 | -2.137503524 |
| RPRD1A | regulation of nuclear pre-mRNA domain containing 1A | 1.861777838 | CRHBP | corticotropin releasing hormone binding protein | -2.137503524 |
| CCRL2 | C-C motif chemokine receptor like 2 | 1.86175579 | TOPBP1 | topoisomerase (DNA) II binding protein 1 | -2.137503524 |
| CCT7 | chaperonin containing TCP1 subunit 7 | 1.861636037 | SLC35A3 | solute carrier family 35 member A3 | -2.137503524 |
| ZFP217 | zinc finger protein 217(Zfp217) | 1.861097096 | CACNB4 | calcium voltage-gated channel auxiliary subunit beta 4 | -2.137503524 |
| ACTN4 | actinin alpha 4 | 1.859689938 | TASP1 | taspase 1 | -2.137503524 |
| KCNA3 | potassium voltage-gated channel subfamily A member 3 | 1.859135363 | HMBOX1 | homeobox containing 1 | -2.145313833 |
| CUL7 | cullin 7 | 1.858597911 | ZFP62 | ZFP62 zinc finger protein | -2.145677455 |
| LRRC59 | leucine rich repeat containing 59 | 1.857543219 | PCDHB4 | protocadherin beta 4 | -2.148666128 |
| PHTF2 | putative homeodomain transcription factor 2 | 1.855602651 | SLC35F3 | solute carrier family 35 member F3 | -2.15120644 |
| KDELC1 | KDEL motif containing 1 | 1.852556218 | AW549877 | expressed sequence AW549877(AW549877) | -2.151324826 |
| SEC24D | SEC24 homolog D, COPII coat complex component | 1.8483841 | GIMAP9 | GTPase, IMAP family member 9(Gimap9) | -2.152400921 |
| OLFR222 | olfactory receptor 222(Olfr222) | 1.847996907 | ZFP329 | zinc finger protein 329(Zfp329) | -2.153805336 |
| OLFR118 | olfactory receptor 118(Olfr118) | 1.847996907 | KRT74 | keratin 74 | -2.153805336 |
| CASKIN2 | CASK interacting protein 2 | 1.847996907 | REG3A | regenerating family member 3 alpha | -2.153805336 |
| TPK1 | thiamin pyrophosphokinase 1 | 1.847996907 | RAB4A | RAB4A, member RAS oncogene family | -2.154308231 |
| NOL3 | nucleolar protein 3 | 1.847996907 | CECR5 | cat eye syndrome chromosome region, candidate 5 | -2.155682653 |
| UBA6 | ubiquitin like modifier activating enzyme 6 | 1.847388943 | ESM1 | endothelial cell specific molecule 1 | -2.157156463 |
| RAVER1 | ribonucleoprotein, PTB binding 1 | 1.846151947 | HS6ST1 | heparan sulfate 6-O-sulfotransferase 1 | -2.164820712 |
| NAT10 | N-acetyltransferase 10 | 1.843300131 | DDB2 | damage specific DNA binding protein 2 | -2.168338824 |
| HIST1H3H | histone cluster 1, H3h | 1.842055889 | 5430435G22RIK | Description Not Found | -2.169925001 |
| SNX8 | sorting nexin 8 | 1.840985134 | ALOX12B | arachidonate 12-lipoxygenase, 12R type | -2.169925001 |
| POLR3K | polymerase (RNA) III subunit K | 1.839538616 | SLC34A3 | solute carrier family 34 member 3 | -2.169925001 |
| WDR55 | WD repeat domain 55 | 1.835957408 | TNS4 | tensin 4 | -2.169925001 |
| WDR93 | WD repeat domain 93 | 1.830541464 | CANX | calnexin | -2.169925001 |
| PLSCR1 | phospholipid scramblase 1 | 1.828635636 | BET1 | Bet1 golgi vesicular membrane trafficking protein | -2.169925001 |
| ARL6 | ADP ribosylation factor like GTPase 6 | 1.827819025 | BEST2 | bestrophin 2 | -2.169925001 |
| NOL9 | nucleolar protein 9 | 1.827819025 | USP28 | ubiquitin specific peptidase 28 | -2.172998154 |
| PNKD | paroxysmal nonkinesigenic dyskinesia | 1.827819025 | PDE4B | phosphodiesterase 4B | -2.173614018 |
| TMEM139 | transmembrane protein 139 | 1.827819025 | CNOT4 | CCR4-NOT transcription complex subunit 4 | -2.177917792 |
| ASPH | aspartate beta-hydroxylase | 1.827819025 | NECAP1 | NECAP endocytosis associated 1 | -2.178043245 |
| LZTFL1 | leucine zipper transcription factor like 1 | 1.827819025 | JUN | Jun proto-oncogene, AP-1 transcription factor subunit | -2.178565309 |
| RHEBL1 | Ras homolog enriched in brain like 1 | 1.827819025 | SLC10A7 | solute carrier family 10 member 7 | -2.17990909 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| CHCHD5 | coiled-coil-helix-coiled-coil-helix domain containing 5 | 1.82552849 | IL17A | interleukin 17A | −2.181702586 |
| GPD2 | glycerol-3-phosphate dehydrogenase 2 | 1.824148697 | ERICH1 | glutamate rich 1 | −2.182286216 |
| STK39 | serine/threonine kinase 39 | 1.823608879 | HN1L | hematological and neurological expressed 1-like | −2.185866545 |
| MAGED2 | MAGE family member D2 | 1.820863253 | SLFNL1 | schlafen like 1 | −2.185866545 |
| TBC1D9B | TBC1 domain family member 9B | 1.813219568 | MYOD1 | myogenic differentiation 1 | −2.185866545 |
| LSS | lanosterol synthase (2,3-oxidosqualene-lanosterol cyclase) | 1.809540228 | TRIM35 | tripartite motif containing 35 | −2.185866545 |
| OLFR859 | olfactory receptor 859(Olfr859) | 1.807354922 | CHRNE | cholinergic receptor nicotinic epsilon subunit | −2.186397884 |
| OLFR1225 | olfactory receptor 1225(Olfr1225) | 1.807354922 | PHF21A | PHD finger protein 21A | −2.190943197 |
| IFNA11 | interferon alpha 11(Ifna11) | 1.807354922 | HIST1H2AE | histone cluster 1, H2ae | −2.196698179 |
| ARG1 | arginase 1 | 1.807354922 | SATB1 | SATB homeobox 1 | −2.198659952 |
| ASCL3 | achaete-scute family bHLH transcription factor 3 | 1.807354922 | LCN8 | lipocalin 8 | −2.201633861 |
| AGA | aspartylglucosaminidase | 1.807354922 | ABCG5 | ATP binding cassette subfamily G member 5 | −2.201633861 |
| MAP3K12 | mitogen-activated protein kinase kinase kinase 12 | 1.806530545 | KRBA1 | KRAB-A domain containing 1 | −2.202959029 |
| COMMD10 | COMM domain containing 10 | 1.802771724 | CD274 | CD274 molecule | −2.206081393 |
| STYX | serine/threonine/tyrosine interacting protein | 1.801251483 | DYRK2 | dual specificity tyrosine phosphorylation regulated kinase 2 | −2.206730511 |
| EPHA6 | EPH receptor A6 | 1.797583147 | ZFP292 | zinc finger protein 292(Zfp292) | −2.209453366 |
| SERPINA3F | serine (or cysteine) peptidase inhibitor, clade A, member 3F(Serpina3f) | 1.794445043 | PRX | periaxin | −2.209453366 |
| PUS10 | pseudouridylate synthase 10 | 1.791814071 | SPAG1 | sperm associated antigen 1 | −2.209453366 |
| RASL12 | RAS like family 12 | 1.791652715 | ASGR2 | asialoglycoprotein receptor 2 | −2.209784456 |
| MRPL51 | mitochondrial ribosomal protein L51 | 1.787631232 | PTEN | phosphatase and tensin homolog | −2.215013513 |
| OLFR1306 | olfactory receptor 1306(Olfr1306) | 1.786596362 | IL1A | interleukin 1 alpha | −2.217230716 |
| BCL2A1C | B cell leukemia/lymphoma 2 related protein A1c(Bcl2a1c) | 1.786596362 | TPCN2 | two pore segment channel 2 | −2.217230716 |
| HOXD1 | homeobox D1 | 1.786596362 | IKBKB | inhibitor of kappa light polypeptide gene enhancer in B-cells, kinase beta | −2.217230716 |
| MEMO1 | mediator of cell motility 1 | 1.786596362 | ST6GAL1 | ST6 beta-galactoside alpha-2,6-sialyltransferase 1 | −2.218342351 |
| ARCN1 | archain 1 | 1.786596362 | TMEM161A | transmembrane protein 161A | −2.232660757 |
| NUDT10 | nudix hydrolase 10 | 1.786596362 | STK32B | serine/threonine kinase 32B | −2.232660757 |
| SLC4A4 | solute carrier family 4 member 4 | 1.786596362 | CHST14 | carbohydrate sulfotransferase 14 | −2.232660757 |
| DHRS4 | dehydrogenase/reductase 4 | 1.786596362 | AQP3 | aquaporin 3 (Gill blood group) | −2.232660757 |
| TOM1 | target of myb1 membrane trafficking protein | 1.786596362 | RASSF3 | Ras association domain family member 3 | −2.233505898 |
| TST | thiosulfate sulfurtransferase | 1.786596362 | OTUD7B | OTU deubiquitinase 7B | −2.242923867 |
| RIPK2 | receptor interacting serine/threonine kinase 2 | 1.784428584 | AP3M2 | adaptor related protein complex 3 mu 2 subunit | −2.247481244 |

TABLE 2-continued

Differentially regulated genes in CD8⁺4-1BB⁺LAG-3⁺ TILs

| Gene | Gene Description | Log2-Fold Change | Gene Symbol | Gene Description | Log2-Fold Change |
|---|---|---|---|---|---|
| NAIP2 | NLR family, apoptosis inhibitory protein 2(Naip2) | 1.780351745 | PSMA6 | proteasome subunit alpha 6 | -2.247927513 |
| OLFR133 | olfactory receptor 133(Olfr133) | 1.77946628 | PRCC | papillary renal cell carcinoma (translocation-associated) | -2.247927513 |
| NBR1 | NBR1, autophagy cargo receptor | 1.776995396 | ZFP688 | zinc finger protein 688(Zfp688) | -2.262218541 |
| GLIS1 | GLIS family zinc finger 1 | 1.776512203 | DOCK11 | dedicator of cytokinesis 11 | -2.262218541 |
| SLC35A2 | solute carrier family 35 member A2 | 1.776232819 | PLA2G4F | phospholipase A2 group IVF | -2.263034406 |
| AU022252 | expressed sequence AU022252(AU022252) | 1.774559318 | MYPN | myopalladin | -2.263034406 |
| OLFR64 | olfactory receptor 64(Olfr64) | 1.773991786 | FRS2 | fibroblast growth factor receptor substrate 2 | -2.263034406 |
| PPAPDC2 | Description Not Found | 1.771983065 | STARD6 | StAR related lipid transfer domain containing 6 | -2.263034406 |
| DIS3 | DIS3 homolog, exosome endoribonuclease and 3'-5' exoribonuclease | 1.771375295 | WSCD2 | WSC domain containing 2 | -2.270653766 |
| 4931440F15RIK | Description Not Found | 1.770829046 | TLE1 | transducin like enhancer of split 1 | -2.272631746 |
| ZFP771 | zinc finger protein 771(Zfp771) | 1.77019569 | HDHD3 | haloacid dehalogenase like hydrolase domain containing 3 | -2.272966802 |
| HMBS | hydroxymethylbilane synthase | 1.769676967 | 1700029J07RIK | Description Not Found | -2.277984747 |
| RCC1 | regulator of chromosome condensation 1 | 1.768267605 | CLEC2D | C-type lectin domain family 2 member D | -2.277984747 |
| SPAG5 | sperm associated antigen 5 | 1.767980257 | PPM1G | protein phosphatase, Mg2+/Mn2+ dependent 1G | -2.277984747 |
| TSPAN31 | tetraspanin 31 | 1.767626782 | CDKN1B | cyclin dependent kinase inhibitor 1B | -2.280970508 |
| PCDHGB8 | protocadherin gamma subfamily B, 8(Pcdhgb8) | 1.765534746 | OASL1 | 2'-5' oligoadenylate synthetase-like 1(Oasl1) | -2.28169825 |
| PRL2B1 | prolactin family 2, subfamily b, member 1(Prl2b1) | 1.765534746 | G0S2 | G0/G1 switch 2 | -2.282045463 |
| OBOX5 | oocyte specific homeobox 5(Obox5) | 1.765534746 | TMEM17 | transmembrane protein 17 | -2.285402219 |
| PIK3R3 | phosphoinositide-3-kinase regulatory subunit 3 | 1.765534746 | BLVRB | biliverdin reductase B | -2.290619427 |
| MAP3K4 | mitogen-activated protein kinase kinase kinase 4 | 1.765534746 | GOSR1 | golgi SNAP receptor complex member 1 | -2.290897209 |
| LRRC30 | leucine rich repeat containing 30 | 1.765534746 | ZFP26 | zinc finger protein 26(Zfp26) | -2.292781749 |
| EN2 | engrailed homeobox 2 | 1.765534746 | CXCL2 | C-X-C motif chemokine ligand 2 | -2.292781749 |
| HOOK3 | hook microtubule-tethering protein 3 | 1.765534746 | SNX7 | sorting nexin 7 | -2.292781749 |
| MYO9A | myosin IXA | 1.765534746 | ZDHHC23 | zinc finger DHHC-type containing 23 | -2.292781749 |
| STX7 | syntaxin 7 | 1.765060364 | GALNT6 | polypeptide N-acetylgalactosaminyltransferase 6 | -2.292781749 |
| ATM | ATM serine/threonine kinase | 1.763504031 | AMPD1 | adenosine monophosphate deaminase 1 | -2.297844157 |
| KCNK6 | potassium two pore domain channel subfamily K member 6 | 1.763385753 | GIMAP5 | GTPase, IMAP family member 5 | -2.303246615 |
| PQLC3 | PQ loop repeat containing 3 | 1.759954577 | ATP5F1 | ATP synthase, H+ transporting, mitochondrial Fo complex subunit B1 | -2.305399163 |
| KIFAP3 | kinesin associated protein 3 | 1.758843168 | LHFPL2 | lipoma HMGIC fusion partner-like 2 | -2.307428525 |
| E2F4 | E2F transcription factor 4 | 1.757752886 | KIF1B | kinesin family member 1B | -2.313231129 |
| ETV5 | ETS variant 5 | 1.757709335 | TLE6 | transducin like enhancer of split 6 | -2.321928095 |

TABLE 2-continued

Differentially regulated genes in CD8$^+$4-1BB$^+$LAG-3$^+$ TILs

| Gene | Gene Description | Log2-Fold Change | Gene Symbol | Gene Description | Log2-Fold Change |
|---|---|---|---|---|---|
| GTF2E2 | general transcription factor IIE subunit 2 | 1.75666387 | SHF | Src homology 2 domain containing F | −2.330691998 |
| GPR150 | G protein-coupled receptor 150 | 1.75547927 | NGFR | nerve growth factor receptor | −2.331438521 |
| E130308A19RIK | RIKEN cDNA E130308A19 gene(E130308A19Rik) | 1.754887502 | KLRA4 | killer cell lectin-like receptor, subfamily A, member 4(Klra4) | −2.334485632 |
| DPYSL4 | dihydropyrimidinase like 4 | 1.754887502 | ITGAE | integrin subunit alpha E | −2.335948972 |
| FNBP1 | formin binding protein 1 | 1.75468902 | PQLC2 | PQ loop repeat containing 2 | −2.336141568 |
| TMOD4 | tropomodulin 4 | 1.754064107 | KLRB1A | killer cell lectin-like receptor subfamily B member 1A(Klrb1a) | −2.336283388 |
| ERLIN1 | ER lipid raft associated 1 | 1.751154691 | IRF9 | interferon regulatory factor 9 | −2.336308285 |
| ENOPH1 | enolase-phosphatase 1 | 1.748447442 | GATA3 | GATA binding protein 3 | −2.338971433 |
| RAB31 | RAB31, member RAS oncogene family | 1.746215332 | RSAD2 | radical S-adenosyl methionine domain containing 2 | −2.33997952 |
| HOXA6 | homeobox A6 | 1.745184623 | RNF215 | ring finger protein 215 | −2.341976415 |
| TAS2R126 | taste receptor, type 2, member 126(Tas2r126) | 1.744161096 | IL7R | interleukin 7 receptor | −2.343395577 |
| AGXT2 | alanine-glyoxylate aminotransferase 2 | 1.744161096 | ACP5 | acid phosphatase 5, tartrate resistant | −2.345270806 |
| STK32C | serine/threonine kinase 32C | 1.744161096 | STYXL1 | serine/threonine/tyrosine interacting-like 1 | −2.346956889 |
| P2RY2 | purinergic receptor P2Y2 | 1.744161096 | NOXO1 | NADPH oxidase organizer 1 | −2.35030956 |
| NWD1 | NACHT and WD repeat domain containing 1 | 1.744161096 | IGFALS | insulin like growth factor binding protein acid labile subunit | −2.358664554 |
| UQCRQ | ubiquinol-cytochrome c reductase complex III subunit VII | 1.744161096 | STIM1 | stromal interaction molecule 1 | −2.359335599 |
| PPP1R3A | protein phosphatase 1 regulatory subunit 3A | 1.744161096 | TMEM186 | transmembrane protein 186 | −2.361030771 |
| GOLT1A | golgi transport 1A | 1.744161096 | OLFR1043 | olfactory receptor 1043(Olfr1043) | −2.364572432 |
| EZH1 | enhancer of zeste 1 polycomb repressive complex 2 subunit | 1.744161096 | D8ERTD82E | DNA segment, Chr 8, ERATO Doi 82, expressed(D8Ertd82e) | −2.364572432 |
| MTHFD2 | methylenetetrahydrofolate dehydrogenase (NADP+ dependent) 2, methenyltetrahydrofolate cyclohydrolase | 1.744154314 | MYOG | myogenin | −2.364572432 |
| PGRMC1 | progesterone receptor membrane component 1 | 1.742545062 | NCLN | nicalin | −2.364572432 |
| DNAJB12 | DnaJ heat shock protein family (Hsp40) member B12 | 1.741863621 | MTSS1 | metastasis suppressor 1 | −2.364572432 |
| DNAJC11 | DnaJ heat shock protein family (Hsp40) member C11 | 1.738767837 | TRMU | tRNA 5-methylaminomethyl-2-thiouridylate methyltransferase | −2.364572432 |
| TOMM6 | translocase of outer mitochondrial membrane 6 | 1.738448709 | EMILIN2 | elastin microfibril interfacer 2 | −2.369119767 |
| RPS6KL1 | ribosomal protein S6 kinase like 1 | 1.738393453 | MPV17L | MPV17 mitochondrial inner membrane protein like | −2.371558863 |
| CDC73 | cell division cycle 73 | 1.73665741 | WWC2 | WW and C2 domain containing 2 | −2.371558863 |
| NDC80 | NDC80, kinetochore complex component | 1.732078892 | TMEM178 | transmembrane protein 178(Tmem178) | −2.374005585 |
| TACC3 | transforming acidic coiled-coil containing protein 3 | 1.731372884 | TPCN1 | two pore segment channel 1 | −2.375232208 |
| CPSF3 | cleavage and polyadenylation specific factor 3 | 1.727926568 | LRRC45 | leucine rich repeat containing 45 | −2.377207351 |
| ARID3A | AT-rich interaction domain 3A | 1.726471722 | 1110059G10RIK | Description Not Found | −2.377915929 |
| LLPH | LLP homolog, long-term synaptic facilitation | 1.726107859 | MCOLN2 | mucolipin 2 | −2.378511623 |

TABLE 2-continued

Differentially regulated genes in CD8⁺4-1BB⁺LAG-3⁺ TILs

| Gene | Gene Description | Log2-Fold Change | Gene Symbol | Gene Description | Log2-Fold Change |
| --- | --- | --- | --- | --- | --- |
| PCNA | proliferating cell nuclear antigen | 1.725441599 | DDX58 | DEXD/H-box helicase 58 | −2.378511623 |
| GJC2 | gap junction protein gamma 2 | 1.722978517 | H2-OA | histocompatibility 2, O region alpha locus(H2-Oa) | −2.382329516 |
| OLFR373 | olfactory receptor 373(Olfr373) | 1.722466024 | RARG | retinoic acid receptor gamma | −2.388827772 |
| H2-T24 | histocompatibility 2, T region locus 24(H2-T24) | 1.722466024 | SERPINB1A | serine (or cysteine) peptidase inhibitor, clade B, member 1a(Serpinb1a) | −2.392317423 |
| AKAP7 | A-kinase anchoring protein 7 | 1.722466024 | GHRL | ghrelin/obestatin prepropeptide | −2.392317423 |
| NDUFB7 | NADH: ubiquinone oxidoreductase subunit B7 | 1.722466024 | ZMAT4 | zinc finger matrin-type 4 | −2.392317423 |
| PRR11 | proline rich 11 | 1.722466024 | BTBD6 | BTB domain containing 6 | −2.392897478 |
| TJP1 | tight junction protein 1 | 1.722466024 | KLRA16 | killer cell lectin-like receptor, subfamily A, member 16(Klra16) | −2.394534969 |
| S100A3 | S100 calcium binding protein A3 | 1.722466024 | EPS15L1 | epidermal growth factor receptor pathway substrate 15 like 1 | −2.397012831 |
| KRT78 | keratin 78 | 1.718729711 | VCPIP1 | valosin containing protein interacting protein 1 | −2.397303585 |
| GMDS | GDP-mannose 4,6-dehydratase | 1.717904741 | RRP7A | ribosomal RNA processing 7 homolog A | −2.404992223 |
| PDGFB | platelet derived growth factor subunit B | 1.714400534 | IL1B | interleukin 1 beta | −2.40599236 |
| SLC36A1 | solute carrier family 36 member 1 | 1.714297338 | NAT14 | N-acetyltransferase 14 (putative) | −2.40599236 |
| RSU1 | Ras suppressor protein 1 | 1.712647036 | SLC40A1 | solute carrier family 40 member 1 | −2.40599236 |
| STX12 | syntaxin 12 | 1.711911478 | RAB37 | RAB37, member RAS oncogene family | −2.40599236 |
| SLC25A34 | solute carrier family 25 member 34 | 1.711494907 | IL17RA | interleukin 17 receptor A | −2.40599236 |
| AFG3L2 | AFG3 like matrix AAA peptidase subunit 2 | 1.711057 | BACE1 | beta-secretase 1 | −2.40599236 |
| RPL24 | ribosomal protein L24 | 1.709193708 | CTNS | cystinosin, lysosomal cystine transporter | −2.40599236 |
| UBE3C | ubiquitin protein ligase E3C | 1.708789682 | IFIT3 | interferon induced protein with tetratricopeptide repeats 3 | −2.411404504 |
| CAR12 | carbonic anhydrase 12(Car12) | 1.70867626 | ZFYVE21 | zinc finger FYVE-type containing 21 | −2.412378292 |
| ZFP207 | zinc finger protein 207(Zfp207) | 1.707603009 | 1700016D06RIK | Description Not Found | −2.419538892 |
| XIST | X inactive specific transcript (non-protein coding) | 1.706065607 | STK25 | serine/threonine kinase 25 | −2.419538892 |
| NCAPD2 | non-SMC condensin I complex subunit D2 | 1.705012178 | PLEKHJ1 | pleckstrin homology domain containing J1 | −2.419538892 |
| ZSWIM2 | zinc finger SWIM-type containing 2 | 1.704802998 | TGIF2 | TGFB induced factor homeobox 2 | −2.419538892 |
| CASP1 | caspase 1 | 1.70065942 | SLC25A29 | solute carrier family 25 member 29 | −2.419538892 |
| OLFR701 | olfactory receptor 701(Olfr701) | 1.700439718 | DAPL1 | death associated protein like 1 | −2.419661316 |
| CBLC | Cbl proto-oncogene C | 1.700439718 | P2RX4 | purinergic receptor P2X 4 | −2.425748008 |
| HIST1H2AC | histone cluster 1, H2ac | 1.700439718 | 1700001O22RIK | Description Not Found | −2.426264755 |
| EPHA10 | EPH receptor A10 | 1.700439718 | C9 | complement component 9 | −2.429615964 |
| NDUFC2 | NADH: ubiquinone oxidoreductase subunit C2 | 1.700439718 | KLF13 | Kruppel like factor 13 | −2.430628023 |
| DLG1 | discs large MAGUK scaffold protein 1 | 1.700439718 | GADD45A | growth arrest and DNA damage inducible alpha | −2.432591239 |
| SCN10A | sodium voltage-gated channel alpha subunit 10 | 1.700439718 | OLFR788 | olfactory receptor 788(Olfr788) | −2.432959407 |
| RGL3 | ral guanine nucleotide dissociation stimulator like 3 | 1.700439718 | FADS6 | fatty acid desaturase 6 | −2.432959407 |
| TMCO3 | transmembrane and coiled-coil domains 3 | 1.700439718 | CHCHD2 | coiled-coil-helix-coiled-coil-helix domain containing 2 | −2.432959407 |

TABLE 2-continued

Differentially regulated genes in CD8⁺4-1BB⁺LAG-3⁺ TILs

| Gene | Gene Description | Log2-Fold Change | Gene Symbol | Gene Description | Log2-Fold Change |
|---|---|---|---|---|---|
| BCL2L14 | BCL2 like 14 | 1.700439718 | MPPE1 | metallophosphoesterase 1 | −2.432959407 |
| THOP1 | thimet oligopeptidase 1 | 1.700290033 | CHAC1 | ChaC glutathione specific gamma-glutamylcyclotransferase 1 | −2.432959407 |
| MTIF3 | mitochondrial translational initiation factor 3 | 1.698305331 | 2310011J03RIK | Description Not Found | −2.435017448 |
| XDH | xanthine dehydrogenase | 1.697717724 | LRSAM1 | leucine rich repeat and sterile alpha motif containing 1 | −2.437473925 |
| ANXA9 | annexin A9 | 1.697184071 | SIRPA | signal regulatory protein alpha | −2.443125132 |
| OLFR1502 | olfactory receptor 1502(Olfr1502) | 1.694046727 | CYP24A1 | cytochrome P450 family 24 subfamily A member 1 | −2.44625623 |
| HCFC2 | host cell factor C2 | 1.693780609 | NQO1 | NAD(P)H quinone dehydrogenase 1 | −2.44625623 |
| DIDO1 | death inducer-obliterator 1 | 1.693596948 | HRH4 | histamine receptor H4 | −2.44625623 |
| PGAM1 | phosphoglycerate mutase 1 | 1.689846917 | NUDCD1 | NudC domain containing 1 | −2.44625623 |
| RASGEF1C | RasGEF domain family member 1C | 1.689299161 | CCND1 | cyclin D1 | −2.447924527 |
| SLC25A42 | solute carrier family 25 member 42 | 1.686774817 | ADAM22 | ADAM metallopeptidase domain 22 | −2.452858965 |
| CPT2 | carnitine palmitoyltransferase 2 | 1.686364794 | MDK | midkine (neurite growth-promoting factor 2) | −2.456149035 |
| MAD2L1 | MAD2 mitotic arrest deficient-like 1 (yeast) | 1.686161103 | STX1A | syntaxin 1A | −2.456729828 |
| NQO2 | NAD(P)H quinone dehydrogenase 2 | 1.685558757 | HEMK1 | HemK methyltransferase family member 1 | −2.459431619 |
| HIP1R | huntingtin interacting protein 1 related | 1.685473307 | B4GALT7 | beta-1,4-galactosyltransferase 7 | −2.459431619 |
| ALOX12E | arachidonate lipoxygenase, epidermal(Alox12e) | 1.684373244 | ASXL2 | additional sex combs like 2, transcriptional regulator | −2.459431619 |
| LMAN1 | lectin, mannose binding 1 | 1.683514205 | TLR7 | toll like receptor 7 | −2.46052038 |
| ASB3 | ankyrin repeat and SOCS box containing 3 | 1.680142991 | TDP1 | tyrosyl-DNA phosphodiesterase 1 | −2.464461869 |
| XKR5 | XK related 5 | 1.679254438 | 1700025G04RIK | Description Not Found | −2.469303076 |
| ZFP235 | zinc finger protein 235(Zfp235) | 1.678071905 | SLC16A6 | solute carrier family 16 member 6 | −2.471045434 |
| OLFR971 | olfactory receptor 971(Olfr971) | 1.678071905 | DOXL2 | diamine oxidase-like protein 2(Doxl2) | −2.472487771 |
| OLFR374 | olfactory receptor 374(Olfr374) | 1.678071905 | PKD1L3 | polycystin 1 like 3, transient receptor potential channel interacting | −2.472487771 |
| NOS1AP | nitric oxide synthase 1 adaptor protein | 1.678071905 | ZC3H11A | zinc finger CCCH-type containing 11A | −2.472487771 |
| GALM | galactose mutarotase | 1.678071905 | LY6K | lymphocyte antigen 6 complex, locus K | −2.472487771 |
| MEGF9 | multiple EGF like domains 9 | 1.678071905 | KLF7 | Kruppel like factor 7 | −2.474755307 |
| CCDC66 | coiled-coil domain containing 66 | 1.678071905 | BTLA | B and T lymphocyte associated | −2.475604026 |
| LRRC40 | leucine rich repeat containing 40 | 1.678071905 | CDON | cell adhesion associated, oncogene regulated | −2.485426827 |
| RALA | RALA Ras like proto-oncogene A | 1.678071905 | DDC | dopa decarboxylase | −2.485426827 |
| YIPF4 | Yip1 domain family member 4 | 1.678071905 | GTF2A2 | general transcription factor IIA subunit 2 | −2.485426827 |
| TAL2 | T-cell acute lymphocytic leukemia 2 | 1.678071905 | DTX4 | deltex E3 ubiquitin ligase 4 | −2.485426827 |
| LRRC8A | leucine rich repeat containing 8 family member A | 1.678071905 | GSTK1 | glutathione S-transferase kappa 1 | −2.486195934 |
| APOM | apolipoprotein M | 1.678071905 | OLFR213 | olfactory receptor 213(Olfr213) | −2.489125048 |
| KCNG3 | potassium voltage-gated channel modifier subfamily G member 3 | 1.678071905 | PDE5A | phosphodiesterase 5A | −2.490571469 |
| CNN1 | calponin 1 | 1.678071905 | TOB1 | transducer of ERBB2, 1 | −2.496763907 |
| STAC2 | SH3 and cysteine rich domain 2 | 1.678071905 | 1700109H08RIK | Description Not Found | −2.498250868 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| SFRP2 | secreted frizzled related protein 2 | 1.678071905 | LEFTY1 | left-right determination factor 1 | -2.498250868 |
| SERPINB9E | serine (or cysteine) peptidase inhibitor, clade B, member 9e(Serpinb9e) | 1.670169131 | SNAPC4 | small nuclear RNA activating complex polypeptide 4 | -2.500878922 |
| TFB1M | transcription factor B1, mitochondrial | 1.668946692 | RNF41 | ring finger protein 41 | -2.503551585 |
| SLC25A10 | solute carrier family 25 member 10 | 1.668856925 | KLHL34 | kelch like family member 34 | -2.504620392 |
| BID | BH3 interacting domain death agonist | 1.667992567 | SSH2 | slingshot protein phosphatase 2 | -2.505492762 |
| MRPS27 | mitochondrial ribosomal protein S27 | 1.667295766 | CAMK2B | calcium/calmodulin dependent protein kinase II beta | -2.507047355 |
| NEDD4 | neural precursor cell expressed, developmentally down-regulated 4, E3 ubiquitin protein ligase | 1.666756592 | IRF7 | interferon regulatory factor 7 | -2.507590939 |
| VANGL2 | VANGL planar cell polarity protein 2 | 1.666756592 | SCML4 | sex comb on midleg-like 4 (Drosophila) | -2.523118672 |
| UBE2R2 | ubiquitin conjugating enzyme E2 R2 | 1.666641116 | EPB4.1 | Description Not Found | -2.523561956 |
| KLHL30 | kelch like family member 30 | 1.666519523 | PARP12 | poly(ADP-ribose) polymerase family member 12 | -2.523561956 |
| FBXO36 | F-box protein 36 | 1.665588375 | CACNB3 | calcium voltage-gated channel auxiliary subunit beta 3 | -2.529877218 |
| DCT | dopachrome tautomerase | 1.664016818 | NRG4 | neuregulin 4 | -2.53318567 |
| CCDC120 | coiled-coil domain containing 120 | 1.663931727 | OLFR1383 | olfactory receptor 1383(Olfr1383) | -2.5360529 |
| TMEM38B | transmembrane protein 38B | 1.663455268 | PTGR1 | prostaglandin reductase 1 | -2.5360529 |
| ENDOD1 | endonuclease domain containing 1 | 1.663327923 | NFAM1 | NFAT activating protein with ITAM motif 1 | -2.5360529 |
| PTPRD | protein tyrosine phosphatase, receptor type D | 1.663215776 | ARL4C | ADP ribosylation factor like GTPase 4C | -2.5360529 |
| ARL3 | ADP ribosylation factor like GTPase 3 | 1.661690196 | LACE1 | lactation elevated 1 | -2.5360529 |
| CDC37 | cell division cycle 37 | 1.661567827 | CDC14B | cell division cycle 14B | -2.545350645 |
| MKKS | McKusick-Kaufman syndrome | 1.66106548 | GUCA1A | guanylate cyclase activator 1A | -2.548436625 |
| CHN2 | chimerin 2 | 1.660998764 | KIF21B | kinesin family member 21B | -2.554588852 |
| CRTAP | cartilage associated protein | 1.659431912 | ARID3B | AT-rich interaction domain 3B | -2.558087884 |
| CXCR6 | C-X-C motif chemokine receptor 6 | 1.657515938 | HBA-A1 | hemoglobin alpha, adult chain 1(Hba-a1) | -2.560714954 |
| BUB1B | BUB1 mitotic checkpoint serine/threonine kinase B | 1.65691495 | CSF2RB2 | colony stimulating factor 2 receptor, beta 2, low-affinity (granulocyte-macrophage)(Csf2rb2) | -2.560714954 |
| B430306N03RIK | RIKEN cDNA B430306N03 gene(B430306N03Rik) | 1.655351829 | ATP6V1B1 | ATPase H+ transporting V1 subunit B1 | -2.560714954 |
| OLFR1262 | olfactory receptor 1262(Olfr1262) | 1.655351829 | PCSK1N | proprotein convertase subtilisin/kexin type 1 inhibitor | -2.560714954 |
| SLC38A5 | solute carrier family 38 member 5 | 1.655351829 | ZFP667 | zinc finger protein 667(Zfp667) | -2.566670372 |
| VAT1L | vesicle amine transport 1-like | 1.655351829 | SH3BP1 | SH3 domain binding protein 1 | -2.566734604 |
| HOXB7 | homeobox B7 | 1.655351829 | FFAR2 | free fatty acid receptor 2 | -2.572889668 |
| GAN | gigaxonin | 1.655351829 | EEF2K | eukaryotic elongation factor 2 kinase | -2.572889668 |
| MMP28 | matrix metallopeptidase 28 | 1.655351829 | SLPI | secretory leukocyte peptidase inhibitor | -2.574721828 |
| METTL10 | methyltransferase like 10 | 1.655351829 | CMA1 | chymase 1 | -2.584962501 |
| SIX4 | SIX homeobox 4 | 1.655351829 | ASCL1 | achaete-scute family bHLH transcription factor 1 | -2.584962501 |
| TDRD6 | tudor domain containing 6 | 1.655351829 | ACPP | acid phosphatase, prostate | -2.584962501 |

TABLE 2-continued

Differentially regulated genes in CD8$^+$4-1BB$^+$LAG-3$^+$ TILs

| Gene | Gene Description | Log2-Fold Change | Gene Symbol | Gene Description | Log2-Fold Change |
|---|---|---|---|---|---|
| COMMD5 | COMM domain containing 5 | 1.654604999 | CLCNKB | chloride voltage-gated channel Kb | -2.596935142 |
| PRDX4 | peroxiredoxin 4 | 1.651923925 | FBXW7 | F-box and WD repeat domain containing 7 | -2.596935142 |
| HS3ST3A1 | heparan sulfate-glucosamine 3-sulfotransferase 3A1 | 1.649298274 | OLIG3 | oligodendrocyte transcription factor 3 | -2.596935142 |
| CALCA | calcitonin related polypeptide alpha | 1.649067786 | WHRN | whirlin | -2.606789951 |
| SLC12A2 | solute carrier family 12 member 2 | 1.648449243 | DNAJC14 | DnaJ heat shock protein family (Hsp40) member C14 | -2.608809243 |
| TJP2 | tight junction protein 2 | 1.644145647 | PIGT | phosphatidylinositol glycan anchor biosynthesis class T | -2.611031218 |
| LRRC16B | Description Not Found | 1.64385619 | AP1G2 | adaptor related protein complex 1 gamma 2 subunit | -2.614709844 |
| AP3S2 | adaptor related protein complex 3 sigma 2 subunit | 1.64385619 | SAA2 | serum amyloid A2 | -2.62058641 |
| PSMD9 | proteasome 26S subunit, non-ATPase 9 | 1.64385619 | USP30 | ubiquitin specific peptidase 30 | -2.62058641 |
| PARD6G | par-6 family cell polarity regulator gamma | 1.643379419 | RPE65 | retinal pigment epithelium specific protein 65 | -2.632268216 |
| CIAPIN1 | cytokine induced apoptosis inhibitor 1 | 1.643219709 | CML1 | Description Not Found | -2.634891632 |
| CKAP5 | cytoskeleton associated protein 5 | 1.642747156 | SLC6A19 | solute carrier family 6 member 19 | -2.640930751 |
| E430025E21RIK | RIKEN cDNA E430025E21 gene(E430025E21Rik) | 1.641902626 | FGF15 | fibroblast growth factor 15(Fgf15) | -2.64385619 |
| PIAS3 | protein inhibitor of activated STAT 3 | 1.641884484 | HERC3 | HECT and RLD domain containing E3 ubiquitin protein ligase 3 | -2.64385619 |
| USP1 | ubiquitin specific peptidase 1 | 1.640233791 | ADAMTSL4 | ADAMTS like 4 | -2.64385619 |
| RAB3GAP2 | RAB3 GTPase activating non-catalytic protein subunit 2 | 1.639592623 | HYAL3 | hyaluronoglucosaminidase 3 | -2.64385619 |
| CSRP2 | cysteine and glycine rich protein 2 | 1.639046229 | SLC15A2 | solute carrier family 15 member 2 | -2.648217996 |
| MOV10 | Mov10 RISC complex RNA helicase | 1.638073837 | UFSP1 | UFM1-specific peptidase 1 (inactive) | -2.649553823 |
| GM1965 | predicted gene 1965(Gm1965) | 1.637881562 | 6430573F11RIK | Description Not Found | -2.655351829 |
| POMGNT1 | protein O-linked mannose N-acetylglucosaminyltransferase 1 (beta 1,2-) | 1.636237884 | DNM3OS | DNM3 opposite strand/antisense RNA | -2.655351829 |
| FIGNL1 | fidgetin like 1 | 1.633950492 | F2RL1 | F2R like trypsin receptor 1 | -2.655351829 |
| TMEM177 | transmembrane protein 177 | 1.633475547 | SNX33 | sorting nexin 33 | -2.666654581 |
| ALX4 | ALX homeobox 4 | 1.632864872 | CXCL9 | C-X-C motif chemokine ligand 9 | -2.666756592 |
| OLFR533 | olfactory receptor 533(Olfr533) | 1.632268216 | TEAD2 | TEA domain transcription factor 2 | -2.666756592 |
| H2-M10.3 | histocompatibility 2, M region locus 10.3(H2-M10.3) | 1.632268216 | QSOX1 | quiescin sulfhydryl oxidase 1 | -2.666756592 |
| GPX7 | glutathione peroxidase 7 | 1.632268216 | TLR13 | toll-like receptor 13(Tlr13) | -2.678071905 |
| STXBP6 | syntaxin binding protein 6 | 1.632268216 | SCD3 | stearoyl-coenzyme A desaturase 3(Scd3) | -2.678071905 |
| RAB33A | RAB33A, member RAS oncogene family | 1.632268216 | SDC3 | syndecan 3 | -2.678071905 |
| PDCL3 | phosducin like 3 | 1.632268216 | GRPR | gastrin releasing peptide receptor | -2.678071905 |
| GPR20 | G protein-coupled receptor 20 | 1.632268216 | MAFK | MAF bZIP transcription factor K | -2.678071905 |
| GSTA2 | glutathione S-transferase alpha 2 | 1.632268216 | DIRC2 | disrupted in renal carcinoma 2 | -2.678071905 |
| ADCY10 | adenylate cyclase 10 (soluble) | 1.632268216 | ZCCHC12 | zinc finger CCHC-type containing 12 | -2.67833354 |
| PEX12 | peroxisomal biogenesis factor 12 | 1.632268216 | ADCY6 | adenylate cyclase 6 | -2.680886921 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| IQCC | IQ motif containing C | 1.632268216 | ECM1 | extracellular matrix protein 1 | −2.68345512 |
| ENPP1 | ectonucleotide pyrophosphatase/phosphodiesterase 1 | 1.632086279 | AFP | alpha fetoprotein | −2.689299161 |
| ADAL | adenosine deaminase-like | 1.630664126 | GP5 | glycoprotein V platelet | −2.689299161 |
| SCRN2 | secernin 2 | 1.630566247 | GAB3 | GRB2 associated binding protein 3 | −2.691405681 |
| CEP78 | centrosomal protein 78 | 1.629851642 | USP2 | ubiquitin specific peptidase 2 | −2.693334369 |
| SLC25A15 | solute carrier family 25 member 15 | 1.629798606 | PLXNB1 | plexin B1 | −2.700439718 |
| ADSSL1 | adenylosuccinate synthase like 1 | 1.628272149 | PODXL2 | podocalyxin like 2 | −2.700799925 |
| TM6SF2 | transmembrane 6 superfamily member 2 | 1.627758638 | RAD9B | RAD9 checkpoint clamp component B | −2.70103836 |
| TUBG1 | tubulin gamma 1 | 1.624511879 | AKAP10 | A-kinase anchoring protein 10 | −2.705977902 |
| FASTK | Fas activated serine/threonine kinase | 1.623336662 | PIGW | phosphatidylinositol glycan anchor biosynthesis class W | −2.716990894 |
| RBBP5 | RB binding protein 5, histone lysine methyltransferase complex subunit | 1.622163711 | COL12A1 | collagen type XII alpha 1 chain | −2.722466024 |
| 1700071K01RIK | Description Not Found | 1.621465074 | GPR137B | G protein-coupled receptor 137B | −2.733354341 |
| SLC25A33 | solute carrier family 25 member 33 | 1.621282718 | IMMP2L | inner mitochondrial membrane peptidase subunit 2 | −2.733354341 |
| MDM4 | MDM4, p53 regulator | 1.62058641 | PIK3CB | phosphatidylinositol-4,5-bisphosphate 3-kinase catalytic subunit beta | −2.737320423 |
| TOP2A | topoisomerase (DNA) II alpha | 1.620374948 | TGFBI | transforming growth factor beta induced | −2.740276443 |
| OLFR139 | olfactory receptor 139(Olfr139) | 1.619731323 | ZFP106 | zinc finger protein 106(Zfp106) | −2.744161096 |
| PAPLN | papilin, proteoglycan like sulfated glycoprotein | 1.618762248 | ARNTL | aryl hydrocarbon receptor nuclear translocator like | −2.744161096 |
| PACSIN2 | protein kinase C and casein kinase substrate in neurons 2 | 1.617401771 | HS3ST3B1 | heparan sulfate-glucosamine 3-sulfotransferase 3B1 | −2.744161096 |
| TRDMT1 | tRNA aspartic acid methyltransferase 1 | 1.615239219 | OASL2 | 2'-5' oligoadenylate synthetase-like 2(Oasl2) | −2.744892108 |
| 4932438H23RIK | Description Not Found | 1.614681809 | PRDX6 | peroxiredoxin 6 | −2.75084462 |
| SPAG9 | sperm associated antigen 9 | 1.614567709 | RASA2 | RAS p21 protein activator 2 | −2.751203108 |
| RPA3 | replication protein A3 | 1.61436984 | HOXB2 | homeobox B2 | −2.754887502 |
| GNPTAB | N-acetylglucosamine-1-phosphate transferase alpha and beta subunits | 1.613298199 | TULP3 | tubby like protein 3 | −2.754887502 |
| SNX9 | sorting nexin 9 | 1.609251493 | MFRP | membrane frizzled-related protein | −2.754887502 |
| OLFR550 | olfactory receptor 550(Olfr550) | 1.609195813 | MEN1 | menin 1 | −2.757556689 |
| ZFP160 | zinc finger protein 160(Zfp160) | 1.608809243 | C330021F23RIK | RIKEN cDNA C330021F23 gene(C330021F23Rik) | −2.762199201 |
| TAS2R129 | taste receptor, type 2, member 129(Tas2r129) | 1.608809243 | CSTAD | CSA-conditional, T cell activation-dependent protein(Cstad) | −2.765534746 |
| OLFR371 | olfactory receptor 371(Olfr371) | 1.608809243 | ALDH5A1 | aldehyde dehydrogenase 5 family member A1 | −2.773022439 |
| OLFR281 | olfactory receptor 281(Olfr281) | 1.608809243 | EPM2AIP1 | EPM2A interacting protein 1 | −2.773468928 |
| OLFR195 | olfactory receptor 195(Olfr195) | 1.608809243 | PDE8B | phosphodiesterase 8B | −2.776103988 |
| OLFR142 | olfactory receptor 142(Olfr142) | 1.608809243 | DMRTA1 | DMRT like family A1 | −2.776184379 |
| PRSS3 | protease, serine 3 | 1.608809243 | LYPD6B | LY6/PLAUR domain containing 6B | −2.780048768 |
| CX3CL1 | C-X3-C motif chemokine ligand 1 | 1.608809243 | CD300E | CD300e molecule | −2.786596362 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| TMPRSS6 | transmembrane protease, serine 6 | 1.608809243 | NPFF | neuropeptide FF-amide peptide precursor | -2.786596362 |
| ALK | anaplastic lymphoma receptor tyrosine kinase | 1.608809243 | FASTKD1 | FAST kinase domains 1 | -2.793765229 |
| ITGA9 | integrin subunit alpha 9 | 1.608809243 | OLFR802 | olfactory receptor 802(Olfr802) | -2.797012978 |
| TIMM13 | translocase of inner mitochondrial membrane 13 | 1.608809243 | HIVEP1 | human immunodeficiency virus type I enhancer binding protein 1 | -2.797012978 |
| MSH5 | mutS homolog 5 | 1.608809243 | HIC1 | hypermethylated in cancer 1 | -2.797012978 |
| XPO4 | exportin 4 | 1.605818241 | TRIM33 | tripartite motif containing 33 | -2.802009226 |
| MED21 | mediator complex subunit 21 | 1.603309406 | SELL | selectin L | -2.803274253 |
| CHST12 | carbohydrate sulfotransferase 12 | 1.602612589 | EPHX1 | epoxide hydrolase 1 | -2.803758579 |
| 6030408B16RIK | Description Not Found | 1.602195565 | BCL9 | B-cell CLL/lymphoma 9 | -2.807354922 |
| SLU7 | SLU7 homolog, splicing factor | 1.601548066 | STAT2 | signal transducer and activator of transcription 2 | -2.808521822 |
| CDK5RAP2 | CDK5 regulatory subunit associated protein 2 | 1.601120229 | ELMO3 | engulfment and cell motility 3 | -2.812498225 |
| CASP7 | caspase 7 | 1.6002402 | HDC | histidine decarboxylase | -2.815167456 |
| KIF22 | kinesin family member 22 | 1.599011705 | AI317395 | Description Not Found | -2.817623258 |
| E2F1 | E2F transcription factor 1 | 1.598449678 | RPL14 | ribosomal protein L14 | -2.817623258 |
| MXI1 | MAX interactor 1, dimerization protein | 1.597690116 | SNAI1 | snail family transcriptional repressor 1 | -2.818256244 |
| DONSON | downstream neighbor of SON | 1.596935142 | NUPR1 | nuclear protein 1, transcriptional regulator | -2.827819025 |
| TBX22 | T-box 22 | 1.596935142 | IGSF8 | immunoglobulin superfamily member 8 | -2.827819025 |
| INPPL1 | inositol polyphosphate phosphatase like 1 | 1.596300192 | SLC12A7 | solute carrier family 12 member 7 | -2.827819025 |
| CSE1L | chromosome segregation 1 like | 1.59586273 | RENBP | renin binding protein | -2.837431463 |
| NDFIP2 | Nedd4 family interacting protein 2 | 1.594709608 | ZFP553 | zinc finger protein 553(Zfp553) | -2.837943242 |
| LYPD6 | LY6/PLAUR domain containing 6 | 1.592962293 | LRFN2 | leucine rich repeat and fibronectin type III domain containing 2 | -2.837943242 |
| DDX49 | DEAD-box helicase 49 | 1.592190323 | HP | haptoglobin | -2.839737506 |
| MGLL | monoglyceride lipase | 1.590948822 | TOMM40 | translocase of outer mitochondrial membrane 40 | -2.847996907 |
| NR4A3 | nuclear receptor subfamily 4 group A member 3 | 1.59092994 | GABARAPL2 | GABA type A receptor associated protein like 2 | -2.847996907 |
| LRRN3 | leucine rich repeat neuronal 3 | 1.590360181 | TMEM86A | transmembrane protein 86A | -2.855497819 |
| PTPRK | protein tyrosine phosphatase, receptor type K | 1.587927102 | LRP1 | LDL receptor related protein 1 | -2.857980995 |
| OLFR1212 | olfactory receptor 1212(Olfr1212) | 1.584962501 | ATXN1 | ataxin 1 | -2.857980995 |
| KLHL2 | kelch like family member 2 | 1.584962501 | FAS | Fas cell surface death receptor | -2.861524641 |
| UBE2G2 | ubiquitin conjugating enzyme E2 G2 | 1.584962501 | ZDHHC18 | zinc finger DHHC-type containing 18 | -2.882740655 |
| GRIN2A | glutamate ionotropic receptor NMDA type subunit 2A | 1.584962501 | LARGE | Description Not Found | -2.887525271 |
| INHA | inhibin alpha subunit | 1.584962501 | SP5 | Sp5 transcription factor | -2.887525271 |
| RNPC3 | RNA binding region (RNP1, RRM) containing 3 | 1.584962501 | ATG7 | autophagy related 7 | -2.895440528 |
| XKR7 | XK related 7 | 1.584962501 | DNAJC27 | DnaJ heat shock protein family (Hsp40) member C27 | -2.897240426 |
| STX19 | syntaxin 19 | 1.584962501 | PCSK4 | proprotein convertase subtilisin/kexin type 4 | -2.900866808 |
| SLC5A5 | solute carrier family 5 member 5 | 1.584962501 | RNF141 | ring finger protein 141 | -2.902073579 |

TABLE 2-continued

Differentially regulated genes in CD8$^+$4-1BB$^+$LAG-3$^+$ TILs

| Gene | Gene Description | Log2-Fold Change | Gene Symbol | Gene Description | Log2-Fold Change |
|---|---|---|---|---|---|
| VPS37C | VPS37C, ESCRT-I subunit | 1.584022655 | GRAP2 | GRB2-related adaptor protein 2 | -2.904150467 |
| ERMP1 | endoplasmic reticulum metallopeptidase 1 | 1.582531434 | VIPR1 | vasoactive intestinal peptide receptor 1 | -2.904484098 |
| ZFP790 | zinc finger protein 790(Zfp790) | 1.581046002 | CAR15 | carbonic anhydrase 15(Car15) | -2.906890596 |
| AA467197 | expressed sequence AA467197(AA467197) | 1.579947242 | RELL2 | RELT like 2 | -2.906890596 |
| UBE2Z | ubiquitin conjugating enzyme E2 Z | 1.57976541 | HECA | hdc homolog, cell cycle regulator | -2.916545968 |
| SOAT2 | sterol O-acyltransferase 2 | 1.577460518 | DPM1 | dolichyl-phosphate mannosyltransferase polypeptide 1, catalytic subunit | -2.933100475 |
| ZMAT5 | zinc finger matrin-type 5 | 1.576986214 | AOC2 | amine oxidase, copper containing 2 | -2.936235748 |
| CDCA3 | cell division cycle associated 3 | 1.576323153 | HIST2H2BE | histone cluster 2, H2be | -2.936320631 |
| NEUROD2 | neuronal differentiation 2 | 1.576266476 | ACAD10 | acyl-CoA dehydrogenase family member 10 | -2.942514505 |
| WDR35 | WD repeat domain 35 | 1.576120636 | NT5E | 5'-nucleotidase ecto | -2.944039663 |
| TWSG1 | twisted gastrulation BMP signaling modulator 1 | 1.5758728 | SSH1 | slingshot protein phosphatase 1 | -2.944858446 |
| PPT1 | palmitoyl-protein thioesterase 1 | 1.575321868 | SEMA4F | ssemaphorin 4F | -2.948329995 |
| IRF8 | interferon regulatory factor 8 | 1.574489283 | NKD2 | naked cuticle homolog 2 | -2.953960396 |
| PLEKHG5 | pleckstrin homology and RhoGEF domain containing G5 | 1.574066379 | TCEB3 | transcription elongation factor B subunit 3 | -2.95419631 |
| CDC20 | cell division cycle 20 | 1.573718243 | HDAC4 | histone deacetylase 4 | -2.95419631 |
| MFI2 | antigen p97 (melanoma associated) identified by monoclonal antibodies 133.2 and 96.5(Mfi2) | 1.572889668 | PCNX | pecanex homolog (Drosophila)(Pcnx) | -2.972692654 |
| HDAC9 | histone deacetylase 9 | 1.571625208 | ARL5C | ADP ribosylation factor like GTPase 5C | -2.972692654 |
| ASF1B | anti-silencing function 1B histone chaperone | 1.570544039 | 1600014C10RIK | Description Not Found | -2.981852653 |
| B3GNT1 | Description Not Found | 1.569171715 | ANKRD23 | ankyrin repeat domain 23 | -2.981852653 |
| SLC25A14 | solute carrier family 25 member 14 | 1.569127395 | CLOCK | clock circadian regulator | -2.985543793 |
| FYN | FYN proto-oncogene, Src family tyrosine kinase | 1.567462919 | SFI1 | SFI1 centrin binding protein | -2.986410935 |
| SERPINB6B | serine (or cysteine) peptidase inhibitor, clade B, member 6b(Serpinb6b) | 1.567348435 | HEY1 | hes related family bHLH transcription factor with YRPW motif 1 | -2.987632559 |
| TOP1MT | topoisomerase (DNA) I, mitochondrial | 1.567180597 | ATP11C | ATPase phospholipid transporting 11C | -2.99095486 |
| CCDC50 | coiled-coil domain containing 50 | 1.566273906 | NUDCD3 | NudC domain containing 3 | -3 |
| ZFP414 | zinc finger protein 414(Zfp414) | 1.565776574 | CDC25A | cell division cycle 25 A | -3.000238201 |
| OGFOD2 | 2-oxoglutarate and iron dependent oxygenase domain containing 2 | 1.565512016 | OLFR135 | olfactory receptor 135(Olfr135) | -3.017921908 |
| CTNNAL1 | catenin alpha like 1 | 1.563586461 | RC3H1 | ring finger and CCCH-type domains 1 | -3.019621529 |
| CREB3L2 | cAMP responsive element binding protein 3 like 2 | 1.561361122 | NSG2 | neuron specific gene family member 2(Nsg2) | -3.020466888 |
| OLFR492 | olfactory receptor 492(Olfr492) | 1.560714954 | ID1 | inhibitor of DNA binding 1, HLH protein | -3.026800059 |
| OLFR1312 | olfactory receptor 1312(Olfr1312) | 1.560714954 | CYP2D22 | cytochrome P450, family 2, subfamily d, polypeptide 22(Cyp2d22) | -3.044282215 |
| UPK2 | uroplakin 2 | 1.560714954 | H2AFJ | H2A histone family member J | -3.044297135 |
| RESP18 | regulated endocrine specific protein 18 | 1.560714954 | TGFBR3 | transforming growth factor beta receptor 3 | -3.053111336 |
| CRCT1 | cysteine rich C-terminal 1 | 1.560714954 | IRS2 | insulin receptor substrate 2 | -3.061776198 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| NEUROD4 | neuronal differentiation 4 | 1.560714954 | ADCY7 | adenylate cyclase 7 | −3.06608919 |
| SENP1 | SUMO1/sentrin specific peptidase 1 | 1.560714954 | HYI | hydroxypyruvate isomerase (putative) | −3.072315809 |
| MR1 | major histocompatibility complex, class I-related | 1.560714954 | TRIP4 | thyroid hormone receptor interactor 4 | −3.078951341 |
| BIVM | basic, immunoglobulin-like variable motif containing | 1.560714954 | D730001G18RIK | RIKEN cDNA D730001G18 gene(D730001G18Rik) | −3.087462841 |
| KPNA2 | karyopherin subunit alpha 2 | 1.560714954 | PRR7 | proline rich 7 (synaptic) | −3.087462841 |
| BAG2 | BCL2 associated athanogene 2 | 1.560714954 | GFPT2 | glutamine-fructose-6-phosphate transaminase 2 | −3.09592442 |
| SLC12A8 | solute carrier family 12 member 8 | 1.560714954 | SCMH1 | sex comb on midleg homolog 1 (Drosophila) | −3.100136671 |
| SCN7A | sodium voltage-gated channel alpha subunit 7 | 1.560714954 | ANKRD12 | ankyrin repeat domain 12 | −3.107456458 |
| SLC5A7 | solute carrier family 5 member 7 | 1.560714954 | PTPRV | protein tyrosine phosphatase, receptor type, V(Ptprv) | −3.112700133 |
| ENPEP | glutamyl aminopeptidase | 1.560714954 | TMEM135 | transmembrane protein 135 | −3.112700133 |
| ANGPTL4 | angiopoietin like 4 | 1.56060777 | AKAP3 | A-kinase anchoring protein 3 | −3.11460665 |
| OSBPL3 | oxysterol binding protein like 3 | 1.559778376 | CBR2 | carbonyl reductase 2(Cbr2) | −3.129283017 |
| MCFD2 | multiple coagulation factor deficiency 2 | 1.559617874 | CXCL16 | C-X-C motif chemokine ligand 16 | −3.129283017 |
| MAP2K1 | mitogen-activated protein kinase kinase 1 | 1.558556708 | MBTD1 | mbt domain containing 1 | −3.145677455 |
| ING2 | inhibitor of growth family member 2 | 1.557223521 | UBE2J2 | ubiquitin conjugating enzyme E2 J2 | −3.161887682 |
| CDCA5 | cell division cycle associated 5 | 1.55643411 | STK36 | serine/threonine kinase 36 | −3.161887682 |
| MAP3K7 | mitogen-activated protein kinase kinase kinase 7 | 1.554463905 | SLC14A1 | solute carrier family 14 member 1 (Kidd blood group) | −3.16922072 |
| GSTT3 | glutathione S-transferase, theta 3(Gstt3) | 1.55048277 | CTSE | cathepsin E | −3.177917792 |
| PFN2 | profilin 2 | 1.549690793 | HSD3B7 | hydroxy-delta-5-steroid dehydrogenase, 3 beta- and steroid delta-isomerase 7 | −3.177917792 |
| HPS4 | HPS4, biogenesis of lysosomal organelles complex 3 subunit 2 | 1.549115647 | 3010003L21RIK | Description Not Found | −3.179249632 |
| CAPN8 | calpain 8 | 1.548436625 | BAI1 | Description Not Found | −3.186461055 |
| RAB11FIP5 | RAB11 family interacting protein 5 | 1.548436625 | ZFP451 | zinc finger protein 451(Zfp451) | −3.187711618 |
| CD9 | CD9 molecule | 1.548429184 | CCDC28B | coiled-coil domain containing 28B | −3.192207249 |
| CCR6 | C-C motif chemokine receptor 6 | 1.548250633 | MCF2L | MCF.2 cell line derived transforming sequence like | −3.199672345 |
| ALG2 | ALG2, alpha-1,3/1,6-mannosyltransferase | 1.547992668 | BCL6 | B-cell CLL/lymphoma 6 | −3.201024389 |
| BCDIN3D | BCDIN3 domain containing RNA methyltransferase | 1.546046129 | PFKFB4 | 6-phosphofructo-2-kinase/fructose-2,6-biphosphatase 4 | −3.204935584 |
| NT5DC3 | 5'-nucleotidase domain containing 3 | 1.54522349 | PROS1 | protein S (alpha) | −3.209453366 |
| DNAJC18 | DnaJ heat shock protein family (Hsp40) member C18 | 1.544626916 | CTSH | cathepsin H | −3.21628737 |
| SH3RF1 | SH3 domain containing ring finger 1 | 1.544156019 | CRTC3 | CREB regulated transcription coactivator 3 | −3.217230716 |
| RGS16 | regulator of G-protein signaling 16 | 1.541382294 | TNKS | tankyrase | −3.217230716 |
| NCAPH | non-SMC condensin I complex subunit H | 1.540788228 | GRM6 | glutamate metabotropic receptor 6 | −3.224966365 |
| USP14 | ubiquitin specific peptidase 14 | 1.540333713 | SPSB1 | splA/ryanodine receptor domain and SOCS box containing 1 | −3.255500733 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| RFT1 | RFT1 homolog | 1.54031759 | PARP8 | poly(ADP-ribose) polymerase family member 8 | −3.263034406 |
| SLC31A1 | solute carrier family 31 member 1 | 1.540275536 | KCNRG | potassium channel regulator | −3.263034406 |
| TCTEX1D2 | Tctex1 domain containing 2 | 1.538332378 | POU6F1 | POU class 6 homeobox 1 | −3.268517714 |
| TTF2 | transcription termination factor 2 | 1.537871953 | REV3L | REV3 like, DNA directed polymerase zeta catalytic subunit | −3.270528942 |
| ZFP7 | zinc finger protein 7(Zfp7) | 1.5360529 | TCF7 | transcription factor 7 (T-cell specific, HMG-box) | −3.272419178 |
| G6PD2 | glucose-6-phosphate dehydrogenase 2(G6pd2) | 1.5360529 | NME4 | NME/NM23 nucleoside diphosphate kinase 4 | −3.283551423 |
| DEFB14 | defensin beta 14(Defb14) | 1.5360529 | PLAUR | plasminogen activator, urokinase receptor | −3.285402219 |
| SLC18A3 | solute carrier family 18 member A3 | 1.5360529 | CD4 | CD4 molecule | −3.285402219 |
| AHNAK2 | AHNAK nucleoprotein 2 | 1.5360529 | ZMYND11 | zinc finger MYND-type containing 11 | −3.293186363 |
| HOXC12 | homeobox C12 | 1.5360529 | ARMCX5 | armadillo repeat containing, X-linked 5 | −3.298404158 |
| CEACAM16 | carcinoembryonic antigen related cell adhesion molecule 16 | 1.5360529 | LPHN1 | Description Not Found | −3.300123725 |
| MOSPD3 | motile sperm domain containing 3 | 1.5360529 | PIK3IP1 | phosphoinositide-3 -kinase interacting protein 1 | −3.307428525 |
| DCTN1 | dynactin subunit 1 | 1.5360529 | ERDR1 | erythroid differentiation regulator 1(Erdr1) | −3.317651188 |
| MYB | MYB proto-oncogene, transcription factor | 1.5360529 | PLD4 | phospholipase D family member 4 | −3.328444792 |
| GLIPR1L2 | GLI pathogenesis-related 1 like 2 | 1.5360529 | BMF | Bcl2 modifying factor | −3.336283388 |
| ALDH1A3 | aldehyde dehydrogenase 1 family member A3 | 1.5360529 | GALNT11 | polypeptide N-acetylgalactosaminyltransferase 11 | −3.345118795 |
| SLC2A8 | solute carrier family 2 member 8 | 1.5360529 | LCN2 | lipocalin 2 | −3.378511623 |
| SRC | SRC proto-oncogene, non-receptor tyrosine kinase | 1.5360529 | PAG1 | phosphoprotein membrane anchor with glycosphingolipid microdomains 1 | −3.385431037 |
| ZCCHC17 | zinc finger CCHC-type containing 17 | 1.535618518 | DTX1 | deltex E3 ubiquitin ligase 1 | −3.425576064 |
| HNRNPUL1 | heterogeneous nuclear ribonucleoprotein U like 1 | 1.534420207 | RFFL | ring finger and FYVE-like domain containing E3 ubiquitin protein ligase | −3.426684082 |
| TRIM68 | tripartite motif containing 68 | 1.533057052 | MAFF | MAF bZIP transcription factor F | −3.429615964 |
| TPST1 | tyrosylprotein sulfotransferase 1 | 1.53140111 | TOR1AIP2 | torsin 1A interacting protein 2 | −3.432316325 |
| OLFR922 | olfactory receptor 922(Olfr922) | 1.531260941 | SNN | stannin | −3.432316325 |
| FIG4 | FIG4 phosphoinositide 5-phosphatase | 1.530442167 | CLEC4N | C-type lectin domain family 4, member n(Clec4n) | −3.433567144 |
| SETMAR | SET domain and mariner transposase fusion gene | 1.530442167 | RREB1 | ras responsive element binding protein 1 | −3.443780274 |
| GSTM5 | glutathione S-transferase mu 5 | 1.530053218 | CCDC84 | coiled-coil domain containing 84 | −3.445188687 |
| TUBA3B | tubulin, alpha 3B(Tuba3b) | 1.527986221 | ID3 | inhibitor of DNA binding 3, HLH protein | −3.46350285 |
| PDCL | phosducin like | 1.527807072 | BC065397 | cDNA sequence BC065397(BC065397) | −3.465974465 |
| SMPDL3B | sphingomyelin phosphodiesterase acid like 3B | 1.527243888 | VRK1 | vaccinia related kinase 1 | −3.46760555 |
| ABHD14A | abhydrolase domain containing 14A | 1.527213882 | HOXD13 | homeobox D13 | −3.491853096 |
| TIPIN | TIMELESS interacting protein | 1.526972991 | MAPK8IP2 | mitogen-activated protein kinase 8 interacting protein 2 | −3.491853096 |
| DSCC1 | DNA replication and sister chromatid cohesion 1 | 1.525986429 | HOXA5 | homeobox A5 | −3.517275693 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| PSMD1 | proteasome 26S subunit, non-ATPase 1 | 1.525574957 | HIST1H1A | histone cluster 1, H1a | -3.523561956 |
| BZRAP1 | benzodiazepine receptor associated protein 1(Bzrap1) | 1.524166255 | MAML1 | mastermind like transcriptional coactivator 1 | -3.523603553 |
| ENO3 | enolase 3 | 1.523778831 | PTPDC1 | protein tyrosine phosphatase domain containing 1 | -3.526694846 |
| E330034G19RIK | RIKEN cDNA E330034G19 gene(E330034G19Rik) | 1.523561956 | TNFRSF12A | tumor necrosis factor receptor superfamily member 12A | -3.528725998 |
| GABRP | gamma-aminobutyric acid type A receptor pi subunit | 1.523561956 | TNIP2 | TNFAIP3 interacting protein 2 | -3.539158811 |
| SLC14A2 | solute carrier family 14 member 2 | 1.523561956 | HIST2H4 | histone cluster 2, H4(Hist2h4) | -3.540773411 |
| YWHAE | tyrosine 3-monooxygenase/tryptophan 5-monooxygenase activation protein epsilon | 1.522478712 | PIM2 | Pim-2 proto-oncogene, serine/threonine kinase | -3.557655155 |
| EHBP1L1 | EH domain binding protein 1 like 1 | 1.522282169 | DOK7 | docking protein 7 | -3.567781854 |
| CHGB | chromogranin B | 1.51924262 | TNFSF14 | tumor necrosis factor superfamily member 14 | -3.588895735 |
| TXNRD2 | thioredoxin reductase 2 | 1.519008256 | TDRKH | tudor and KH domain containing | -3.590961241 |
| NCF1 | neutrophil cytosolic factor 1 | 1.518873761 | FIBCD1 | fibrinogen C domain containing 1 | -3.608656121 |
| OAF | out at first homolog | 1.517431856 | RBBP9 | RB binding protein 9, serine hydrolase | -3.608809243 |
| FAM110A | family with sequence similarity 110 member A | 1.517263583 | DERL1 | derlin 1 | -3.617651119 |
| ANGEL1 | angel homolog 1 (*Drosophila*) | 1.515832566 | LENG9 | leukocyte receptor cluster member 9 | -3.62058641 |
| RTN4IP1 | reticulon 4 interacting protein 1 | 1.515760776 | TRPC2 | transient receptor potential cation channel subfamily C member 2, pseudogene | -3.62058641 |
| LAMP2 | lysosomal associated membrane protein 2 | 1.515709038 | CCDC134 | coiled-coil domain containing 134 | -3.632268216 |
| KRT4 | keratin 4 | 1.514299789 | OAS2 | 2'-5'-oligoadenylate synthetase 2 | -3.632268216 |
| PAFAH1B3 | platelet activating factor acetylhydrolase 1b catalytic subunit 3 | 1.5142935 | 2410127L17RIK | Description Not Found | -3.646738698 |
| STT3A | STT3A, catalytic subunit of the oligosaccharyltransferase complex | 1.513537695 | RSAD1 | radical S-adenosyl methionine domain containing 1 | -3.649220471 |
| PRKAR1B | protein kinase cAMP-dependent type I regulatory subunit beta | 1.51340003 | H2-DMB1 | histocompatibility 2, class II, locus Mb1(H2-DMb1) | -3.649615459 |
| HIST1H2BB | histone cluster 1, H2bb | 1.512941595 | IFT81 | intraflagellar transport 81 | -3.673839056 |
| ZFP39 | zinc finger protein 39(Zfp39) | 1.511385424 | MID1 | midline 1 | -3.683696454 |
| PLK1 | polo like kinase 1 | 1.511151166 | DEPDC1B | DEP domain containing 1B | -3.683696454 |
| 1700028P14RIK | Description Not Found | 1.510961919 | SMAD3 | SMAD family member 3 | -3.716296166 |
| D10BWG1379E | Description Not Found | 1.510961919 | UBTD1 | ubiquitin domain containing 1 | -3.716990894 |
| TREM3 | triggering receptor expressed on myeloid cells 3(Trem3) | 1.510961919 | FBXO44 | F-box protein 44 | -3.738767837 |
| GM128 | predicted gene 128(Gm128) | 1.510961919 | KCNMB4 | potassium calcium-activated channel subfamily M regulatory beta subunit 4 | -3.741951111 |
| OLFR741 | olfactory receptor 741(Olfr741) | 1.510961919 | FAIM3 | Description Not Found | -3.754887502 |
| OLFR523 | olfactory receptor 523(Olfr523) | 1.510961919 | CCM2 | CCM2 scaffolding protein | -3.754887502 |
| DCPP1 | demilune cell and parotid protein 1(Dcpp1) | 1.510961919 | DAG1 | dystroglycan 1 | -3.760220946 |
| RPRML | reprimo like | 1.510961919 | FCGR3 | Fc receptor, IgG, low affinity III(Fcgr3) | -3.776103988 |

TABLE 2-continued

Differentially regulated genes in CD8$^+$4-1BB$^+$LAG-3$^+$ TILs

| Gene | Gene Description | Log2-Fold Change | Gene Symbol | Gene Description | Log2-Fold Change |
|---|---|---|---|---|---|
| CHRD | chordin | 1.510961919 | ZNRF1 | zinc and ring finger 1, E3 ubiquitin protein ligase | -3.776103988 |
| C5AR1 | complement component 5a receptor 1 | 1.510961919 | TLR1 | toll like receptor 1 | -3.786596362 |
| APOA2 | apolipoprotein A2 | 1.510961919 | HSD17B11 | hydroxysteroid 17-beta dehydrogenase 11 | -3.789207575 |
| PRG2 | proteoglycan 2, pro eosinophil major basic protein | 1.510961919 | ZPBP | zona pellucida binding protein | -3.887525271 |
| VCAM1 | vascular cell adhesion molecule 1 | 1.510961919 | ZSWIM3 | zinc finger SWIM-type containing 3 | -3.892391026 |
| LY6G5B | lymphocyte antigen 6 complex, locus G5B | 1.510961919 | SOCS1 | suppressor of cytokine signaling 1 | -3.892391026 |
| AIM2 | absent in melanoma 2 | 1.510961919 | KLF9 | Kruppel like factor 9 | -3.902021342 |
| DMBX1 | diencephalon/mesencephalon homeobox 1 | 1.510961919 | AHSA2 | AHA1, activator of heat shock 90 kDa protein ATPase homolog 2 (yeast) | -3.904760449 |
| HCN2 | hyperpolarization activated cyclic nucleotide gated potassium channel 2 | 1.510961919 | DDHD1 | DDHD domain containing 1 | -3.914086097 |
| MRGPRF | MAS related GPR family member F | 1.510961919 | CNKSR3 | CNKSR family member 3 | -3.930737338 |
| CYTH4 | cytohesin 4 | 1.510961919 | CPEB2 | cytoplasmic polyadenylation element binding protein 2 | -4.017516295 |
| ANGPTL3 | angiopoietin like 3 | 1.510961919 | TRP53BP2 | transformation related protein 53 binding protein 2(Trp53bp2) | -4.021932279 |
| DHX29 | DEAH-box helicase 29 | 1.510667738 | FAM178A | family with sequence similarity 178, member A(Fam178a) | -4.03562391 |
| PMPCB | peptidase, mitochondrial processing beta subunit | 1.509477625 | RCN3 | reticulocalbin 3 | -4.03562391 |
| HRH3 | histamine receptor H3 | 1.508554002 | SPTLC2 | serine palmitoyltransferase long chain base subunit 2 | -4.040015679 |
| ZFP282 | zinc finger protein 282(Zfp282) | 1.507419453 | ZFP810 | zinc finger protein 810(Zfp810) | -4.070389328 |
| TBC1D7 | TBC1 domain family member 7 | 1.504847821 | NAGA | alpha-N-acetylgalactosaminidase | -4.074676686 |
| ARSB | arylsulfatase B | 1.504845728 | KLRA20 | killer cell lectin-like receptor subfamily A, member 20(Klra20) | -4.078951341 |
| RAD17 | RAD17 checkpoint clamp loader component | 1.504177542 | STK11IP | serine/threonine kinase 11 interacting protein | -4.083213368 |
| CMTM7 | CKLF like MARVEL transmembrane domain containing 7 | 1.503297831 | KLF4 | Kruppel like factor 4 | -4.084306687 |
| NFKB2 | nuclear factor kappa B subunit 2 | 1.500363085 | INADL | Description Not Found | -4.086667018 |
| TOP3A | topoisomerase (DNA) III alpha | -1.50007357 | URM1 | ubiquitin related modifier 1 | -4.0907078 |
| RAB33B | RAB33B, member RAS oncogene family | -1.50054042 | PELI1 | pellino E3 ubiquitin protein ligase 1 | -4.093813673 |
| LYSMD1 | LysM domain containing 1 | -1.500614885 | FBLN1 | fibulin 1 | -4.098032083 |
| POLG2 | polymerase (DNA) gamma 2, accessory subunit | -1.500707646 | HR | hair growth associated | -4.135452784 |
| TGIF1 | TGFB induced factor homeobox 1 | -1.501196523 | ASB6 | ankyrin repeat and SOCS box containing 6 | -4.137503524 |
| RELL1 | RELT like 1 | -1.50300255 | SLC27A5 | solute carrier family 27 member 5 | -4.141596278 |
| CYP26B1 | cytochrome P450 family 26 subfamily B member 1 | -1.50439813 | PPP1R3F | protein phosphatase 1 regulatory subunit 3F | -4.14974712 |
| PTRH2 | peptidyl-tRNA hydrolase 2 | -1.504678598 | AB124611 | cDNA sequence AB124611(AB124611) | -4.173373402 |
| ZKSCAN3 | zinc finger with KRAB and SCAN domains 3 | -1.504916722 | CD40 | CD40 molecule | -4.181897643 |
| SP8 | Sp8 transcription factor | -1.505999092 | SMAD5 | SMAD family member 5 | -4.183883459 |
| SAMD14 | sterile alpha motif domain containing 14 | -1.506272343 | COL23A1 | collagen type XXIII alpha 1 chain | -4.221103725 |
| MX2 | MX dynamin like GTPase 2 | -1.507268463 | ZFP595 | zinc finger protein 595(Zfp595) | -4.228818691 |

TABLE 2-continued

Differentially regulated genes in CD8⁺4-1BB⁺LAG-3⁺ TILs

| Gene | Gene Description | Log2-Fold Change | Gene Symbol | Gene Description | Log2-Fold Change |
|---|---|---|---|---|---|
| OCRL | OCRL, inositol polyphosphate-5-phosphatase | −1.507638755 | PECAM1 | platelet and endothelial cell adhesion molecule 1 | −4.232789973 |
| SYNJ2BP | synaptojanin 2 binding protein | −1.507669173 | TMEM138 | transmembrane protein 138 | −4.241228289 |
| CPLX4 | complexin 4 | −1.508554002 | RFX2 | regulatory factor X2 | −4.244125943 |
| LGALS9 | galectin 9 | −1.509246723 | KCTD12 | potassium channel tetramerization domain containing 12 | −4.247846204 |
| TAZ | tafazzin | −1.509269953 | TRIM56 | tripartite motif containing 56 | −4.262008929 |
| 2310002L09RIK | Description Not Found | −1.510961919 | EIF4EBP2 | eukaryotic translation initiation factor 4E binding protein 2 | −4.263034406 |
| ZFP97 | zinc finger protein 97(Zfp97) | −1.510961919 | RALGPS2 | Ral GEF with PH domain and SH3 binding motif 2 | −4.279842694 |
| OLFR1494 | olfactory receptor 1494(Olfr1494) | −1.510961919 | TGM2 | transglutaminase 2 | −4.293161941 |
| BC030867 | cDNA sequence BC030867(BC030867) | −1.510961919 | ENC1 | ectodermal-neural cortex 1 | −4.311067102 |
| CEACAM9 | carcinoembryonic antigen-related cell adhesion molecule 9(Ceacam9) | −1.510961919 | LRIG1 | leucine rich repeats and immunoglobulin like domains 1 | −4.375039431 |
| LRIT1 | leucine rich repeat, Ig-like and transmembrane domains 1 | −1.510961919 | PRM1 | protamine 1 | −4.375039431 |
| KLK5 | kallikrein related peptidase 5 | −1.510961919 | DUSP7 | dual specificity phosphatase 7 | −4.383538076 |
| KRT27 | keratin 27 | −1.510961919 | SERTAD3 | SERTA domain containing 3 | −4.399171094 |
| CACNG4 | calcium voltage-gated channel auxiliary subunit gamma 4 | −1.510961919 | KCNC1 | potassium voltage-gated channel subfamily C member 1 | −4.409390936 |
| IL13RA1 | interleukin 13 receptor subunit alpha 1 | −1.510961919 | UBE2D3 | ubiquitin conjugating enzyme E2 D3 | −4.462706751 |
| TMEM121 | transmembrane protein 121 | −1.510961919 | SEPP1 | selenoprotein P, plasma, 1 | −4.463383458 |
| HIST1H2AA | histone cluster 1, H2aa | −1.510961919 | ADRB2 | adrenoceptor beta 2 | −4.463910999 |
| MPZL3 | myelin protein zero like 3 | −1.510961919 | PPP1R13B | protein phosphatase 1 regulatory subunit 13B | −4.471417658 |
| TGFB2 | transforming growth factor beta 2 | −1.510961919 | ARRDC3 | arrestin domain containing 3 | −4.504620392 |
| IFT74 | intraflagellar transport 74 | −1.510961919 | GNGT2 | G protein subunit gamma transducin 2 | −4.531381461 |
| FCRL1 | Fc receptor like 1 | −1.510961919 | SIAH1A | seven in absentia 1A(Siah1a) | −4.539158811 |
| ADRB1 | adrenoceptor beta 1 | −1.510961919 | XPC | XPC complex subunit, DNA damage recognition and repair factor | −4.563768278 |
| MAGI2 | membrane associated guanylate kinase, WW and PDZ domain containing 2 | −1.510961919 | HIPK1 | homeodomain interacting protein kinase 1 | −4.683696454 |
| SCG5 | secretogranin V | −1.510961919 | H2-OB | histocompatibility 2, O region beta locus(H2-Ob) | −4.700439718 |
| GCK | glucokinase | −1.510961919 | BACH2 | BTB domain and CNC homolog 2 | −4.716990894 |
| ASB10 | ankyrin repeat and SOCS box containing 10 | −1.510961919 | MAP1LC3A | microtubule associated protein 1 light chain 3 alpha | −4.722466024 |
| SELE | selectin E | −1.510961919 | LRRFIP1 | LRR binding FLU interacting protein 1 | −4.761551232 |
| IGFBP3 | insulin like growth factor binding protein 3 | −1.510961919 | ATP10D | ATPase phospholipid transporting 10D (putative) | −4.766581958 |
| TPT1 | tumor protein, translationally-controlled 1 | −1.510961919 | IGFBP4 | insulin like growth factor binding protein 4 | −4.790993785 |
| ROCK1 | Rho associated coiled-coil containing protein kinase 1 | −1.510961919 | TMEM108 | transmembrane protein 108 | −4.865423978 |
| OGFRL1 | opioid growth factor receptor-like 1 | −1.510961919 | PTK2 | protein tyrosine kinase 2 | −4.875719796 |
| TMEM38A | transmembrane protein 38A | −1.510961919 | CLEC11A | C-type lectin domain family 11 member A | −4.897240426 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| RLTPR | Description Not Found | −1.51227339 | LRP12 | LDL receptor related protein 12 | −4.955029571 |
| ITPKC | inositol-trisphosphate 3-kinase C | −1.512389725 | GCNT2 | glucosaminyl (N-acetyl) transferase 2, I-branching enzyme (I blood group) | −4.958842675 |
| TLE4 | transducin like enhancer of split 4 | −1.51341989 | F10 | coagulation factor X | −4.965784285 |
| PDE4D | phosphodiesterase 4D | −1.513667908 | DBP | D-box binding PAR bZIP transcription factor | −4.966549451 |
| A130010J15RIK | Description Not Found | −1.514296211 | ABCG1 | ATP binding cassette subfamily G member 1 | −5.002252452 |
| RNF167 | ring finger protein 167 | −1.514765492 | WDR78 | WD repeat domain 78 | −5.017921908 |
| CCBL1 | Description Not Found | −1.515626494 | DNAJC6 | DnaJ heat shock protein family (Hsp40) member C6 | −5.017921908 |
| HSD17B1 | hydroxysteroid 17-beta dehydrogenase 1 | −1.516875069 | AFF4 | AF4/FMR2 family member 4 | −5.033423002 |
| OSM | oncostatin M | −1.517234668 | TNFRSF26 | tumor necrosis factor receptor superfamily, member 26(Tnfrsf26) | −5.040015679 |
| RHPN1 | rhophilin, Rho GTPase binding protein 1 | −1.517275693 | GFOD2 | glucose-fructose oxidoreductase domain containing 2 | −5.070389328 |
| TAS2R105 | taste receptor, type 2, member 105(Tas2r105) | −1.517431856 | TYROBP | TYRO protein tyrosine kinase binding protein | −5.114783447 |
| NIPBL | NIPBL, cohesin loading factor | −1.517569618 | TMEM176B | transmembrane protein 176B | −5.118941073 |
| CXCR3 | C-X-C motif chemokine receptor 3 | −1.519325267 | ZFP710 | zinc finger protein 710(Zfp710) | −5.159871337 |
| SMURF1 | SMAD specific E3 ubiquitin protein ligase 1 | −1.520263252 | ENPP4 | ectonucleotide pyrophosphatase/ phosphodiesterase 4 (putative) | −5.181897643 |
| RNF208 | ring finger protein 208 | −1.52126647 | MAPK8 | mitogen-activated protein kinase 8 | −5.259272487 |
| ITGA5 | integrin subunit alpha 5 | −1.523517983 | TNFRSF25 | tumor necrosis factor receptor superfamily member 25 | −5.289096702 |
| USP18 | ubiquitin specific peptidase 18 | −1.524814077 | LCN4 | lipocalin 4(Lcn4) | −5.366322214 |
| PIP5K1A | phosphatidylinositol-4-phosphate 5-kinase type 1 alpha | −1.525074369 | CRIM1 | cysteine rich transmembrane BMP regulator 1 | −5.369815424 |
| STRBP | spermatid perinuclear RNA binding protein | −1.52561213 | RTP4 | receptor transporter protein 4 | −5.444600814 |
| GRAMD2 | GRAM domain containing 2 | −1.52652805 | PRNP | prion protein | −5.495055528 |
| ZFP101 | zinc finger protein 101(Zfp101) | −1.526555668 | ZFP747 | zinc finger protein 747(Zfp747) | −5.496654083 |
| RUNDC1 | RUN domain containing 1 | −1.526563287 | CD7 | CD7 molecule | −5.504620392 |
| SLC13A3 | solute carrier family 13 member 3 | −1.528487927 | ARHGAP26 | Rho GTPase activating protein 26 | −5.548436625 |
| CCDC94 | coiled-coil domain containing 94 | −1.528487927 | S100A9 | S100 calcium binding protein A9 | −5.557655155 |
| MRPS14 | mitochondrial ribosomal protein S14 | −1.528962318 | AQP9 | aquaporin 9 | −5.572889668 |
| NEU4 | neuraminidase 4 (sialidase) | −1.529820947 | CXCR5 | C-X-C motif chemokine receptor 5 | −5.573647187 |
| PCGF1 | polycomb group ring finger 1 | −1.53059536 | CCNO | cyclin O | −5.574404309 |
| PNPLA7 | patatin like phospholipase domain containing 7 | −1.53207883 | LYNX1 | Ly6/neurotoxin 1 | −5.666756592 |
| SPATA19 | spermatogenesis associated 19 | −1.533014103 | CLDN10 | claudin 10 | −5.782015335 |
| AP4B1 | adaptor related protein complex 4 beta 1 subunit | −1.533821865 | AMIGO2 | adhesion molecule with Ig-like domain 2 | −5.83541884 |
| BC068281 | cDNA sequence BC068281(BC068281) | −1.5360529 | CD79B | CD79b molecule | −5.94016675 |
| GK2 | glycerol kinase 2 | −1.5360529 | USP53 | ubiquitin specific peptidase 53 | −5.980710829 |
| PIGM | phosphatidylinositol glycan anchor biosynthesis class M | −1.5360529 | IKBKE | inhibitor of kappa light polypeptide gene enhancer in B-cells, kinase epsilon | −6.005624549 |

TABLE 2-continued

Differentially regulated genes in CD8+4-1BB+LAG-3+ TILs

| Gene | Gene Description | Log2-Fold Change | Gene Symbol | Gene Description | Log2-Fold Change |
|---|---|---|---|---|---|
| FKBP6 | FK506 binding protein 6 | −1.5360529 | ALOX5AP | arachidonate 5-lipoxygenase activating protein | −6.008988783 |
| EVI5 | ecotropic viral integration site 5 | −1.5360529 | GGT1 | gamma-glutamyltransferase 1 | −6.010108453 |
| BCL11A | B-cell CLL/lymphoma 11A | −1.5360529 | CAMK2D | calcium/calmodulin dependent protein kinase II delta | −6.047669251 |
| PER1 | period circadian clock 1 | −1.537278499 | RAB3D | RAB3D, member RAS oncogene family | −6.156841525 |
| BTBD9 | BTB domain containing 9 | −1.537451456 | MAP3K8 | mitogen-activated protein kinase kinase kinase 8 | −6.376776572 |
| USP38 | ubiquitin specific peptidase 38 | −1.537763627 | NOTCH4 | notch 4 | −6.495055528 |
| LRRC57 | leucine rich repeat containing 57 | −1.538083341 | MACROD1 | MACRO domain containing 1 | −6.581200582 |
| 5830415F09RIK | Description Not Found | −1.53855912 | RNF144A | ring finger protein 144A | −6.632268216 |
| EGR2 | early growth response 2 | −1.540038325 | PDE2A | phosphodiesterase 2A | −6.86913112 |
| GMEB2 | glucocorticoid modulatory element binding protein 2 | −1.541122795 | THA1 | threonine aldolase 1(Tha1) | −6.885086225 |
| PIK3R4 | phosphoinositide-3-kinase regulatory subunit 4 | −1.541975323 | APP | amyloid beta precursor protein | −6.940754047 |
| KRR1 | KRR1, small subunit processome component homolog | −1.54225805 | FAM109A | family with sequence similarity 109 member A | −6.968666793 |
| COL9A1 | collagen type IX alpha 1 | −1.54225805 | LRG1 | leucine rich alpha-2-glycoprotein 1 | −6.995484519 |
| POLD4 | polymerase (DNA) delta 4, accessory subunit | −1.542654605 | IL11RA1 | interleukin 11 receptor, alpha chain 1(Il11ra1) | −7.016251155 |
| ACSS2 | acyl-CoA synthetase short-chain family member 2 | −1.544045378 | CNR2 | cannabinoid receptor 2 | −7.213347282 |
| PDLIM1 | PDZ and LIM domain 1 | −1.544785186 | NUAK2 | NUAK family kinase 2 | −7.369815424 |
| A430107P09RIK | Description Not Found | −1.544921568 | GPR146 | G protein-coupled receptor 146 | −7.577806447 |
| SLC38A11 | solute carrier family 38 member 11 | −1.546222547 | | | |

*Log 2Fold Change=log 2(4+L+/4−L−)

To investigate the molecular pathways between these three populations, gene ontology networks were grouped into nodes and the most significant pathways within each node were determined (FIG. 6A). Gene ontology (GO) terms shared between our dysfunctional T cell dataset and the published hypofunctional T cell dataset were greatly enriched in cell cycle genes, consistent with the observation that the dysfunctional population is largely Ki67+. GO terms shared between dysfunctional and exhausted gene sets encompassed effector programs such as regulation of cell killing, chemotaxis, interferon-γ production. GO terms shared between hypofunctional and exhausted gene sets consisted of cell cycle pathways, negative regulation of lymphocytes, and interferon-γ production. These data indicate that while some conserved molecular programs likely exist in these dysfunctional differentiation states, many pathways may be differentially regulated between chronic viral infections and in the tumor context.

Figure 6C:
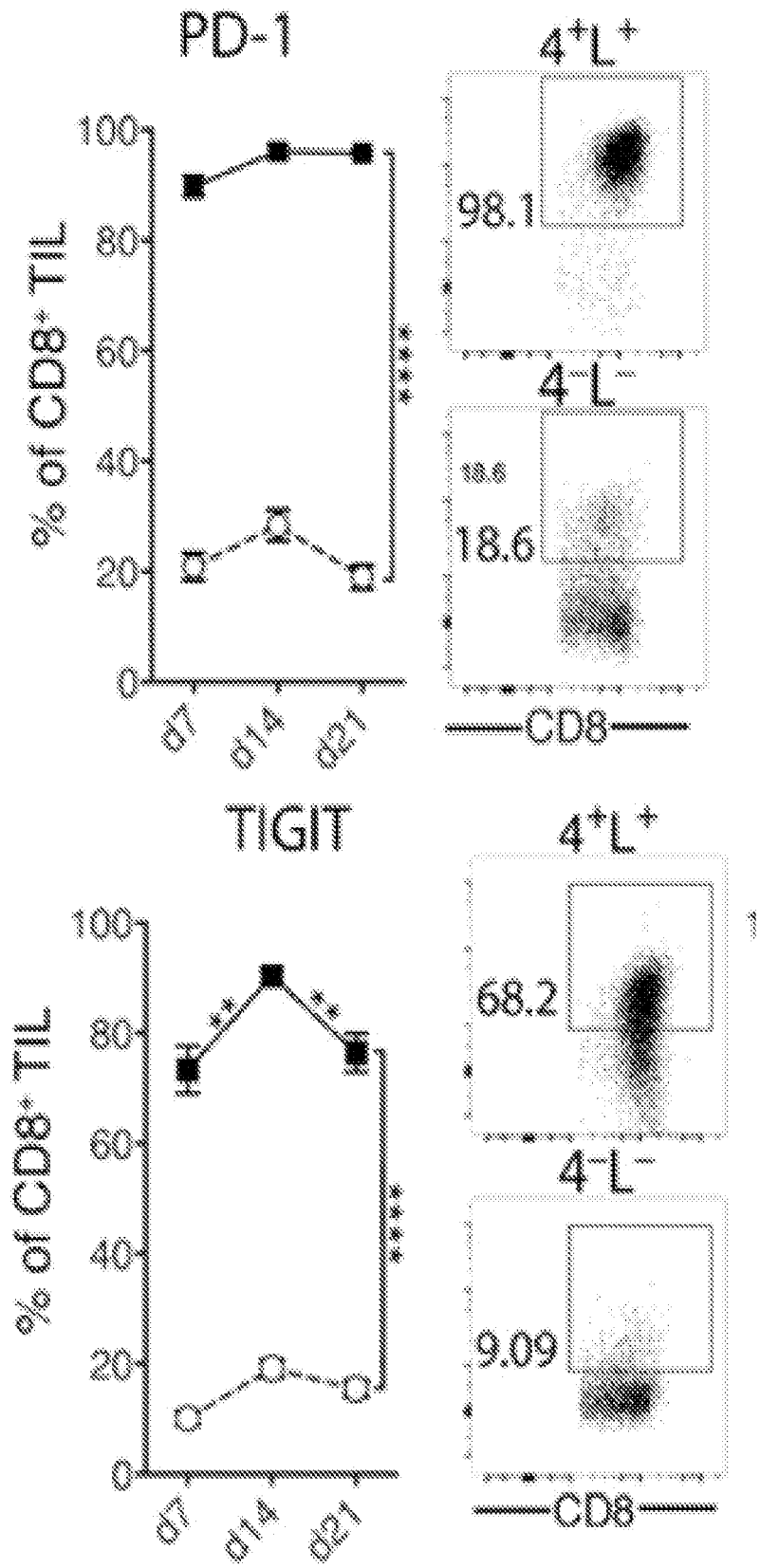
Figure 6C:
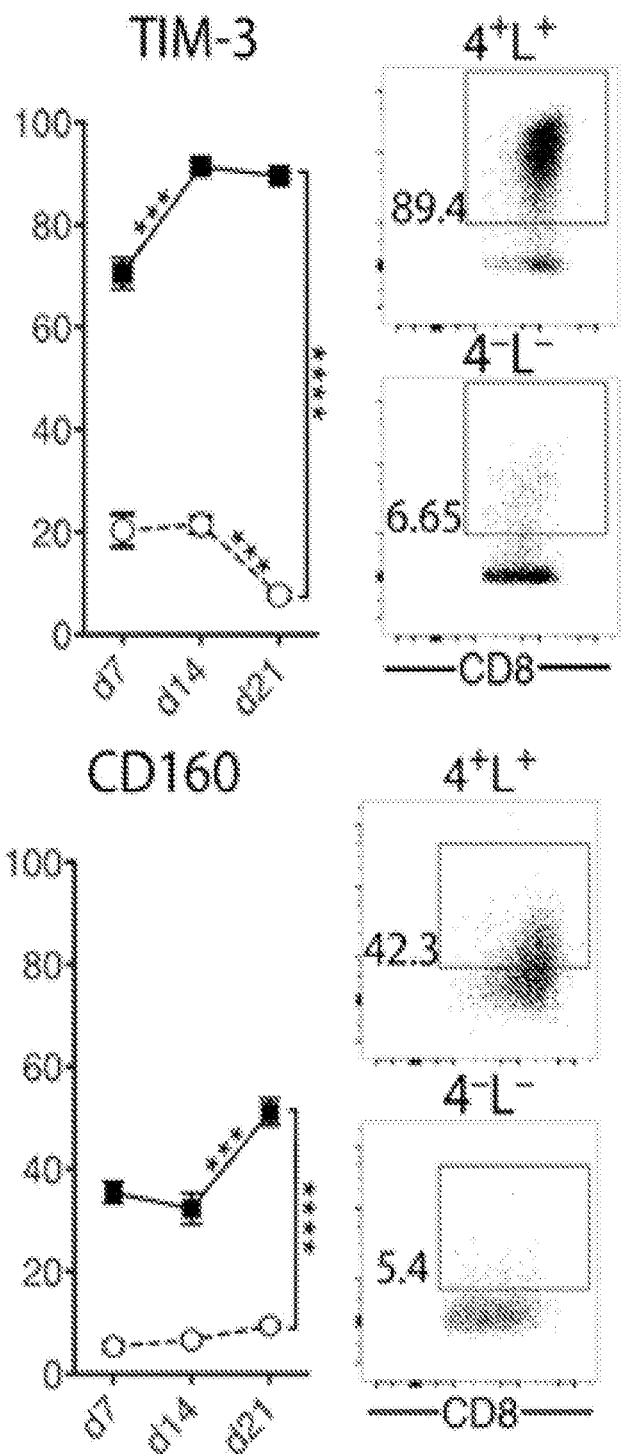
Figure 6C:
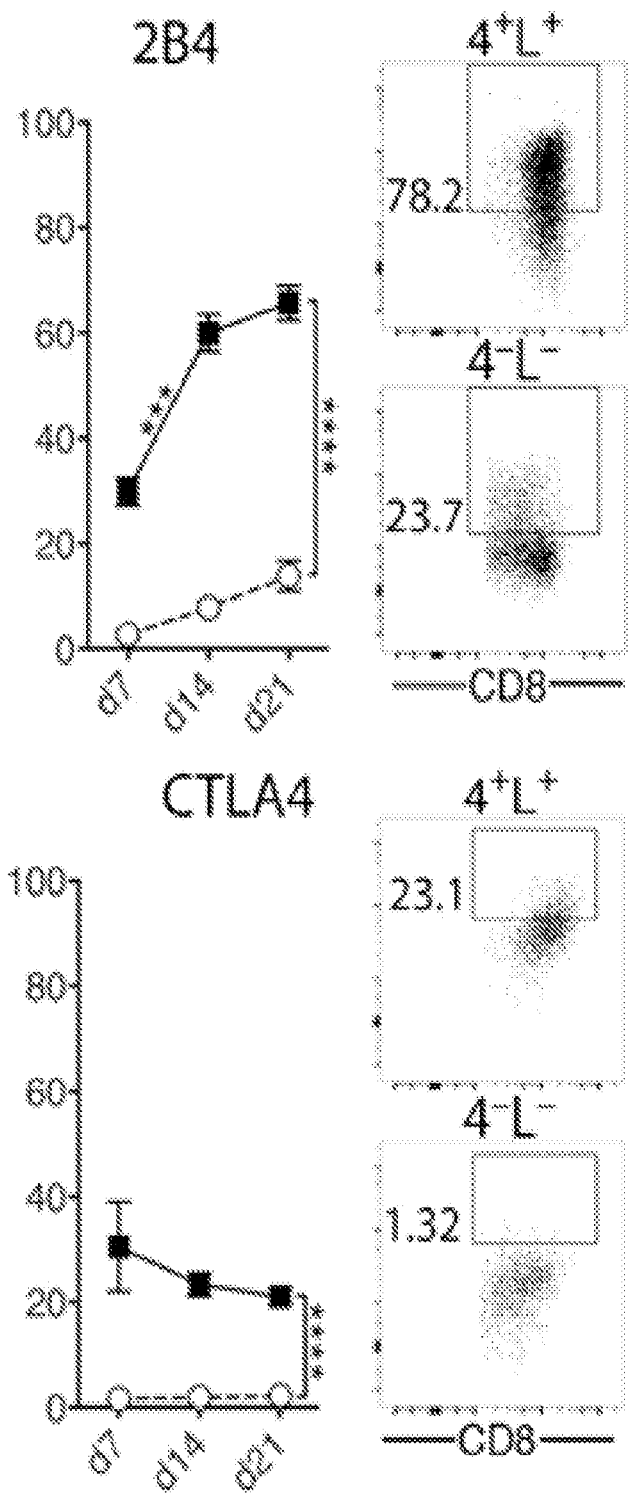
Figure 6C:
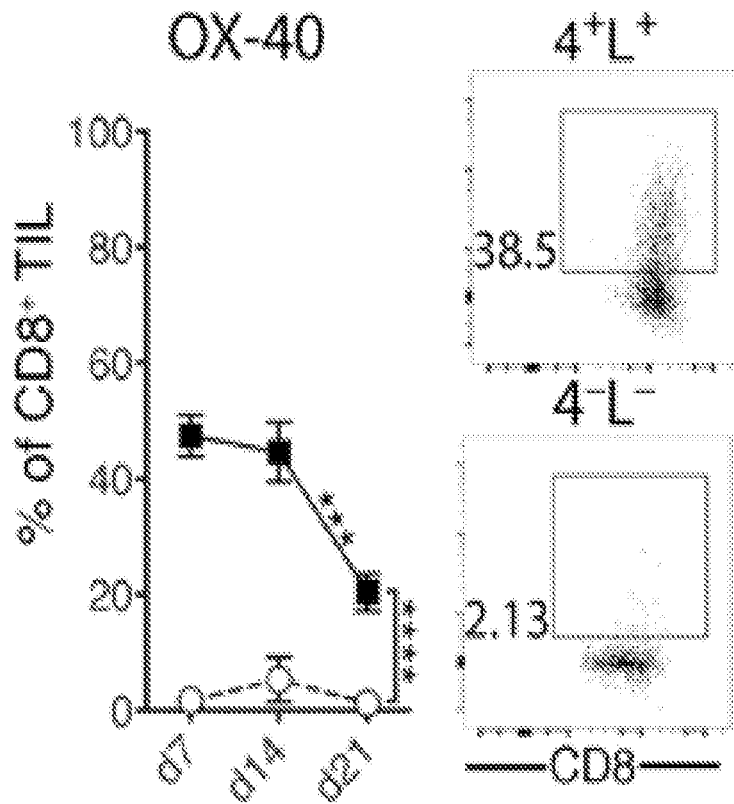
Figure 6C:
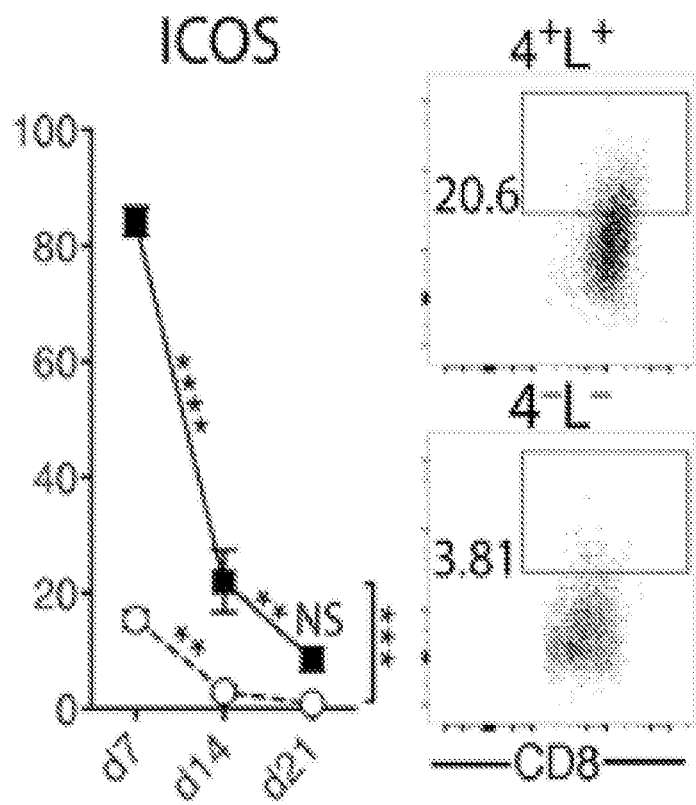
Figure 6C:
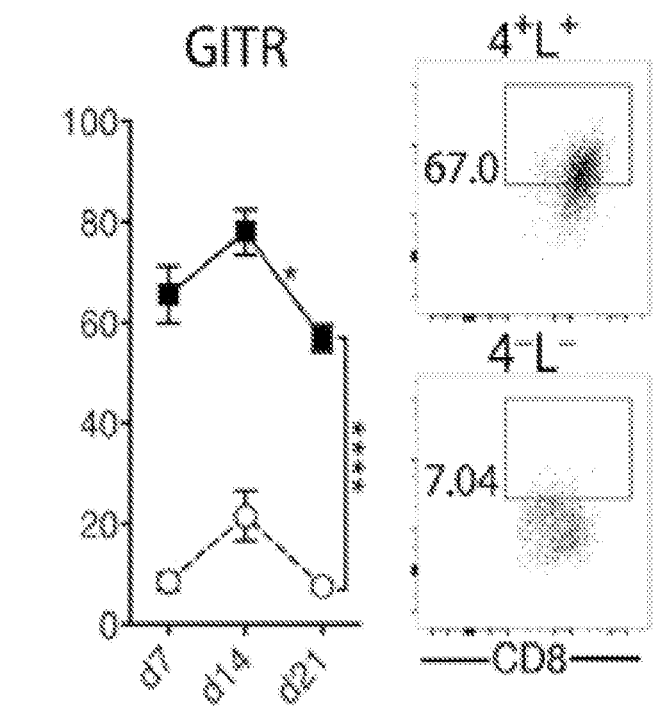
Figure 6C:
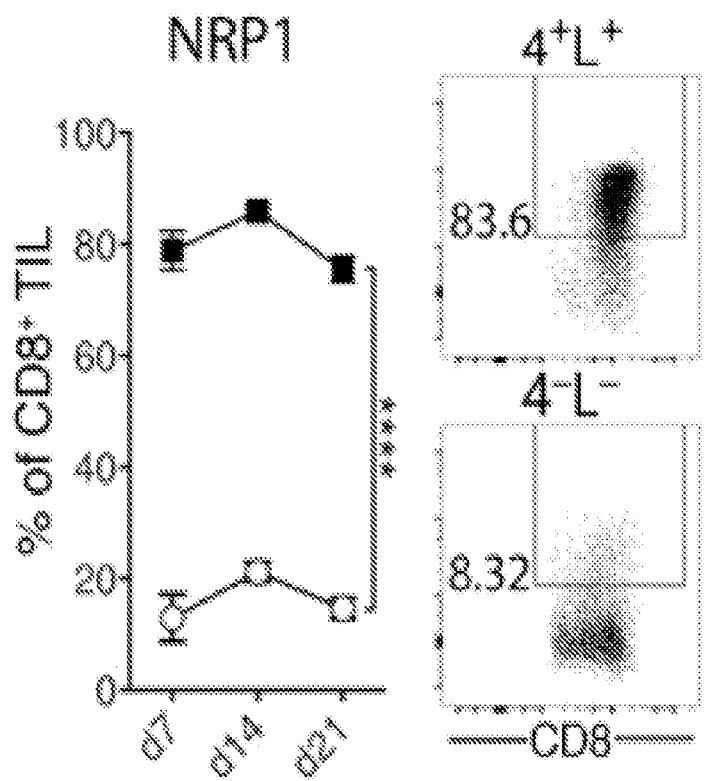

While many inhibitory receptors, including Pdcd1 (PD-1), Havcr2 (TIM-3), Cd244 (2B4), Klre1, and Lag3 were shared between all data sets; the co-stimulatory receptors Tnfrsf4 (OX-40) and Tnfrsf9 (4-1BB) were upregulated in dysfunctional and hypofunctional CD8+ TIL data sets. Therefore, to enrich in potential markers and therapeutic targets on tumor specific CD8+ TILs, the complete cell surface phenotype of the 4-1BB+LAG-3+CD8 TIL population was characterized. Comparing the different CD8+ TIL subpopulations, several additional upregulated co-stimulatory receptors were found: Tnfrsf18 (GITR), Nkg2d (KLRK1) and Cd27. The transcript for Nrp1 (neuropilin-1), which encodes for a cell surface receptor protein implicated in CD4+ Treg function (Sarris et al., 2008; incorporated by reference in its entirety), was also highly expressed. Expression of many of these molecules was confirmed by flow cytometry at day 7, 14 and 21 after tumor inoculation (FIG. 6C). The analysis was extended to include the co-stimulatory molecules ICOS and CD160 and the inhibitory receptor T cell immunoreceptor with Ig and ITIM domains (TIGIT) because ICOS and CD160 were close to the cutoff value and no probe was present for TIGIT in the gene array. In addition, recent reports indicate that targeting these receptors can be therapeutic in murine models of cancer (Johnston et al., 2014; Fan et al., 2014; incorporated by reference in their entireties). PD-1, TIGIT, TIM-3, CD27 and NRP1 were expressed the majority of the 4-1BB+LAG-3+ TIL population and expression was maintained over time. 2B4, CD160, CTLA4, OX-40, and GITR subdivided a lesser fraction of the 4-1BB+LAG-3+ population. The expression of several inhibitory receptors, 2B4, TIM3 and CD160 increased over this 3-week time frame while expression of the co-stimulatory receptors, ICOS and OX-40, decreased (FIG. 6C).

Figure 6D:
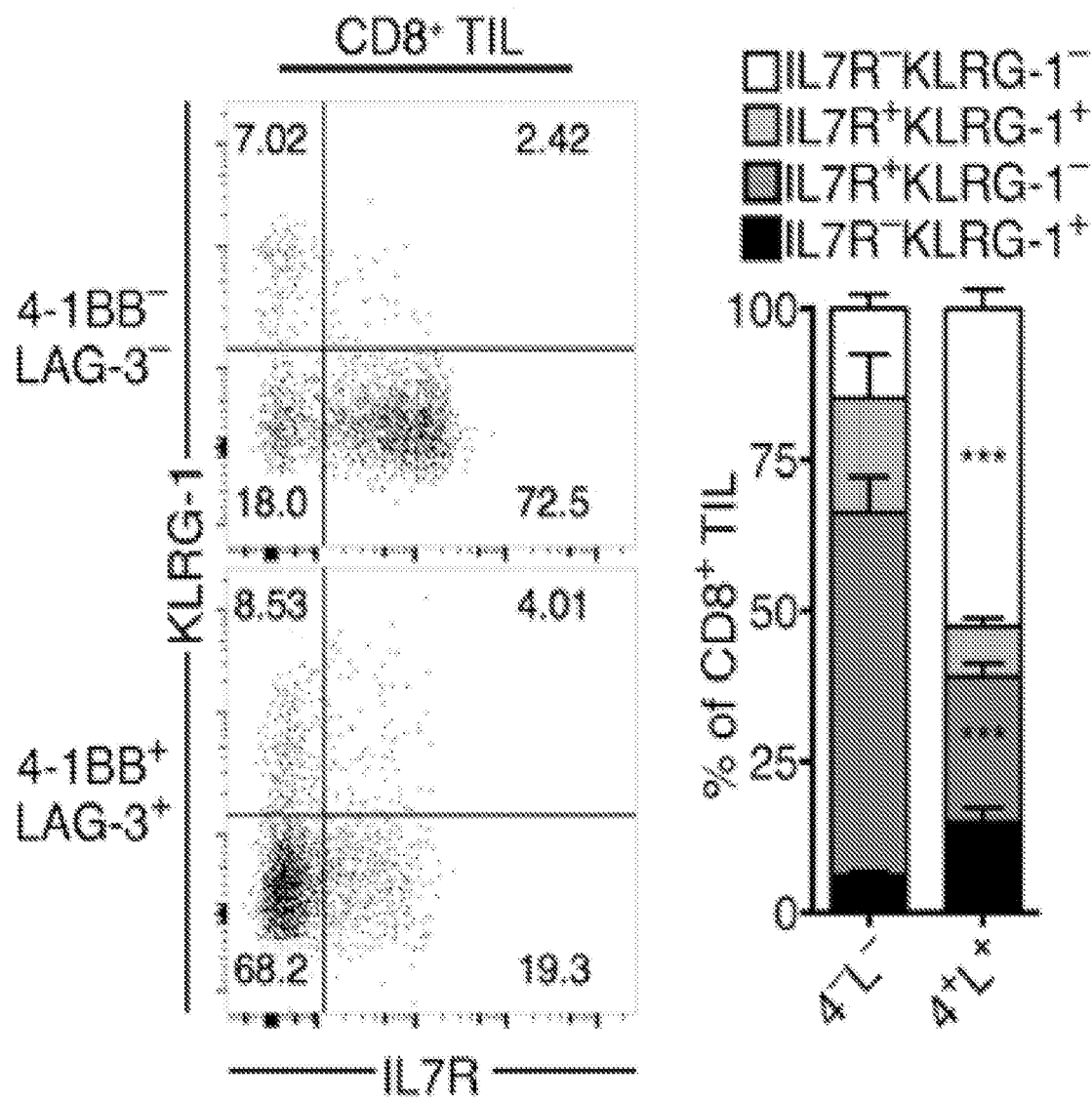
Figure 11:
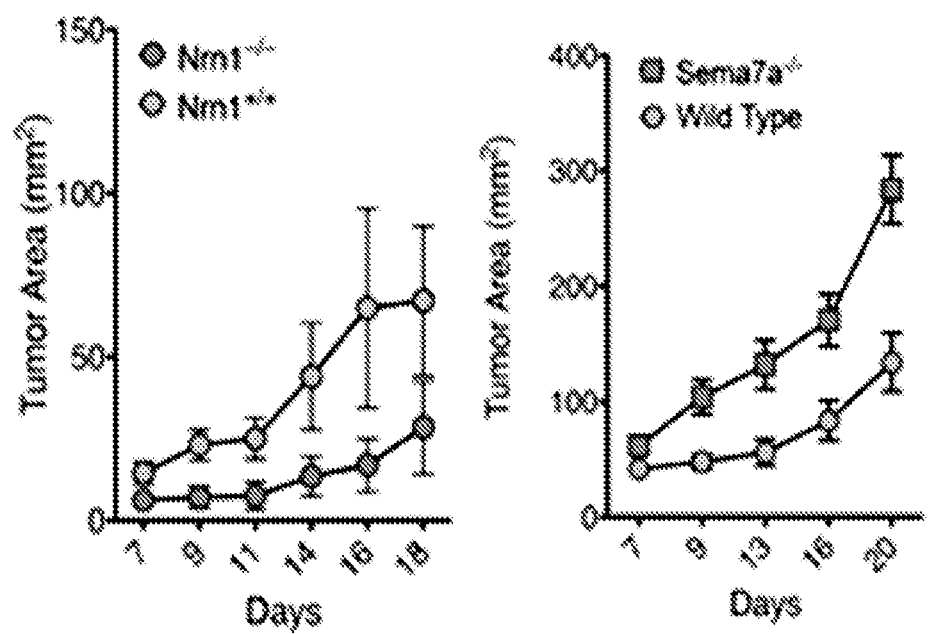
FIG. 11A-E. Nrn1, CRTAM and Sema7a are regulators of anti-tumor immunity. (A) Tumor growth measured in mm2. Nrn1$^{-/-}$ or Sema7a$^{-/-}$ and littermate control mice were engrafted with 2×106 B16.SIY cells subcutaneously. (B) Gene expression analysis of Nrn1 in T cell subsets of the spleen, TdLN and Tumor. (C) Representative flow plot and summary of IFN-g production of WT, Nrn1$^{-/-}$ or (D) CRTAM$^{-/-}$ 2C T cells on day 7. Briefly, on the same day as tumor inoculation, 1×10$^6$ Cell Trace Violet-labeled 2C T cells were transferred into mice by tail vein injection. On day 7, whole TdLN suspensions were restimulated with SIY peptide for 12 hours and analyzed for cell trace dilution and IFN-g production. (E) Mice that received 1×10$^6$ Nrn1$^{-/-}$ 2 C T cells are more likely to exhibit complete tumor control compared to mice that received the same number of WT 2C T cells. Adoptive transfer of T cells was performed the same way as in (C).
Figure 11:
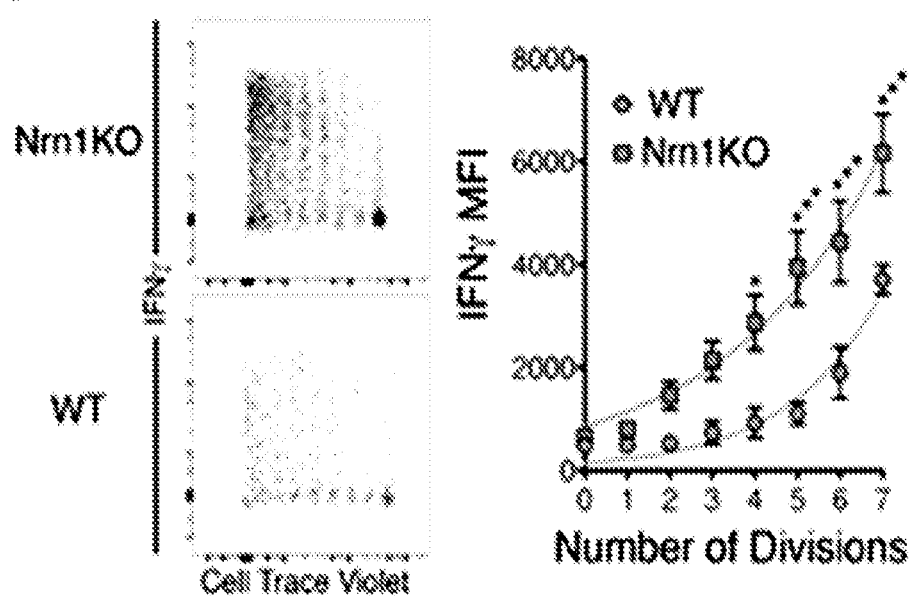
Figure 11:
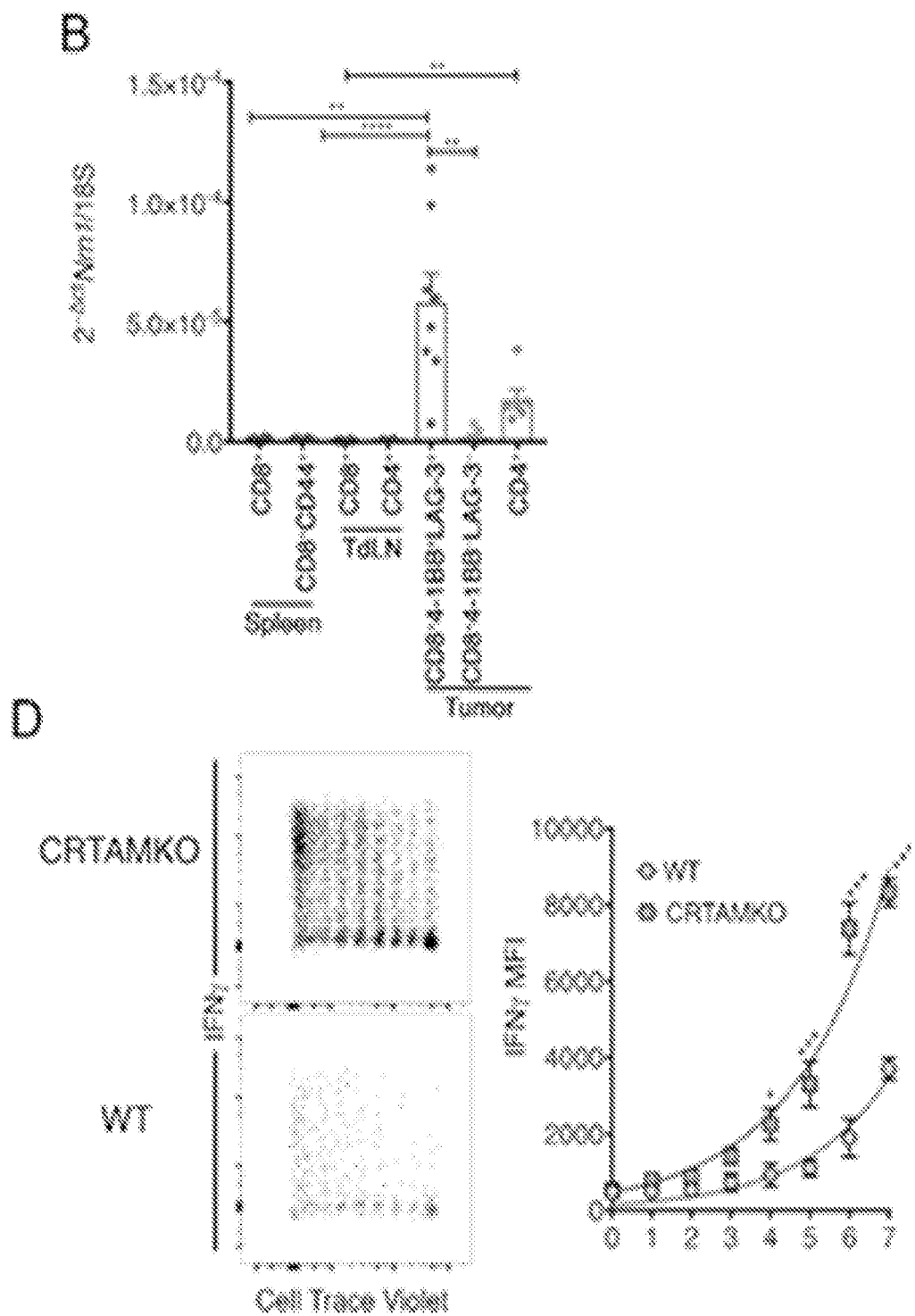
Figure 11:
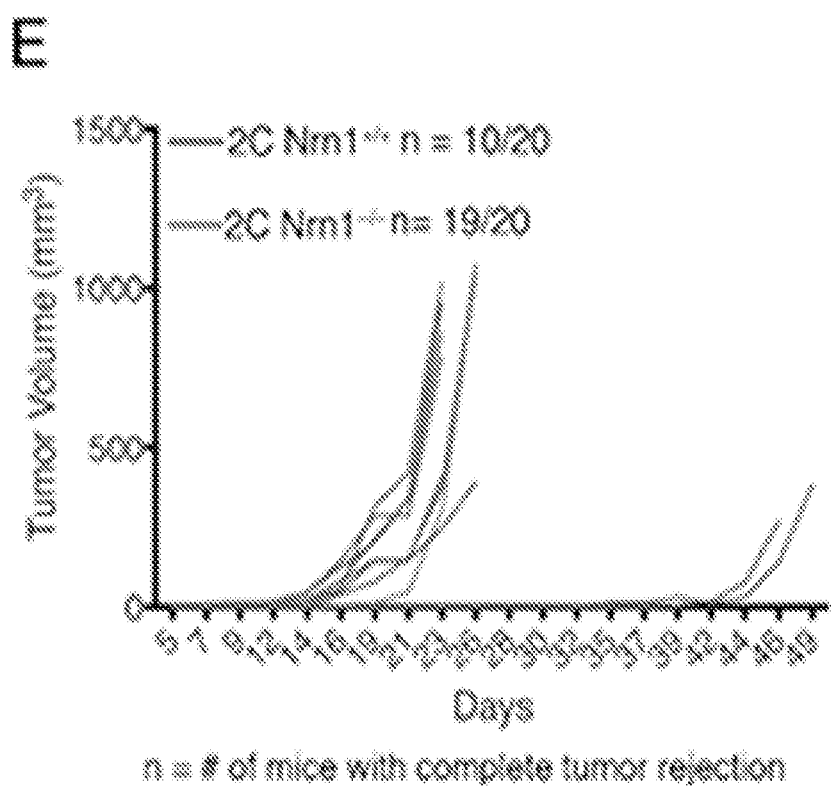
Figure 12:
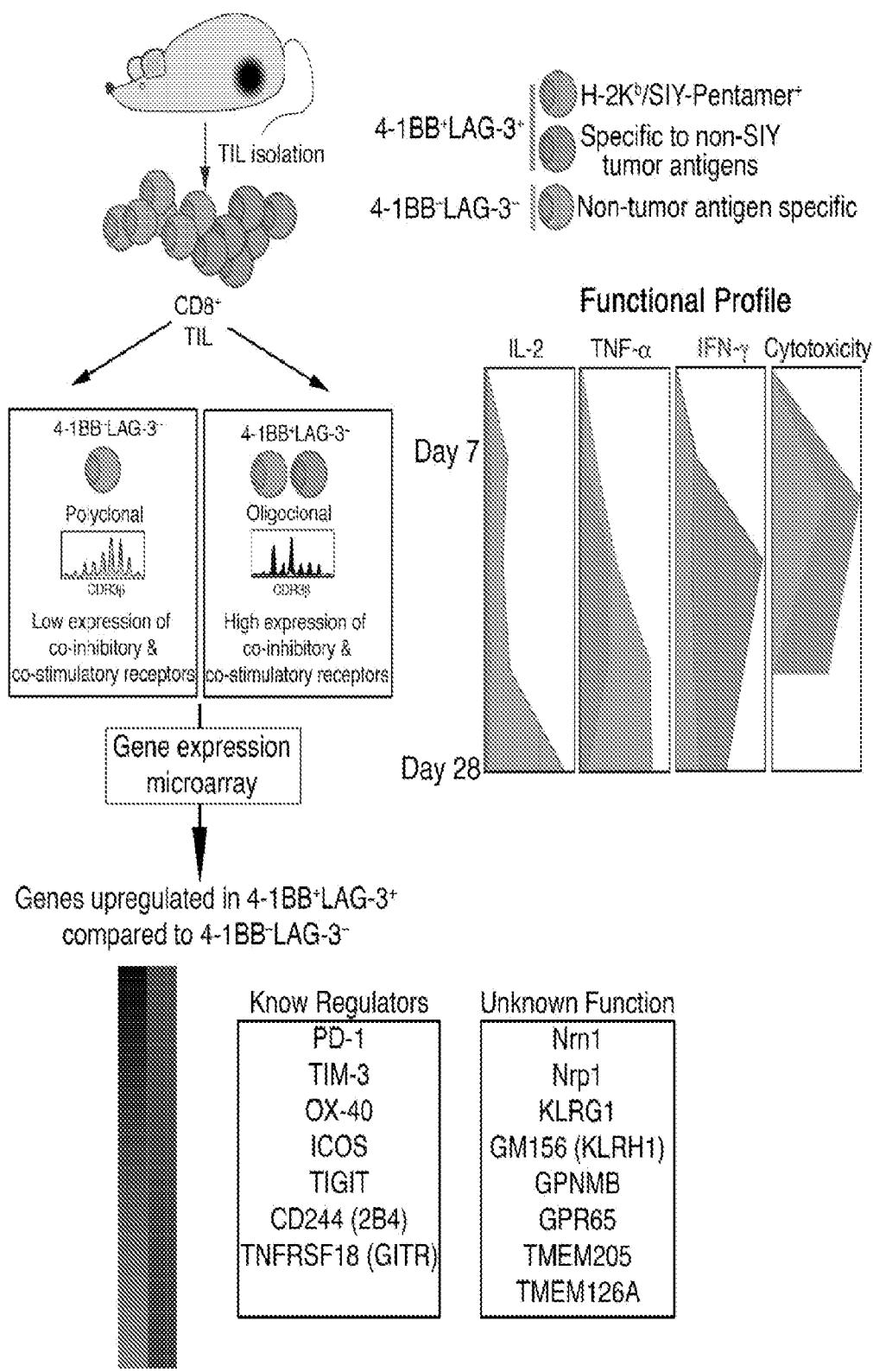
FIG. 12. Exemplary experimental protocol and data.

To address if the dysfunctional CD8+ TILs are terminally-differentiated short term effector cells or memory-like cells, the expression of KLRG-1 and IL-7Rα (Joshi et al., 2007). Most of the CD8$^+$ TIL were negative for KLRG-1 expression and there was no difference between the 4-1BB$^+$LAG-3$^+$ and 4-1BB$^-$LAG-3$^-$ populations. However, the majority of the 4-1BB$^+$LAG-3$^+$ TIL did not express the IL-7 receptor (IL-7Rα) compared to their negative counter parts (FIG. 6D). These results indicate that the 4-1BB$^-$LAG-3$^-$ TIL, which are not apparently specific for antigens expressed in the tumor microenvironment, are more memory-like, yet at the same time the tumor antigen-specific LAG-3$^+$4-1BB$^+$ subset has not fully acquired a terminal effector phenotype. Functional Relevance of Genes that are Differentially Regulated in CD8$^+$ 4-1BB$^+$LAG-3$^+$ TILs The gene array results in Table 2 provide a list of genes characterizing CD8$^+$ 4-1BB$^+$LAG-3$^+$ TILs. The list includes therapeutic targets and additional markers of anti-tumor immunity. Experiments conducted during development of embodiments herein to test the functional relevance of these additional targets/markers (FIG. 11). Data indicate that the array has identified targets for immunotherapy, using knockout mice (e.g., PD-1, TIM-3, OX-40ICOS, TIGIT, CD244, TNFRSF18, Nrn1, Nrp1, KLRG1, GM156, GPNMB, GPR65, TMEM205, and TMEM126A, CRTAM, Sema7a, etc.). Experiments demonstrate that Nrn1 and CRTAM are negative regulators of the anti-tumor immune response, as knockout mice lacking either of these molecules showed improved immune-mediated tumor control in vivo. In contrast, Sema7a is a positive regulator of anti-tumor immune responses, as knockout mice lacking this molecule show diminished immune-mediated tumor control in vivo (FIG. 11). These experiments indicate that agonists of Sema7a signaling and antagonists of Nrn1 and/or CRTAM should be useful therapeutics for the treatment of cancer.

Figure 7:
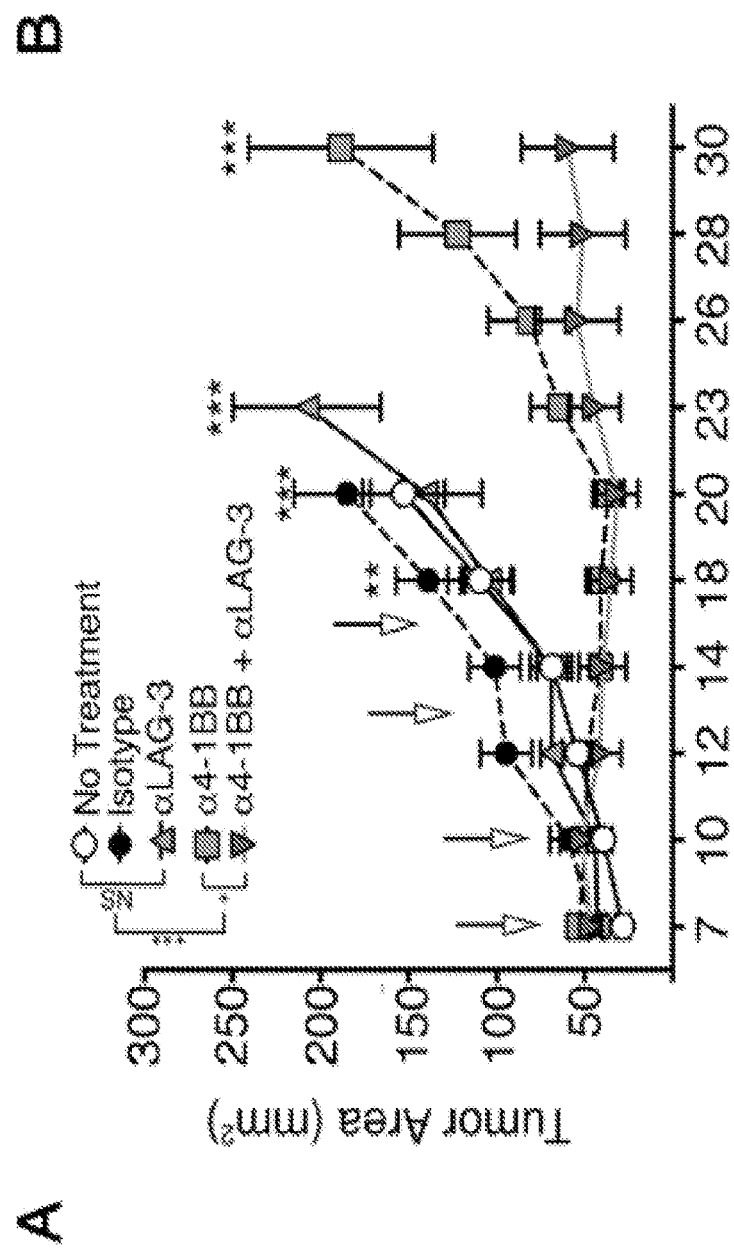
FIG. 7A-G. Anti-4-1BB and anti-LAG-3 acts synergistically to control tumor outgrowth and restore TIL function. (A) Tumor outgrowth measured in mm$^2$. Arrows indicate on which days mice received antibody therapy. Statistical significance at indicate time points is in comparison to anti-4-1BB+anti-LAG-3 treatment. n=5; two independent experiments. (B) Composition of H-2K$^b$/SIY$^+$CD8$^+$ TILS on day 14. Mice received antibody doses (100 μg each) on days 7, 10, 13 and 16. n=5; two independent experiments. (C-F) Representative flow plot and summary of NRP1/2B4 (C and E) and KLRG-1/IL-7Rα (D and F) expression in H-2K$^b$/SIY$^+$CD8$^+$ TILS without FTY720 (C and D) and with FTY720 (E and F) on day 14 after tumor inoculation. Mice received antibody treatment as in (A and B) and FTY720 was administered at a dose of 25 µg/mouse by gavage starting one day before treatment and continuing one dose per day until analysis (day 6 to day 13). n=5; two-independent experiments. (G) IL-2 production after treatment. Sorted cells from treated or untreated day 14 B16.SIY tumor bearing mice were stimulated in vitro for 12 hours and analyzed for Il-2 transcript by qRT-PCR. Protein concentration was determined by the bead-based LEGENDplex immunoassay and normalized to cell number. Two tumors on opposite flanks pooled per mouse. n=2-3; two independent experiments. A two-way ANOVA with Bonferroni post-hoc test was used for all analyses. *:P<0.05, :P<0.01, *:P<0.001.
Figure 7:
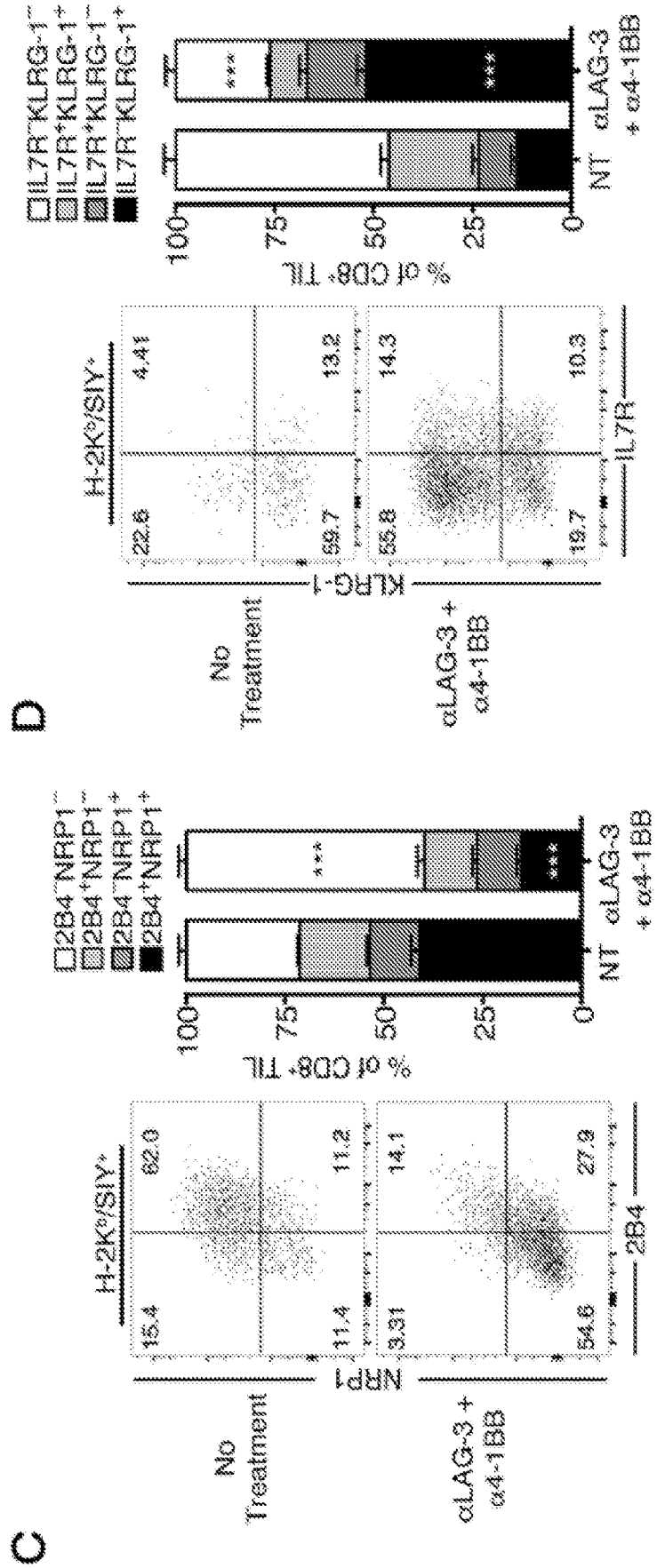
Figure 7:
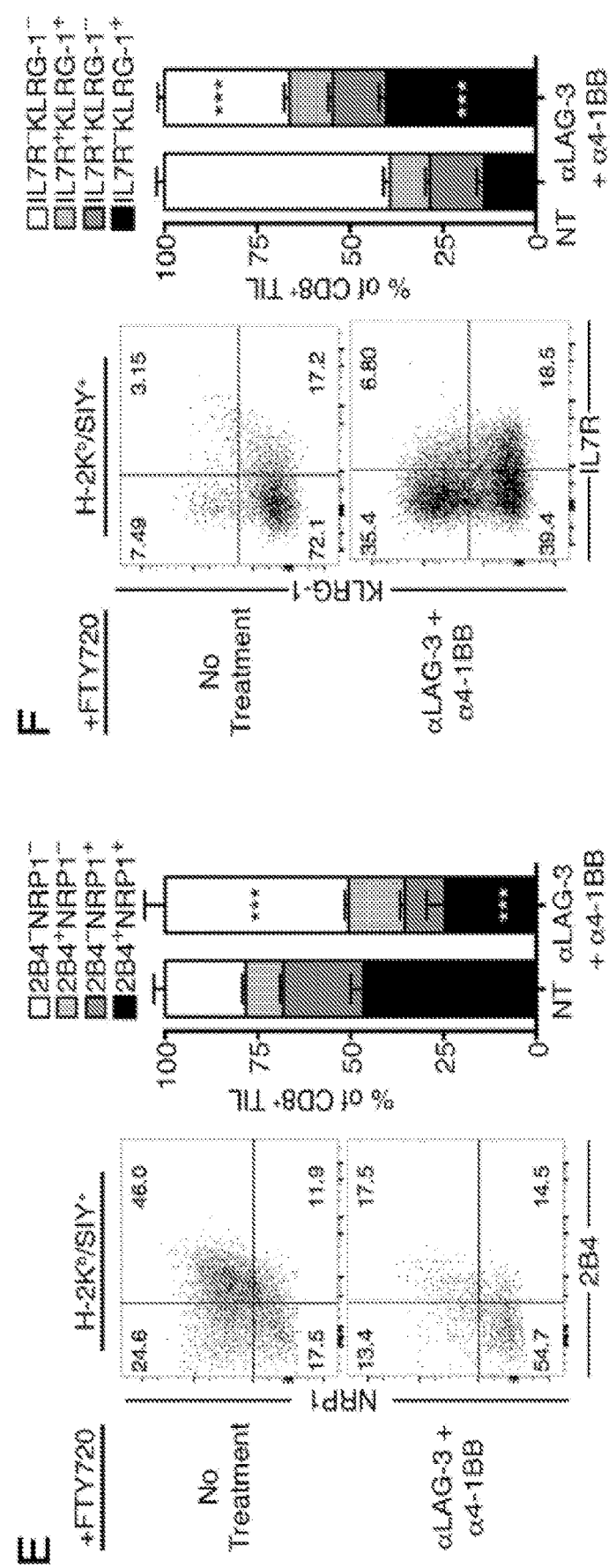
Figure 7:
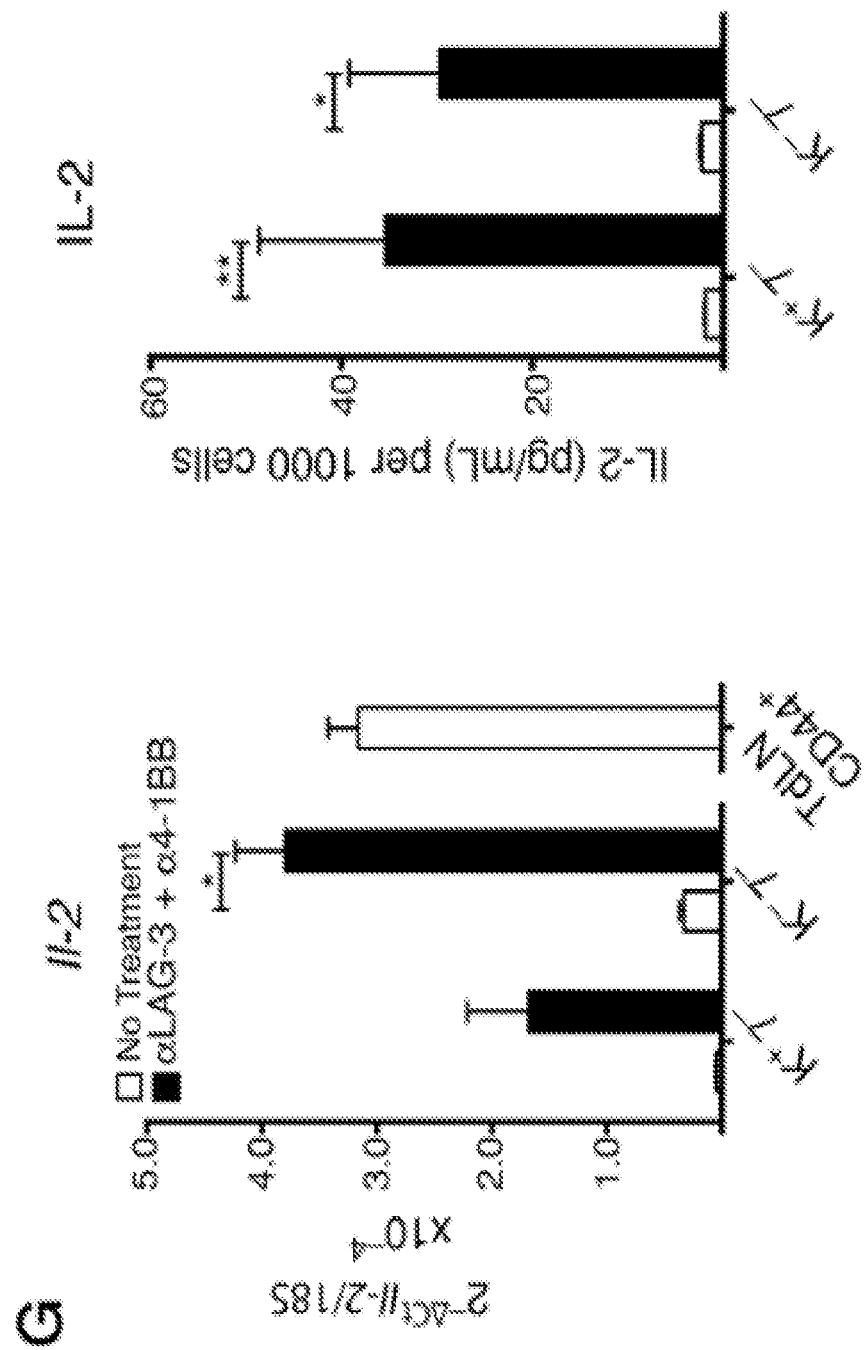

Targeting 4-1BB and LAG-3 Exerts Anti-Tumor Activity In Vivo and Normalizes the Function and Phenotypic Composition of CD8$^+$ TILs Experiments were conducted during development of embodiments herein to assess whether targeting these receptors might have therapeutic utility. To this end, an agonistic anti-4-1BB mAb was administered alone or in combination with a blocking anti-LAG-3 mAb in mice bearing established B16.SIY tumors. While each antibody treatment alone had some therapeutic effect as reflected by slower tumor growth, the combination was particularly potent (FIG. 7A). Analysis of the tumor microenvironment revealed that improved tumor control with the combination therapy was accompanied by an increase in the number of CD8$^+$ TILs specific for the SIY antigen (FIG. 7B), consistent with results reported previously with anti-PD-L1+anti-CTLA-4 mAb (Spranger et al., 2014b; Twyman-Saint Victor et al., 2015; incorporated by reference in their entireties).

It was next examined whether the therapeutic effect of anti-4-1BB+anti-LAG-3 mAbs was associated with a loss of phenotypic markers defining dysfunctional T cells in the steady state. Due to concern that re-analyzing the T cells for expression of LAG-3 and 4-1BB might be problematic, as the administered Abs could theoretically modulate the target receptors from the cell surface, the coordinate expression of additional receptors as identified above by gene expression profiling was taken advantage of Preliminary analyses of the bulk TIL subpopulations revealed decreased expression of NRP1 and 2B4 following anti-LAG-3+anti-4-1BB treatment (data not shown). Co-expression of 2B4 and NRP1 on SIY-reactive CD8$^+$ TILs identified by pentamer staining was analyzed. A 2.7-fold-decrease in the co-expression of 2B4 and NRP1 was observed upon anti-4-1BB+ and anti-LAG-3 mAb treatment (FIG. 7C), indicating a loss of the surface phenotype associated with T cell dysfunction. To determine whether this change was accompanied by a shift towards an effector phenotype, expression of KLGR-1 was examined. Indeed, a marked increase in KLGR-1 expression was observed on the SIY-reactive TIL following treatment, and a 3.7-fold increase in the KLRG-1$^{hi}$IL-7RA$^{lo}$ population was observed (FIG. 7D).

Figure 9:
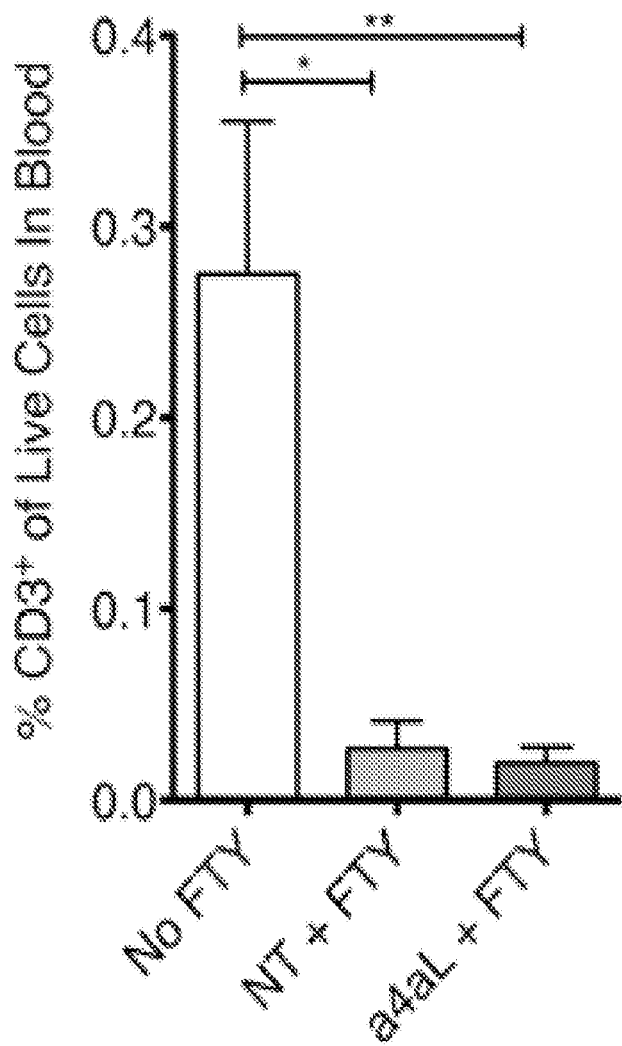
FIG. 9. CD3+ T cells on day 14 after FTY720 administration.

To eliminate the possibility that treatment with anti-LAG-3+anti-4-1BB mAbs was not altering the phenotype of T cells already within the tumor but rather was supporting recruitment of newly primed functional T cells from secondary lymphoid organs, the S1PR inhibitor FTY720, which prevents T cell egress from lymph nodes (Halin et al., 2005; incorporated by reference in its entirety), was utilized. The efficacy of anti-PD-L1-based immunotherapies was preserved in the presence of FTY720, arguing for re-functionalization of TIL as the major mechanism of action (Spranger et al., 2014a; incorporated by reference in its entirety). FTY720 administration was started on day 6 after tumor inoculation, 24 hours before the start of anti-LAG-3+anti-4-1BB treatment, and continued every day until TIL analysis on day 14. Peripheral blood analyzed at the same time point revealed marked depletion of circulating T cells (FIG. 9). Despite this loss of circulating T cells, the down regulation of 2B4 and NRP1 and the shift towards the KLRG1$^{hi}$IL-7RA$^{lo}$ phenotype was nonetheless preserved (FIGS. 7E and F).

To examine functional restoration of the TIL, the KLRG-1$^{lo}$IL-7RA$^{lo}$ and KLRG-1 IL-7RA$^{lo}$ CD8$^+$ TIL populations were sorted from B16.SIY tumors on day 14 following treatment and analyzed for IL-2 after restimulation in vitro. Indeed, the KLRG-1$^{lo}$IL-7RA$^{lo}$ and KLRG-1$^{hi}$IL-7RA$^{lo}$ populations showed an increased capacity to produce IL-2 upon stimulation (FIG. 7G). The relative level of Il-2 mRNA was comparable between the two CD8$^+$ TIL populations and control CD8$^+$CD44$^+$ TdLN T cells. Collectively, these data indicate that anti-4-1BB/anti-LAG-3 combinatorial treatment induces significant changes in the phenotype profile and promotes functional restoration of tumor antigen-specific CD8$^+$ T cells already present within the tumor microenvironment.

REFERENCES

The following references, some of which are cited above, are herein incorporated by references in their entireties.

Ahmadzadeh, M., L. A. Johnson, B. Heemskerk, J. R. Wunderlich, M. E. Dudley, D. E. White, and S. A. Rosenberg. 2009. Tumor antigen-specific CD8 T cells infiltrating the tumor express high levels of PD-1 and are functionally impaired. Blood. 114:1537-1544. doi:10.1182/blood-2008-12-195792.

Baitsch, L., A. Legat, L. Barba, S. A. Fuertes Marraco, J.-P. Rivals, P. Baumgaertner, C. Christiansen-Jucht, H. Bouzourene, D. Rimoldi, H. Pircher, N. Rufer, M. Matter, O. Michielin, and D. E. Speiser. 2012. Extended co-expression of inhibitory receptors by human CD8 T-cells depending on differentiation, antigen-specificity and anatomical localization. PLoS ONE. 7:e30852. doi:10.1371/journal.pone.0030852.

Baitsch, L., P. Baumgaertner, E. Devêvre, S. K. Raghav, A. Legat, L. Barba, S. Wieckowski, H. Bouzourene, B. Deplancke, P. Romero, N. Rufer, and D. E. Speiser. 2011. Exhaustion of tumor-specific CD8$^+$ T cells in metastases from melanoma patients. J. Clin. Invest. 121:2350-2360. doi:10.1172/JCI46102.

Blackburn, S. D., H. Shin, W. N. Haining, T. Zou, C. J. Workman, A. Polley, M. R. Betts, G. J. Freeman, D. A. A. Vignali, and E. J. Wherry. 2009. Coregulation of CD8+ T cell exhaustion by multiple inhibitory receptors during chronic viral infection. Nature Publishing Group. 10:29-37. doi:10.1038/ni.1679.

Brown, I. E., C. Blank, J. Kline, A. K. Kacha, and T. F. Gajewski. 2006. Homeostatic proliferation as an isolated variable reverses CD8+ T cell anergy and promotes tumor rejection. Journal of Immunology (Baltimore, Md.: 1950). 177:4521-4529.

Clouthier, D. L., A. C. Zhou, and T. H. Watts. 2014. Anti-GITR agonist therapy intrinsically enhances CD8 T cell responses to chronic lymphocytic choriomeningitis virus (LCMV), thereby circumventing LCMV-induced downregulation of costimulatory GITR ligand on APC. The Journal of Immunology. 193:5033-5043. doi:10.4049/jimmunol.1401002.

Crawford, A., J. M. Angelosanto, C. Kao, T. A. Doering, P. M. Odorizzi, B. E. Barnett, and E. J. Wherry. 2014. Molecular and Transcriptional Basis of CD4(+) T Cell Dysfunction during Chronic Infection. Immunity. 40:289-302. doi:10.1016/j.immuni.2014.01.005.

Cunningham, C. R., A. Champhekar, M. V. Tullius, B. J. Dillon, A. Zhen, J. R. de la Fuente, J. Herskovitz, H. Elsaesser, L. M. Snell, E. B. Wilson, J. C. de la Torre, S. G. Kitchen, M. A. Horwitz, S. J. Bensinger, S. T. Smale, and D. G. Brooks. 2016. Type I and Type II Interferon Coordinately Regulate Suppressive Dendritic Cell Fate and Function during Viral Persistence. PLoS Pathog. 12:e1005356. doi:10.1371/journal.ppat.1005356.

Currier, J. R., and M. A. Robinson. 2001. Spectratype/Immunoscope Analysis of the Expressed TCR Repertoire. John Wiley & Sons, Inc., Hoboken, N. J., USA. 92544 pp.

Diamond, M. S., M. Kinder, H. Matsushita, M. Mashayekhi, G. P. Dunn, J. M. Archambault, H. Lee, C. D. Arthur, J. M. White, U. Kalinke, K. M. Murphy, and R. D. Schreiber. 2011. Type I interferon is selectively required by dendritic cells for immune rejection of tumors. J. Exp. Med. 208:1989-2003. doi:10.1084/jem.20101158.

Doering, T. A., A. Crawford, J. M. Angelosanto, M. A. Paley, C. G. Ziegler, and E. J. Wherry. 2012. Network analysis reveals centrally connected genes and pathways involved in CD8+ T cell exhaustion versus memory. Immunity. 37:1130-1144. doi:10.1016/j.immuni.2012.08.021.

Evaristo, C., S. Spranger, S. E. Barnes, M. L. Miller, L. L. Molinero, F. L. Locke, T. F. Gajewski, and M.-L. Alegre. 2016. Cutting Edge: Engineering Active IKKβ in T Cells Drives Tumor Rejection. The Journal of Immunology. 196:2933-2938. doi: 10.4049/jimmunol.1501144.

Fan, X., S. A. Quezada, M. A. Sepulveda, P. Sharma, and J. P. Allison. 2014. Engagement of the ICOS pathway markedly enhances efficacy of CTLA-4 blockade in cancer immunotherapy. J. Exp. Med. 211:715-725. doi:10.1084/jem.20130590.

Fourcade, J., Z. Sun, O. Pagliano, P. Guillaume, I. F. Luescher, C. Sander, J. M. Kirkwood, D. Olive, V. Kuchroo, and H. M. Zarour. 2012. CD8(+) T cells specific for tumor antigens can be rendered dysfunctional by the tumor microenvironment through upregulation of the inhibitory receptors BTLA and PD-1. Cancer Res. 72:887-896. doi:10.1158/0008-5472.CAN-11-2637.

Fridman, W. H., F. Pagès, C. Sautès-Fridman, and J. Galon. 2012. The immune contexture in human tumours: impact on clinical outcome. Nature Publishing Group. 12:298-306. doi:10.1038/nrc3245.

Fuertes, M. B., A. K. Kacha, J. Kline, S.-R. Woo, D. M. Kranz, K. M. Murphy, and T. F. Gajewski. 2011. Host type I IFN signals are required for antitumor CD8+ T cell responses through CD8{alpha}+dendritic cells. J. Exp. Med. 208:2005-2016. doi:10.1084/jem.20101159.

Gajewski, T. F. 2007a. The expanding universe of regulatory T cell subsets in cancer. Immunity. 27:185-187. doi: 10.1016/j.immuni.2007.08.001.

Gajewski, T. F. 2007b. Failure at the Effector Phase: Immune Barriers at the Level of the Melanoma Tumor Microenvironment. Clin. Cancer Res. 13:5256-5261. doi:10.1158/1078-0432.CCR-07-0892.

Gajewski, T. F., H. Schreiber, and Y.-X. Fu. 2013. Innate and adaptive immune cells in the tumor microenvironment. Nat Immunol. 14:1014-1022. doi:10.1038/ni.2703.

Gajewski, T. F., Y. Meng, C. Blank, I. E. Brown, A. K. Kacha, J. Kline, and H. Harlin. 2006. Immune resistance orchestrated by the tumor microenvironment. Immunological Reviews. 1-15.

Goldszmid, R. S., A. Dzutsev, and G. Trinchieri. 2014. Host Immune Response to Infection and Cancer: Unexpected Commonalities. Cell Host and Microbe. 15:295-305. doi: 10.1016/j.chom.2014.02.003.

Gros, A., P. F. Robbins, X. Yao, Y. F. Li, S. Turcotte, E. Tran, J. R. Wunderlich, A. Mixon, S. Farid, M. E. Dudley, K.-I. Hanada, J. R. Almeida, S. Darko, D. C. Douek, J. C. Yang, and S. A. Rosenberg. 2014. PD-1 identifies the patient-specific CD8$^+$ tumor-reactive repertoire infiltrating human tumors. J. Clin. Invest. 124:2246-2259. doi: 10.1172/JCI73639.

Halin, C., M. L. Scimone, R. Bonasio, J.-M. Gauguet, T. R. Mempel, E. Quackenbush, R. L. Proia, S. Mandala, and U. H. von Andrian. 2005. The S1P-analog FTY720 differentially modulates T-cell homing via HEV: T-cell-expressed S1P1 amplifies integrin activation in peripheral lymph nodes but not in Peyer patches. Blood. 106:1314-1322. doi:10.1182/blood-2004-09-3687.

Harlin, H., T. V. Kuna, A. C. Peterson, Y. Meng, and T. F. Gajewski. 2006. Tumor progression despite massive influx of activated CD8+ T cells in a patient with malignant melanoma ascites. Cancer Immunol Immunother. 55:1185-1197. doi:10.1007/s00262-005-0118-2.

Harlin, H., Y. Meng, A. C. Peterson, Y. Zha, M. Tretiakova, C. Slingluff, M. McKee, and T. F. Gajewski. 2009. Chemokine expression in melanoma metastases associated with CD8+ T-cell recruitment. Cancer Res. 69:3077-3085. doi:10.1158/0008-5472.CAN-08-2281.

Hoelzinger, D. B., S. E. Smith, N. Mirza, A. L. Dominguez, S. Z. Manrique, and J. Lustgarten. 2010. Blockade of CCL1 Inhibits T Regulatory Cell Suppressive Function Enhancing Tumor Immunity without Affecting T Effector Responses. The Journal of Immunology. 184:6833-6842. doi:10.4049/jimmunol.0904084.

Jenkins, M. K., D. M. Pardoll, J. Mizuguchi, T. M. Chused, and R. H. Schwartz. 1987. Molecular events in the induction of a nonresponsive state in interleukin 2-producing helper T-lymphocyte clones. PNAS. 84:5409-5413.

Johnston, R. J., L. Comps-Agrar, J. Hackney, X. Yu, M. Huseni, Y. Yang, S. Park, V. Javinal, H. Chiu, B. Irving, D. L. Eaton, and J. L. Grogan. 2014. The immunoreceptor TIGIT regulates antitumor and antiviral CD8(+) T cell effector function. Cancer Cell. 26:923-937. doi:10.1016/j.ccell.2014.10.018.

Joshi, N. S., W. Cui, A. Chandele, H. K. Lee, D. R. Urso, J. Hagman, L. Gapin, and S. M. Kaech. 2007. Inflammation Directs Memory Precursor and Short-Lived Effector CD8+ T Cell Fates via the Graded Expression of T-bet Transcription Factor. Immunity. 27:281-295. doi:10.1016/j.immuni.2007.07.010.

Kaech, S. M., J. T. Tan, E. J. Wherry, B. T. Konieczny, C. D. Surh, and R. Ahmed. 2003. Selective expression of the interleukin 7 receptor identifies effector CD8 T cells that give rise to long-lived memory cells. Nat Immunol. 4:1191-1198. doi:10.1038/ni1009.

Kearse, M., R. Moir, A. Wilson, S. Stones-Havas, M. Cheung, S. Sturrock, S. Buxton, A. Cooper, S. Markowitz, C. Duran, T. Thierer, B. Ashton, P. Meintjes, and A. Drummond. 2012. Geneious Basic: an integrated and extendable desktop software platform for the organization and analysis of sequence data. Bioinformatics. 28:1647-1649. doi:10.1093/bioinformatics/bts199.

Kim, J.-O., H. W. Kim, K.-M. Baek, and C.-Y. Kang. 2003. NF-κB and AP-1 regulate activation-dependent CD137 (4-1BB) expression in T cells. FEBS Letters. 541:163-170. doi:10.1016/S0014-5793(03)00326-0.

Kline, J., L. Zhang, L. Battaglia, K. S. Cohen, and T. F. Gajewski. 2012. Cellular and molecular requirements for rejection of B16 melanoma in the setting of regulatory T cell depletion and homeostatic proliferation. The Journal of Immunology. 188:2630-2642. doi:10.4049/jimmunol.1100845.

Kuchroo, V. K., A. C. Anderson, and C. Petrovas. 2014. Coinhibitory receptors and CD8 T cell exhaustion in chronic infections. Current Opinion in HIV and AIDS. 9:439-445. doi:10.1097/COH.0000000000000088.

Larkin, J., F. S. Hodi, and J. D. Wolchok. 2015. Combined Nivolumab and Ipilimumab or Monotherapy in Untreated Melanoma. New England Journal of Medicine. 373:1270-1271. doi:10.1056/NEJMc1509660.

Li, S., T. Miao, M. Sebastian, P. Bhullar, E. Ghaffari, M. Liu, A. L. J. Symonds, and P. Wang. 2012. The transcription factors Egr2 and Egr3 are essential for the control of inflammation and antigen-induced proliferation of B and T cells. Immunity. 37:685-696. doi:10.1016/j.immuni.2012.08.001.

Martinez, G. J., R. M. Pereira, T. Äijö, E. Y. Kim, F. Marangoni, M. E. Pipkin, S. Togher, V. Heissmeyer, Y. C. Zhang, S. Crotty, E. D. Lamperti, K. M. Ansel, T. R. Mempel, H. Lähdesmäki, P. G. Hogan, and A. Rao. 2015. The Transcription Factor NFAT Promotes Exhaustion of Activated CD8+ T Cells. Immunity. 42:265-278. doi:10.1016/j.immuni.2015.01.006.

Odorizzi, P. M., K. E. Pauken, M. A. Paley, A. Sharpe, and E. J. Wherry. 2015. Genetic absence of PD-1 promotes accumulation of terminally differentiated exhausted CD8+ T cells. J. Exp. Med. 439:jem.20142237-1137. doi:10.1084/jem.20142237.

Palazón, A., I. Martinez-Forero, A. Teijeira, A. Morales-Kastresana, C. Alfaro, M. F. Sanmamed, J. L. Perez-Gracia, I. Peñuelas, S. Hervás-Stubbs, A. Rouzaut, M. O. de Landázuri, M. Jure-Kunkel, J. Aragonés, and I. Melero. 2012. The HIF-1α hypoxia response in tumor-infiltrating T lymphocytes induces functional CD137 (4-1BB) for immunotherapy. Cancer Discov. 2:608-623. doi:10.1158/2159-8290.CD-11-0314.

Pardoll, D. M. 2012. The blockade of immune checkpoints in cancer immunotherapy. 1-13. doi:10.1038/nrc3239.

Pauken, K. E., and E. J. Wherry. 2015. Overcoming T cell exhaustion in infection and cancer. Trends in Immunology. 36:265-276. doi:10.1016/j.it.2015.02.008.

Pearce, E. L., M. C. Poffenberger, C. H. Chang, and R. G. Jones. 2013. Fueling immunity: insights into metabolism and lymphocyte function. Science.

Plaisier, S. B., R. Taschereau, J. A. Wong, and T. G. Graeber. 2010. Rank-rank hypergeometric overlap: identification of statistically significant overlap between gene-expression signatures. Nucl. Acids Res. 38:e169-e169. doi:10.1093/nar/gkq636.

Rosenblatt, J. D., and J. L. Stein. 2014. RRHO: Test overlap using the Rank-Rank Hypergeometric test.

Safford, M., S. Collins, M. A. Lutz, A. Allen, C.-T. Huang, J. Kowalski, A. Blackford, M. R. Horton, C. Drake, R. H. Schwartz, and J. D. Powell. 2005. Egr-2 and Egr-3 are negative regulators of T cell activation. Nat Immunol. 6:472-480. doi:10.1038/ni1193.

Sarkar, S., V. Kalia, W. N. Haining, B. T. Konieczny, S. Subramaniam, and R. Ahmed. 2008. Functional and genomic profiling of effector CD8 T cell subsets with distinct memory fates. J. Exp. Med. 205:625-640. doi:10.1084/jem.20071641.

Sarris, M., K. G. Andersen, F. Randow, L. Mayr, and A. G. Betz. 2008. Neuropilin-1 Expression on Regulatory T Cells Enhances Their Interactions with Dendritic Cells during Antigen Recognition. Immunity. 28:402-413. doi:10.1016/j.immuni.2008.01.012.

Schietinger, A., and P. D. Greenberg. 2014. Tolerance and exhaustion: defining mechanisms of T cell dysfunction. Trends in Immunology. 35:51-60. doi:10.1016/j.it.2013.10.001.

Schietinger, A., M. Philip, V. E. Krisnawan, E. Y. Chiu, J. J. Delrow, R. S. Basom, P. Lauer, D. G. Brockstedt, S. E. Knoblaugh, G. J. Hammerling, T. D. Schell, N. Garbi, and P. D. Greenberg. 2016. Tumor-Specific T Cell Dysfunction Is a Dynamic Antigen-Driven Differentiation Program Initiated Early during Tumorigenesis. Immunity. doi:10.1016/j.immuni.2016.07.011.

Schwartz, R. H. 2003. T C ELLA NERGY*. Annu. Rev. Immunol. 21:305-334. doi:10.1146/annurev.immunol.21.120601.141110.

Schwartz, R. H., D. L. Mueller, M. K. Jenkins, and H. Quill. 1989. T-cell clonal anergy. Cold Spring Harb. Symp. Quant. Biol. 54 Pt 2:605-610.

Shannon, P., A. Markiel, O. Ozier, N. S. Baliga, J. T. Wang, D. Ramage, N. Amin, B. Schwikowski, and T. Ideker. 2003. Cytoscape: a software environment for integrated models of biomolecular interaction networks. Genome Res. 13:2498-2504. doi:10.1101/gr.1239303.

Snell, L. M., and D. G. Brooks. 2015. New insights into type I interferon and the immunopathogenesis of persistent viral infections. Curr. Opin. Immunol. 34:91-98. doi:10.1016/j.coi.2015.03.002.

Spiotto, M. T., P. Yu, D. A. Rowley, M. I. Nishimura, S. C. Meredith, T. F. Gajewski, Y.-X. Fu, and H. Schreiber. 2002. Increasing Tumor Antigen Expression Overcomes "Ignorance" to Solid Tumors via Crosspresentation by Bone Marrow-Derived Stromal Cells. Immunity. 17:737-747. doi:10.1016/S1074-7613(02)00480-6.

Spranger, S., H. K. Koblish, and B. Horton. 2014a. Mechanism of tumor rejection with doublets of CTLA-4, PD-1/PD-L1, or IDO blockade involves restored IL-2 production and proliferation of CD8+ T cells directly . . . Journal for . . . .

Spranger, S., H. K. Koblish, B. Horton, P. A. Scherle, R. Newton, and T. F. Gajewski. 2014b. Mechanism of tumor rejection with doublets of CTLA-4, PD-1/PD-L1, or IDO blockade involves restored IL-2 production and proliferation of CD8(+) T cells directly within the tumor microenvironment. J Immunother Cancer. 2:3. doi:10.1186/2051-1426-2-3.

Spranger, S., R. M. Spaapen, Y. Zha, J. Williams, Y. Meng, T. T. Ha, and T. F. Gajewski. 2013. Up-Regulation of PD-L1, IDO, and Tregs in the Melanoma Tumor Microenvironment Is Driven by CD8+ T Cells. Science Translational Medicine. 5:200ra116-200ra116. doi:10.1126/scitranslmed.3006504.

Sumitomo, S., K. Fujio, T. Okamura, and K. Yamamoto. 2013. Egr2 and Egr3 are the unique regulators for systemic autoimmunity. jak-stat. 2:e23952. doi:10.4161/jkst.23952.

Tumeh, P. C., C. L. Harview, J. H. Yearley, I. P. Shintaku, E. J. M. Taylor, L. Robert, B. Chmielowski, M. Spasic, G. Henry, V. Ciobanu, A. N. West, M. Carmona, C. Kivork, E. Seja, G. Cherry, A. J. Gutierrez, T. R. Grogan, C. Mateus, G. Tomasic, J. A. Glaspy, R. O. Emerson, H. Robins, R. H. Pierce, D. A. Elashoff, C. Robert, and A. Ribas. 2014. PD-1 blockade induces responses by inhibiting adaptive immune resistance. Nature. 515:568-571. doi:10.1038/nature13954.

Twyman-Saint Victor, C., A. J. Rech, A. Maity, R. Rengan, K. E. Pauken, E. Stelekati, J. L. Benci, B. Xu, H. Dada, P. M. Odorizzi, R. S. Herati, K. D. Mansfield, D. Patsch, R. K. Amaravadi, L. M. Schuchter, H. Ishwaran, R. Mick, D. A. Pryma, X. Xu, M. D. Feldman, T. C. Gangadhar, S. M. Hahn, E. J. Wherry, R. H. Vonderheide, and A. J. Minn. 2015. Radiation and dual checkpoint blockade activate non-redundant immune mechanisms in cancer. Nature. 520:373-377. doi:10.1038/nature14292.

Vesely, M. D., M. H. Kershaw, R. D. Schreiber, and M. J. Smyth. 2011. Natural Innate and Adaptive Immunity to Cancer. Annu. Rev. Immunol. 29:235-271. doi:10.1146/annurev-immunol-031210-101324.

Waugh, K. A., S. M. Leach, B. L. Moore, T. C. Bruno, J. D. Buhrman, and J. E. Slansky. 2016. Molecular Profile of Tumor-Specific CD8+ T Cell Hypofunction in a Transplantable Murine Cancer Model. The Journal of Immunology. 197:1477-1488. doi: 10.4049/jimmunol.1600589.

Wherry, E. J., and M. Kurachi. 2015. Molecular and cellular insights into T cell exhaustion. Nat Rev Immunol. 15:486-499. doi:10.1038/nri3862.

Wherry, E. J., S.-J. Ha, S. M. Kaech, W. N. Haining, S. Sarkar, V. Kalia, S. Subramaniam, J. N. Blattman, D. L. Barber, and R. Ahmed. 2007. Molecular signature of CD8+ T cell exhaustion during chronic viral infection. Immunity. 27:670-684. doi: 10.1016/j.immuni.2007.09.006.

Wu, X., H. Zhang, Q. Xing, J. Cui, J. Li, Y. Li, Y. Tan, and S. Wang. 2014. PD-1(+) CD8(+) T cells are exhausted in tumours and functional in draining lymph nodes of colorectal cancer patients. Br. J. Cancer. 111:1391-1399. doi:10.1038/bjc.2014.416.

Zajac, A. J., J. N. Blattman, K. Murali-Krishna, D. J. Sourdive, M. Suresh, J. D. Altman, and R. Ahmed. 1998. Viral immune evasion due to persistence of activated T cells without effector function. J. Exp. Med. 188:2205-2213. doi:10.1084/jem.188.12.2205.

Zha, Y., R. Marks, A. W. Ho, A. C. Peterson, S. Janardhan, I. Brown, K. Praveen, S. Stang, J. C. Stone, and T. F. Gajewski. 2006. T cell anergy is reversed by active Ras and is regulated by diacylglycerol kinase-alpha. Nat Immunol. 7:1166-1173. doi:10.1038/ni1394.

Zhang, L., T. F. Gajewski, and J. Kline. 2009. PD-1/PD-L1 interactions inhibit antitumor immune responses in a murine acute myeloid leukemia model. Blood. 114:1545-1552. doi:10.1182/blood-2009-03-206672.

Zheng, Y., Y. Zha, G. Driessens, F. Locke, and T. F. Gajewski. 2012. Transcriptional regulator early growth response gene 2 (Egr2) is required for T cell anergy in vitro and in vivo. Journal of Experimental Medicine. 209:2157-2163. doi: 10.1084/jem.20120342.

Zheng, Y., Y. Zha, R. M. Spaapen, R. Mathew, K. Barr, A. Bendelac, and T. F. Gajewski. 2013. Egr2-dependent gene expression profiling and ChIP-Seq reveal novel biologic targets in T cell anergy. Mol. Immunol. 55:283-291. doi:10.1016/j.molimm.2013.03.006.

The invention claimed is:

1. A method of treating dysfunctional tumor antigen-specific CD8+ T cells in a subject in need thereof with a solid tumor cancer comprising identifying dysfunctional T cells by testing said cells for expression of GPNMB; and administering to the subject an antibody or antibody fragment that specifically targets dysfunctional tumor antigen-specific CD8+ T cells, wherein the antibody or antibody fragment targets GPNMB expressed on the surface of the T cells, and wherein the dysfunctional tumor antigen-specific CD8+ T cells are within a tumor microenvironment.

2. The method of claim 1, wherein the tumor allows T cell infiltration, but is resistant to immunotherapies.

3. The method of claim 1, further comprising contacting the dysfunctional tumor antigen-specific CD8+ T cells with an anti-4-1BB and/or anti-LAG3 agent.

4. The method of claim 3, wherein the anti-4-1BB and/or anti-LAG3 agent is an antibody, antibody fragment, or antibody mimetic molecule.

5. The method of claim 1, further comprising co-administration of an additional therapeutic agent.

6. The method of claim 5, wherein the additional therapeutic agent is a chemotherapeutic or an immunotherapeutic agent.

7. The method of claim 6, wherein the additional therapeutic agent is an immunotherapeutic agent selected from the list consisting of cell-based therapies, monoclonal antibody (mAb) therapy, cytokine therapy, and adjuvant treatment.

8. The method of claim 7, wherein the immunotherapeutic agent is a mAb therapy selected from the list consisting of anti-CTLA-4 monoclonal antibodies and/or anti-PD-L1 monoclonal antibodies.

9. The method of claim 7, wherein the immunotherapeutic agent is a cell-based therapy selected from the list consisting of dendritic-cell therapy and T-cell therapy.

10. The method of claim 5, wherein the additional therapeutic agent targets PD-1, TIM-3, OX-40ICOS, TIGIT, CD244, TNFRSF18, Nrn1, Nrp1, KLRG1, GM156, GPNMB, GPR65, TMEM205, and TMEM126A, Nrn1, CRTAM and/or Sema7a.

11. The method of claim 1, wherein the antibody or antibody fragment is an anti-Nrn1 antibody, antibody fragment, or antibody mimetic molecule.

12. The method of claim 1, wherein the antibody or antibody fragment is an anti-Sema7a antibody, antibody fragment, or antibody mimetic molecule.

13. The method of claim 1, wherein the antibody or antibody fragment is an anti-CRTAM antibody, antibody fragment, or antibody mimetic molecule.

* * * * *

SEQUENCE LISTING

<160> NUMBER OF SEQ ID NOS: 60

<210> SEQ ID NO 1
<211> LENGTH: 24
<212> TYPE: DNA
<213> ORGANISM: Artificial sequence
<220> FEATURE:
<223> OTHER INFORMATION: Synthetic

<400> SEQUENCE: 1
ctcaaacaag gagaccttgg gtgg                                        24

<210> SEQ ID NO 2
<211> LENGTH: 24
<212> TYPE: DNA
<213> ORGANISM: Artificial sequence
<220> FEATURE:
<223> OTHER INFORMATION: Synthetic

<400> SEQUENCE: 2
cagacagctc caagctactt ttac                                        24

<210> SEQ ID NO 3
<211> LENGTH: 24
<212> TYPE: DNA
<213> ORGANISM: Artificial sequence

```
<220> FEATURE:
<223> OTHER INFORMATION: Synthetic

<400> SEQUENCE: 3
atgagccagg gcagaacctt gtac                                          24

<210> SEQ ID NO 4
<211> LENGTH: 24
<212> TYPE: DNA
<213> ORGANISM: Artificial sequence
<220> FEATURE:
<223> OTHER INFORMATION: Synthetic

<400> SEQUENCE: 4
gaaattcagt cctctgaggc agga                                          24

<210> SEQ ID NO 5
<211> LENGTH: 24
<212> TYPE: DNA
<213> ORGANISM: Artificial sequence
<220> FEATURE:
<223> OTHER INFORMATION: Synthetic

<400> SEQUENCE: 5
ctaaagcctg atgactcggc caca                                          24

<210> SEQ ID NO 6
<211> LENGTH: 24
<212> TYPE: DNA
<213> ORGANISM: Artificial sequence
<220> FEATURE:
<223> OTHER INFORMATION: Synthetic

<400> SEQUENCE: 6
ctttggagct agaggactct gccg                                          24

<210> SEQ ID NO 7
<211> LENGTH: 24
<212> TYPE: DNA
<213> ORGANISM: Artificial sequence
<220> FEATURE:
<223> OTHER INFORMATION: Synthetic

<400> SEQUENCE: 7
ccttggaact ggaggactct gcta                                          24

<210> SEQ ID NO 8
<211> LENGTH: 24
<212> TYPE: DNA
<213> ORGANISM: Artificial sequence
<220> FEATURE:
<223> OTHER INFORMATION: Synthetic

<400> SEQUENCE: 8
gcccagaaga acgagatggc cgtt                                          24

<210> SEQ ID NO 9
<211> LENGTH: 30
<212> TYPE: DNA
<213> ORGANISM: Artificial sequence
<220> FEATURE:
<223> OTHER INFORMATION: Synthetic

<400> SEQUENCE: 9
ggattctgct aaaacaaacc agacatctgt                                    30
```

<210> SEQ ID NO 10
<211> LENGTH: 24
<212> TYPE: DNA
<213> ORGANISM: Artificial sequence
<220> FEATURE:
<223> OTHER INFORMATION: Synthetic

<400> SEQUENCE: 10
gcttcccttt ctcagacagc tgta                                              24

<210> SEQ ID NO 11
<211> LENGTH: 24
<212> TYPE: DNA
<213> ORGANISM: Artificial sequence
<220> FEATURE:
<223> OTHER INFORMATION: Synthetic

<400> SEQUENCE: 11
gctaccccct ctcagacatc agtg                                              24

<210> SEQ ID NO 12
<211> LENGTH: 23
<212> TYPE: DNA
<213> ORGANISM: Artificial sequence
<220> FEATURE:
<223> OTHER INFORMATION: Synthetic

<400> SEQUENCE: 12
ggcttctccc tctcagacat ctt                                               23

<210> SEQ ID NO 13
<211> LENGTH: 24
<212> TYPE: DNA
<213> ORGANISM: Artificial sequence
<220> FEATURE:
<223> OTHER INFORMATION: Synthetic

<400> SEQUENCE: 13
ctctctctac attggctctg cagg                                              24

<210> SEQ ID NO 14
<211> LENGTH: 24
<212> TYPE: DNA
<213> ORGANISM: Artificial sequence
<220> FEATURE:
<223> OTHER INFORMATION: Synthetic

<400> SEQUENCE: 14
cttcgaatca agtctgtaga gccg                                              24

<210> SEQ ID NO 15
<211> LENGTH: 24
<212> TYPE: DNA
<213> ORGANISM: Artificial sequence
<220> FEATURE:
<223> OTHER INFORMATION: Synthetic

<400> SEQUENCE: 15
tgaagatcca gagcagcggg cccc                                              24

<210> SEQ ID NO 16
<211> LENGTH: 29
<212> TYPE: DNA
<213> ORGANISM: Artificial sequence
<220> FEATURE:
<223> OTHER INFORMATION: Synthetic

```
<400> SEQUENCE: 16
ccactctgaa gattcaacct acagaaccc                                          29

<210> SEQ ID NO 17
<211> LENGTH: 24
<212> TYPE: DNA
<213> ORGANISM: Artificial sequence
<220> FEATURE:
<223> OTHER INFORMATION: Synthetic

<400> SEQUENCE: 17
caagatccag tctgcaaagc aggg                                               24

<210> SEQ ID NO 18
<211> LENGTH: 24
<212> TYPE: DNA
<213> ORGANISM: Artificial sequence
<220> FEATURE:
<223> OTHER INFORMATION: Synthetic

<400> SEQUENCE: 18
gcacggagaa gctgcttctc agcc                                               24

<210> SEQ ID NO 19
<211> LENGTH: 21
<212> TYPE: DNA
<213> ORGANISM: Artificial sequence
<220> FEATURE:
<223> OTHER INFORMATION: Synthetic

<400> SEQUENCE: 19
gcatatcttg aagacagagg c                                                  21

<210> SEQ ID NO 20
<211> LENGTH: 27
<212> TYPE: DNA
<213> ORGANISM: Artificial sequence
<220> FEATURE:
<223> OTHER INFORMATION: Synthetic

<400> SEQUENCE: 20
ctctgaaaat ccaacccaca gcactgg                                            27

<210> SEQ ID NO 21
<211> LENGTH: 24
<212> TYPE: DNA
<213> ORGANISM: Artificial sequence
<220> FEATURE:
<223> OTHER INFORMATION: Synthetic

<400> SEQUENCE: 21
tctgaagaag acgactcagc actg                                               24

<210> SEQ ID NO 22
<211> LENGTH: 24
<212> TYPE: DNA
<213> ORGANISM: Artificial sequence
<220> FEATURE:
<223> OTHER INFORMATION: Synthetic

<400> SEQUENCE: 22
gcaaggcctg gagacagcag tatc                                               24

<210> SEQ ID NO 23
```

```
<211> LENGTH: 19
<212> TYPE: DNA
<213> ORGANISM: Artificial sequence
<220> FEATURE:
<223> OTHER INFORMATION: Synthetic

<400> SEQUENCE: 23
tgctttggga agctccagt                                                    19

<210> SEQ ID NO 24
<211> LENGTH: 20
<212> TYPE: DNA
<213> ORGANISM: Artificial sequence
<220> FEATURE:
<223> OTHER INFORMATION: Synthetic

<400> SEQUENCE: 24
ccggtcttaa gcacagacct                                                   20

<210> SEQ ID NO 25
<211> LENGTH: 19
<212> TYPE: DNA
<213> ORGANISM: Artificial sequence
<220> FEATURE:
<223> OTHER INFORMATION: Synthetic

<400> SEQUENCE: 25
ctacccggtg gaagacctc                                                    19

<210> SEQ ID NO 26
<211> LENGTH: 19
<212> TYPE: DNA
<213> ORGANISM: Artificial sequence
<220> FEATURE:
<223> OTHER INFORMATION: Synthetic

<400> SEQUENCE: 26
tcaatcggct gcaagatgt                                                    19

<210> SEQ ID NO 27
<211> LENGTH: 21
<212> TYPE: DNA
<213> ORGANISM: Artificial sequence
<220> FEATURE:
<223> OTHER INFORMATION: Synthetic

<400> SEQUENCE: 27
agatccaaca acgaggagac a                                                 21

<210> SEQ ID NO 28
<211> LENGTH: 19
<212> TYPE: DNA
<213> ORGANISM: Artificial sequence
<220> FEATURE:
<223> OTHER INFORMATION: Synthetic

<400> SEQUENCE: 28
tcaccatgaa acccactgc                                                    19

<210> SEQ ID NO 29
<211> LENGTH: 21
<212> TYPE: DNA
<213> ORGANISM: Artificial sequence
<220> FEATURE:
<223> OTHER INFORMATION: Synthetic

<400> SEQUENCE: 29
``` cacccctagcc taacctcaac c                                              21

<210> SEQ ID NO 30
<211> LENGTH: 20
<212> TYPE: DNA
<213> ORGANISM: Artificial sequence
<220> FEATURE:
<223> OTHER INFORMATION: Synthetic

<400> SEQUENCE: 30
ctggcagatc cagtcctgtt                                                 20

<210> SEQ ID NO 31
<211> LENGTH: 20
<212> TYPE: DNA
<213> ORGANISM: Artificial sequence
<220> FEATURE:
<223> OTHER INFORMATION: Synthetic

<400> SEQUENCE: 31
atgagggagg agagcggtat                                                 20

<210> SEQ ID NO 32
<211> LENGTH: 20
<212> TYPE: DNA
<213> ORGANISM: Artificial sequence
<220> FEATURE:
<223> OTHER INFORMATION: Synthetic

<400> SEQUENCE: 32
agaaaaccat catgccaggt                                                 20

<210> SEQ ID NO 33
<211> LENGTH: 18
<212> TYPE: DNA
<213> ORGANISM: Artificial sequence
<220> FEATURE:
<223> OTHER INFORMATION: Synthetic

<400> SEQUENCE: 33
atcctcgcgg tgcaaata                                                   18

<210> SEQ ID NO 34
<211> LENGTH: 19
<212> TYPE: DNA
<213> ORGANISM: Artificial sequence
<220> FEATURE:
<223> OTHER INFORMATION: Synthetic

<400> SEQUENCE: 34
ccggggagat ctcatcaaa                                                  19

<210> SEQ ID NO 35
<211> LENGTH: 24
<212> TYPE: DNA
<213> ORGANISM: Artificial sequence
<220> FEATURE:
<223> OTHER INFORMATION: Synthetic

<400> SEQUENCE: 35
tgaagacaca ctacctgact cctg                                            24

<210> SEQ ID NO 36
<211> LENGTH: 21
<212> TYPE: DNA

```
<213> ORGANISM: Artificial sequence
<220> FEATURE:
<223> OTHER INFORMATION: Synthetic

<400> SEQUENCE: 36
gctgctcact gtgaaggaag t                                             21

<210> SEQ ID NO 37
<211> LENGTH: 20
<212> TYPE: DNA
<213> ORGANISM: Artificial sequence
<220> FEATURE:
<223> OTHER INFORMATION: Synthetic

<400> SEQUENCE: 37
caatctgtac cccgaggaga                                               20

<210> SEQ ID NO 38
<211> LENGTH: 19
<212> TYPE: DNA
<213> ORGANISM: Artificial sequence
<220> FEATURE:
<223> OTHER INFORMATION: Synthetic

<400> SEQUENCE: 38
ctgtagccca cgtcgtagc                                                19

<210> SEQ ID NO 39
<211> LENGTH: 21
<212> TYPE: DNA
<213> ORGANISM: Artificial sequence
<220> FEATURE:
<223> OTHER INFORMATION: Synthetic

<400> SEQUENCE: 39
gctgctcact gtgaaggaag t                                             21

<210> SEQ ID NO 40
<211> LENGTH: 19
<212> TYPE: DNA
<213> ORGANISM: Artificial sequence
<220> FEATURE:
<223> OTHER INFORMATION: Synthetic

<400> SEQUENCE: 40
tcaccatgaa acccactgc                                                19

<210> SEQ ID NO 41
<211> LENGTH: 20
<212> TYPE: DNA
<213> ORGANISM: Artificial sequence
<220> FEATURE:
<223> OTHER INFORMATION: Synthetic

<400> SEQUENCE: 41
tcttgctgtg gcaattcaga                                               20

<210> SEQ ID NO 42
<211> LENGTH: 18
<212> TYPE: DNA
<213> ORGANISM: Artificial sequence
<220> FEATURE:
<223> OTHER INFORMATION: Synthetic

<400> SEQUENCE: 42
gctgcaggga agatggac                                                 18
```

<210> SEQ ID NO 43
<211> LENGTH: 20
<212> TYPE: DNA
<213> ORGANISM: Artificial sequence
<220> FEATURE:
<223> OTHER INFORMATION: Synthetic

<400> SEQUENCE: 43
gaacggtact ggcgtctgtc                                              20

<210> SEQ ID NO 44
<211> LENGTH: 21
<212> TYPE: DNA
<213> ORGANISM: Artificial sequence
<220> FEATURE:
<223> OTHER INFORMATION: Synthetic

<400> SEQUENCE: 44
aatgttgatc atgccatctc c                                            21

<210> SEQ ID NO 45
<211> LENGTH: 21
<212> TYPE: DNA
<213> ORGANISM: Artificial sequence
<220> FEATURE:
<223> OTHER INFORMATION: Synthetic

<400> SEQUENCE: 45
cgcagacagc tgagtagttc c                                            21

<210> SEQ ID NO 46
<211> LENGTH: 20
<212> TYPE: DNA
<213> ORGANISM: Artificial sequence
<220> FEATURE:
<223> OTHER INFORMATION: Synthetic

<400> SEQUENCE: 46
tcatgcaacg cttagactgg                                              20

<210> SEQ ID NO 47
<211> LENGTH: 20
<212> TYPE: DNA
<213> ORGANISM: Artificial sequence
<220> FEATURE:
<223> OTHER INFORMATION: Synthetic

<400> SEQUENCE: 47
agcagcagct attggagacc                                              20

<210> SEQ ID NO 48
<211> LENGTH: 20
<212> TYPE: DNA
<213> ORGANISM: Artificial sequence
<220> FEATURE:
<223> OTHER INFORMATION: Synthetic

<400> SEQUENCE: 48
tgaaaacctc ctccctctt                                               20

<210> SEQ ID NO 49
<211> LENGTH: 19
<212> TYPE: DNA
<213> ORGANISM: Artificial sequence
<220> FEATURE:

<223> OTHER INFORMATION: Synthetic

<400> SEQUENCE: 49
acccagttca tgccatcct                                                19

<210> SEQ ID NO 50
<211> LENGTH: 21
<212> TYPE: DNA
<213> ORGANISM: Artificial sequence
<220> FEATURE:
<223> OTHER INFORMATION: Synthetic

<400> SEQUENCE: 50
cagcttgttg tccaaatcgt c                                             21

<210> SEQ ID NO 51
<211> LENGTH: 20
<212> TYPE: DNA
<213> ORGANISM: Artificial sequence
<220> FEATURE:
<223> OTHER INFORMATION: Synthetic

<400> SEQUENCE: 51
acaggtgaag caggtctcgt                                               20

<210> SEQ ID NO 52
<211> LENGTH: 21
<212> TYPE: DNA
<213> ORGANISM: Artificial sequence
<220> FEATURE:
<223> OTHER INFORMATION: Synthetic

<400> SEQUENCE: 52
gcccttaaag actgcatcac a                                             21

<210> SEQ ID NO 53
<211> LENGTH: 19
<212> TYPE: DNA
<213> ORGANISM: Artificial sequence
<220> FEATURE:
<223> OTHER INFORMATION: Synthetic

<400> SEQUENCE: 53
tcgaaggcca tgtcatctg                                                19

<210> SEQ ID NO 54
<211> LENGTH: 20
<212> TYPE: DNA
<213> ORGANISM: Artificial sequence
<220> FEATURE:
<223> OTHER INFORMATION: Synthetic

<400> SEQUENCE: 54
cccacaatgt gttgcagttc                                               20

<210> SEQ ID NO 55
<211> LENGTH: 20
<212> TYPE: DNA
<213> ORGANISM: Artificial sequence
<220> FEATURE:
<223> OTHER INFORMATION: Synthetic

<400> SEQUENCE: 55
tggggaatgc attttaccat                                               20

```
<210> SEQ ID NO 56
<211> LENGTH: 21
<212> TYPE: DNA
<213> ORGANISM: Artificial sequence
<220> FEATURE:
<223> OTHER INFORMATION: Synthetic

<400> SEQUENCE: 56
ccgatgtcca tcacattctc t                                             21

<210> SEQ ID NO 57
<211> LENGTH: 18
<212> TYPE: DNA
<213> ORGANISM: Artificial sequence
<220> FEATURE:
<223> OTHER INFORMATION: Synthetic

<400> SEQUENCE: 57
ttgagatcca tgccgttg                                                 18

<210> SEQ ID NO 58
<211> LENGTH: 20
<212> TYPE: DNA
<213> ORGANISM: Artificial sequence
<220> FEATURE:
<223> OTHER INFORMATION: Synthetic

<400> SEQUENCE: 58
tggggaatgc attttaccat                                               20

<210> SEQ ID NO 59
<211> LENGTH: 20
<212> TYPE: DNA
<213> ORGANISM: Artificial sequence
<220> FEATURE:
<223> OTHER INFORMATION: Synthetic

<400> SEQUENCE: 59
agcagcagct attggagacc                                               20

<210> SEQ ID NO 60
<211> LENGTH: 20
<212> TYPE: DNA
<213> ORGANISM: Artificial sequence
<220> FEATURE:
<223> OTHER INFORMATION: Synthetic

<400> SEQUENCE: 60
gcagagggtg acggatgtag                                               20
```